United States Patent
King et al.

(10) Patent No.: US 10,226,522 B2
(45) Date of Patent: Mar. 12, 2019

(54) COMPOSITIONS AND METHODS FOR THE TREATMENT OR PREVENTION OF TUBERCULOSIS

(71) Applicants: GlobeImmune, Inc., Louisville, CO (US); Colorado State University Research Foundation, Fort Collins, CO (US)

(72) Inventors: Thomas H. King, Denver, CO (US); Zhimin Guo, Superior, CO (US); Ian M. Orme, Fort Collins, CO (US)

(73) Assignees: GLOBEIMMUNE, INC., Louisville, CO (US); COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 0 days.

(21) Appl. No.: 14/914,790

(22) PCT Filed: Aug. 29, 2014

(86) PCT No.: PCT/US2014/053449
§ 371 (c)(1),
(2) Date: Feb. 26, 2016

(87) PCT Pub. No.: WO2015/031778
PCT Pub. Date: Mar. 5, 2015

(65) Prior Publication Data
US 2016/0213767 A1 Jul. 28, 2016

Related U.S. Application Data

(60) Provisional application No. 61/872,498, filed on Aug. 30, 2013, provisional application No. 62/016,541, filed on Jun. 24, 2014.

(51) Int. Cl.
*A61K 39/04* (2006.01)
*C07K 14/35* (2006.01)
*A61K 39/39* (2006.01)
*A61K 9/00* (2006.01)
*A61K 39/00* (2006.01)

(52) U.S. Cl.
CPC .......... *A61K 39/04* (2013.01); *A61K 9/0019* (2013.01); *A61K 39/39* (2013.01); *C07K 14/35* (2013.01); *A61K 2039/521* (2013.01); *A61K 2039/523* (2013.01)

(58) Field of Classification Search
None
See application file for complete search history.

(56) References Cited

U.S. PATENT DOCUMENTS

| | | |
|---|---|---|
| 4,775,622 A | 10/1988 | Hitzeman et al. |
| 5,234,830 A | 8/1993 | Oshima et al. |
| 5,310,654 A | 5/1994 | Isberg et al. |
| 5,413,914 A | 5/1995 | Franzusoff |
| 5,830,463 A | 11/1998 | Duke et al. |
| 5,858,378 A | 1/1999 | Bostwick |
| 5,919,651 A | 7/1999 | Hitzeman et al. |
| 7,083,787 B2 | 8/2006 | Duke et al. |
| 7,439,042 B2 | 10/2008 | Duke et al. |
| 7,465,454 B2 | 12/2008 | Franzusoff et al. |
| 7,563,447 B2 | 7/2009 | Franzusoff et al. |
| 7,595,060 B2 | 9/2009 | Duke et al. |
| 7,625,569 B2 | 12/2009 | Duke et al. |
| 7,632,511 B2 | 12/2009 | Duke et al. |
| 7,736,642 B2 * | 6/2010 | Duke .......... A61K 39/145 424/184.1 |
| 2002/0044948 A1 | 4/2002 | Samir et al. |
| 2003/0035810 A1 | 2/2003 | Caplan |
| 2007/0172503 A1 | 7/2007 | Selitrennikoff et al. |
| 2007/0224208 A1 | 9/2007 | Guo et al. |
| 2008/0003239 A1 | 1/2008 | Duke et al. |
| 2009/0074805 A1 | 3/2009 | Duke et al. |
| 2009/0098154 A1 | 4/2009 | Franzusoff et al. |
| 2009/0124549 A1 | 5/2009 | Lewinsohn et al. |
| 2009/0142366 A1 | 6/2009 | Franzusoff et al. |
| 2009/0142367 A1 | 6/2009 | Franzusoff et al. |
| 2009/0304741 A1 | 12/2009 | Duke et al. |
| 2010/0034840 A1 | 2/2010 | Apelian et al. |
| 2010/0104604 A1 | 4/2010 | Selitrennikoff et al. |
| 2010/0111912 A1 | 5/2010 | Apelian et al. |
| 2010/0150963 A1 | 6/2010 | Duke et al. |
| 2010/0189749 A1 | 7/2010 | Franzusoff et al. |
| 2010/0196411 A1 | 8/2010 | Duke et al. |

(Continued)

FOREIGN PATENT DOCUMENTS

| | | |
|---|---|---|
| CN | 101438166 | 5/2009 |
| CN | 102666575 | 9/2012 |

(Continued)

OTHER PUBLICATIONS

International Search Report and Written Opinion for International (PCT) Patent Application No. PCT/US14/53449 dated Feb. 13, 2015, 11 pages.
International Preliminary Report of Patentability for International (PCT) Patent Application No. PCT/US2014/053449 dated Mar. 10, 2016, 7 pages.
Bertholet et al., "A Defined Tuberculosis Vaccine Candidate Boosts BCG and Protects Against Multidrug Resistant *Mycobacterium tuberculosis*," Science Translational Medicine, 2010, vol. 2, Iss. 53, pp. 53-74.
Bizzini et al. "Use of live *Saccharomyces cerevisiae* cells as a biological response modifier in experimental infections," FEMS Microbiology Immunology, 1990, vol. 64, pp. 155-168.
Brake et al. "alpha-Factor-directed synthesis and secretion of mature foreign proteins in *Saccharomyces cerevisiae*," Proceedings of the National Academy of Sciences USA, Aug. 1984, vol. 81, pp. 4642-4646.

(Continued)

*Primary Examiner* — Brian Gangle
(74) *Attorney, Agent, or Firm* — Sheridan Ross P.C.

(57) ABSTRACT

Disclosed are yeast-based immunotherapeutic compositions and fusion proteins for the treatment and/or prevention of TB infection and symptoms thereof, as well as methods of using the yeast-based immunotherapeutic compositions and fusion proteins for the prophylactic and/or therapeutic treatment of TB and/or symptoms thereof.

16 Claims, 9 Drawing Sheets

Specification includes a Sequence Listing.

(56) References Cited

U.S. PATENT DOCUMENTS

| | | |
|---|---|---|
| 2010/0215678 A1 | 8/2010 | Guo et al. |
| 2011/0150909 A1 | 6/2011 | Franzusoff et al. |
| 2011/0256098 A1 | 10/2011 | Apelian et al. |
| 2012/0107347 A1 | 5/2012 | Hodge et al. |
| 2012/0282290 A1 | 11/2012 | Spencer et al. |
| 2012/0321664 A1 | 12/2012 | Bellgrau et al. |

FOREIGN PATENT DOCUMENTS

| | | | |
|---|---|---|---|
| EP | 0414404 | 2/1991 | |
| FR | 2486400 | 1/1982 | |
| WO | WO-2008124647 A2 * | 10/2008 | ............. A61K 39/04 |
| WO | WO 2010/065626 | 6/2010 | |
| WO | WO 2011/115914 | 9/2011 | |
| WO | WO 2012/019127 | 2/2012 | |
| WO | WO 2012/083302 | 6/2012 | |
| WO | WO 2012/109404 | 8/2012 | |
| WO | WO 2012/125998 | 9/2012 | |
| WO | WO 2012/174220 | 12/2012 | |
| WO | WO 2013/025972 | 2/2013 | |
| WO | WO 2014/160747 | 10/2014 | |

OTHER PUBLICATIONS

Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

Henao-Tamayo et al. "Memory T cell subsets in tuberculosis: What should we be targeting?," Tuberculosis, 2014, vol. 94, Iss. 5, pp. 455-461.

Klepfer et al. "Characterization of rabies glycoprotein expressed in yeast," Archives of Virology, 1993, vol. 128, pp. 269-286.

Lu, et al., "Mutation-Selective Tumor Remission with Ras-Targeted, Whole Yeast-Based Immunotherapy," Cancer Research, 2004, vol. 64, pp. 5084-5088.

Moore et al., "Novel yeast-based vaccine 1-40, against HIV-SF2 gp160 promotes a cytotoxic 43-62 cell response.", FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.

Ordway et al. "*Mycobacterium bovis* BCG-Mediated Protection against W-Beijing Strains of *Mycobacterium tuberculosis* Is Diminished Concomitant with the Emergence of Regulatory T Cells," Clinical and Vaccine Immunology, 2011, vol. 18, No. 9, pp. 1527-1535.

Orme, "Development of new vaccines and drugs for TB: limitations and potential strategic errors," Future Microbiology, 2011, vol. 6, No. 2, pp. 161-177.

Orme, "Vaccine Development for Tuberculosis: Current Progress," Drugs, 2013, vol. 73, Iss. 10, pp. 1015-1024.

Schreuder et al. "Yeast expressing hepatitis B virus surface antigen determinants on its surface: implications for a possible oral vaccine," Vaccine, Apr. 1996, vol. 14, No. 5, pp. 383-388.

Sinai et al. "Enhancement of Resistance to Infectious Diseases by Oral Administration of Brewer's Yeast," Infection and Immunity, May 1974, vol. 9, No. 5, pp. 781-787.

Stubbs, et al., "Whole Recombinant Yeast Vaccine Activates Dendritic Cells and Elicits Protective Cell-Mediated Immunity," National Medicine, May 2001, vol. 7, No. 5, pp. 1-5.

Turner et al., "Effective Preexposure Tuberculosis Vaccines Fail to Protect When They Are Given in an Immunotherapeutic Mode," Infection and Immunity, 2000, vol. 68, No. 3, pp. 1706-1709.

Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.

Official Action (with English translation) for Taiwanese Patent Application No. 103130016 dated Mar. 31, 2018, 22 pages.

* cited by examiner

COMPOSITIONS AND METHODS FOR THE TREATMENT OR PREVENTION OF TUBERCULOSIS

CROSS-REFERENCE TO RELATED APPLICATIONS

This application is a national stage application under 35 U.S.C. 371 of PCT Application No. PCT/US2014/053449 having an international filing date of Aug. 29, 2014, which designated the United States, which PCT application claims the benefit of priority under 35 U.S.C. § 119(e) to U.S. Provisional Patent Application No. 61/872,498, filed Aug. 30, 2013 and to U.S. Provisional Patent Application No. 62/016,541, filed Jun. 24, 2014. The entire disclosure of each of PCT Application No. PCT/US2014/053449, U.S. Provisional Patent Application No. 61/872,498 and U.S. Provisional Patent Application No. 62/016,541 is incorporated herein by reference.

GOVERNMENT RIGHTS

This invention was made with Government support under Grant No. 1 R01 AI105053-01 awarded by the National Institute of Allergy and Infectious Disease of the National Institutes of Health. The Government of the United States has certain rights in this invention.

STATEMENT REGARDING JOINT RESEARCH AGREEMENT

This invention was made by or on behalf of parties to a Research Subaward Agreement, under Grant No. 1 R01 AI105053-01 awarded by the National Institute of Allergy and Infectious Disease of the National Institutes of Health, executed Oct. 3, 2013. The parties to the Research Subaward Agreement are: GlobeImmune, Inc. (Prime Recipient) and Colorado State University (Subrecipient).

REFERENCE TO A SEQUENCE LISTING

This application contains a Sequence Listing submitted electronically as a text file by EFS-Web. The text file, named "3923-45-PCT_ST25", has a size in bytes of 192 KB, and was recorded on Aug. 25, 2014. The information contained in the text file is incorporated herein by reference in its entirety pursuant to 37 CFR § 1.52(e)(5).

FIELD OF THE INVENTION

The present invention generally relates to yeast-based immunotherapeutic compositions and methods for preventing and/or treating tuberculosis.

BACKGROUND OF THE INVENTION

Tuberculosis ("TB", short for *tubercle bacillus*, also referred to as "MTB"), is caused by *Mycobacterium* infection, most typically, *Mycobacterium tuberculosis*, and ranks in the top three etiologies of infectious disease mortality. Drug resistant strains make this pathogen especially dangerous as both a general health hazard and a potential bioterrorism agent. Tuberculosis primarily impacts the lungs, although it can also affect other parts of the body, such as the brain, the kidneys, or the spine, and it is spread by transmission of respiratory fluids through the air (e.g., as a result of coughing or sneezing by an infected person). While many TB infections are latent (asymptomatic), approximately 10% of these latent infections eventually become active disease which, when untreated, kills more than 50% of infected patients.

Approximately one third of the world's population is thought to have been infected with *M. tuberculosis*. Although the absolute number of TB cases has been decreasing since the early-mid 2000's, according to the Centers for Disease Control (CDC), nearly 9 million people around the world became sick with TB disease in 2011, and there were around 1.4 million TB-related deaths worldwide. Moreover, TB is a leading killer of people who are TB infected. Also according to the CDC, a total of 10,528 TB cases (a rate of 3.4 cases per 100,000 persons) were reported in the United States in 2011. Therefore, there remains a need worldwide for preventative and therapeutic treatments for TB.

The treatment of TB is difficult and requires administration of multiple antibiotics over a long period of time (e.g., 6-9 months). Accordingly, patient compliance with the completion of treatment can be challenging. Moreover, antibiotic resistance is a problem, where multiple drug-resistant tuberculosis (MDR-TB) infections (caused by an organism that is resistant to at least isoniazid and rifampin, currently the two most potent TB drugs) continue to increase in prevalence. In addition, although rare, cases are also emerging of extensively drug-resistant TB (XDR TB), a type of MDR TB that is resistant to isoniazid and rifampin, plus any fluoroquinolone and at least one of three injectable second-line drugs (i.e., amikacin, kanamycin, or capreomycin).

Prevention of tuberculosis in the United States is addressed primarily through TB screening and monitoring programs and in other regions of the world, is addressed by vaccination with the Bacillus Calmette-Guérin (BCG) vaccine. The BCG vaccine is a live vaccine originally derived from a strain of *Mycobacterium bovis* that was attenuated by Calmette and Guerin at the Pasteur Institute in Lille, France in the early 1900's. While the BCG vaccine showed some effect in certain pediatric cases, the vaccine has not been shown to be effective in adult TB, its efficacy wanes in teenagers and young adults, and the vaccine can interfere with tuberculin skin tests, which is a primary means of detection of TB used in screening methods of prevention.

It is known that CD4+ Th1 cells target intracellular pathogens such as *M. tuberculosis* via the production of interferon (IFN) gamma, and that the generation of CD8+ cytotoxic T cells (CTLs) is critical in combating TB (Billeskov et al, *J. Immunol.* 179:3973-81 (2007); Elvang et al, PLoS One 4:5139 (2009)). However, CD4+ Th1 and CD8+ T cells alone do not explain the resistance/susceptibility to TB as might be expected from a disease that also manifests itself extracellularly. It is now apparent that extracellular targeting of TB falls within the purview of a CD4+ T cell subset named Th17 for the cytokine it secretes, IL-17 (Hunter et al., *Nat Rev Immunol* 5, 521-31 (2005)). The magnitude of the Th17 response has been associated with clinical outcome (Khader et al., *Nat Immunol* 8:369-77 (2007)) and disease severity in TB (Chen et al, *J. Clin. Immunol.* published online 2010). If both Th1 and Th17 responses are required for productive immunity (Khader et al., supra (2007); Khader and Cooper, *Cytokine* 41:79-83 (2008)), TB may successfully escape from the immune system by thwarting either pathway. Indeed, it has been reported that TB can lead to downregulation of the IL-6 receptor on T cells (Chen et al., supra, 2010), IL-6 being a key cytokine in the induction of Th17 cells, thus negating the Th17 pathway and subverting an important component of the immune armamentarium. Finally, recent studies by Ordway et al. (*Clin Vaccine Immunol.* 2011 September; 18(9): 1527-35, Epub 2011 Jul. 27) showed that BCG vaccination significantly delayed but did not prevent the emergence of the Treg population of CD4+ T cells, further diminishing long-term protection. This paper compared the host immune responses to two highly virulent W-Beijing strains in control mice and in mice previously vaccinated with the Bacillus Calmette-Guérin (BCG) TB vaccine. Results showed that the CD4+ effector T cell response peaks at around one month post-challenge, then wanes by day 60 concomitant with an increase in the frequency of Treg cells (CD4+Foxp3+ cells) in the lungs, draining lymph nodes, and spleen.

An effective post-exposure vaccine has been an ambition of many researchers in the field for years. Such vaccines have not, however, been widely successful or have not yet been proven efficacious in humans. For example, certain vaccines evaluated by scientists at Colorado State University that focused on antigens found in short-term culture filtrates, e.g., a subunit vaccine consisting of mid-log-phase culture filtrate proteins (CFP) from *M. tuberculosis* emulsified in MPL-TeoA adjuvant and supplemented with recombinant interleukin 2 (rIL-2) or a DNA vaccine encoding antigen 85A (Turner et al., supra 2000), were not successful in modulating the course of an aerosol infection with *M. tuberculosis*. In 2010, Bertholet et al., reported a recombinant subunit vaccine for TB, called ID93, which combines four antigens belonging to families of Mtb proteins associated with virulence (Rv2608, Rv3619, Rv3620) or latency (Rv1813) in a stable oil in water monophosphoryl lipid A-based adjuvant. In three animal models for TB, the vaccine was immunogenic and showed protection from challenge with virulent TB strains in two of the models. However, recombinant proteins are generally not immunogenic alone, and adjuvant development for the successful use of recombinant proteins such as ID93 in humans remains a challenge. While such adjuvants are the subject of ongoing investigation and clinical trials, it remains to be seen whether a subunit vaccine such as ID93 will be efficacious in humans as a pre- or post-exposure vaccine. Several other vaccine candidates are in development, but none have yet shown efficacy in a human clinical trial. In February 2013, the most advanced new vaccine against TB, a recombinant modified vaccinia virus Ankara expressing antigen 85A and developed by researchers at Oxford University, was reported to be unable to confer significant protection against tuberculosis or *M. tuberculosis* infection in infants (Tameris et al., *Lancet.* 2013 Mar. 23; 381(9871):1021-8).

Part of the challenge in developing a pre- or post-exposure vaccine lies in antigen selection. An exhaustive study by investigators at Colorado State University (CSU) in 2000 (Turner et al., supra 2000) indicated that there was no apparent material benefit from post-exposure vaccines based on certain "immunodominant" antigens of *M. tuberculosis* in the therapeutic setting. A review of antigens and current vaccines in development can be found in Orme et al. (*Drugs* (2013) 73:1015-1024). While immunodominant antigens still remain the focus of many TB vaccine efforts, investigators at CSU have recently also focused on antigens made by the bacillus under stress conditions (e.g., necrosis, host nitric oxide production, etc); these include what are regarded by some as "latency" antigens. Included in such latency antigens are antigens involved in a specific action by bacilli in primary lung granulomas to produce proteins for the purpose of accumulating iron. The CSU investigators have extensively defined the pathology of the disease process in guinea pigs infected by low dose aerosol with *M. tuberculosis*. One study, in which iron distribution in the primary lesion (as part of the dystrophic calcification process) was a primary focus, produced the surprising observation that both extracellular bacilli in the necrotic center, as well as bacilli probably still in macrophages on the rim of this structure (Lenaerts et al, 2007; Basaraba et al, 2008; Orme et al, 2011), were surrounded by ferric iron. These investigators had noticed previously that mice chronically infected with TB had T cells in the lungs that recognized bacterial ferritin and produced IFN-γ. A subsequent fusion protein vaccine was made that included this antigen, and it had modest protective activity in the guinea pig post-exposure model. The CSU investigators report a recombinant subunit vaccine formed from "iron accumulation" proteins (also referred to herein as "iron metabolism antigens"), namely Rv1909, Rv2359, and Rv2711 (Orme, *Drugs* (2013) 73:1015-1024).

Finally, as discussed in detail in Orme et al., 2011, supra, the prevailing view of the pathogenesis of TB, which has been in place for many years, is that inflammation drives cellular recruitment and granuloma formation, and the granulomas become neovascularized. The center of the lesion develops necrosis, while lymphocytes are held at the periphery of the lesions. These lesions can then cavitate, releasing bacilli into the airways. However, more current, alternative models of TB infection supported by more recent data, point to the primary lesion and its necrosis being not an end point, but rather a very early event, independent of the generation of acquired immunity. In this model, collapse of local vasculature allow bacilli to persist and survive, perhaps in primitive biofilms, secondary lesions form in the lungs, T cell immunity drops off despite survival of bacilli, and some of these lesions erode into adjacent airways or blood vessels, allowing the dissemination and escape of the TB infection. These differences in the view of pathogenesis of TB relate directly to how a prophylactic or therapeutic vaccine should be designed, again leading back to the idea that targeting immunodominant antigens based on primary lesions has not resulted in an efficacious vaccine to date. Indeed, a lack of understanding of the biology of the tuberculosis pathogen has been a major obstacle in vaccine development.

Therefore, there remains a need in the art for an improved pre- and/or post-exposure vaccine for TB.

SUMMARY OF THE INVENTION

One embodiment of the invention relates to an immunotherapeutic composition comprising: (a) a yeast vehicle; and (b) a fusion protein comprising at least one TB antigen. The TB antigen can include, but is not limited to, a TB protein selected from: Rv0125, Rv1196, Rv1411 (Rv1411c), Rv1738, Rv1813, Rv1909 (Rv1909c), Rv2032, Rv2359, Rv2608, Rv2660, Rv2711, Rv3130, Rv3619, Rv3620, Rv3841, Ag85A, Ag85B, TB10.4 and ESAT-6. In one aspect, the fusion protein comprises a TB antigen from one or more of Rv1738, Rv2032, Rv3130 or Rv3841. In one aspect, the fusion protein comprises a TB antigen from two or more of Rv1738, Rv2032, Rv3130 or Rv3841. In one aspect, the fusion protein comprises a TB antigen from each of Rv1738, Rv2032, Rv3130 and Rv3841. In one aspect, the fusion protein comprises a TB antigen from one or more of Rv2359, Rv2711 or Rv1909c. In one aspect, the fusion protein comprises a TB antigen from two or more of Rv2359, Rv2711 and Rv1909c. In one aspect, the fusion protein comprises a TB antigen from each of Rv2359, Rv2711 and Rv1909c. In one aspect, the fusion protein comprises a TB antigen from at least one of Rv2359, Rv2711 or Rv1909c, and a TB antigen from at least one or more of Rv1738, Rv2032, Rv3130 and Rv3841. In a further embodiment related to any of the above aspects of the invention, the fusion protein further comprises a TB antigen from from Rv1411c. In one aspect, the fusion protein comprises a TB antigen from each of Rv2032, Rv1411c, and Rv2359.

Another embodiment of the invention relates to an immunotherapeutic composition comprising: (a) a yeast vehicle; and (b) a fusion protein comprising TB antigens, wherein the TB antigens comprise or consist of an amino acid sequence that is at least 80% identical to an amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In another embodiment, the TB antigens comprise or consist of an amino acid sequence that is at least 85% identical to an amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In another embodiment, the TB antigens comprise or consist of an amino acid sequence that is at least 90% identical, 91% identical, 92% identical, 93% identical, or 94% identical, to an amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In another embodiment, the TB antigens comprise or consist of an amino acid sequence that is at least 95% identical, 96% identical, 97% identical, 98% identical, or 99% identical, to an amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In another embodiment, the TB antigens comprise or consist of an amino acid sequence that is at least 99% identical to an amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In another embodiment, the TB antigens comprise or consist of an amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In one aspect, the TB antigen comprises or consists of an amino acid sequence of SEQ ID NO:13. In one aspect, the TB antigen comprises or consists of an amino acid sequence of SEQ ID NO:31. In one aspect, the TB antigen comprises or consists of an amino acid sequence of SEQ ID NO:43.

In one aspect of any of these embodiments of the invention related to an immunotherapeutic composition, the fusion protein comprises or consists of an amino acid sequence selected from: SEQ ID NO:6, SEQ ID NO:9, SEQ ID NO:12, SEQ ID NO:15, SEQ ID NO:18, SEQ ID NO:21, SEQ ID NO:25, SEQ ID NO:27, SEQ ID NO:30, SEQ ID NO:33, SEQ ID NO:36, SEQ ID NO:39, SEQ ID NO:42, SEQ ID NO:45 or SEQ ID NO:48. In one aspect, the fusion protein comprises or consists of an amino acid sequence of SEQ ID NO:15. In one aspect, the fusion protein comprises or consists of an amino acid sequence of SEQ ID NO:33. In one aspect, the fusion protein comprises or consists of an amino acid sequence of SEQ ID NO:45.

In any of the above-described embodiments and aspects of the invention, in one further aspect, the yeast vehicle is a whole yeast. In one aspect, the yeast vehicle is a whole, killed or inactivated yeast. In one aspect, the yeast vehicle is a whole, heat-inactivated yeast.

In any of the above-described embodiments and aspects of the invention, in one further aspect, the yeast is from a yeast genus selected from the group consisting of: *Saccharomyces, Candida, Cryptococcus, Hansenula, Kluyveromyces, Pichia, Rhodotorula, Schizosaccharomyces* and *Yarrowia*. In one aspect, the yeast is from *Saccharomyces*. In one aspect, the yeast is from *Saccharomyces cerevisiae*.

In any of the above-described embodiments and aspects of the invention, in one further aspect, the composition is formulated in a pharmaceutically acceptable excipient suitable for administration to a subject by injection.

Yet another embodiment of the invention relates to an immunotherapeutic composition comprising: (a) a whole, heat-inactivated yeast from *Saccharomyces cerevisiae*; and (b) a TB fusion protein expressed by the yeast, wherein the fusion protein comprises or consists of an amino acid sequence selected from: SEQ ID NO:6, SEQ ID NO:9, SEQ ID NO:12, SEQ ID NO:15, SEQ ID NO:18, SEQ ID NO:21, SEQ ID NO:25, SEQ ID NO:27, SEQ ID NO:30, SEQ ID NO:33, SEQ ID NO:36, SEQ ID NO:39, SEQ ID NO:42, SEQ ID NO:45 or SEQ ID NO:48. In one aspect, the fusion protein comprises or consists of an amino acid sequence of SEQ ID NO:15. In one aspect, the fusion protein comprises or consists of an amino acid sequence of SEQ ID NO:33. In one aspect, the fusion protein comprises or consists of an amino acid sequence of SEQ ID NO:45.

Another embodiment of the invention relates to a fusion protein comprising TB antigens, wherein the TB antigens comprise or consist of an amino acid sequence that is at least 80% identical to an amino acid sequence of: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In one aspect, the TB antigens comprise or consist of an amino acid sequence that is at least 85% identical to an amino acid sequence of: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In one aspect, the TB antigens comprise or consist of an amino acid sequence that is at least 90% identical, 91% identical, 92% identical, 93% identical, or 94% identical, to an amino acid sequence of: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In one aspect, the TB antigens comprise or consist of an amino acid sequence that is at least 95% identical, 96% identical, 97% identical, 98% identical, or 99% identical, to an amino acid sequence of: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In one aspect, the TB antigens comprise or consist of an amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46. In one aspect, the fusion protein comprises or consists of an amino acid sequence selected from SEQ ID NO:6, SEQ ID NO:9, SEQ ID NO:12, SEQ ID NO:15, SEQ ID NO:18, SEQ ID NO:21, SEQ ID NO:25, SEQ ID NO:27, SEQ ID NO:30, SEQ ID NO:33, SEQ ID NO:36, SEQ ID NO:39, SEQ ID NO:42, SEQ ID NO:45 or SEQ ID NO:48.

Another embodiment of the invention relates to a recombinant nucleic acid molecule comprising a nucleic acid sequence encoding any of the fusion proteins described above or elsewhere herein.

Another embodiment of the invention relates to an isolated recombinant cell transfected with such a recombinant nucleic acid molecule as described above or elsewhere herein. In one aspect, the cell is a yeast cell.

Yet another embodiment of the invention relates to a composition comprising the isolated recombinant cell described above or elsewhere herein.

Another embodiment of the invention relates to a method to treat tuberculosis (TB) infection or at least one symptom resulting from TB infection in a subject. The method includes the step of administering to a subject that has been infected with TB at least one of any of the immunotherapeutic compositions described above or elsewhere herein. The administration of the composition to the subject reduces TB infection or at least one symptom resulting from TB infection in the subject. In one aspect, the method further includes a step of administering to the subject one or more additional agents useful for treating or ameliorating a symptom of TB infection. In one aspect, the additional agent is a chemotherapeutic drug or antibiotic. Such additional agents can include, but are not limited to, isoniazid (INH), rifampin (RIF), rifapentine (RPT), ethambutol (EMB), pyrazinamide (PZA) and BCG vaccine. In one aspect, the agent is BCG vaccine, and the BCG vaccine is administered prior to administration of the immunotherapeutic composition. In one aspect, the method further includes Directly Observed Therapy (DOT). In one aspect of this embodiment of the invention, the subject has latent TB infection. In one aspect, the subject has active TB infection. In one aspect of this embodiment of the invention, the administration of the immunotherapeutic composition to the subject is effective to enhance or synergize with the efficacy of an agent useful for treating or ameliorating a symptom of TB infection or delay progression of TB infection and/or symptoms thereof sufficient to increase the effectiveness of treatment with the agent or sufficient to allow additional time for the agent to provide a therapeutic benefit to the subject. In one aspect, administration of the composition to the subject reduces or delays the formation of secondary tuberculosis lesions in the lungs of the subject, as compared to in the absence of the composition. In one aspect, administration of the composition to the subject reduces or delays the dissemination of the TB infection to lymph nodes or other tissues or organs, as compared to in the absence of the composition. In one aspect, administration of the composition to the subject elicits an antigen-specific, cellular immune response against one or more TB antigens. None of these aspects of the invention are necessarily exclusive of other aspects of the invention.

Another embodiment of the invention relates to a method to treat an individual or population of individuals who have been exposed to an organism that causes TB. The method includes the step of administering to the individual or population of individuals at least one of any of the immunotherapeutic compositions described above or elsewhere herein. In one aspect, the method further includes a step of administering to the subject one or more additional agents useful for treating or ameliorating a symptom of TB infection. In one aspect, the additional agent is a chemotherapeutic drug or antibiotic. Such additional agents can include, but are not limited to, isoniazid (INH), rifampin (RIF), rifapentine (RPT), ethambutol (EMB), pyrazinamide (PZA) and BCG vaccine. In one aspect, the method further includes Directly Observed Therapy (DOT).

Another embodiment of the invention relates to a method to prevent or delay the onset or severity of TB infection in a subject. The method includes a step of administering to a subject that has not been infected with TB at least one of any of the immunotherapeutic compositions described above or elsewhere herein. In one aspect, the method further includes administering BCG vaccine to the subject. In one aspect, the BCG vaccine is administered prior to administering the immunotherapeutic composition.

Yet another embodiment of the invention relates to a method to immunize a population of individuals against TB. The method includes a step of administering to the population of individuals at least one of any of the immunotherapeutic compositions described above or elsewhere herein. In one aspect, the method further includes a step of administering BCG vaccine to the population of individuals. In one aspect, the method further includes administering BCG vaccine to the population of individuals. In one aspect, the BCG vaccine is administered to the population of individuals prior to administering the immunotherapeutic composition.

In one aspect of any of the methods described above or elsewhere herein, the immunotherapeutic composition is administered at a dose from between 1 Y.U. and 80 Y.U. In one aspect, the immunotherapeutic composition is administered by subcutaneous injection.

Another embodiment of the invention relates to any of the immunotherapeutic compositions described above or elsewhere herein for use to treat TB infection or a symptom thereof.

Yet another embodiment of the invention relates to any of the immunotherapeutic compositions described above or elsewhere herein for use to prevent TB infection or a symptom thereof.

Another embodiment of the invention relates to the use of any of the immunotherapeutic compositions described above or elsewhere herein in the preparation of a medicament to treat TB infection or a symptom thereof.

Yet another embodiment of the invention relates to the use of any of the immunotherapeutic compositions described above or elsewhere herein in the preparation of a medicament to prevent TB infection or a symptom thereof.

DETAILED DESCRIPTION OF THE INVENTION

Figure 1A:
FIG. 1A is a schematic drawing showing the organization of a fusion protein for expression in a yeast-based immunotherapeutic composition, comprising an N-terminal stability peptide (gray), a TB antigen from rv2359 (white), and a C-terminal hexahistidine peptide (black).

This invention generally relates to compositions and methods for preventing and/or treating tuberculosis (TB), e.g., infection by a strain of mycobacteria, usually *Mycobacterium tuberculosis*, and sequelae of the infection. The invention includes a yeast-based immunotherapeutic composition (also referred to as "yeast-based tuberculosis immunotherapy" or "yeast-based TB immunotherapy" or "yeast-based TB immunotherapeutic") comprising a yeast vehicle and TB antigen(s) that have been designed to elicit a prophylactic and/or therapeutic immune response against TB infection in an individual, and the use of such compositions to prevent and/or treat TB infection and related symptoms thereof. The invention also includes the recombinant nucleic acid molecules used in the yeast-based compositions of the invention, as well as the proteins and fusion proteins encoded thereby, for use in any immunotherapeutic composition and/or any therapeutic or prophylactic protocol for TB infection, including any therapeutic or prophylactic protocol that combines the TB-specific yeast-based compositions of the invention with any one or more other therapeutic or prophylactic compositions, agents, drugs, compounds, and/or protocols for TB infection.

The present invention describes a yeast-based TB immunotherapy and method of use of such immunotherapy in order to: prevent, reduce or eliminate detectable infection by TB mycobacteria; reduce, eliminate and/or delay the formation of secondary tuberculosis lesions; reduce, eliminate and/or delay dissemination of the TB mycobacteria to the lymph nodes or other organs or body systems; extend survival of the infected subject; ameliorate TB infection or symptoms sufficient to improve the efficacy of chemotherapeutic or other TB drugs in eradicating or treating the infection; ameliorate at least one symptom of the infection in the individual; delay or prevent the onset and/or severity of symptoms and/or downstream sequelae caused by the infection, reduce organ or physiological system damage resulting from the infection, improve immune responses, including long term memory immune responses against the TB organism (mycobacterium), and/or improve the general health of the individual or population of individuals infected with TB. The yeast-based TB immunotherapy compositions of the invention are believed to be useful to synergize with TB chemotherapy and thereby shorten treatment for active TB disease or latent tuberculosis infection.

The present inventors have developed innovative solutions to problem areas in the development of a vaccine approach to TB, which includes the use of a vaccine (immunotherapy) platform, i.e., yeast-based immunotherapy, that specifically targets the T cell pathway(s) that are relevant for immunity against TB, combined with the choice of novel target antigens (described below) with the potential for greater clinical utility, and the design of these antigens for expression in the yeast-based immunotherapeutic. The experiments described herein also describe preclinical testing of the vaccine in animal models of TB, and the evaluation of the vaccine in newly emerging, highly virulent multi-drug resistant (MDR) strains of *M. tuberculosis*. A yeast-based TB immunotherapeutic of the invention has the additional advantage that it can be manufactured rapidly at large scale with excellent stability, characteristics not shared with other immunotherapies, such as viral vector-based immunotherapy and some adjuvanted subunit therapies.

The yeast-based, TB-specific immunotherapeutic compositions of the invention are unique among various types of immunotherapy, in that these compositions induce innate immune responses as well as adaptive immune responses that specifically target TB. Yeast-based immunotherapy induces $CD4^+$-dependent Th17 and Th1 T cell responses, as well as antigen-specific $CD8^+$ T cell responses. As discussed above, the production of all of these types of cellular immune responses is believed to be important for long term control of TB. In addition, yeast-based immunotherapy reduces the number or activity of regulatory T cells (Treg) in a pathway that involves the production of IL-6 which, in the presence of TGFβ (mice) or IL1β (humans), drives the formation of Th17 cells, at the expense of Tregs. An added benefit of Th17 cell production is that these cells secrete several cytokines, including IL-21, that increase the durability of CD8+ T cells, and other cytokines that result in macrophage/neutrophil mediated clearance of extracellular pathogens. Yeast-based immunotherapy also elicits IL-12 production by antigen presenting cells, and this promotes the Th1 cell subset, ultimately leading to better CTL responses which are key to the elimination of intracellular pathogens such as TB. Accordingly, the breadth of the immune response elicited by yeast-based immunotherapy represents an ideal platform with which to address the challenge of providing a post-exposure (and pre-exposure) vaccine.

Moreover, the particular TB antigens targeted by the compositions of the invention are different than those used by many prior vaccines, and are believed to have a greater potential for clinical efficacy than antigens targeted by vaccines described previously (discussed in more detail below). For example, although immunodominant antigens used in previously described vaccines may be used in the yeast-based immunotherapeutics of the invention, the preferred antigens are not immunodominant antigens, but rather those made by the bacillus under stress conditions (e.g., necrosis, host nitric oxide production, etc). These antigens include what are regarded by some as "latency" antigens. Preferred antigens for use in a yeast-based immunotherapeutic of the invention include TB antigens involved in a specific action by bacilli in primary lung granulomas to produce proteins for the purpose of accumulating iron, as well as other TB antigens that are present or emerge under conditions of low-dose nitric oxide and hypoxia (conditions that mimic those encountered by mycobacteria during the latent stage of infection), which can include, but are not limited to, antigens associated with NAD(P)H reductase activity, triacylglycerol synthase accumulation in macrophages, bacterioferritin/iron uptake, and toll-like receptor agonists. By targeting such antigens, the present inventors, without being bound by theory, believe that instead of primarily targeting destruction or reduction of the primary lesion, the yeast-based immunotherapeutics of the invention are useful to: (i) reduce, ameliorate and/or delay the formation or severity of secondary tuberculosis lesions, (ii) reduce, ameliorate and/or delay the dissemination of the *M. tuberculosis* bacilli to lymph nodes and other organs, (iii) extend survival of the infected subject, (iv) provide long-lasting, protective immunity against *M. tuberculosis* infection, and, (v) enhance the efficacy of other drugs used to treat infection. Indeed, an important goal of the immunotherapy of the invention is to ameliorate or delay the progress of the infection and damage to tissues and organs in order to extend survival long enough to allow antimicrobial chemotherapeutic agents to bring the infection under control.

Yeast-based immunotherapeutic compositions are administered as biologics or pharmaceutically acceptable compositions. Accordingly, rather than using yeast as an antigen production system followed by purification of the antigen from the yeast (e.g., to form a subunit, or recombinant protein vaccine), the entire yeast vehicle as described herein must be suitable for, and formulated for, administration to a patient. Accordingly, the yeast-based immunotherapeutic compositions of the invention contain readily detectable yeast DNA and contain substantially more than 5% yeast protein; generally, yeast-based immunotherapeutics of the invention contain more than 70%, more than 80%, or generally more than 90% yeast protein as a percentage of the total protein in the yeast cells.

Yeast-based immunotherapeutic compositions are administered to a patient in order to immunize the patient for therapeutic and/or prophylactic purposes. In one embodiment of the invention, the yeast-based compositions are formulated for administration in a pharmaceutically acceptable excipient or formulation. The composition should be formulated, in one aspect, to be suitable for administration to a human subject (e.g., the manufacturing conditions should be suitable for use in humans, and any excipients or formulations used to finish the composition and/or prepare the dose of the immunotherapeutic for administration should be suitable for use in humans). In one aspect of the invention, yeast-based immunotherapeutic compositions are formulated for administration by injection of the patient or subject, such as by a parenteral route (e.g., by subcutaneous, intraperitoneal, intramuscular or intradermal injection, or another suitable parenteral route). In one embodiment, the yeast-based immunotherapeutic compositions are lyophilized for storage, to be formulated later in an appropriate injectable diluent.

In one embodiment, the yeast express the antigen (e.g., detectable by a Western blot), and the antigen is not predicted to be aggregated and is not designed to be aggregated in the yeast. Accordingly, the antigen does not form inclusion bodies in the yeast, and/or does not form very large particles (VLPs) or other large antigen particles in the yeast. In another embodiment, the antigen is produced as a soluble protein in the yeast, and/or is not secreted from the yeast or is not substantially or primarily secreted from the yeast. In all of the embodiments of the invention described herein, the yeast-based immunotherapeutics should be readily phagocytosed by dendritic cells of the immune system, and the yeast and antigens readily processed by such dendritic cells, in order to elicit an effective immune response against tuberculosis-causing organisms (e.g., *M. tuberculosis*).

Compositions of the Invention

One embodiment of the present invention relates to a yeast-based immunotherapy composition which can be used to prevent and/or treat TB infection and/or to alleviate at least one symptom or sequela resulting from the TB infection. According to the present invention, a "TB infection" refers to an infection of a subject by one or more strains of organism that causes tuberculosis, and is most often an infection by one or more strains of *Mycobacterium tuberculosis*. The composition comprises: (a) a yeast vehicle; and (b) one or more antigens comprising TB protein(s) and/or immunogenic domain(s) thereof. According to the present invention, a "TB protein" is a protein from an organism that causes tuberculosis, and is most often a protein from a *Mycobacterium tuberculosis* organism (i.e., a protein that is expressed by, produced by, or forms part of such an organism, such that targeting the protein effectively targets the organism). A "TB antigen" is an antigen (defined below) that comprises a TB protein or at least one immunogenic domain (defined below) of a TB protein. In conjunction with the yeast vehicle, the TB proteins are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more such TB proteins are loaded into a yeast vehicle or otherwise complexed with, attached to, mixed with or administered with a yeast vehicle as described herein to form a composition of the present invention. According to the present invention, reference to a "heterologous" protein or "heterologous" antigen, including a heterologous fusion protein, in connection with a yeast vehicle of the invention, means that the protein or antigen is not a protein or antigen that is naturally expressed by the yeast, although a fusion protein that includes heterologous antigen or heterologous protein may also include yeast sequences or proteins or portions thereof that are also naturally expressed by yeast (e.g., an alpha factor prepro sequence as described herein).

One embodiment of the invention relates to TB antigens designed for expression and use in a yeast-based immunotherapy composition of the invention. Such TB antigens include fusion proteins, which are comprised of at least one TB protein or immunogenic domain thereof, in fusion with an N-terminal and/or C-terminal peptide (described below). Fusion proteins and/or the recombinant nucleic acid molecules encoding such proteins, can also be used in, in combination with, or to produce, a non-yeast-based immunotherapeutic composition, which may include, without limitation, a DNA vaccine, a protein subunit vaccine, a recombinant viral-based immunotherapeutic composition, a killed or inactivated pathogen vaccine, and/or a dendritic cell vaccine. In another embodiment, such fusion proteins or TB antigens can be used in a diagnostic assay for TB and/or to generate antibodies against TB. Described herein are exemplary TB fusion proteins providing selected portions of TB antigens, including, for example, iron accumulation antigens including, but not limited to, Rv1909, Rv2359, and Rv2711, and/or arrangements of any one, two, or all three of these antigens; and also including, for example, hypoxia pool antigens including, but not limited to, Rv1738, Rv2032, Rv3130, and Rv3841, and/or arrangements of any one, two, three, four or more of these antigens; and also including, for example, TB antigens that are TLR agonists including, but not limited to, Rv1411c. Also described herein are additional exemplary TB fusion proteins providing selected portions of different types of TB antigens, including, but not limited to, a fusion protein comprising an iron accumulation antigen, a TLR agonist TB antigen, and a hypoxia pool antigen. Antigens comprising immunodominant TB antigens are also described herein, including, but not limited to, Ag85A.

TB Antigens and Constructs

One embodiment of the invention relates to novel TB antigens and fusion proteins and recombinant nucleic acid molecules encoding these antigens and proteins. Described herein are various TB antigens for use in a yeast-based immunotherapeutic composition or other composition (e.g., other immunotherapeutic or diagnostic composition) that provide one, two, or multiple (three, four, five, six, seven, eight, nine or more) antigens from one or more proteins, which may be provided as separate antigens or contained within the same fusion protein and encoded by the same recombinant nucleic acid construct (recombinant nucleic acid molecule). The antigens used in the compositions of the invention include at least one TB protein or immunogenic domain thereof for immunizing an animal (prophylactically or therapeutically). The composition can include one, two, three, four, a few, several or a plurality of TB antigens, including one, two, three, four, five, six, seven, eight, nine, ten, or more immunogenic domains of one, two, three, four or more TB proteins. In some embodiments, the antigen is a fusion protein. In one aspect of the invention, fusion protein can include two or more proteins. In one aspect, the fusion protein can include two or more immunogenic domains and/or two or more epitopes of one or more proteins. An immunotherapeutic composition containing such antigens may provide antigen-specific immunization in a broad range of patients.

The present invention describes novel yeast immunotherapeutic compositions containing specific *M. tuberculosis* antigens, alone or in unique combinations, which antigens can include, but are not limited to, Rv0125, Rv1196, Rv1411 (Rv1411c), Rv1738, Rv1813, Rv1909 (Rv1909c), Rv2032, Rv2359, Rv2608, Rv2660, Rv2711, Rv3130, Rv3619, Rv3620, Rv3841, Ag85A, Ag85B, TB10.4 and ESAT-6 (early secreted antigenic target 6). In one embodiment of the invention, a yeast-based immunotherapeutic composition for the prevention or treatment of TB includes one or more iron accumulation antigens, provided alone, or in combination with other TB antigens, in the form of a fusion protein and/or as individual antigens expressed by yeast to form novel TB vaccines. In one aspect, the iron accumulation antigens include, but are not limited to, Rv1909, Rv2359, and/or Rv2711, which may be produced alone or in combinations of any two or all three of these antigens, and/or which may be combined in a fusion protein with other TB antigens, such as any one or more of the hypoxia pool antigens described herein, and/or the TLR agonist antigen described herein. In one embodiment of the invention, a yeast-based immunotherapeutic composition for the prevention or treatment of TB includes one or more hypoxia pool antigens, in the form of a fusion protein and/or as individual antigens expressed by yeast to form novel TB vaccines. In one aspect, the hypoxia pool antigens include, but are not limited to: Rv1738, Rv2032, Rv3130, and/or Rv3841, which may be produced alone or in combinations of any two, three, or all four of these antigens, and/or which may be combined in a fusion protein with other TB antigens, such as any one or more of the iron accumulation antigens described herein, and/or the TLR agonist antigen described herein. In one embodiment, a yeast-based immunotherapeutic composition for the prevention or treatment of TB includes one or more TB antigens that is a toll like receptor (TLR) agonist, in the form of a fusion protein and/or as individual antigens expressed by yeast to form novel TB vaccines. In one aspect, the TLR agonist antigen includes, but is not limited to, Rv1411c which may be produced alone or in combination with one or more other TB antigens, such as any one or more of the hypoxia pool antigens described herein and/or any one or more of the iron accumulation antigens described herein. According to the present invention, additional TB antigens that can be used in a yeast-based immunotherapy composition, in addition to the hypoxia pool antigens, the iron accumulation antigens, and/or the TLR agonist antigens described herein, include, but are not limited to, the antigens known in the art as: Ag85A, Ag85B, TB10.4, Rv1196, Rv0125, ESAT-6, Rv2660, Rv1813, Rv2608, Rv3619, and Rv3620.

In one aspect of the invention, TB antigens for use in a yeast-based composition of the invention include, as separate antigens or as fusions of any combination of these antigens, Rv1909c, Rv2359, Rv2711, Rv1738, Rv2032, Rv3130, Rv3841, Rv1411c, Ag85A, Ag85B, ESAT6, and/or TB10.4. In one aspect of the invention, the antigens are full-length individual antigens. In one aspect, the antigens are fusions of various domains of the antigens, such as conserved immunogenic regions of the antigens fused to one another. Examples of fusion proteins encompassed by the invention include, but are not limited to, Ag85-ESAT6-TB10.4 fusions, Rv2359-Rv2711-Rv1909c fusions, Rv1738-Rv2032-Rv3130-Rv3841 fusions, Rv2032-Rv3841 fusions, Rv2032-Rv1411c-Rv2359 fusions or Rv2032-Rv1411c-Rv2711 fusions. Fusion proteins have the advantage of being easier to manufacture in a yeast-based immunotherapy composition and are easier to administer as a single vaccine. Single antigen constructs may have the advantage that natural antigen sequences sometimes accumulate to higher levels in yeast and/or are processed more efficiently by the immune system. In general, for use in a yeast-based immunotherapeutic composition, growth rate and antigen expression within the yeast must be optimized using a variety of antigen constructs, arrangement of antigens within the fusion protein (when a fusion protein is used), promoters, media, and transcriptional induction methods. In addition, immunological testing performed in vitro, ex vivo and/or in vivo is used to identify the most promising candidate(s).

Recombinant nucleic acid molecules and the proteins encoded thereby, including fusion proteins, as one embodiment of the invention, may be used in yeast-based immunotherapy compositions, or for any other suitable purpose for TB antigen(s), including in an in vitro assay, for the production of antibodies, or in another immunotherapy composition, including another vaccine, that is not based on the yeast-based immunotherapy described herein. Expression of the proteins by yeast is one preferred embodiment, although other expression systems may be used to produce the proteins for applications other than a yeast-based immunotherapy composition.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-12 amino acids (i.e., a peptide) and as large as: a full length protein, a multimer, a fusion protein, a chimeric protein, a whole cell, a whole microorganism, or any portions thereof (e.g., lysates of whole cells or extracts of microorganisms). In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism.

When the antigen is to be expressed in yeast, an antigen is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or is at least 25-50 amino acids in length, at least 30-50 amino acids in length, or at least 35-50 amino acids in length, or at least 40-50 amino acids in length, or at least 45-50 amino acids in length. Smaller proteins may be expressed, and considerably larger proteins (e.g., hundreds of amino acids in length or even a few thousand amino acids in length) may be expressed. In one aspect, a full-length protein, or a structural or functional domain thereof, or an immunogenic domain thereof, that is lacking one or more amino acids from the N- and/or the C-terminus may be expressed (e.g., lacking between about 1 and about 20 amino acids from the N- and/or the C-terminus). Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). An "TB antigen" is an antigen derived, designed, or produced from one or more TB proteins such that targeting the antigen also targets the organism causing tuberculosis (e.g., *Mycobacterium tuberculosis*).

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, an immunogen elicits a cell-mediated immune response, including a $CD4^+$ T cell response (e.g., Th1, Th2 and/or Th17) and/or a $CD8^+$ T cell response (e.g., a CTL response), and/or decreases the number or frequency of Treg (regulatory T cells).

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains are not restricted to linear sequences within a protein; for example, in the case of a humoral immune response, immunogenic domains can contain linear epitopes and/or conformational epitopes.

A "functional domain" of a given protein is a portion or functional unit of the protein that includes sequence or structure that is directly or indirectly responsible for at least one biological or chemical function associated with, ascribed to, or performed by the protein. For example, a functional domain can include an active site for enzymatic activity, a ligand binding site, a receptor binding site, a binding site for a molecule or moiety such as calcium, a phosphorylation site, or a transactivation domain.

A "structural domain" of a given protein is a portion of the protein or an element in the protein's overall structure that has an identifiable structure (e.g., it may be a primary or tertiary structure belonging to and indicative of several proteins within a class or family of proteins), is self-stabilizing and/or may fold independently of the rest of the protein. A structural domain is frequently associated with or features prominently in the biological function of the protein to which it belongs.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is actually recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be from 8 amino acids up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

In any of the TB antigens described herein for use in a yeast-based immunotherapy composition, including any of the fusion proteins, the following additional embodiments can apply. First, an N-terminal expression sequence and/or a C-terminal tag are optional, and if used, may be selected from several different sequences described below to improve expression, stability, and/or allow for identification and/or purification of the protein. In one aspect, one or both of the N- or C-terminal sequences are omitted altogether. In addition, many different promoters suitable for use in yeast are known in the art and are encompassed for use to express TB antigens according to the present invention. Furthermore, short intervening linker sequences (e.g., 1, 2, 3, 4, or 5, or larger, amino acid peptides) may be introduced between portions of the fusion protein for a variety of reasons, including the for the introduction of restriction enzyme sites to facilitate cloning and/or for future manipulation of the constructs. Finally, as discussed in detail elsewhere herein, the sequences described herein are exemplary, and may be modified as described in detail elsewhere herein to substitute, add, or delete sequences in order to accommodate preferences for a protein from a particular TB strain, or consensus sequences and inclusion of preferred T cell epitopes, including dominant and/or subdominant T cell epitopes.

As discussed above, optionally, proteins, including fusion proteins, which are used as a component of the yeast-based immunotherapeutic composition of the invention, can be produced using constructs that are particularly useful for improving or enhancing the expression, or the stability of expression, of recombinant antigens in yeast. Typically, the desired antigenic protein(s) or peptide(s) are fused at their amino-terminal (N-terminal) end to: (a) a specific synthetic peptide that stabilizes the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to alpha factor, wherein either fusion partner provides improved stability of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). An exemplary synthetic sequence that enhances the stability of expression of an antigen in a yeast cell and/or prevents post-translational modification of the protein in the yeast includes the sequence M-A-D-E-A-P (SEQ ID NO:1). In addition to the enhanced stability of the expression product, these fusion partners do not appear to negatively impact the immune response against the immunizing antigen in the construct, meaning that the presence of the N-terminal peptide in the fusion protein does not compete with the TB antigen with respect to the elicitation of an immune response against the target TB organism. In addition, the synthetic fusion peptides can be designed to provide an epitope that can be recognized by a selection agent, such as an antibody. In one embodiment, the TB antigen is linked at the N-terminus to a yeast protein, such as an alpha factor prepro sequence (also referred to as the alpha factor signal leader sequence, the amino acid sequence of which is exemplified herein by SEQ ID NO:2 or SEQ ID NO:3). Other sequences for yeast alpha factor prepro sequence are known in the art and are encompassed for use in the present invention.

In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., hexahistidine) or any other short epitope tag. Peptides attached to the C-terminus of an antigen according to the invention can be used with or without the addition of the N-terminal peptides discussed herein.

The TB sequences used to design fusion proteins described herein are based on isolates of particular TB proteins. However, it is an embodiment of the invention to add to or substitute into any portion of a TB antigen described herein that is based on or derived from one particular strain or isolate, with a corresponding sequence, or even a single or small amino acid substitution, insertion or deletion that occurs in a corresponding sequence, from any other TB strain(s) or isolate(s). In one embodiment, a TB antigen can be produced by substituting an entire sequence(s) of a TB antigen described herein with the corresponding sequence(s) from one or more different TB strain/isolates. Adding to or substituting a sequence from one TB strain for another, for example, allows for the customization of the immunotherapeutic composition, for example, in order to target the TB sequences that are most prevalent in a particular region or country. Similarly, it is also an embodiment of the invention to use all or a portion of a consensus sequence derived from, determined from, or published for, a given TB strain to make changes in the sequence of a given TB antigen to more closely or exactly correspond to the consensus sequence. According to the present invention and as generally understood in the art, a "consensus sequence" is typically a sequence based on the most common nucleotide or amino acid at a particular position of a given sequence after multiple sequences are aligned.

As a particular example of the above-mentioned types of modifications, a TB antigen can be modified to change a T cell epitope in a given sequence from one isolate to correspond more closely or exactly with a T cell epitope from a different isolate, or to correspond more closely or exactly with a consensus sequence for the T cell epitope. Such T cell epitopes can include dominant epitopes and/or sub-dominant epitopes. Alignments of major TB proteins across exemplary sequences from various strains can be readily generated using publicly available software, which will inform the generation of consensus sequences, for example. Furthermore, consensus sequences for many TB proteins have been published.

According to any embodiment of the present invention, reference to a "full-length" protein (or a full-length functional domain, a full-length structural domain, or a full-length immunological domain) includes the full-length amino acid sequence of the protein or functional domain, structural domain or immunological domain, as described herein or as otherwise known or described in a publicly available sequence. A protein or domain that is "near full-length", which is also a type of homologue of a protein, differs from a full-length protein or domain, by the addition or deletion or omission of 1, 2, 3, 4, 5, 6, 7, 8, 9, or 10 amino acids from the N- and/or C-terminus of such a full-length protein or full-length domain. General reference to a protein or domain can include both full-length and near full-length proteins, as well as other homologues thereof. For example, and for clarity, many of the amino acid sequences of TB antigens described herein, as compared to the native TB protein, are "near-full-length" TB proteins, in that the methionine at position 1 is not included in the amino acid sequence (i.e., the TB protein sequence is referenced from position 2 with respect to the native protein), since N- and C-terminal sequences are typically appended to the TB protein to produce a fusion protein for expression in yeast, and thus the methionine at position 1 of the native protein is often omitted to facilitate the fusion protein construction.

In one aspect, the TB antigen has an amino acid sequence comprising or consisting of at least 50%, 55%, 60%, 65%, 70%, 75%, 80%, 85%, 90%, 91%, 92%, 93%, 94%, 95%, 96%, 97%, 98%, or 99% of the linear sequence of a full-length or near-full-length TB protein, or of a functional, structural or immunogenic domain thereof. In one aspect, the TB antigen comprises or consists of an amino acid sequence that is at least 50%, 55%, 60%, 65%, 70%, 75%, 80%, 85%, 90%, 91%, 92%, 93%, 94%, 95%, 96%, 97%, 98%, or 99% identical to a full-length or near-full-length TB protein, or a functional, structural or immunogenic domain thereof.

In one embodiment of the invention, the TB antigen(s) for use in a composition or method of the invention is a fusion protein comprising TB antigens, wherein the TB antigens comprise or consist of one or more TB antigens referred to as "iron accumulation antigens", or at least one functional, structural or immunogenic domain thereof. TB iron accumulation antigens useful in the present invention include: Rv2359, Rv2711 and Rv1909. One example of a yeast-based immunotherapeutic composition comprising TB iron accumulation antigens useful in the present invention is described herein. In this embodiment, yeast (e.g., *Saccharomyces cerevisiae*) were engineered to express a fusion protein comprising an antigen from the TB Rv2359 protein, under the control of the copper-inducible promoter, CUP1. The TB antigen is a single polypeptide having the amino acid sequence of SEQ ID NO:4. As discussed above, fusion proteins containing TB antigens and useful in the present invention can be constructed using any of the N-terminal and/or C-terminal sequences as described herein, and/or amino acid linkers can be introduced between proteins or domains in the fusion protein. In one aspect of the TB antigen represented by SEQ ID NO:4, an N-terminal sequence selected from SEQ ID NO:1, SEQ ID NO:2 or SEQ ID NO:3 is appended to the N-terminus of SEQ ID NO:4. In one aspect, a hexahistidine tag is appended to the C-terminus of SEQ ID NO:4. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:6. SEQ ID NO:6 has the following sequence elements fused in frame from N- to C-terminus: 1) the amino acid sequence of the N-terminal peptide of SEQ ID NO:1 (positions 1-6 of SEQ ID NO:6); 2) a two amino acid linker sequence of Thr-Ser (positions 7-8 of SEQ ID NO:6); 3) the amino acid sequence of the Rv2359 antigen of SEQ ID NO:4 (positions 9-137 of SEQ ID NO:6); and 4) a hexahistidine tag (positions 138-143 of SEQ ID NO:6). The fusion protein represented by SEQ ID NO:6 is encoded by a recombinant nucleic acid molecule for insertion into a vector that has the nucleic acid sequence of SEQ ID NO:5. A yeast-based immunotherapeutic composition of the invention that expresses SEQ ID NO:6 can be referred to herein as GI-19001.

As another example of a yeast-based immunotherapeutic composition comprising TB iron accumulation antigens useful in the present invention, yeast (e.g., *Saccharomyces cerevisiae*) were engineered to express a fusion protein comprising an antigen from the TB Rv2711 protein, under the control of the copper-inducible promoter, CUP1. The TB antigen is a single polypeptide having the amino acid sequence of SEQ ID NO:7. In one aspect of the TB antigen represented by SEQ ID NO:7, an N-terminal sequence selected from SEQ ID NO:1, SEQ ID NO:2 or SEQ ID NO:3 is appended to the N-terminus of SEQ ID NO:7. In one aspect, a hexahistidine tag is appended to the C-terminus of SEQ ID NO:7. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:9. SEQ ID NO:9 has the following sequence elements fused in frame from N- to C-terminus: 1) the amino acid sequence of the N-terminal peptide of SEQ ID NO:1 (positions 1-6 of SEQ ID NO:9); 2) a two amino acid linker sequence of Thr-Ser (positions 7-8 of SEQ ID NO:9); 3) the amino acid sequence of the Rv2711 antigen of SEQ ID NO:7 (positions 9-237 of SEQ ID NO:9); and 4) a hexahistidine tag (positions 238-243 of SEQ ID NO:9). The fusion protein represented by SEQ ID NO:9 is encoded by a recombinant nucleic acid molecule for insertion into a vector that has the nucleic acid sequence of SEQ ID NO:8. A yeast-based immunotherapeutic composition of the invention that expresses SEQ ID NO:9 can be referred to herein as GI-19002.

As yet another example of a yeast-based immunotherapeutic composition comprising TB iron accumulation antigens useful in the present invention, yeast (e.g., *Saccharomyces cerevisiae*) were engineered to express a fusion protein comprising an antigen from the TB Rv1909c protein, under the control of the copper-inducible promoter, CUP1. The TB antigen is a single polypeptide having the amino acid sequence of SEQ ID NO:10. In one aspect of the TB antigen represented by SEQ ID NO:10, an N-terminal sequence selected from SEQ ID NO:1, SEQ ID NO:2 or SEQ ID NO:3 is appended to the N-terminus of SEQ ID NO:10. In one aspect, a hexahistidine tag is appended to the C-terminus of SEQ ID NO:10. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:12. SEQ ID NO:12 has the following sequence elements fused in frame from N- to C-terminus: 1) the amino acid sequence of the N-terminal peptide of SEQ ID NO:1 (positions 1-6 of SEQ ID NO:12); 2) a two amino acid linker sequence of Thr-Ser (positions 7-8 of SEQ ID NO:12); 3) the amino acid sequence of the Rv1909c antigen of SEQ ID NO:10 (positions 9-155 of SEQ ID NO:12); and 4) a hexahistidine tag (positions 156-161 of SEQ ID NO:12). The fusion protein represented by SEQ ID NO:12 is encoded by a recombinant nucleic acid molecule for insertion into a vector that has the nucleic acid sequence of SEQ ID NO:11. A yeast-based immunotherapeutic composition of the invention that expresses SEQ ID NO:12 can be referred to herein as GI-19003.

As another example of a yeast-based immunotherapeutic composition comprising TB iron accumulation antigens useful in the present invention, yeast (e.g., *Saccharomyces cerevisiae*) were engineered to express a fusion protein comprising three different iron accumulation TB antigens, fused to form a single fusion protein, under the control of the copper-inducible promoter, CUP1. The TB antigen in this protein is a single polypeptide comprising a TB antigen from Rv2359, a TB antigen from Rv2711, and a TB antigen from Rv1909c, having the amino acid sequence of SEQ ID NO:13. In one aspect of the TB antigen represented by SEQ ID NO:13, an N-terminal sequence selected from SEQ ID NO:1, SEQ ID NO:2 or SEQ ID NO:3 is appended to the N-terminus of SEQ ID NO:13. In one aspect, a hexahistidine tag is appended to the C-terminus of SEQ ID NO:13. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:15. SEQ ID NO:15 has the following sequence elements fused in frame from N- to C-terminus: 1) the amino acid sequence of the N-terminal peptide of SEQ ID NO:1 (positions 1-6 of SEQ ID NO:15); 2) a two amino acid linker sequence of Thr-Ser (positions 7-8 of SEQ ID NO:15); 3) the amino acid sequence of the Rv2359 antigen of SEQ ID NO:4 (positions 9-137 of SEQ ID NO:15); 4) the amino acid sequence of the Rv2711 antigen of SEQ ID NO:7 (positions 138-366 of SEQ ID NO:15); 5) the amino acid sequence of the Rv1909c antigen of SEQ IDS NO:10 (positions 367-513 of SEQ ID NO:15); and 6) a hexahistidine tag (positions 514-519 of SEQ ID NO:15). The fusion protein represented by SEQ ID NO:15 is encoded by a recombinant nucleic acid molecule for insertion into a vector that has the nucleic acid sequence of SEQ ID NO:14. The combination of the TB antigens in the amino acid sequence represented by SEQ ID NO:13 or SEQ ID NO:15 can also be referred to herein as the "3-iron fusion". A yeast-based immunotherapeutic composition of the invention that expresses SEQ ID NO:15 can be referred to herein as GI-19004 or "3-iron Tarm" or "Tarm 3-iron".

As another example of a yeast-based immunotherapeutic composition for TB useful in the present invention, yeast (e.g., *Saccharomyces cerevisiae*) were engineered to express a fusion protein comprising an antigen from the TB ESAT-6 protein, under the control of the copper-inducible promoter, CUP1. The TB antigen is a single polypeptide having the amino acid sequence of SEQ ID NO:16. In one aspect of the TB antigen represented by SEQ ID NO:16, an N-terminal sequence selected from SEQ ID NO:1, SEQ ID NO:2 or SEQ ID NO:3 is appended to the N-terminus of SEQ ID NO:16. In one aspect, a hexahistidine tag is appended to the C-terminus of SEQ ID NO:16. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:18. SEQ ID NO:18 has the following sequence elements fused in frame from N- to C-terminus: 1) the amino acid sequence of the N-terminal peptide of SEQ ID NO:1 (positions 1-6 of SEQ ID NO:18); 2) a two amino acid linker sequence of Thr-Ser (positions 7-8 of SEQ ID NO:18); 3) the amino acid sequence of the ESAT-6 antigen of SEQ ID NO:16 (positions 9-102 of SEQ ID NO:18); and 4) a hexahistidine tag (positions 103-108 of SEQ ID NO:18). The fusion protein represented by SEQ ID NO:18 is encoded by a recombinant nucleic acid molecule for insertion into a vector that has the nucleic acid sequence of SEQ ID NO:17. A yeast-based immunotherapeutic composition of the invention that expresses SEQ ID NO:18 can be referred to herein as GI-19005.

In one embodiment of the invention, the TB antigen(s) for use in a composition or method of the invention is a fusion protein comprising TB antigens, wherein the TB antigens comprise or consist of one or more TB antigens referred to as "hypoxia pool antigens", or at least one functional, structural or immunogenic domain thereof. TB hypoxia pool antigens useful in the present invention include, but are not limited to: Rv1738, Rv2032, Rv3130, and Rv3841.

One example of a yeast-based immunotherapeutic composition comprising TB hypoxia pool antigens useful in the present invention is described herein. In this embodiment, yeast (e.g., *Saccharomyces cerevisiae*) were engineered to express a fusion protein comprising an antigen from the Rv1738 protein, under the control of the copper-inducible promoter, CUP1. The TB antigen is a single polypeptide having the amino acid sequence of SEQ ID NO:19. In one aspect of the TB antigen represented by SEQ ID NO:19, an N-terminal sequence selected from SEQ ID NO:1, SEQ ID NO:2 or SEQ ID NO:3 is appended to the N-terminus of SEQ ID NO:19 or to positions 2-94 of SEQ ID NO:19. In one aspect, a hexahistidine tag is appended to the C-terminus of SEQ ID NO:19 or to positions 2-94 of SEQ ID NO:19. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:21. SEQ ID NO:21 has the following sequence elements fused in frame from N- to C-terminus: 1) the amino acid sequence of the N-terminal peptide of SEQ ID NO:1 (positions 1-6 of SEQ ID NO:21); 2) a two amino acid linker sequence of Thr-Ser (positions 7-8 of SEQ ID NO:21); 3) the amino acid sequence of the Rv1738 antigen of positions 2-94 of SEQ ID NO:19 (positions 9-101 of SEQ ID NO:21); and 4) a hexahistidine tag (positions 102-107 of SEQ ID NO:21). The fusion protein represented by SEQ ID NO:21 is encoded by a recombinant nucleic acid molecule for insertion into a vector that has the nucleic acid sequence of SEQ ID NO:20.

As yet another example of a yeast-based immunotherapeutic composition comprising TB hypoxia pool antigens useful in the present invention, yeast (e.g., *Saccharomyces cerevisiae*) were engineered to express a fusion protein comprising an antigen from the TB Rv2032 protein, under the control of the copper-inducible promoter, CUP1. The TB Rv2032 protein is a putative NAD(P)H nitroreductase. In one aspect, this antigen is inactivated by mutation to abolish FMN binding. In one aspect, the inactivating mutation is a single amino acid substitution at position 14 of the full-length TB Rv2032 amino acid sequence, which substitutes a non-alanine amino acid for the alanine in the native protein. In one aspect, the non-alanine amino acid residue is an arginine (i.e., A14R mutation). The TB antigen based on Rv2032 is a single polypeptide having the amino acid sequence of SEQ ID NO:22. SEQ ID NO:22 contains an inactivating mutation, which is a substitution of an arginine for the alanine that occurs in the native Rv2032 sequence, which is at position 13 of SEQ ID NO:22. In one aspect of the TB antigen represented by SEQ ID NO:22, an N-terminal sequence selected from SEQ ID NO:1, SEQ ID NO:2 or SEQ ID NO:3 is appended to the N-terminus of SEQ ID NO:22 or to positions 2-331 of SEQ ID NO:22. In one aspect, a hexahistidine tag is appended to the C-terminus of SEQ ID NO:22 or to positions 2-331 of SEQ ID NO:22. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:24. SEQ ID NO:24 has the following sequence elements fused in frame from N- to C-terminus: 1) the amino acid sequence of the N-terminal peptide of SEQ ID NO:1 (positions 1-6 of SEQ ID NO:24); 2) a two amino acid linker sequence of Thr-Ser (positions 7-8 of SEQ ID NO:24); 3) the amino acid sequence of the Rv2032 antigen of positions 2-331 of SEQ ID NO:22 (positions 9-338 of SEQ ID NO:24); and 4) a hexahistidine tag (positions 339-344 of SEQ ID NO:24). SEQ ID NO:24 contains an inactivating mutation, which is a substitution of an arginine for the alanine that occurs in the native Rv2032 sequence, which is at position 21 of SEQ ID NO:24. The fusion protein represented by SEQ ID NO:24 is encoded by a recombinant nucleic acid molecule for insertion into a vector that has the nucleic acid sequence of SEQ ID NO:23.

As yet another example of a yeast-based immunotherapeutic composition comprising TB hypoxia pool antigens useful in the present invention, yeast (e.g., *Saccharomyces cerevisiae*) were engineered to express a fusion protein comprising an antigen from the TB Rv3130 protein, under the control of the copper-inducible promoter, CUP1. Rv3130 is a proposed triacyglycerol synthase (Sirakova and Dubey, 2006, *Microbiol.* 152(Pt9):2717-2725). The TB antigen is a single polypeptide having the amino acid sequence of SEQ ID NO:25. In one aspect of the TB antigen represented by SEQ ID NO:25, an N-terminal sequence selected from SEQ ID NO:1, SEQ ID NO:2 or SEQ ID NO:3 is appended to the N-terminus of SEQ ID NO:25 or to positions 2-463 of SEQ ID NO:25. In one aspect, a hexahistidine tag is appended to the C-terminus of SEQ ID NO:25 or to positions 2-463 of SEQ ID NO:25. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:27. SEQ ID NO:27 has the following sequence elements fused in frame from N- to C-terminus: 1) the amino acid sequence of the N-terminal peptide of SEQ ID NO:1 (positions 1-6 of SEQ ID NO:27); 2) a two amino acid linker sequence of Thr-Ser (positions 7-8 of SEQ ID NO:27); 3) the amino acid sequence of the Rv3130 antigen of positions 2-463 of SEQ ID NO:25 (positions 9-470 of SEQ ID NO:27); and 4) a hexahistidine tag (positions 471-476 of SEQ ID NO:27). The fusion protein represented by SEQ ID NO:27 is encoded by a recombinant nucleic acid molecule for insertion into a vector that has the nucleic acid sequence of SEQ ID NO:26.

As yet another example of a yeast-based immunotherapeutic composition comprising TB hypoxia pool antigens useful in the present invention, yeast (e.g., *Saccharomyces cerevisiae*) were engineered to express a fusion protein comprising an antigen from the TB Rv3841 protein, under the control of the copper-inducible promoter, CUP1. Rv3841 has a proposed function of compartmentalizing iron in the form of a bioavailable ferric mineral inside the protein's hollow cavity (the protein has a spherical multi-subunit structure) (Biochemistry, 2012, 51(49)9900-9910). In one aspect, this antigen is inactivated by mutation to abolish metal binding. In one aspect, the inactivating mutation is a deletion of the amino acid motif "EXXH", which is "ERNH" at positions 55-58 in the native Rv3841 protein. The TB antigen is a single polypeptide having the amino acid sequence of SEQ ID NO:28. SEQ ID NO:28 includes a four amino acid deletion of the ERNH sequence, which sequence would have otherwise occurred between positions 53 and 54 with respect to SEQ ID NO:28. In one aspect of the TB antigen represented by SEQ ID NO:28, an N-terminal sequence selected from SEQ ID NO:1, SEQ ID NO:2 or SEQ ID NO:3 is appended to the N-terminus of SEQ ID NO:28 or to positions 2-181 of SEQ ID NO:28. In one aspect, a hexahistidine tag is appended to the C-terminus of SEQ ID NO:28 or to positions 2-181 of SEQ ID NO:28. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:30. SEQ ID NO:30 has the following sequence elements fused in frame from N- to C-terminus: 1) the amino acid sequence of the N-terminal peptide of SEQ ID NO:1 (positions 1-6 of SEQ ID NO:30); 2) a two amino acid linker sequence of Thr-Ser (positions 7-8 of SEQ ID NO:30); 3) the amino acid sequence of the Rv3841 antigen of positions 2-181 of SEQ ID NO:28 (positions 9-183 of SEQ ID NO:30); and 4) a hexahistidine tag (positions 184-189 of SEQ ID NO:30). SEQ ID NO:30 includes a four amino acid deletion of the ERNH sequence, which sequence would have otherwise occurred between positions 61 and 62 with respect to SEQ ID NO:30. The fusion protein represented by SEQ ID NO:30 is encoded by a recombinant nucleic acid molecule for insertion into a vector that has the nucleic acid sequence of SEQ ID NO:29.

As another example of a yeast-based immunotherapeutic composition comprising TB hypoxia pool antigens useful in the present invention, yeast (e.g., *Saccharomyces cerevisiae*) were engineered to express a fusion protein comprising four different hypoxia pool TB antigens, fused to form a single fusion protein, under the control of the copper-inducible promoter, CUP1. The TB antigen in this protein is a single polypeptide comprising a TB antigen from Rv1738, a TB antigen from Rv2032, a TB antigen from Rv3130, and a TB antigen from Rv3841, having the amino acid sequence of SEQ ID NO:31. In one aspect of the TB antigen represented by SEQ ID NO:31, an N-terminal sequence selected from SEQ ID NO:1, SEQ ID NO:2 or SEQ ID NO:3 is appended to the N-terminus of SEQ ID NO:31. In one aspect, a hexahistidine tag is appended to the C-terminus of SEQ ID NO:31. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:33. SEQ ID NO:33 has the following sequence elements fused in frame from N- to C-terminus: 1) the amino acid sequence of the N-terminal peptide of SEQ ID NO:1 (positions 1-6 of SEQ ID NO:33); 2) a two amino acid linker sequence of Thr-Ser (positions 7-8 of SEQ ID NO:33); 3) the amino acid sequence of the Rv1738 antigen of positions 2-94 of SEQ ID NO:19 (positions 9-101 of SEQ ID NO:33); 4) the amino acid sequence of the Rv2032 antigen of positions 2-331 of SEQ ID NO:22 (positions 102-431 of SEQ ID NO:33); 5) the amino acid sequence of the Rv3130 antigen of positions 2-463 of SEQ ID NO:25 (positions 432-893 of SEQ ID NO:33); 6) the amino acid sequence of the Rv3841 antigen of positions 2-181 of SEQ ID NO:28 (positions 894-1068 of SEQ ID NO:33); and 7) a hexahistidine tag (positions 1069-1074 of SEQ ID NO:33). The deactivating mutations described above for each of the Rv2032 antigen (SEQ ID NO:22) and the Rv3841 antigen (SEQ ID NO:28) are also included in this fusion protein. The fusion protein represented by SEQ ID NO:33 is encoded by a recombinant nucleic acid molecule for insertion into a vector that has the nucleic acid sequence of SEQ ID NO:32. The combination of the TB antigens in the amino acid sequence represented by SEQ ID NO:31 or SEQ ID NO:33 can also be referred to herein as the "hypoxia 4-gene fusion".

As yet another example of a yeast-based immunotherapeutic composition comprising TB hypoxia pool antigens useful in the present invention, yeast (e.g., *Saccharomyces cerevisiae*) were engineered to express a fusion protein comprising two different hypoxia pool TB antigens, fused to form a single fusion protein, under the control of the copper-inducible promoter, CUP1. The TB antigen in this protein is a single polypeptide comprising a TB antigen from Rv2032 and a TB antigen from Rv3841, having the amino acid sequence of SEQ ID NO:34. In one aspect of the TB antigen represented by SEQ ID NO:34, an N-terminal sequence selected from SEQ ID NO:1, SEQ ID NO:2 or SEQ ID NO:3 is appended to the N-terminus of SEQ ID NO:34. In one aspect, a hexahistidine tag is appended to the C-terminus of SEQ ID NO:34. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:36. SEQ ID NO:36 has the following sequence elements fused in frame from N- to C-terminus: 1) the amino acid sequence of the N-terminal peptide of SEQ ID NO:1 (positions 1-6 of SEQ ID NO:36); 2) a two amino acid linker sequence of Thr-Ser (positions 7-8 of SEQ ID NO:36); 3) the amino acid sequence of the Rv2032 antigen of positions 2-331 of SEQ ID NO:22 (positions 9-338 of SEQ ID NO:36); 4) the amino acid sequence of the Rv3841 antigen of positions 2-181 of SEQ ID NO:28 (positions 339-513 of SEQ ID NO:36); and 5) a hexahistidine tag (positions 514-519 of SEQ ID NO:36). The deactivating mutations described above for each of the Rv2032 antigen (SEQ ID NO:22) and the Rv3841 antigen (SEQ ID NO:28) are also included in this fusion protein. The fusion protein represented by SEQ ID NO:36 is encoded by a recombinant nucleic acid molecule for insertion into a vector that has the nucleic acid sequence of SEQ ID NO:35.

As another example of a yeast-based immunotherapeutic composition for TB useful in the present invention, yeast (e.g., *Saccharomyces cerevisiae*) were engineered to express a fusion protein comprising the TB Ag85a protein, under the control of the copper-inducible promoter, CUP1. The TB antigen is a single polypeptide having the amino acid sequence of SEQ ID NO:37. In one aspect of the TB antigen represented by SEQ ID NO:37, an N-terminal sequence selected from SEQ ID NO:1, SEQ ID NO:2 or SEQ ID NO:3 is appended to the N-terminus of SEQ ID NO:37. In one aspect, a hexahistidine tag is appended to the C-terminus of SEQ ID NO:37. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:39. SEQ ID NO:39 has the following sequence elements fused in frame from N- to C-terminus: 1) the amino acid sequence of the N-terminal peptide of SEQ ID NO:1 (positions 1-6 of SEQ ID NO:39); 2) a two amino acid linker sequence of Thr-Ser (positions 7-8 of SEQ ID NO:39); 3) the amino acid sequence of the Ag85a antigen of SEQ ID NO:37 (positions 9-345 of SEQ ID NO:39); and 4) a hexahistidine tag (positions 346-351 of SEQ ID NO:39). The fusion protein represented by SEQ ID NO:39 is encoded by a recombinant nucleic acid molecule for insertion into a vector that has the nucleic acid sequence of SEQ ID NO:38.

In one embodiment of the invention, the TB antigen(s) for use in a composition or method of the invention is a fusion protein comprising TB antigens, wherein the TB antigens comprise or consist of one or more TB antigens referred to as "Toll-Like Receptor agonists" or "TLR agonists", or at least one functional, structural or immunogenic domain thereof. TB TLR agonist antigens useful in the present invention include Rv1411c. In one example of a yeast-based immunotherapeutic composition for TB useful in the present invention, yeast (e.g., *Saccharomyces cerevisiae*) were engineered to express a fusion protein comprising the TB Rv1411c protein, under the control of the copper-inducible promoter, CUP1. The TB antigen is a single polypeptide having the amino acid sequence of SEQ ID NO:40. Rv1411c is a membrane protein and a TLR-2 ligand that inhibits MHC class II antigen presentation in macrophages (Gehring et al., 2004, *J. Immunol.* 173(4):2660-2668). Accordingly, for use in the present invention, it is desirable, in one aspect, to abrogate the agonist activity of the protein, since an immune response against TB is ultimately desired. Potential sites for mutation that would abrogate binding include a valine at position 91 with respect to the native TB protein, which may, for example, be mutated to a tryptophan or other non-valine residue in order to block the binding pocket for the TLR2 agonist lipid (Drage and Tsai, 2010, *Nature Structural Mol. Biol.* 17(9):1088-1095). Additional valine residues in the native protein could also be mutated to block TLR activity (e.g., at positions 194 and 217 with respect to the native protein or SEQ ID NO:40), but mutation of one valine residue is sufficient to inactivate the protein. The amino acid sequence of SEQ ID NO:40 contains the inactivating mutation of a valine to a tryptophan corresponding to position 91 (V91W) in the native protein (also occurring at position 91 with respect to SEQ ID NO:40). In one aspect of the TB antigen represented by SEQ ID NO:40, an N-terminal sequence selected from SEQ ID NO:1, SEQ ID NO:2 or SEQ ID NO:3 is appended to the N-terminus of SEQ ID NO:40. In one aspect, a hexahistidine tag is appended to the C-terminus of SEQ ID NO:40. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:42. SEQ ID NO:42 has the following sequence elements fused in frame from N- to C-terminus: 1) the amino acid sequence of the N-terminal peptide of SEQ ID NO:1 (positions 1-6 of SEQ ID NO:1 (positions 1-6 of SEQ ID NO:42); 2) a two amino acid linker sequence of Thr-Ser (positions 7-8 of SEQ ID NO:42); 3) the amino acid sequence of the Rv1411c antigen of SEQ ID NO:40 (positions 9-244 of SEQ ID NO:42); and 4) a hexahistidine tag (positions 245-250 of SEQ ID NO:42). The fusion protein represented by SEQ ID NO:42 is encoded by a recombinant nucleic acid molecule for insertion into a vector that has the nucleic acid sequence of SEQ ID NO:41.

As yet another example of a yeast-based immunotherapeutic composition comprising a variety of TB antigens useful in the present invention, yeast (e.g., *Saccharomyces cerevisiae*) were engineered to express a fusion protein comprising one hypoxia pool TB antigen (Rv2032), one TLR agonist protein (Rv1411c) and one iron accumulation antigen (Rv2359), fused to form a single fusion protein, under the control of the copper-inducible promoter, CUP1, the TB antigen fusion protein having the amino acid sequence of SEQ ID NO:43. In one aspect of the TB antigen represented by SEQ ID NO:43, an N-terminal sequence selected from SEQ ID NO:1, SEQ ID NO:2 or SEQ ID NO:3 is appended to the N-terminus of SEQ ID NO:43. In one aspect, a hexahistidine tag is appended to the C-terminus of SEQ ID NO:43. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:45. SEQ ID NO:45 has the following sequence elements fused in frame from N- to C-terminus: 1) the amino acid sequence of the N-terminal peptide of SEQ ID NO:1 (positions 1-6 of SEQ ID NO:45); 2) a two amino acid linker sequence of Thr-Ser (positions 7-8 of SEQ ID NO:45); 3) the amino acid sequence of the Rv2032 antigen of positions 2-331 of SEQ ID NO:22 (positions 9-338 of SEQ ID NO:45); 4) the amino acid sequence of the Rv1411c antigen of SEQ ID NO:40 (positions 339-574 of SEQ ID NO:45); 5) the amino acid sequence of the Rv2359 protein of SEQ ID NO:4 (positions 575-703 of SEQ ID NO:45); and 6) a hexahistidine tag (positions 704-709 of SEQ ID NO:45). The deactivating mutations described above for each of the Rv2032 antigen (SEQ ID NO:22) and the Rv1411c antigen (SEQ ID NO:40) are also included in this fusion protein. The fusion protein represented by SEQ ID NO:45 is encoded by a recombinant nucleic acid molecule for insertion into a vector that has the nucleic acid sequence of SEQ ID NO:44.

As yet another example of a yeast-based immunotherapeutic composition comprising a variety of TB antigens useful in the present invention, yeast (e.g., *Saccharomyces cerevisiae*) are engineered to express a fusion protein comprising one hypoxia pool TB antigen (Rv2032), one TLR agonist protein (Rv1411c) and one iron accumulation antigen (Rv2711), fused to form a single fusion protein, under the control of the copper-inducible promoter, CUP1, the TB antigen fusion protein having the amino acid sequence of SEQ ID NO:46. In one aspect of the TB antigen represented by SEQ ID NO:46, an N-terminal sequence selected from SEQ ID NO:1, SEQ ID NO:2 or SEQ ID NO:3 is appended to the N-terminus of SEQ ID NO:46. In one aspect, a hexahistidine tag is appended to the C-terminus of SEQ ID NO:46. In any of the above aspects, a short peptide linker is inserted between the N-terminal sequence and the TB antigen sequence and/or between the TB antigen sequence and the C-terminal sequence. One such fusion protein designed for expression by yeast and described in the Examples is represented here by SEQ ID NO:48. SEQ ID NO:48 has the following sequence elements fused in frame from N- to C-terminus: 1) the amino acid sequence of the N-terminal peptide of SEQ ID NO:1 (positions 1-6 of SEQ ID NO:48); 2) a two amino acid linker sequence of Thr-Ser (positions 7-8 of SEQ ID NO:48); 3) the amino acid sequence of the Rv2032 antigen of positions 2-331 of SEQ ID NO:22 (positions 9-338 of SEQ ID NO:48); 4) the amino acid sequence of the Rv1411c antigen of SEQ ID NO:40 (positions 339-574 of SEQ ID NO:48); 5) the amino acid sequence of the Rv2711 protein of SEQ ID NO:7 (positions 575-803 of SEQ ID NO:48); and 6) a hexahistidine tag (positions 804-809 of SEQ ID NO:48). The deactivating mutations described above for each of the Rv2032 antigen (SEQ ID NO:22) and the Rv1411c antigen (SEQ ID NO:40) are also included in this fusion protein. The fusion protein represented by SEQ ID NO:48 is encoded by a recombinant nucleic acid molecule for insertion into a vector that has the nucleic acid sequence of SEQ ID NO:47.

Agonist Antigens.

In some aspects of the invention, amino acid insertions, deletions, and/or substitutions can be made for one, two, three, four, five, six, seven, eight, nine, ten, or more amino acids of a wild-type or reference TB protein, provided that the resulting TB protein, when used as an antigen in a yeast-TB immunotherapeutic composition of the invention, elicits an immune response against the target or wild-type or reference TB protein, which may include an enhanced immune response, a diminished immune response, or a substantially similar immune response.

For example, the invention includes the use of TB agonist antigens (also referred to herein as "Altered Peptide Ligands" (APLs), which are TB antigens that may include one or more T cell epitopes, and particularly, cytotoxic T lymphocyte (CTL) epitopes, that have been mutated by substitution of one or more amino acid residues for a different amino acid residue(s). The purpose of the mutation is to elicit a T cell response against the TB agonist epitope that is enhanced/amplified/improved as compared to the response against the native antigen, which may be achieved by improving the avidity or affinity of the epitope for an MHC molecule or for the T cell receptor that recognizes the epitope in the context of MHC presentation. TB antigen agonists may therefore improve the potency or efficiency of a T cell response against native TB proteins that infect a host.

The invention also includes homologues of any of the above-described fusion proteins, as well as the use of homologues, variants, or mutants of the individual TB proteins or portions thereof (including any functional and/or immunogenic domains) that are part of such fusion proteins or otherwise described herein. In one aspect, the invention includes the use of fusion proteins or individual (single) TB proteins or TB antigens, comprising or consisting of amino acid sequences that are at least 85%, 86%, 87%, 88%, 89%, 90%, 91%, 92%, 93%, 94%, 95%, 96%, 97%, 98%, or 99% identical to the amino acid sequence of any one of the fusion proteins or individual TB proteins or TB antigens, respectively, described herein, including any of the TB proteins, TB antigens and fusion proteins referenced by a specific sequence identifier herein (e.g., any one of SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, SEQ ID NO:45, SEQ ID NO:46 or SEQ ID NO:48), over the full length of the protein, or with respect to a defined segment in the protein or a domain thereof (immunogenic domain or functional domain (i.e., a domain with at least one biological activity)) that forms part of the protein.

Another aspect of the invention includes a TB antigen comprising, consisting essentially of, or consisting of, an amino acid sequence represented by any one or more of: SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16 SEQ ID NO:18, SEQ ID NO:19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, SEQ ID NO:45, SEQ ID NO:46 or SEQ ID NO:48. The TB antigen is suitable for use in any of the embodiments of the invention described herein, including in a yeast-based immunotherapy composition described herein.

Yeast-Based Immunotherapy Compositions.

In various embodiments of the invention, the invention includes the use of at least one "yeast-based immunotherapeutic composition" (which phrase may be used interchangeably with "yeast-based immunotherapy product", "yeast-based immunotherapy composition", "yeast-based composition", "yeast-based immunotherapeutic", "yeast-based vaccine", or derivatives of these phrases). An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. A yeast-based immunotherapeutic composition useful in the present invention can, for example, elicit an immune response in an individual such that the individual is protected from TB infection and/or is treated for TB infection or for symptoms resulting from TB infection.

Yeast-based immunotherapy compositions of the invention may be used in either "prophylactic" or "therapeutic" settings. When provided prophylactically, the compositions of the present invention are provided in advance of any symptom of active TB infection (defined below), but may include both pre-exposure and post-exposure scenarios, when an active infection is not yet detected or emerged. Such a composition could be administered at birth or in infancy, in early or late childhood, or to adults, particularly adults who may be at higher risk of becoming infected with TB (e.g., by virtue of geographical location, medical history, or field of work), or who are believed or known to have been exposed to TB but have not yet developed active infection. The prophylactic administration of the yeast-TB immunotherapy compositions serves to prevent subsequent TB infection, to prevent, delay or attenuate active TB infection or disease, to resolve an infection more quickly or more completely if active TB infection subsequently ensues, and/ or to ameliorate the symptoms of active TB infection if it subsequently ensues.

When provided therapeutically, the compositions of the invention are provided once active infection (also referred to as TB disease) develops in an individual post-exposure. Such a composition could be administered to any individual (infant, child, adult) who has been identified as having active TB infection (TB disease). When provided therapeutically, one goal of the therapy is to ameliorate, reduce or eliminate at least one symptom of the TB infection and preferably, to eliminate the infection or reduce the microorganism burden in the individual, provide a long lasting remission of infection, and/or provide long term immunity against subsequent TB infections.

As used herein, "pre-exposure" means that an individual has not been exposed to, or is not known to have been exposed to, an organism that causes TB (i.e., does not have a TB infection). As used herein, "post-exposure" means that an individual is known to have been exposed to an organism that causes TB, which is most typically verified by a positive reaction to the tuberculin skin test or to a TB blood test, both tests being well known in the art. Post-exposure individuals can include individuals with a "latent infection" and individuals with an "active infection" or "TB disease". Individuals having a "latent infection" do not feel sick and do not have symptoms of TB disease, but do test positive for TB infection (e.g., by tuberculin skin test or TB blood test). In addition, these individuals typically have normal chest X-rays and negative sputum tests, and are not believed to be infectious (i.e., will not spread the TB organisms to others). Persons with latent TB infection, if untreated, have approximately a 5-10% chance of developing an active infection at some point in their lives. Individuals having an "active infection" or "TB disease" (the terms used interchangeably herein) are persons which test positive for TB infection (by tuberculin skin test or TB blood test) and in whom the TB organisms have begun to multiply and overcome the immune system. In addition, TB disease may be identified by a positive abnormal chest X-ray, positive sputum smear or culture (for the TB organism). Such persons may have unexplained weight loss, loss of appetite, night sweats, fever, fatigue, chills, cough for 3 weeks or longer, cough blood, or have chest pain. These individuals are infectious (i.e., can spread/transmit the infection to others).

Typically, a yeast-based immunotherapy composition includes a yeast vehicle and at least one antigen, which includes one or more TB proteins or an immunogenic domains thereof, the antigen being expressed by, attached to, or mixed with the yeast vehicle, wherein the antigen is heterologous to the yeast. In some embodiments, the antigen is provided as a fusion protein. Several TB fusion proteins suitable for use in the compositions and methods of the invention are described herein. In one aspect of the invention, fusion protein can include two or more different TB proteins. In one aspect, the fusion protein can include two or more immunogenic domains of one or more TB proteins, or two or more epitopes of one or more TB proteins.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. The yeast vehicle can therefore include, but is not limited to, a live intact (whole) yeast microorganism (i.e., a yeast cell having all its components including a cell wall), a killed (dead) or inactivated intact yeast microorganism, or derivatives of intact/whole yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674, incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains).

Genera of yeast strains that may be used in the invention include but are not limited to *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, yeast genera are selected from *Saccharomyces, Hansenula*, and *Pichia*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Han-*

*senula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe. S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

Methods of producing yeast vehicles and expressing, combining and/or associating yeast vehicles with antigens and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from 2 to 3, 4, 5, 6, 7, 8, 9, 10 or more heterologous antigens and or other proteins or agents.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome cl (CYC1), Sec7 protein (SECT) and acid phosphatase (PH05), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SECT; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some embodiments of the invention, yeast are grown under neutral pH conditions, which is described in more detail in PCT Publication No. WO 2008/097863. As used herein, the general use of the term "neutral pH" refers to a pH range between about pH 5.5 and about pH 8, and in one aspect, between about pH 6 and about 8. The use of neutral pH to grow yeast cells means that the yeast cells are grown in neutral pH for the majority or all of the time that they are in culture (i.e., from the start of growth of the yeast to harvest of the yeast). In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5 or 8. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The use of a neutral pH allows for the production of yeast with pliable cell walls and/or yeast that are more sensitive to cell wall digesting enzymes (e.g., glucanase) at all harvest densities, including high cell densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., Th1-type cytokines including, but not limited to, IFN-$\gamma$, interleukin-12 (IL-12), and IL-2, as well as proinflammatory cytokines such as IL-6). In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g., mnn1, och1 and mnn9 mutants), or one could eliminate by mutation the glycosylation acceptor sequences on the target antigen. Alternatively, one could use a yeast with abbreviated glycosylation patterns, e.g., *Pichia*. One can also treat the yeast using methods that reduce or alter the glycosylation.

In one embodiment of the invention, the yeast vehicle and the antigen or other protein are both loaded intracellularly into a carrier such as a dendritic cell or macrophage to form the therapeutic composition or vaccine of the present invention. Alternatively, an antigen or other protein can be loaded into a dendritic cell in the absence of the yeast vehicle.

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat-inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a Th17 response versus a Th1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-α) or agonists or antagonists of type I interferon or a receptor thereof; type II interferon (including IFN-γ) or agonists or antagonists of type II interferon or a receptor thereof; anti-CD40 antibody, CD40L, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill $CD4^+/CD25^+$ T regulatory cells); Flt3 ligand, imiquimod (Aldara™), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, and/or pro-inflammatory agents. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other compounds or compositions that are useful for preventing or treating TB infection or any compounds that treat or ameliorate any symptom of TB infection. A variety of agents, including various antimicrobial chemotherapeutic drugs (e.g., antibiotics) are known to be useful for treating or ameliorating TB infection. In addition, compositions of the invention can be used together with other immunotherapeutic compositions, including prophylactic and/or therapeutic immunotherapy.

Four regimens are currently approved for the treatment of latent TB infection, and include the use of the drugs isoniazid (INH), rifampin (RIF) and rifapentine (RPT). In the first regimen, INH is given for 9 months administered either (1) daily, or (2) twice weekly in conjunction with Directly Observed Therapy (DOT). DOT is the name given to the World Health Organization tuberculosis control strategy and includes (a) government commitment for a system of TB monitoring, recording and training; (b) case detection by sputum smear microscopy; (c) standardized treatment regimen directly observed by a healthcare working for at least the first two months; (d) a regular drug supply; and (e) a standardized recording and reporting system that allows assessment of treatment results. In a second approved regimen for treatment of latent infection, INH is given for 6 months either (1) daily or (2) twice weekly in conjunction with DOT. In a third regimen, INH and RPT are given in combination for 3 months weekly with DOT. Finally, a fourth approved regimen for treatment of latent infection is administration of RIF for 4 months daily.

There are currently 10 drugs approved by the U.S. Food and Drug Administration (FDA) for the treatment of active TB infection (TB disease). The first-line drugs that form the core of most treatment regimens are INH, RIF, ethambutol (EMB) and pyrazinamide (PZA). TB disease treatment usually commences with 2 months of treatment, followed by a choice of several different options for continued treatment of either 4 or 7 months. For example, a preferred regimen includes an initial regimen of daily INH, RIF, PZA and EMB for 8 weeks, followed by a continuation phase of: (1) daily INH and RIF for 18 weeks or twice-weekly INH and RIF for 18 weeks. An alternate protocol includes an initial regimen of daily INH, RIF, PZA and EMB for 2 weeks, followed by all four drugs twice weekly for 6 weeks, followed by a continuation phase of twice-weekly INH and RIF for 18 weeks. Another alternate protocol includes an initial regimen of thrice-weekly INH, RIF, PZA and EMB for 8 weeks, followed by a continuation phase of thrice-weekly INH and RIF for 18 weeks. Drug-resistant TB is defined as TB mycobacteria that are resistant to at least one first-line drug, and multidrug resistant (MDR) TB is resistant to more than one TB drug and at least INH and RIF. Treatment of these forms of TB is more complicated and involves DOT along with one or more drugs identified as suitable for the patient through drug-susceptibility testing.

Any of the methods of administering a yeast-based TB immunotherapy composition of the invention can be combined with administration of the Bacillus Calmette-Guérin (BCG) vaccine. The BCG vaccine is a live vaccine originally derived from a strain of *Mycobacterium bovis* that was attenuated by Calmette and Guerin at the Pasteur Institute in Lille, France in the early 1900's. The BCG vaccine may be administered as a priming immunization, followed by boosters (1, 2, 3, 4, 5 or more) of the yeast-based TB immunotherapy composition. Boosters of BCG vaccine may also be given prior to, concurrently with, or after boosters of the yeast-based TB immunotherapy composition. Alternatively, the yeast-based immunotherapy composition can be used as the priming immunization, followed by boosters of the BCG vaccine. The BCG vaccine is administered by intradermal injection, typically percutaneously utilizing a sterile multiple puncture device or by syringe and needle. The dosage for a human adult is generally $2\text{-}8\times10^5$ cfu, and $1\text{-}4\times10^5$ cfu is a pediatric dose.

The yeast-based TB immunotherapy composition can also be combined with other prophylactic or immunotherapeutic vaccines, such as any of those in development (e.g., adjuvanted subunit vaccines, DNA vaccines, viral vector vaccines, whole cell or attenuated or fragmented mycobacterial vaccines, etc.) in a similar manner (e.g., prime-boost or even concurrent administration).

The invention also includes a kit comprising any of the compositions described herein, or any of the individual components of the compositions described herein.

Methods for Administration or Use of Compositions of the Invention

Compositions of the invention, which can include any one or more (e.g., combinations of two, three, four, five, or more) yeast-based immunotherapeutic compositions described herein, TB antigens including TB proteins and fusion proteins, and/or recombinant nucleic acid molecules encoding such TB proteins or fusion proteins described above, and other compositions comprising such yeast-based compositions, antigens, proteins, fusion proteins, or recombinant molecules described herein, can be used in a variety of in vivo and in vitro methods, including, but not limited to, to treat and/or prevent TB infection and its sequelae, in diagnostic assays for TB, or to produce antibodies against TB.

One embodiment of the invention relates to a method to prevent or to treat TB infection (latent or active), and/or to prevent, ameliorate or treat at least one symptom of TB infection (latent or active), in an individual or population of individuals. The method includes the step of administering to an individual or a population of individuals who are infected with TB one or more immunotherapeutic compositions of the invention. In one aspect, the composition is an immunotherapeutic composition comprising one or more TB antigens as described herein, which can include a yeast-based immunotherapeutic composition. In one embodiment, the individual or population of individuals is a "pre-exposure" individual or population of individuals. In one embodiment, the individual or population of individuals has latent TB infection. In one embodiment, the individual or population of individuals has active TB infection (TB disease). In one aspect, the individual or population of individuals is additionally treated with at least one other preventative and/or therapeutic compound or regimen useful for the treatment of TB infection (latent or active, depending on whether the individual or population of individuals has latent or active TB infection). Such therapeutic compounds and regimens have been described in detail above, and can include any currently approved compound or regimen, or other types of therapies, including without limitation additional immunotherapeutic compositions and regimens.

Another embodiment of the invention relates to a method to immunize an individual or population of individuals against TB in order to prevent TB infection and/or reduce or delay the onset or severity of TB infection in the individual or population of individuals. The method includes the step of administering to an individual or population of individuals that is not infected with TB (or believed not to be infected with TB), a composition of the invention. In one aspect, the composition is an immunotherapeutic composition comprising one or more TB antigens as described herein, including one or more yeast-based immunotherapeutic compositions. In one embodiment, a yeast-based immunotherapeutic of the invention is administered in conjunction with BCG vaccine or other vaccines comprising TB antigens.

As used herein, the phrase "treat" TB infection, or any permutation thereof (e.g., "treated for TB infection", etc.) generally refers to applying or administering a composition of the invention once the infection (latent or active) has occurred, with the goal of: reduction or elimination of detectable TB mycobacteria (e.g., mycobacterial burden in the lung, spleen, lymph node or other organ where TB infection can reside); reduction, elimination and/or delay of the formation of secondary tuberculosis lesions; reduction, elimination, and/or delay of dissemination of the TB mycobacteria to the lymph nodes or other organs or body systems; extension of survival; amelioration of TB infections or symptoms sufficient to improve or synergize with the efficacy or effectiveness or time for introduction of chemotherapeutic other TB drugs in eradicating or treating the infection; reduction or resolution of at least one symptom resulting from the infection in the individual; delaying or preventing the onset and/or severity of symptoms and/or downstream sequelae caused by the infection, reduction of organ or physiological system damage resulting from the infection, improvement of immune responses against the TB organism, improvement of long term memory immune responses against the TB organism, and/or improved general health of the individual or population of individuals. In one aspect of the invention, the administration of the immunotherapeutic composition to the subject is effective to enhance or synergize with the efficacy of an agent useful for treating or ameliorating a symptom of TB infection or delay progression of TB infection and/or symptoms thereof sufficient to increase the effectiveness of treatment with the agent or sufficient to allow additional time for the agent to provide a therapeutic benefit to the subject.

To "prevent" TB infection, or any permutation thereof (e.g., "prevention of TB infection", etc.), generally refers to applying or administering a composition of the invention before an infection with TB has occurred, with the goal of preventing infection by TB mycobacteria, or, should the infection later occur, at least delaying the onset, reducing the severity, and/or reducing the length of infection and/or the physiological damage caused by the infection, including preventing or reducing the severity or incidence of at least one symptom resulting from the infection in the individual, delaying or preventing the formation of secondary TB lesions, delaying or preventing recurrence of the disease, and/or delaying or preventing the onset and/or severity of symptoms and/or downstream sequelae caused by the infection, in an individual or population of individuals.

The present invention includes the delivery (administration, immunization) of one or more immunotherapeutic compositions of the invention, including a yeast-based immunotherapy composition, to a subject. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of infection). Suitable routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). Other routes of administration that modulate mucosal immunity may be useful in the treatment of TB infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response against one or more TB antigens or epitopes, when administered one or more times over a suitable time period. For example, in one embodiment, a single dose of a yeast vehicle of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Y.U. ($1 \times 10^6$ cells) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). In one embodiment, doses include doses between 1 Y.U. and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60 Y.U., 70 Y.U., or 80 Y.U. In one embodiment, the doses are administered at two, three, four or more different sites on the individual but during the same dosing period. For example, a 40 Y.U. dose may be administered via by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1 \times 10^5$ to about $5 \times 10^7$ yeast cell equivalents of a composition per kg body weight of the organism is administered at least 1, 2, 3, 4, 5, 6, 7, 8, 9, 10, or more times over a time period of from weeks, to months, to years. In one embodiment, the doses are administered weekly for 1, 2, 3, 4, 5, 6, 7, 8, 9, 10 or more doses, followed by monthly doses as needed to achieve the desired inhibition or elimination of the TB mycobacterium. In one embodiment, the doses are administered in a 4-weekly protocol (every 4 weeks, or on day 1, week 4, week 8, week 12, etc., for between 2 and 10 doses or longer as determined by the clinician). Additional doses can be administered.

With respect to administration of yeast-based immunotherapeutic compositions described herein, a single composition can be administered to an individual or population of individuals or combination of such compositions can be administered. Accordingly, two or more compositions can be selected in a "spice rack" approach to most effectively prevent or treat TB infection in a given individual or population of individuals. For example, in the TB compositions described herein, a combination of a yeast-based immunotherapeutic containing a Rv1909 antigen can be combined or given concurrently or sequentially administered with a yeast-based immunotherapeutic containing a Rv2359 and/or a Rv2711 antigen. As another example, a combination of a yeast-based immunotherapeutic containing a Rv1738 antigen can be combined or given concurrently or sequentially administered with a yeast-based immunotherapeutic containing an Rv2032 antigen and/or an Rv3130 antigen and/or an Rv3841 antigen. Similar combinations can be concurrently or sequentially administered using any of the TB antigens described elsewhere herein, e.g., any combination of two, three, four or more of yeast-based immunotherapeutics comprising one or more of the following TB antigens: Rv0125, Rv1196, Rv1411 (Rv1411c), Rv1738, Rv1813, Rv1909 (Rv1909c), Rv2032, Rv2359, Rv2608, Rv2660, Rv2711, Rv3130, Rv3619, Rv3620, Rv3841, Ag85A, Ag85B, TB10.4 and ESAT-6. This aspect of the invention is particularly useful when customization or personalization of the treatment or prevention regimen is desirable for a given patient, population of patients, TB strain, geographical region and/or companion therapy.

In one aspect of the invention, one or more additional therapeutic agents are administered sequentially with the yeast-based immunotherapy composition. In another embodiment, one or more additional therapeutic agents are administered before the yeast-based immunotherapy composition is administered. In another embodiment, one or more additional therapeutic agents are administered after the yeast-based immunotherapy composition is administered. In one embodiment, one or more additional therapeutic agents are administered in alternating doses with the yeast-based immunotherapy composition, or in a protocol in which the yeast-based composition is administered at prescribed intervals in between or with one or more consecutive doses of the additional agents, or vice versa. In one embodiment, the yeast-based immunotherapy composition is administered in one or more doses over a period of time prior to commencing the administration of the additional agents. In other words, the yeast-based immunotherapeutic composition is administered as a monotherapy for a period of time, and then the agent administration is added, either concurrently with new doses of yeast-based immunotherapy, or in an alternating fashion with yeast-based immunotherapy. Alternatively, the agent may be administered for a period of time prior to beginning administration of the yeast-based immunotherapy composition. In one aspect, the yeast is engineered to express or carry the agent, or a different yeast is engineered or produced to express or carry the agent.

In one aspect of the invention, when a treatment course of anti-TB compound therapy begins (e.g., any one of the approved drugs or regimens described elsewhere herein), additional doses of the immunotherapeutic composition are administered over the same period of time, or for at least a portion of that time, and may continue to be administered once the course of therapy of the anti-TB compound has ended. However, the dosing schedule for the immunotherapy over the entire period may be, and is expected to typically be, different than that for the anti-TB compound. For example, the immunotherapeutic composition may be administered daily, weekly, biweekly (every two weeks), tri-weekly (every three weeks), monthly, bimonthly, or every 3-6 months, or at longer intervals as determined by the physician, and is most typically administered weekly followed by monthly, biweekly, or monthly, where current anti-TB drugs are administered daily, twice weekly, thrice weekly, or biweekly.

In aspects of the invention, an immunotherapeutic composition and other agents can be administered together (concurrently). As used herein, concurrent use does not necessarily mean that all doses of all compounds are administered on the same day at the same time. Rather, concurrent use means that each of the therapy components (e.g., immunotherapy and anti-TB therapy) are started at approximately the same period (within hours, or up to 1-7 days of each other) and are administered over the same general period of time, noting that each component may have a different dosing schedule (e.g., immunotherapy monthly, anti-TB drugs daily). In addition, before or after the concurrent administration period, any one of the agents or immunotherapeutic compositions can be administered without the other agent(s).

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); Current Protocols in Molecular Biology (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin and W. Orenstein, eds., 3rd edition (1999).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN® products have been generally described (see, e.g., U.S. Pat. No. 5,830,463). Certain yeast-based immunotherapy compositions, and methods of making and generally using the same, are also described in detail, for example, in U.S. Pat. No. 5,830,463, U.S. Pat. No. 7,083,787, U.S. Pat. No. 7,736,642, Stubbs et al., *Nat. Med.* 7:625-629 (2001), Lu et al., Cancer Research 64:5084-5088 (2004), and in Bernstein et al., Vaccine 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background.

Binding can be measured using a variety of methods standard in the art including enzyme immunoassays (e.g., ELISA, immunoblot assays, etc.).

Reference to a protein or polypeptide used in the present invention includes full-length proteins, fusion proteins, or any fragment, domain, conformational epitope, or homologue of such proteins, including functional domains and immunological domains of proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

A homologue may include proteins or domains of proteins that are "near full-length", which means that such a homologue differs from the full-length protein, functional domain or immunological domain (as such protein, functional domain or immunological domain is described herein or otherwise known or described in a publicly available sequence) by the addition of or deletion of 1, 2, 3, 4, 5, 6, 7, 8, 9, or 10 amino acids from the N- and/or the C-terminus of such full-length protein or full-length functional domain or full-length immunological domain.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T.L., Schääffer, A.A., Zhang, J., Zhang, Z., Miller, W. & Lipman, D.J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the production of several yeast-based immunotherapeutic compositions for the treatment or prevention of TB infection.

Figure 1B:
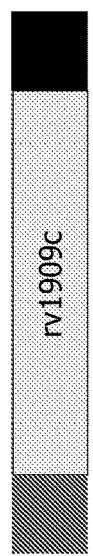
FIG. 1B is a schematic drawing showing the organization of a fusion protein for expression in a yeast-based immunotherapeutic composition, comprising an N-terminal stability peptide (gray), a TB antigen from rv1909c (light gray), and a C-terminal hexahistidine peptide (black).
Figure 1C:
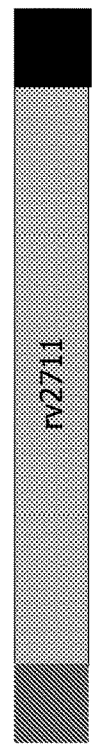
FIG. 1C is a schematic drawing showing the organization of a fusion protein for expression in a yeast-based immunotherapeutic composition, comprising an N-terminal stability peptide (gray), a TB antigen from rv2711 (medium gray), and a C-terminal hexahistidine peptide (black).

In a first experiment, yeast (e.g., *Saccharomyces cerevisiae*) were engineered to express a fusion protein comprising an antigen from the TB Rv2359 protein, under the control of the copper-inducible promoter, CUP1. The TB antigen was a single polypeptide of approximately 130 amino acids represented by SEQ ID NO:4. The fusion protein comprising SEQ ID NO:4 and expressed by the yeast was a single polypeptide, with the following sequence elements fused in frame from N- to C-terminus, represented by SEQ ID NO:6: 1) the amino acid sequence of the N-terminal peptide of SEQ ID NO:1 (positions 1-6 of SEQ ID NO:6); 2) a two amino acid linker sequence of Thr-Ser (positions 7-8 of SEQ ID NO:6); 3) the amino acid sequence of the Rv2359 antigen of SEQ ID NO:4 (positions 9-137 of SEQ ID NO:6); and 4) a hexahistidine tag (positions 138-143 of SEQ ID NO:6). The fusion protein represented by SEQ ID NO:6 is encoded by a recombinant nucleic acid sequence for insertion into a vector that has the nucleic acid sequence of SEQ ID NO:5. This fusion protein is illustrated schematically in FIG. 1A. A yeast-based immunotherapeutic composition of the invention that expresses SEQ ID NO:6 can be referred to herein as GI-19001.

In a second experiment, yeast (e.g., *Saccharomyces cerevisiae*) were engineered to express a fusion protein comprising an antigen from the TB Rv2711 protein, under the control of the copper-inducible promoter, CUP1. The TB antigen was a single polypeptide of approximately 230 amino acids represented by SEQ ID NO:7. The fusion protein comprising SEQ ID NO:7 and expressed by the yeast was a single polypeptide, with the following sequence elements fused in frame from N- to C-terminus, represented by SEQ ID NO:9: 1) the amino acid sequence of the N-terminal peptide of SEQ ID NO:1 (positions 1-6 of SEQ ID NO:9); 2) a two amino acid linker sequence of Thr-Ser (positions 7-8 of SEQ ID NO:9); 3) the amino acid sequence of the Rv2711 antigen of SEQ ID NO:7 (positions 9-237 of SEQ ID NO:9); and 4) a hexahistidine tag (positions 238-243 of SEQ ID NO:9). The fusion protein represented by SEQ ID NO:9 is encoded by a recombinant nucleic acid sequence for insertion into a vector that has the nucleic acid sequence of SEQ ID NO:8. This fusion protein is illustrated schematically in FIG. 1C. A yeast-based immunotherapeutic composition of the invention that expresses SEQ ID NO:9 can be referred to herein as GI-19002.

In a third experiment, yeast (e.g., *Saccharomyces cerevisiae*) were engineered to express a fusion protein comprising an antigen from the TB Rv1909c protein, under the control of the copper-inducible promoter, CUP1. The TB antigen was a single polypeptide of approximately 147 amino acids represented by SEQ ID NO:10. The fusion protein comprising SEQ ID NO:10 and expressed by the yeast was a single polypeptide, with the following sequence elements fused in frame from N- to C-terminus, represented by SEQ ID NO:12: 1) the amino acid sequence of the N-terminal peptide of SEQ ID NO:1 (positions 1-6 of SEQ ID NO:12); 2) a two amino acid linker sequence of Thr-Ser (positions 7-8 of SEQ ID NO:12); 3) the amino acid sequence of the Rv1909c antigen of SEQ ID NO:10 (positions 9-155 of SEQ ID NO:12); and 4) a hexahistidine tag (positions 156-161 of SEQ ID NO:12). The fusion protein represented by SEQ ID NO:12 is encoded by a recombinant nucleic acid sequence for insertion into a vector that has the nucleic acid sequence of SEQ ID NO:11. This fusion protein is illustrated schematically in FIG. 1B. A yeast-based immunotherapeutic composition of the invention that expresses SEQ ID NO:12 can be referred to herein as GI-19003.

Figure 1D:
FIG. 1D is a schematic drawing showing the organization of a fusion protein for expression in a yeast-based immunotherapeutic composition, comprising an N-terminal stability peptide (gray), a TB antigen from rv2359 (white), a TB antigen from rv2711 (medium gray), a TB antigen from rv1909c (light gray) and a C-terminal hexahistidine peptide (black).

In a fourth experiment, yeast (e.g., *Saccharomyces cerevisiae*) were engineered to express an antigen comprising three different iron accumulation TB antigens, fused to form a single fusion protein, under the control of the copper-inducible promoter, CUP1. The TB antigen in this fusion protein is a single polypeptide comprising a TB antigen from Rv2359, a TB antigen from Rv2711, and a TB antigen from Rv1909c, having the amino acid sequence of SEQ ID NO:13. The fusion protein comprising SEQ ID NO:13 and expressed by the yeast was a single polypeptide, with the following sequence elements fused in frame from N- to C-terminus, represented by SEQ ID NO:15: 1) the amino acid sequence of the N-terminal peptide of SEQ ID NO:1 (positions 1-6 of SEQ ID NO:15); 2) a two amino acid linker sequence of Thr-Ser (positions 7-8 of SEQ ID NO:15); 3) the amino acid sequence of the Rv2359 antigen of SEQ ID NO:4 (positions 9-137 of SEQ ID NO:15); 4) the amino acid sequence of the Rv2711 antigen of SEQ ID NO:7 (positions 138-366 of SEQ ID NO:15); 5) the amino acid sequence of the Rv1909c antigen of SEQ IDS NO:10 (positions 367-513 of SEQ ID NO:15); and 6) a hexahistidine tag (positions 514-519 of SEQ ID NO:15). The fusion protein represented by SEQ ID NO:15 is encoded by a recombinant nucleic acid sequence for insertion into a vector that has the nucleic acid sequence of SEQ ID NO:14. The combination of the TB antigens in the amino acid sequence represented by SEQ ID NO:13 or SEQ ID NO:15 can also be referred to herein as the "3-iron fusion". This fusion protein is illustrated schematically in FIG. 1D. A yeast-based immunotherapeutic composition of the invention that expresses SEQ ID NO:15 can be referred to herein as GI-19004.

In a fifth experiment, yeast (e.g., *Saccharomyces cerevisiae*) were engineered to express a fusion protein comprising an antigen from the TB ESAT-6 protein, under the control of the copper-inducible promoter, CUP1. The TB antigen was a single polypeptide of approximately 94 amino acids represented by SEQ ID NO:16. The fusion protein comprising SEQ ID NO:16 and expressed by the yeast was a single polypeptide, with the following sequence elements fused in frame from N- to C-terminus, represented by SEQ ID NO:18: 1) the amino acid sequence of the N-terminal peptide of SEQ ID NO:1 (positions 1-6 of SEQ ID NO:18); 2) a two amino acid linker sequence of Thr-Ser (positions 7-8 of SEQ ID NO:18); 3) the amino acid sequence of the ESAT-6 antigen of SEQ ID NO:16 (positions 9-102 of SEQ ID NO:18); and 4) a hexahistidine tag (positions 103-108 of SEQ ID NO:18). The fusion protein represented by SEQ ID NO:18 is encoded by a recombinant nucleic acid sequence for insertion into a vector that has the nucleic acid sequence of SEQ ID NO:17. A yeast-based immunotherapeutic composition of the invention that expresses SEQ ID NO:18 can be referred to herein as GI-19005.

To produce the five yeast immunotherapy compositions described above, briefly, DNA encoding the TB antigens described above was first codon optimized for expression in yeast, and then inserted behind the CUP1 promoter (pGI-100) in yeast 2 μm expression vectors. The resulting plasmids were introduced into *Saccharomyces cerevisiae* W303α yeast by Lithium acetate/polyethylene glycol transfection, and transfectants were selected on solid minimal plates lacking uracil and leucine (ULDM; uridine and leucine dropout medium). Liquid cultures lacking uridine and leucine (UL2 medium: 20 g/L glucose; 6.7 g/L of yeast nitrogen base containing ammonium sulfate; and 0.04 mg/mL each of histidine, tryptophan, and adenine) were inoculated from plates and starter cultures were grown for 20 h at 30° C., 250 rpm. Primary cultures were used to inoculate final cultures of the same formulation for all cultures except GI-19003) or liquid medium lacking uridine only for GI-19003 (U2 medium: 20 g/L glucose; 6.7 g/L of yeast nitrogen base containing ammonium sulfate; 0.04 mg/mL each of histidine, tryptophan, and adenine; and 0.06 mg/mL of Leucine) and growth was continued until a density or 1.1 to 4.0 YU/mL was reached. Cultures were induced with 500 μM copper sulfate at a starting density of 1-4 YU/ml for 3 hours at 30° C. The cells from each culture were then harvested, PBS-washed and heat-killed at 56° C. for 1 hour in PBS.

After heat-kill of the cultures, the cells were thrice washed in PBS and total protein was isolated by glass bead rupture followed by boiling in SDS lysis buffer. Quantification of total protein was done by Pierce 660 nm protein assay, and TB antigen content was measured by Western blot using an anti-His tag monoclonal antibody probe followed by interpolation to a His-tagged HCV NS3 protein standard curve.

Figure 2:
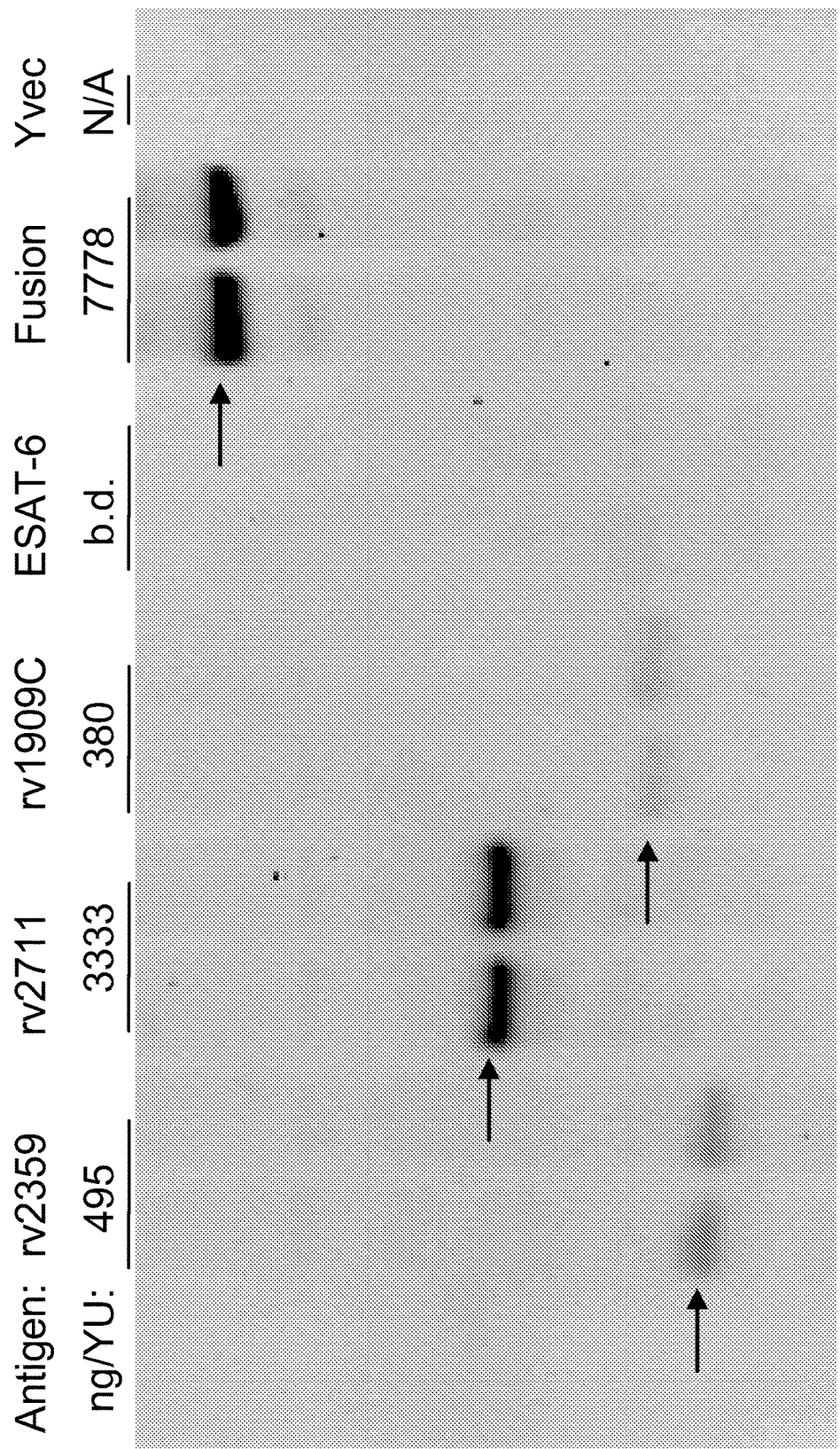
FIG. 2 is a digitized image of a Western blot showing the expression of five different TB antigens in yeast-based immunotherapy compositions (rv2359=fusion protein represented by SEQ ID NO:6; rv2711=fusion protein represented by SEQ ID NO:9; rv1909C=fusion protein represented by SEQ ID NO:12; ESAT-6=fusion protein represented by SEQ ID NO:18; Fusion="3-iron" fusion protein represented by SEQ ID NO:15; Yvec=empty vector yeast (negative control)). Levels of antigen expression are quantified as ng of antigen per YU ($10^7$ yeast cells; b.d.=below detection; N/A=not applicable). Arrows indicate bands showing antigen expression.

Results are shown in FIG. 2. FIG. 2 shows copper inducible expression of the yeast expressing the fusion protein comprising the Rv2359 antigen (GI-19001 expressing SEQ ID NO:6; denoted in FIG. 2 as "rv2359"), the yeast expressing the fusion protein comprising the Rv2711 antigen (GI-19002 expressing SEQ ID NO:9; denoted in FIG. 2 as "rv2711"), the yeast expressing the fusion protein comprising the Rv1 909c antigen (GI-19003 expressing SEQ ID NO:12; denoted in FIG. 2 as "rv1909C"), the yeast expressing the fusion protein comprising the "3-iron fusion" (GI-19004 expressing SEQ ID NO:15; denoted in FIG. 2 as "Fusion"), and a yeast expressing a TB ESAT-6 antigen (GI-19005 expressing SEQ ID NO:18; denoted in FIG. 2 as "ESAT-6"). A control yeast (empty vector) was used as a control (denoted "Yvec" in FIG. 2). 8 µg total protein was loaded per lane. FIG. 2 shows that each of the TB yeast-based immunotherapy compositions expressing an iron accumulation antigen (Rv2359, Rv2711, Rv1909c) of the invention expresses the TB protein, and can be identified by Western blot, but that expression of the ESAT-6 antigen was not detected (b.d.=below the detection limits of this assay). The fusion protein containing all three iron accumulation antigens (3-iron fusion protein or "Fusion") accumulated to a much higher level than any of the individual antigens (calculated: Rv2359=495 ng antigen/$10^7$ yeast cells; Rv2711=3333 ng antigen/$10^7$ yeast cells; Rv1909c=380 ng antigen/$10^7$ yeast cells; Fusion=7778 ng antigen/$10^7$ yeast cells). The yeast known as GI-19004, expressing the 3-iron fusion protein of SEQ ID NO:15, was selected for the experiment described in Example 2.

Example 2

The following example shows the results of immunization of mice with a yeast-based immunotherapeutic composition expressing the 3-iron fusion TB antigen.

Figure 3:
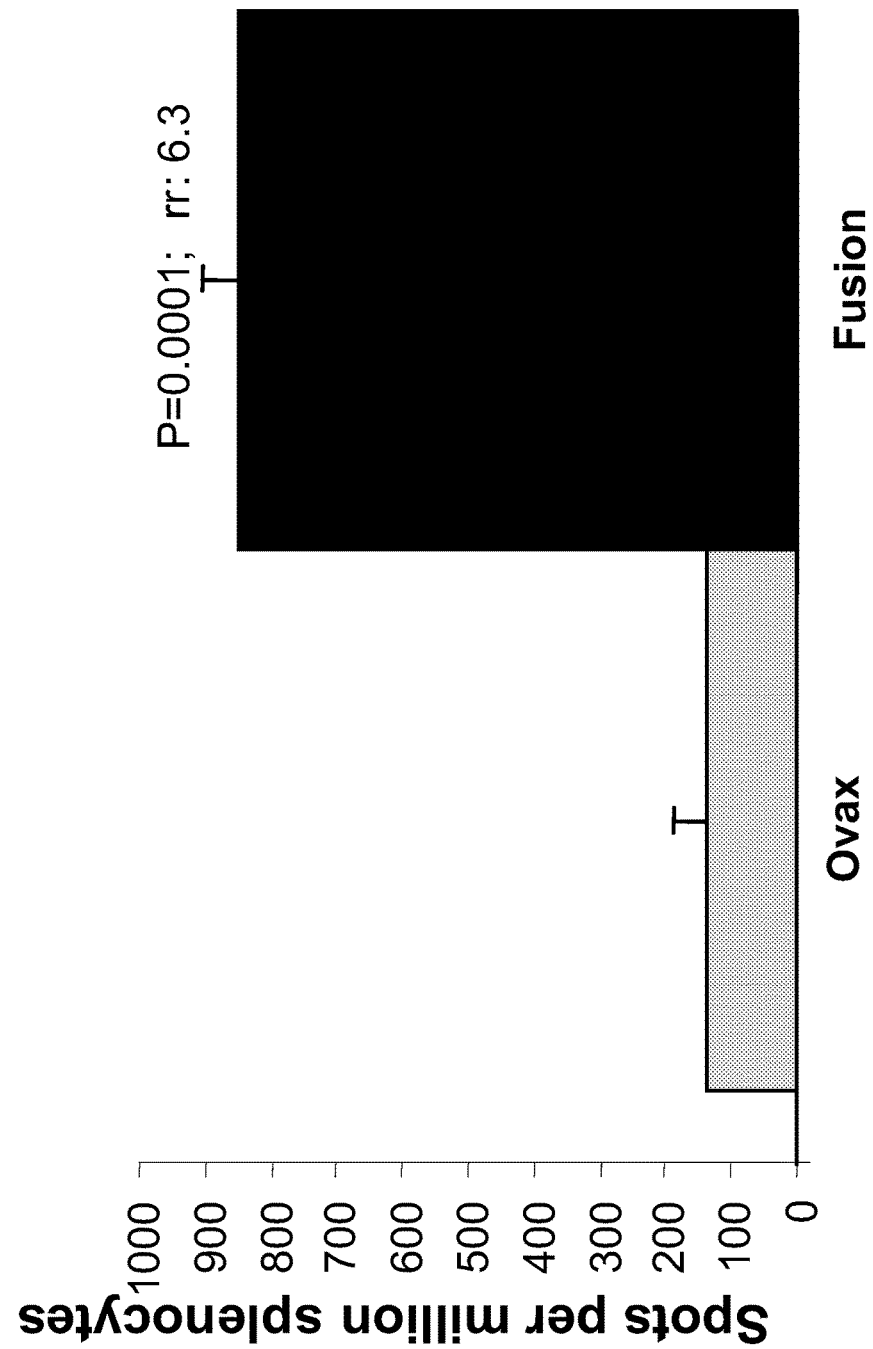
FIG. 3 is a graph showing interferon-γ (IFN-γ) production by splenocytes from mice immunized with GI-19004 (yeast-based immunotherapeutic expressing 3-iron fusion protein, denoted "Fusion"), as compared to control yeast (Ovax, a yeast-based immunotherapeutic expressing the irrelevant antigen, chicken ovalbumin), after in vitro stimulation (IVS) with recombinant TB antigen Rv2359.

Briefly, DBA mice were immunized subcutaneously once per week for 2 weeks with 4 Y.U. ($4 \times 10^7$ yeast cells) of GI-19004, which is the yeast-based immunotherapy composition expressing the "3-iron" fusion protein of SEQ ID NO:15. Seven days later, splenocytes were stimulated in vitro for 4 days with recombinant purified TB iron antigen in the presence of 4 U/ml murine IL-2. In the experiment shown in FIG. 3 (yeast expressing the 3-iron fusion protein of SEQ ID NO:15, denoted "Fusion" in FIG. 3), splenocytes were restimulated with recombinant purified iron antigen rv2359. IFN-γ production was measured by ELISpot assay. Ovax is a control yeast expressing the irrelevant antigen, chicken ovalbumin. FIG. 3 shows that immunization with GI-19004 expressing a fusion protein of three iron accumulation antigens elicits a robust, antigen-specific (rv2359), interferon-γ (IFN-γ) response in immune cells isolated from the mice, indicating a strong cell-mediated immune response and $CD8^+$ T cell response (P value determined using ANOVA; rr: response ratio (ELISpot ratio of the Fusion/Ovax).

Figure 4:
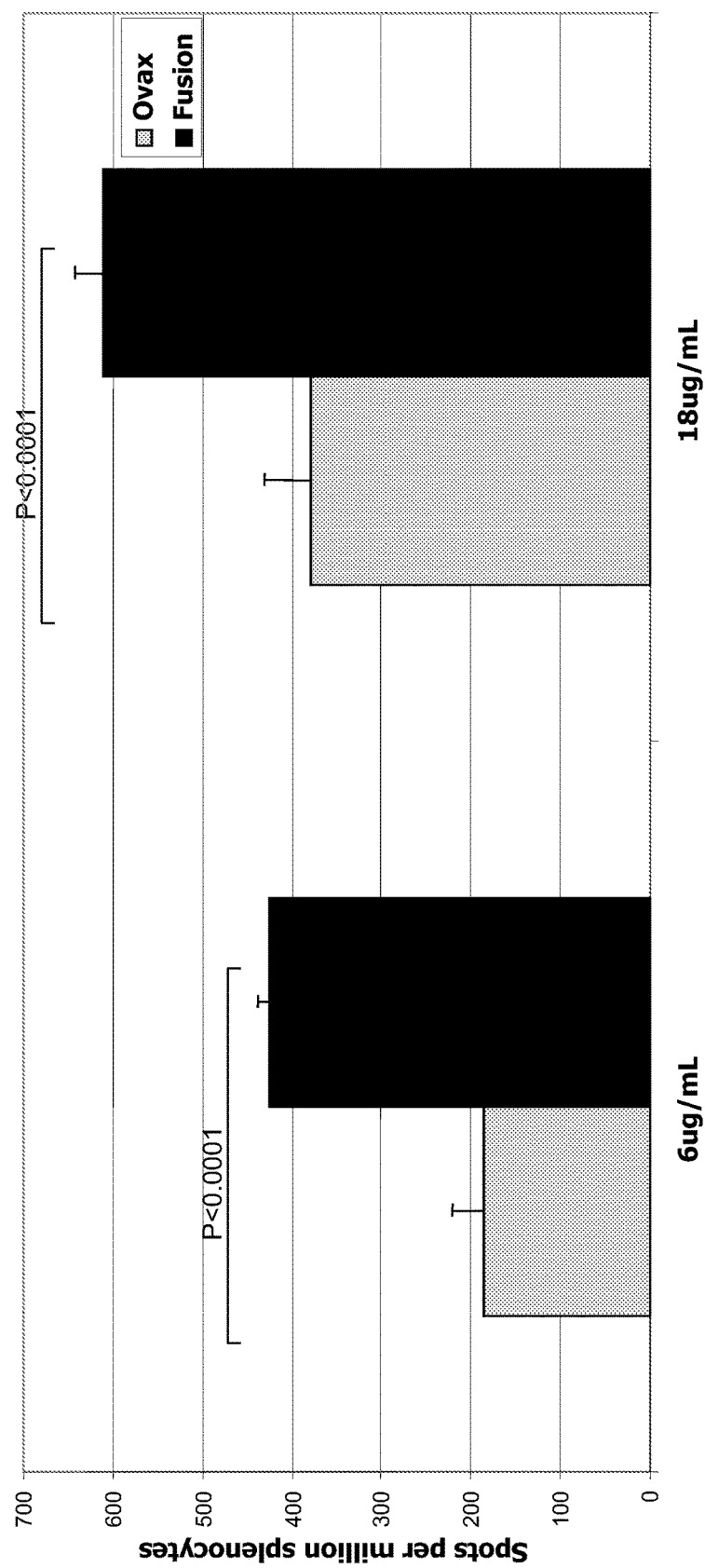
FIG. 4 is a graph showing interferon-γ (IFN-γ) production by splenocytes from mice immunized with GI-19004 (yeast-based immunotherapeutic expressing 3-iron fusion protein, denoted "Fusion"), as compared to control yeast (Ovax), after in vitro stimulation (IVS) with centifugally cleared lysate of live GI-19004, provided at two different concentrations.

FIG. 4 shows the results of additional ELISpot assays performed using splenocytes from mice immunized with GI-19004. In this experiment, mice were immunized as described above for the experiment shown in FIG. 3, and splenocytes were isolated for in vitro stimulation with antigen and evaluation by ELISpot assay. The antigen used for in vitro stimulation of the splenocytes in this experiment was not recombinant Rv2359, but a centifugally cleared lysate of live GI-19004 (expressing the 3-iron fusion, so all three TB antigens, and also containing bulk yeast antigens from the lysate). The lysate antigen was used at a concentration of 6 µg/mL or 18 µg/mL. Ovax (yeast expressing ovalbumin as an irrelevant antigen) served as a control for antigen-specificity. As shown in FIG. 4, immunization with GI-19004 expressing a fusion protein of three iron accumulation antigens elicits a robust, antigen-specific (this time using all three antigens), interferon-γ (IFN-γ) response in immune cells isolated from the mice. The Ovax control response was higher in this experiment due to the presence of the yeast antigens in the lysate, which are shared by all of the yeast-based compositions; however, the response elicited by GI-19004 was statistically significant (P<0.0001) as compared to the response elicited by Ovax.

These experiments show that a yeast-based immunotherapy composition expressing mycobacterial iron accumulation antigens can elicit a robust, antigen-specific, IFN-γ immune response after only two immunizations.

Example 3

The following example describes additional experiments to evaluate yeast-based TB immunotherapy compositions of the invention.

In this experiment, the panel of recombinant yeast expressing TB antigens as described in Example 1 above, in addition to a yeast-based immunotherapy compositions expressing Ag85B, TB10.4, and/or fusions of TB proteins or immunogenic domains thereof (e.g., Ag85B-ESAT6-TB10.4), or yeast-based immunotherapy compositions expressing other antigens as described in Example 4 (produced as described for the other yeast-based immunotherapy compositions described herein), are further optimized for growth and antigen expression. Those candidate immunotherapeutics meeting pre-defined growth and antigen expression criteria are selected for immunological evaluation. Growth rate and antigen expression within the strains are optimized using a variety of promoters, media, and transcriptional induction methods. Second, the yeast vaccine candidates are tested in established in vivo and in vitro correlative assays in mice to demonstrate specificity, potency and potential efficacy, such as the assays used in Example 2. Assays for adaptive, antigen-specific immune responses to the above yeast strains are conducted in mice using classical in vivo and ex vivo tests, as described by previously (Stubbs et al, supra 2001; Lu et al, Cancer Res 64, 5084-8 (2004); Haller et al, Vaccine 25, 1452-63 (2007), Tamburini et al, J. Immunotherapy 35:14-22 (2012)) including: 1) tumor protection, 2) CTL assay, 3) lymphocyte proliferation assay (LPA) and; 4) Th17 stimulation. Tests 1-3 are designed to probe for CD4+ and CD8+ T cell mediated activities that are directed against the TB antigens in the yeast vaccines, while test 4 will indicate the capacity of the TB immunotherapeutics to modulate Treg activity in vaccinated animals. These experiments identify the most immunogenic TB yeast-based immunotherapy products for later testing in Mtb challenge experiments (see additional Examples).

Example 4

The following example describes the production of several additional yeast-based immunotherapeutic compositions for the treatment or prevention of TB infection, including yeast expressing one or more hypoxia pool antigens, yeast expressing TLR agonist antigens, yeast expressing another TB antigen, and yeast expressing combinations of a variety of TB antigens.

In the following experiment, yeast (e.g., *Saccharomyces cerevisiae*) were engineered to express a fusion protein comprising an antigen from the TB hypoxia pool Rv1738 protein, under the control of the copper-inducible promoter, CUP1. The TB antigen was a single polypeptide of approximately 94 amino acids represented by SEQ ID NO:19. The fusion protein comprising SEQ ID NO:19 and expressed by the yeast was a single polypeptide, with the following sequence elements fused in frame from N- to C-terminus, represented by SEQ ID NO:21: 1) the amino acid sequence of the N-terminal peptide of SEQ ID NO:1 (positions 1-6 of SEQ ID NO:21); 2) a two amino acid linker sequence of Thr-Ser (positions 7-8 of SEQ ID NO:21); 3) the amino acid sequence of the Rv1738 antigen of positions 2-94 of SEQ ID NO:19 (positions 9-101 of SEQ ID NO:21); and 4) a hexahistidine tag (positions 102-107 of SEQ ID NO:21). The fusion protein represented by SEQ ID NO:21 is encoded by a recombinant nucleic acid molecule for insertion into a vector that has the nucleic acid sequence of SEQ ID NO:20.

In another experiment, yeast (e.g., *Saccharomyces cerevisiae*) were engineered to express a fusion protein comprising an antigen from the TB hypoxia pool Rv2032 protein, under the control of the copper-inducible promoter, CUP1. The TB antigen was a single polypeptide of approximately 331 amino acids represented by SEQ ID NO:22. SEQ ID NO:22 contains an inactivating mutation, which is a substitution of an arginine for the alanine that occurs in the native Rv2032 sequence, which is at position 13 of SEQ ID NO:22. The fusion protein comprising SEQ ID NO:22 and expressed by the yeast was a single polypeptide, with the following sequence elements fused in frame from N- to C-terminus, represented by SEQ ID NO:24: 1) the amino acid sequence of the N-terminal peptide of SEQ ID NO:1 (positions 1-6 of SEQ ID NO:24); 2) a two amino acid linker sequence of Thr-Ser (positions 7-8 of SEQ ID NO:24); 3) the amino acid sequence of the Rv2032 antigen of positions 2-331 of SEQ ID NO:22 (positions 9-338 of SEQ ID NO:24); and 4) a hexahistidine tag (positions 339-344 of SEQ ID NO:24). SEQ ID NO:24 contains an inactivating mutation, which is a substitution of an arginine for the alanine that occurs in the native Rv2032 sequence, which is at position 21 of SEQ ID NO:24. The fusion protein represented by SEQ ID NO:24 is encoded by a recombinant nucleic acid molecule for insertion into a vector that has the nucleic acid sequence of SEQ ID NO:23.

In another experiment, yeast (e.g., *Saccharomyces cerevisiae*) were engineered to express a fusion protein comprising an antigen from the TB hypoxia pool Rv3130 protein, under the control of the copper-inducible promoter, CUP1. The TB antigen was a single polypeptide of approximately 463 amino acids represented by SEQ ID NO:25. The fusion protein comprising SEQ ID NO:25 and expressed by the yeast was a single polypeptide, with the following sequence elements fused in frame from N- to C-terminus, represented by SEQ ID NO:27: 1) the amino acid sequence of the N-terminal peptide of SEQ ID NO:1 (positions 1-6 of SEQ ID NO:27); 2) a two amino acid linker sequence of Thr-Ser (positions 7-8 of SEQ ID NO:27); 3) the amino acid sequence of the Rv3130 antigen of positions 2-463 of SEQ ID NO:25 (positions 9-470 of SEQ ID NO:27); and 4) a hexahistidine tag (positions 471-476 of SEQ ID NO:27). The fusion protein represented by SEQ ID NO:27 is encoded by a recombinant nucleic acid molecule for insertion into a vector that has the nucleic acid sequence of SEQ ID NO:26.

In another experiment, yeast (e.g., *Saccharomyces cerevisiae*) were engineered to express a fusion protein comprising an antigen from the TB hypoxia pool Rv3841 protein, under the control of the copper-inducible promoter, CUP1. The TB antigen was a single polypeptide of approximately 181 amino acids represented by SEQ ID NO:28. SEQ ID NO:28 includes a four amino acid inactivating deletion of the ERNH sequence, which sequence would have otherwise occurred between positions 53 and 54 with respect to SEQ ID NO:28. The fusion protein comprising SEQ ID NO:28 and expressed by the yeast was a single polypeptide, with the following sequence elements fused in frame from N- to C-terminus, represented by SEQ ID NO:30: 1) the amino acid sequence of the N-terminal peptide of SEQ ID NO:1 (positions 1-6 of SEQ ID NO:30); 2) a two amino acid linker sequence of Thr-Ser (positions 7-8 of SEQ ID NO:30); 3) the amino acid sequence of the Rv3841 antigen of positions 2-181 of SEQ ID NO:28 (positions 9-183 of SEQ ID NO:30); and 4) a hexahistidine tag (positions 184-189 of SEQ ID NO:30). SEQ ID NO:30 includes a four amino acid deletion of the ERNH sequence, which sequence would have otherwise occurred between positions 61 and 62 with respect to SEQ ID NO:30. The fusion protein represented by SEQ ID NO:30 is encoded by a recombinant nucleic acid molecule for insertion into a vector that has the nucleic acid sequence of SEQ ID NO:29.

In another experiment, yeast (e.g., *Saccharomyces cerevisiae*) were engineered to express a fusion protein comprising four different hypoxia pool TB antigens, under the control of the copper-inducible promoter, CUP1. The TB antigens in this protein form a single polypeptide comprising a TB antigen from Rv1738, a TB antigen from Rv2032, a TB antigen from Rv3130, and a TB antigen from Rv3841, having the amino acid sequence of SEQ ID NO:31. The fusion protein comprising SEQ ID NO:31 and expressed by the yeast was a single polypeptide, with the following sequence elements fused in frame from N- to C-terminus, represented by SEQ ID NO:33: 1) the amino acid sequence of the N-terminal peptide of SEQ ID NO:1 (positions 1-6 of SEQ ID NO:33); 2) a two amino acid linker sequence of Thr-Ser (positions 7-8 of SEQ ID NO:33); 3) the amino acid sequence of the Rv1738 antigen of positions 2-94 of SEQ ID NO:19 (positions 9-101 of SEQ ID NO:33); 4) the amino acid sequence of the Rv2032 antigen of positions 2-331 of SEQ ID NO:22 (positions 102-431 of SEQ ID NO:33); 5) the amino acid sequence of the Rv3130 antigen of positions 2-463 of SEQ ID NO:25 (positions 432-893 of SEQ ID NO:33); 6) the amino acid sequence of the Rv3841 antigen of positions 2-181 of SEQ ID NO:28 (positions 894-1068 of SEQ ID NO:33); and 7) a hexahistidine tag (positions 1069-1074 of SEQ ID NO:33). The deactivating mutations described above for each of the Rv2032 antigen (SEQ ID NO:22) and the Rv3841 antigen (SEQ ID NO:28) are also included in this fusion protein. The fusion protein represented by SEQ ID NO:33 is encoded by a recombinant nucleic acid molecule for insertion into a vector that has the nucleic acid sequence of SEQ ID NO:32. The combination of the TB antigens in the amino acid sequence represented by SEQ ID NO:31 or SEQ ID NO:33 can also be referred to herein as the "hypoxia 4-gene fusion".

In another experiment, yeast (e.g., *Saccharomyces cerevisiae*) were engineered to express a fusion protein comprising two different hypoxia pool TB antigens, under the control of the copper-inducible promoter, CUP1. The TB antigens in this protein form a single polypeptide comprising a TB antigen from Rv2032 and a TB antigen from Rv3841, having the amino acid sequence of SEQ ID NO:34. The fusion protein comprising SEQ ID NO:34 and expressed by the yeast was a single polypeptide, with the following sequence elements fused in frame from N- to C-terminus, represented by SEQ ID NO:36: 1) the amino acid sequence of the N-terminal peptide of SEQ ID NO:1 (positions 1-6 of SEQ ID NO:36); 2) a two amino acid linker sequence of Thr-Ser (positions 7-8 of SEQ ID NO:36); 3) the amino acid sequence of the Rv2032 antigen of positions 2-331 of SEQ ID NO:22 (positions 9-338 of SEQ ID NO:36); 4) the amino acid sequence of the Rv3841 antigen of positions 2-181 of SEQ ID NO:28 (positions 339-513 of SEQ ID NO:36); and 5) a hexahistidine tag (positions 514-519 of SEQ ID NO:36). The deactivating mutations described above for each of the Rv2032 antigen (SEQ ID NO:22) and the Rv3841 antigen (SEQ ID NO:28) are also included in this fusion protein. The fusion protein represented by SEQ ID NO:36 is encoded by a recombinant nucleic acid molecule for insertion into a vector that has the nucleic acid sequence of SEQ ID NO:35.

In the following experiment, yeast (e.g., *Saccharomyces cerevisiae*) were engineered to express a fusion protein comprising an antigen from the TB Ag85a protein, under the control of the copper-inducible promoter, CUP1. The TB antigen was a single polypeptide of approximately 337 amino acids represented by SEQ ID NO:37. The fusion protein comprising SEQ ID NO:37 and expressed by the yeast was a single polypeptide, with the following sequence elements fused in frame from N- to C-terminus, represented by SEQ ID NO:39: 1) the amino acid sequence of the N-terminal peptide of SEQ ID NO:1 (positions 1-6 of SEQ ID NO:39); 2) a two amino acid linker sequence of Thr-Ser (positions 7-8 of SEQ ID NO:39); 3) the amino acid sequence of the Ag85a antigen of SEQ ID NO:37 (positions 9-345 of SEQ ID NO:39); and 4) a hexahistidine tag (positions 346-351 of SEQ ID NO:39). The fusion protein represented by SEQ ID NO:39 is encoded by a recombinant nucleic acid molecule for insertion into a vector that has the nucleic acid sequence of SEQ ID NO:38.

In another experiment, yeast (e.g., *Saccharomyces cerevisiae*) were engineered to express a fusion protein comprising an antigen from the TB TLR agonist Rv1411c protein, under the control of the copper-inducible promoter, CUP1. The TB antigen was a single polypeptide of approximately 236 amino acids represented by SEQ ID NO:40. The amino acid sequence of SEQ ID NO:40 contains the inactivating mutation of a valine to a tryptophan corresponding to position 91 (V91W) in the native protein (also occurring at position 91 with respect to SEQ ID NO:40). The fusion protein comprising SEQ ID NO:40 and expressed by the yeast was a single polypeptide, with the following sequence elements fused in frame from N- to C-terminus, represented by SEQ ID NO:42: 1) the amino acid sequence of the N-terminal peptide of SEQ ID NO:1 (positions 1-6 of SEQ ID NO:42); 2) a two amino acid linker sequence of Thr-Ser (positions 7-8 of SEQ ID NO:42); 3) the amino acid sequence of the Rv1411c antigen of SEQ ID NO:40 (positions 9-244 of SEQ ID NO:42); and 4) a hexahistidine tag (positions 245-250 of SEQ ID NO:42). The fusion protein represented by SEQ ID NO:42 is encoded by a recombinant nucleic acid molecule for insertion into a vector that has the nucleic acid sequence of SEQ ID NO:41.

In another experiment, yeast (e.g., *Saccharomyces cerevisiae*) were engineered to express a fusion protein comprising three different TB antigens, under the control of the copper-inducible promoter, CUP1. The TB antigens in this protein form a single polypeptide comprising a TB hypoxia pool antigen from Rv2032, a TB TLR agonist protein from Rv1411c, and a TB iron accumulation antigen from Rv2359, having the amino acid sequence of SEQ ID NO:43. The fusion protein comprising SEQ ID NO:43 and expressed by the yeast was a single polypeptide, with the following sequence elements fused in frame from N- to C-terminus, represented by SEQ ID NO:45: 1) the amino acid sequence of the N-terminal peptide of SEQ ID NO:1 (positions 1-6 of SEQ ID NO:45); 2) a two amino acid linker sequence of Thr-Ser (positions 7-8 of SEQ ID NO:45); 3) the amino acid sequence of the Rv2032 antigen of positions 2-331 of SEQ ID NO:22 (positions 9-338 of SEQ ID NO:45); 4) the amino acid sequence of the Rv1411c antigen of SEQ ID NO:40 (positions 339-574 of SEQ ID NO:45); 5) the amino acid sequence of the Rv2359 protein of SEQ ID NO:4 (positions 575-703 of SEQ ID NO:45); and 6) a hexahistidine tag (positions 704-709 of SEQ ID NO:45). The deactivating mutations described above for each of the Rv2032 antigen (SEQ ID NO:22) and the Rv1411c antigen (SEQ ID NO:40) are also included in this fusion protein. The fusion protein represented by SEQ ID NO:45 is encoded by a recombinant nucleic acid molecule for insertion into a vector that has the nucleic acid sequence of SEQ ID NO:44.

To produce the various yeast immunotherapy compositions described above, briefly, DNA encoding the TB antigens was first codon optimized for expression in yeast, and then inserted behind the CUP1 promoter (pGI-100) in yeast 2 µm expression vectors. The resulting plasmids were introduced into *Saccharomyces cerevisiae* W303a yeast by Lithium acetate/polyethylene glycol transfection, and transfectants were selected on solid minimal plates lacking uracil and leucine (ULDM; uridine and leucine dropout medium), or lacking uracil (UDM). Liquid cultures lacking uridine and leucine (UL2 medium: 20 g/L glucose; 6.7 g/L of yeast nitrogen base containing ammonium sulfate; and 0.04 mg/mL each of histidine, tryptophan, and adenine), or lacking uracil (UDM; same as UL2 but containing 0.06 mg/mL leucine), were inoculated from ULDM and UDM plates, respectively, and starter cultures were grown for 20h at 30° C. (250 rpm). Primary cultures were used to inoculate final cultures of the same formulation for all cultures and growth was continued until a density or 1.1 to 4.0 YU/mL was reached. Cultures were induced with 500 µM copper sulfate at a starting density of 1-4 YU/ml for 4 hours at 30° C. The cells from each culture were then harvested, PBS-washed and heat-killed at 56° C. for 1 hour in PBS.

After heat-kill of the cultures, the cells were thrice washed in PBS and total protein was isolated by glass bead rupture followed by boiling in SDS lysis buffer. Quantification of total protein was done by Pierce 660 nm protein assay, and TB antigen content was measured by Western blot using an anti-His tag monoclonal antibody probe followed by interpolation to a His-tagged HCV NS3 protein standard curve.

Figure 5:
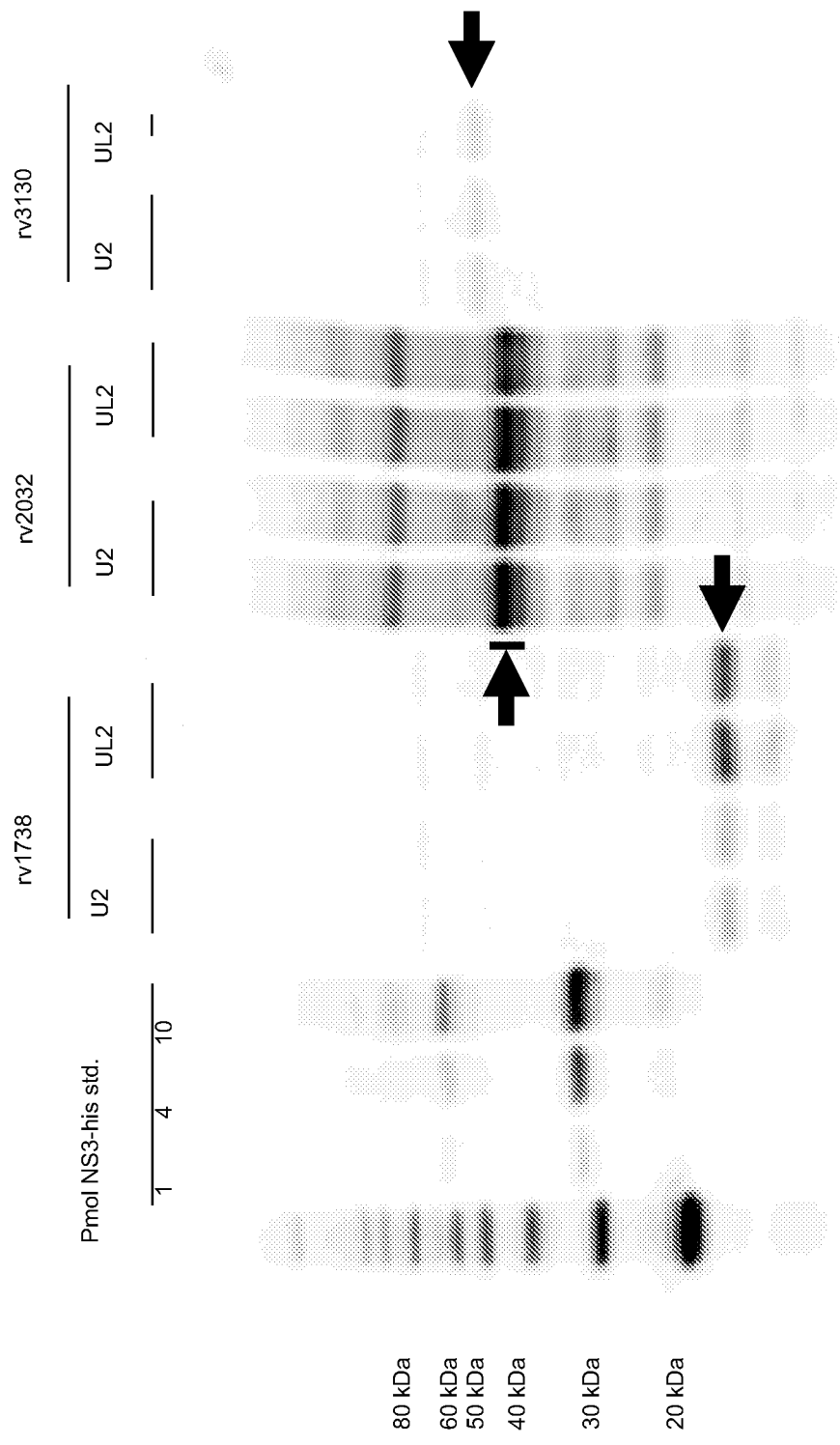
FIG. 5 is a digitized image of a Western blot showing the expression of three different TB antigens in yeast-based immunotherapy compositions in U2 and UL2 media (rv1738=fusion protein represented by SEQ ID NO:21; rv2032=fusion protein represented by SEQ ID NO:24; rv3130=fusion protein represented by SEQ ID NO:27). Arrows indicate bands showing antigen expression. Pmol NS3-his std.=molecular weight standard.

Results showing the expression in both U2 and UL2 media of three of the hypoxia pool antigens by yeast are shown in FIG. 5. FIG. 5 shows copper inducible expression (see arrows) of the yeast expressing the fusion protein comprising the Rv1738 antigen (SEQ ID NO:22; denoted in FIG. 5 as "rv1738"), the yeast expressing the fusion protein comprising the Rv2032 antigen (SEQ ID NO:24; denoted in FIG. 5 as "rv2032"), and the yeast expressing the fusion protein comprising the Rv3130 antigen (SEQ ID NO:27; denoted in FIG. 5 as "rv3130"). FIG. 5 shows that each of the TB yeast-based immunotherapy compositions expressing a hypoxia pool antigen of the invention expresses the TB protein, and can be identified by Western blot. The rv2032 protein is running at a slightly higher molecular weight than expected in this experiment, but this sometimes occurs as primary sequence can influence SDS binding and migration rate in SDS-PAGE gels.

Figure 6:
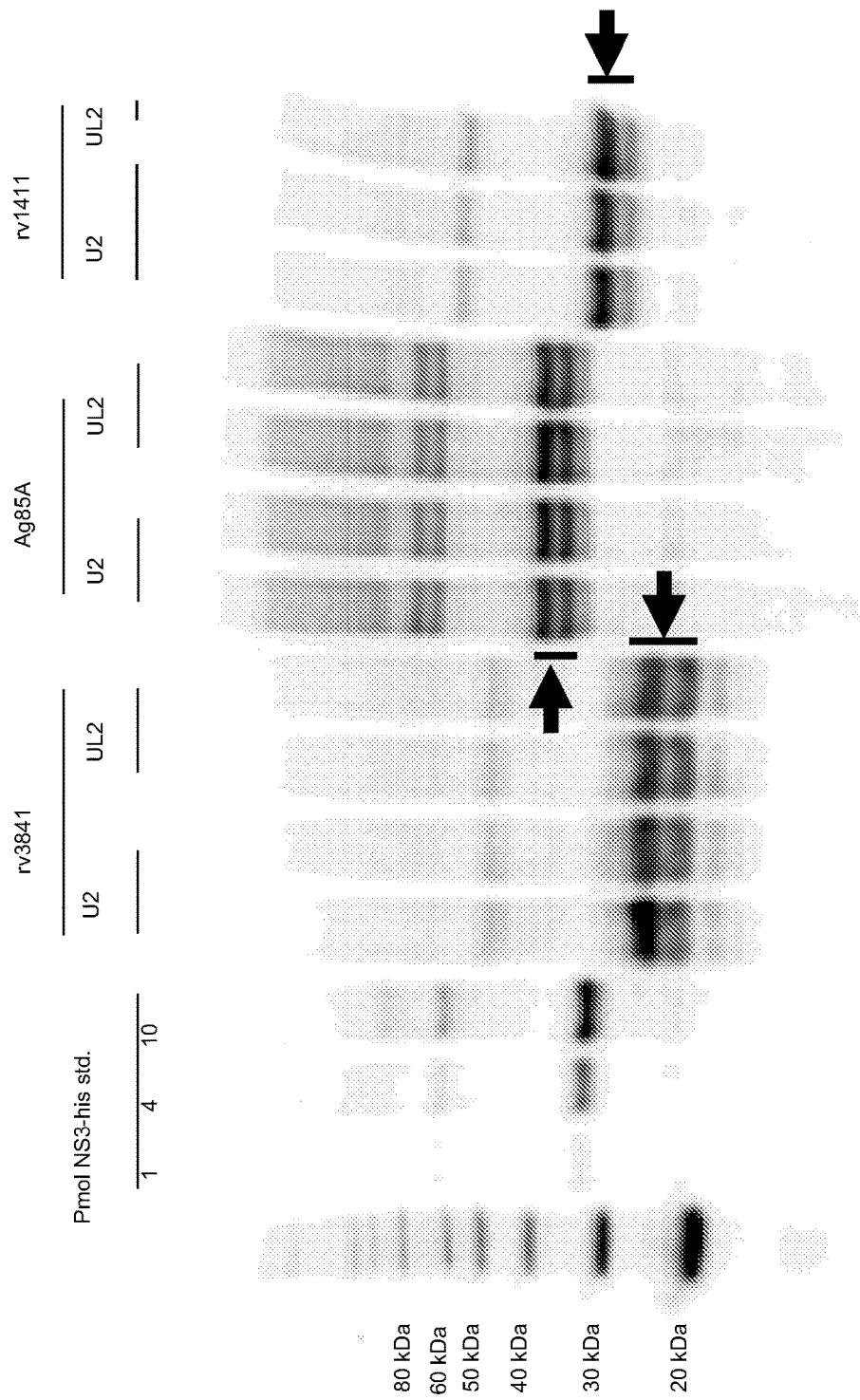
FIG. 6 is a digitized image of a Western blot showing the expression of three different TB antigens in yeast-based immunotherapy compositions in U2 and UL2 media (rv3841=fusion protein represented by SEQ ID NO:30; Ag85A=fusion protein represented by SEQ ID NO:39; rv1411=fusion protein represented by SEQ ID NO:42). Arrows indicate bands showing antigen expression. Pmol NS3-his std.=molecular weight standard used for antigen quantification: HCV NS3 protease fused to a hexahistidine epitope tag.

Results showing the expression in both U2 and UL2 media of TB proteins Rv3841, Ag85A and 1411c are shown in FIG. 6. FIG. 6 shows copper inducible expression (see arrows) of the yeast expressing the fusion protein comprising the TB hypoxia pool Rv3841 antigen (SEQ ID NO:30; denoted in FIG. 6 as "rv3841"), the yeast expressing the fusion protein comprising the Ag85A antigen (SEQ ID NO:39; denoted in FIG. 6 as "Ag85A"), and the yeast expressing the fusion protein comprising the TB TLR agonist Rv1411c antigen (SEQ ID NO:42; denoted in FIG. 6 as "rv1411"). FIG. 6 shows that each of the TB yeast-based immunotherapy compositions expressing a TB antigen of the invention expresses the protein, and can be identified by Western blot.

Figure 7:
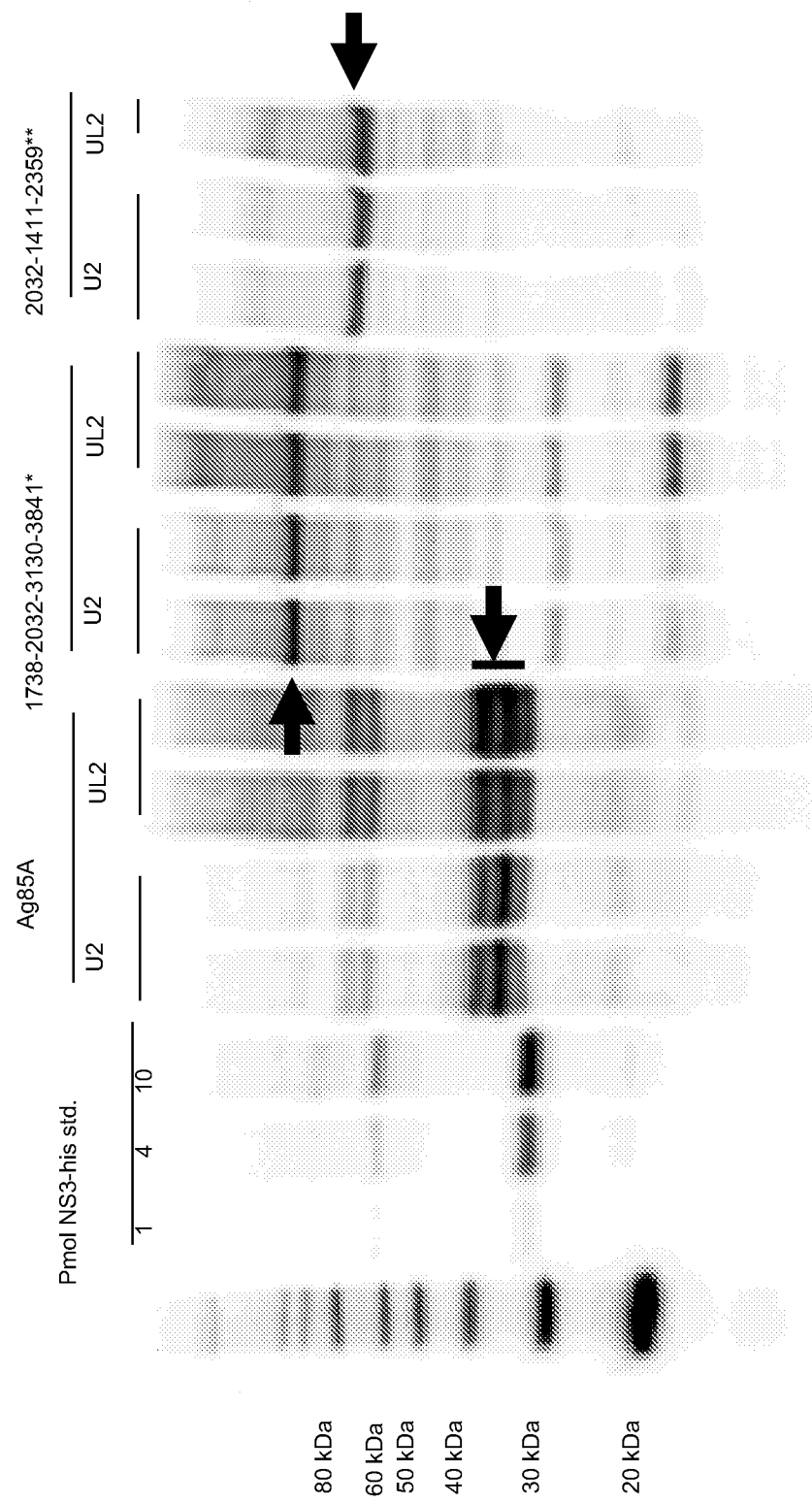
FIG. 7 is a digitized image of a Western blot showing the expression of three different TB antigens in yeast-based immunotherapy compositions in U2 and UL2 media (Ag85A=fusion protein represented by SEQ ID NO:39; 1738-2032-3130-3841*=fusion protein represented by SEQ ID NO:33; 2032-1411-2359**=fusion protein represented by SEQ ID NO:45). Arrows indicate bands showing antigen expression. Pmol NS3-his std.=molecular weight standard.

FIG. 7 shows the expression in both U2 and UL2 media of the TB protein Ag85A, the hypoxia 4-gene fusion (Rv1738-Rv2032-Rv3130-Rv3841), and the hypoxia-TLR-iron fusion (Rv2032-Rv1411c-Rv2359). Specifically FIG. 7 shows copper inducible expression (see arrows) of the yeast expressing the fusion protein comprising the TB antigen Ag85A (SEQ ID NO:39; denoted in FIG. 7 as "Ag85A"), the yeast expressing the "hypoxia 4-gene fusion" protein (SEQ ID NO:33; denoted in FIG. 7 as "1738-2032-3130-3841*"), and the yeast expressing the fusion protein comprising the a hypoxia pool antigen, the TB TLR agonist Rv1411c antigen and a TB iron accumulation antigen (SEQ ID NO:45; denoted in FIG. 7 as "2032-1411-2359**"). FIG. 7 shows that each of the TB yeast-based immunotherapy compositions expressing a TB antigen of the invention expresses the protein, and can be identified by Western blot. This experiment shows some proteolysis of the hypoxia 4-gene fusion, but the antigen expression is nevertheless robust.

Figure 8:
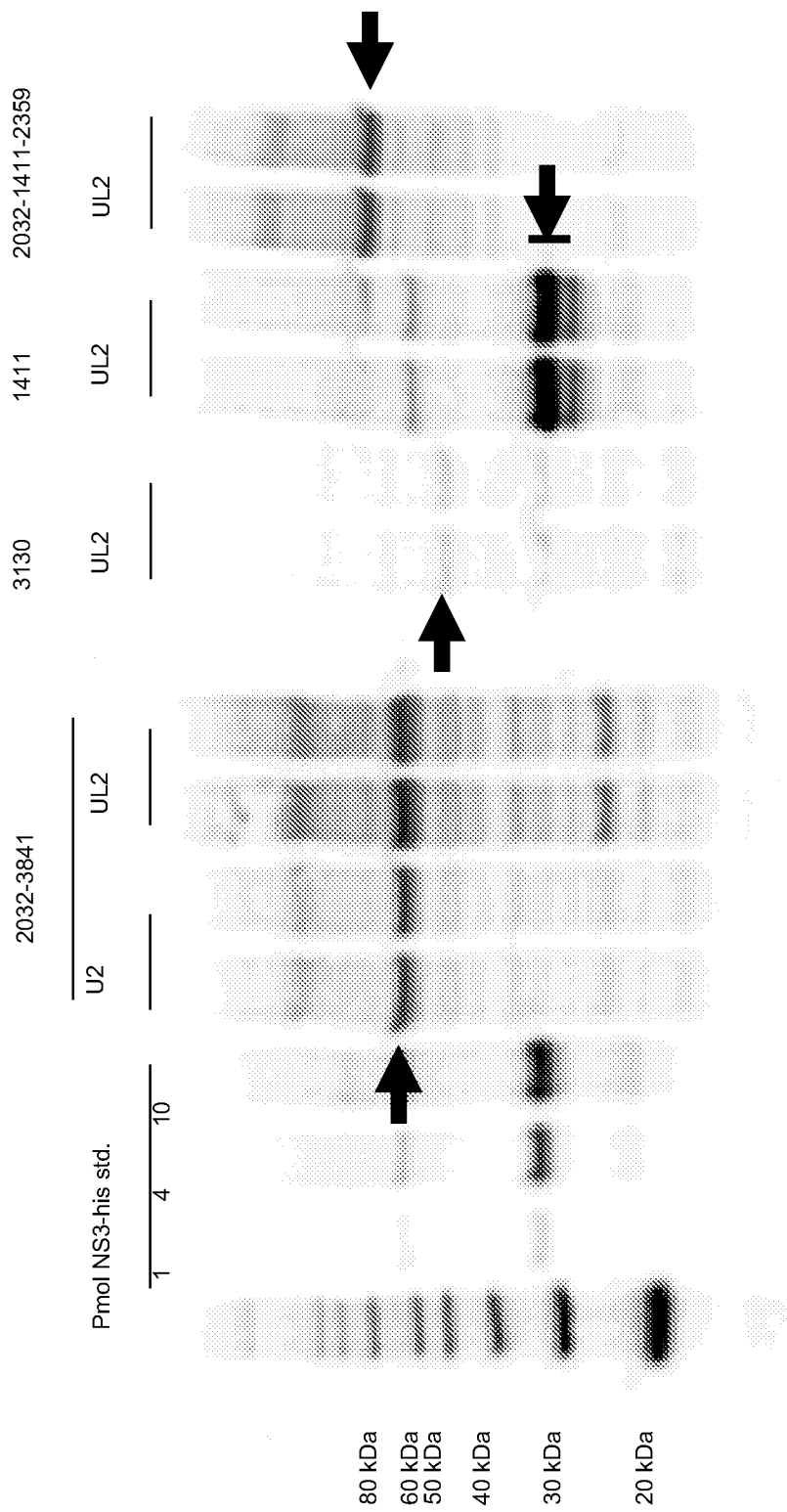
FIG. 8 is a digitized image of a Western blot showing the expression of four different TB antigens in yeast-based immunotherapy compositions in U2 and UL2 media (2032-3841=fusion protein represented by SEQ ID NO:36; 3130=fusion protein represented by SEQ ID NO:27; 1411=fusion protein represented by SEQ ID NO:42; 2032-1411-2359=fusion protein represented by SEQ ID NO:45). Arrows indicate bands showing antigen expression. Pmol NS3-his std.=molecular weight standard.

FIG. 8 shows the expression in both U2 and UL2 media of the TB 2-gene fusion (Rv2032-Rv3841), the TB hypoxia pool antigen Rv3130, the TB TLR agonist Rv1411c, and the hypoxia-TLR-iron fusion (Rv2032-Rv1411c-Rv2359). Specifically FIG. 8 shows copper inducible expression (see arrows) of the yeast expressing the fusion protein comprising hypoxia pool antigens Rv2032 and Rv3841 (SEQ ID NO:36; denoted in FIG. 8 as "2032-3841"), the yeast expressing the Rv3130 protein (SEQ ID NO:27; denoted in FIG. 8 as "3130"), the yeast expressing the Rv1411c protein (SEQ ID NO:42; denoted in FIG. 8 as "1411"), and the yeast expressing the fusion protein comprising the a hypoxia pool antigen, the TB TLR agonist Rv1411c antigen and a TB iron accumulation antigen (SEQ ID NO:45; denoted in FIG. 8 as "2032-1411-2359"). FIG. 8 shows that each of the TB yeast-based immunotherapy compositions expressing a TB antigen of the invention expresses the protein, and can be identified by Western blot.

Figure 9:
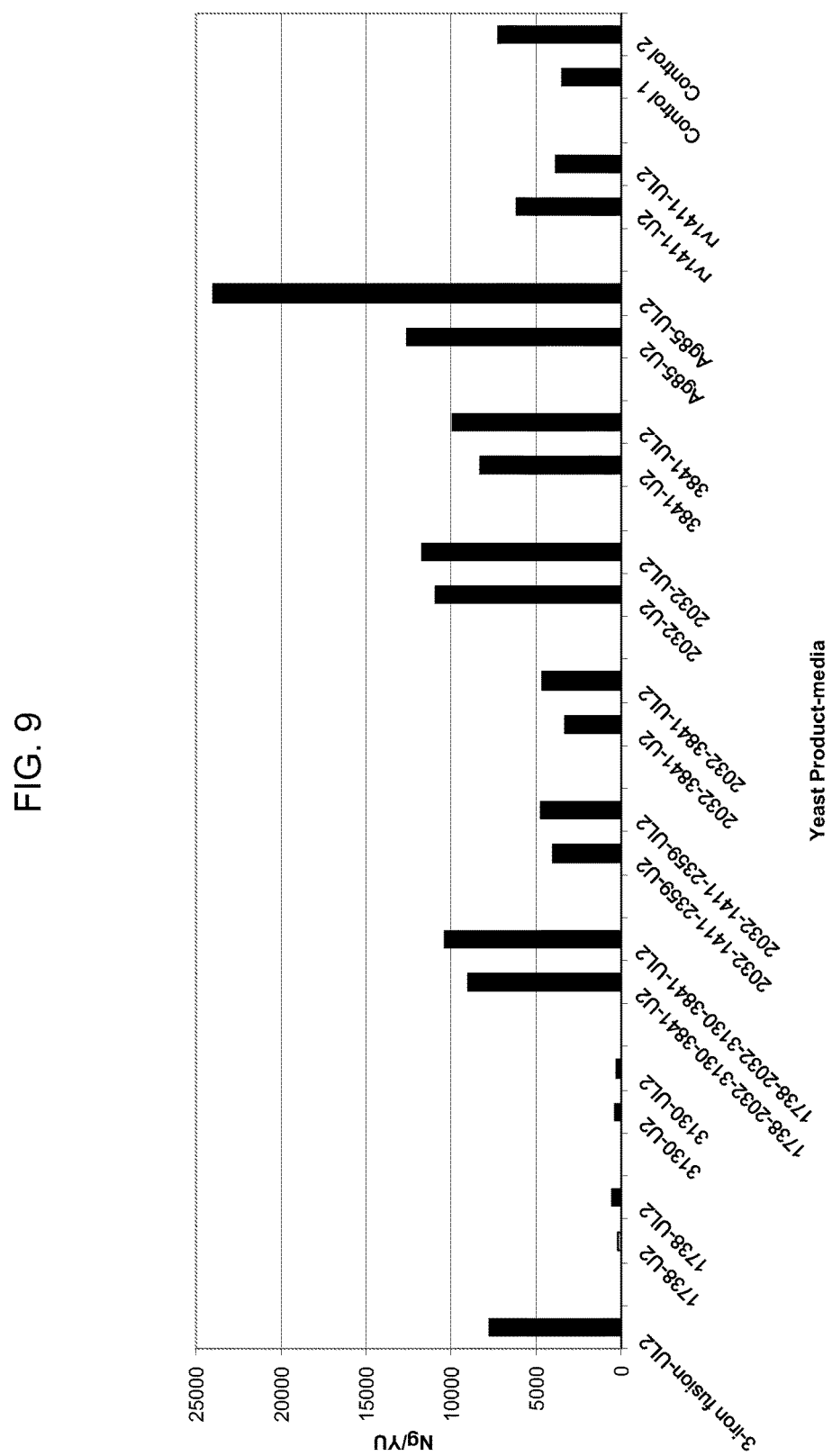
FIG. 9 is a bar graph showing the nanograms (Ng) of expressed TB antigen per Yeast Unit (YU; one YU=$10^7$ yeast cells) for multiple different yeast-based immunotherapy compositions. The fusion proteins represented are: (1) 3-iron fusion represented by SEQ ID NO:15 in UL2 medium (3-iron fusion-UL2); (2) Rv1738 represented by SEQ ID NO:21 in U2 medium (1738-U2); (3) Rv1738 represented by SEQ ID NO:21 in UL2 medium (1738-UL2); (4) Rv3130 represented by SEQ ID NO:27 in U2 medium (3130-U2); (5) Rv3130 represented by SEQ ID NO:27 in UL2 medium (3130-UL2); (6) Rv1738-Rv2032-Rv3130-Rv3841 represented by SEQ ID NO:33 in U2 medium (1738-2032-3130-3841-U2); (7) Rv1738-Rv2032-Rv3130-Rv3841 represented by SEQ ID NO:33 in UL2 medium (1738-2032-3130-3841-UL2); (8) Rv2032-Rv1411-Rv2359 represented by SEQ ID NO:45 in U2 medium (2032-1411-2359-U2); (9) Rv2032-Rv1411-Rv2359 represented by SEQ ID NO:45 in UL2 medium (2032-1411-2359-UL2); (10) Rv2032-Rv3841 represented by SEQ ID NO:36 in U2 medium (2032-3841-U2); (11) Rv2032-Rv3841 represented by SEQ ID NO:36 in UL2 medium (2032-3841-UL2); (12) Rv2032 represented by SEQ ID NO:24 in U2 medium (2032-U2); (13) Rv2032 represented by SEQ ID NO:24 in UL2 medium (2032-UL2); (14) Rv3841 represented by SEQ ID NO:30 in U2 medium (3841-U2); (15) Rv3841 represented by SEQ ID NO:30 in UL2 medium (3841-UL2); (16) Ag85A represented by SEQ ID NO:39 in U2 medium (A85-U2); (17) Ag85A represented by SEQ ID NO:39 in UL2 medium (A85-UL2); (18) Rv1411c represented by SEQ ID NO:42 in U2 medium (1411-U2); (19) Rv1411c represented by SEQ ID NO:42 in UL2 medium (1411-UL2); (20) Control 1 (HCV antigen fusion protein control); and (21) (Cancer antigen fusion protein control).

FIG. 9 is a graph illustrating the expression of various of the fusion proteins described above in Ng/YU; 1 YU=$10^7$ yeast cells). The fusion proteins represented in FIG. 9 are: (1) 3-iron fusion represented by SEQ ID NO:15 in UL2 medium (3-iron fusion-UL2); (2) Rv1738 represented by SEQ ID NO:21 in U2 medium (1738-U2); (3) Rv1738 represented by SEQ ID NO:21 in UL2 medium (1738-UL2); (4) Rv3130 represented by SEQ ID NO:27 in U2 medium (3130-U2); (5) Rv3130 represented by SEQ ID NO:27 in UL2 medium (3130-UL2); (6) Rv1738-Rv2032-Rv3130-Rv3841 represented by SEQ ID NO:33 in U2 medium (1738-2032-3130-3841-U2); (7) Rv1738-Rv2032-Rv3130-Rv3841 represented by SEQ ID NO:33 in UL2 medium (1738-2032-3130-3841-UL2); (8) Rv2032-Rv1411-Rv2359 represented by SEQ ID NO:45 in U2 medium (2032-1411-2359-U2); (9) Rv2032-Rv1411-Rv2359 represented by SEQ ID NO:45 in UL2 medium (2032-1411-2359-UL2); (10) Rv2032-Rv3841 represented by SEQ ID NO:36 in U2 medium (2032-3841-U2); (11) Rv2032-Rv3841 represented by SEQ ID NO:36 in UL2 medium (2032-3841-UL2); (12) Rv2032 represented by SEQ ID NO:24 in U2 medium (2032-U2); (13) Rv2032 represented by SEQ ID NO:24 in UL2 medium (2032-UL2); (14) Rv3841 represented by SEQ ID NO:30 in U2 medium (3841-U2); (15) Rv3841 represented by SEQ ID NO:30 in UL2 medium (3841-UL2); (16) Ag85A represented by SEQ ID NO:39 in U2 medium (A85-U2); (17) Ag85A represented by SEQ ID NO:39 in UL2 medium (A85-UL2); (18) Rv1411c represented by SEQ ID NO:42 in U2 medium (1411-U2); (19) Rv1411c represented by SEQ ID NO:42 in UL2 medium (1411-UL2); (20) Control 1 (HCV antigen fusion protein control); and (21) (Cancer antigen fusion protein control).

In summary, these experiments show that all of the TB fusion proteins were successfully expressed in yeast, some with exceptionally high levels of antigen expression as compared to yeast-based immunotherapy products produced and selected in other pre-clinical research programs. The fusion proteins comprising two or more TB antigens are attractive candidates for preclinical products due to their strong antigen expression in yeast combined with the broad TB sequence representation in a single product.

In another experiment, yeast (e.g., *Saccharomyces cerevisiae*) are engineered to express a fusion protein comprising three different TB antigens, under the control of the copper-inducible promoter, CUP1. The TB antigens in this protein form a single polypeptide comprising one hypoxia pool TB antigen (Rv2032), one TLR agonist protein (Rv1411c) and one iron accumulation antigen (Rv2711), fused to form a single fusion protein, under the control of the copper-inducible promoter, CUP1, the TB antigen fusion protein having the amino acid sequence of SEQ ID NO:46. The fusion protein comprising SEQ ID NO:46 and expressed by the yeast is a single polypeptide, with the following sequence elements fused in frame from N- to C-terminus, represented by SEQ ID NO:48: 1) the amino acid sequence of the N-terminal peptide of SEQ ID NO:1 (positions 1-6 of SEQ ID NO:48); 2) a two amino acid linker sequence of Thr-Ser (positions 7-8 of SEQ ID NO:48); 3) the amino acid sequence of the Rv2032 antigen of positions 2-331 of SEQ ID NO:22 (positions 9-338 of SEQ ID NO:48); 4) the amino acid sequence of the Rv1411c antigen of SEQ ID NO:40 (positions 339-574 of SEQ ID NO:48); 5) the amino acid sequence of the Rv2711 protein of SEQ ID NO:7 (positions 575-803 of SEQ ID NO:48); and 6) a hexahistidine tag (positions 804-809 of SEQ ID NO:48). The deactivating mutations described above for each of the Rv2032 antigen (SEQ ID NO:22) and the Rv1411c antigen (SEQ ID NO:40) are also included in this fusion protein. The fusion protein represented by SEQ ID NO:48 is encoded by a recombinant nucleic acid molecule for insertion into a vector that has the nucleic acid sequence of SEQ ID NO:47.

Example 5

The following example describes testing of yeast-based immunotherapeutics for TB for efficacy in an animal model challenged with strains of highly virulent TB.

In this experiment, the yeast-based immunotherapeutics selected in Examples 2, 3 and/or 4 above are used to test for efficacy in a murine TB challenge model. Mice will be immunized with yeast-based TB immunotherapy compositions and then challenged with two different strains of highly virulent TB, as follows:

Part 1:

Initially, at least two different immunization schemes are used, one that functions well with the benchmark BCG approach and one, used in clinical studies of other yeast-based immunotherapeutics (GlobeImmune, Inc., Louisville, Colo.), to optimally enhance the Th1/Th17 axis. Scheme 1: mice are immunized with yeast subcutaneously (s.c.) at two or more sites (dose determined in Example 3) three times, one month apart, rested for 10-weeks, challenged, then assayed on days 30, 60, and 90 thereafter; or Scheme 2: mice are immunized s.c. weekly for one month, monthly thereafter and assayed on days 30, 60 and 90 after the second monthly immunization.

Mice.

Specific-pathogen-free female, 6- to 8-week-old C57BL/6 mice are purchased from the Jackson Laboratories, Bar Harbor, Me. The mice are maintained in the biosafety level-III biohazard facility at Colorado State University (CSU), and given sterile water and mouse chow ad libitum. All experimental protocols are to be approved by the Animal Care and Use Committee of Colorado State University. Animals are vaccinated s.c. with indicated vaccine candidates (i.e., the selected yeast-based immunotherapeutics) prior to aerosol challenge. Control mice are injected with diluent only. Mice are then challenged by low-dose aerosol exposure to *M. tuberculosis* using a Glas-Col exposure device (Terre Haute, Ind.) calibrated to deliver 50-100 bacteria into the lungs of each mouse. The clinical W-Beijing strain HN878 was kindly provided by Dr B. Kreiswirth (Public Health Research Institute, New Jersey), and the W-Beijing strain SA161 was kindly provided by Dr K. Eisenach (University of Arkansas). Bacterial burden in the lungs of infected animals (n=5) at indicated time points is determined by plating serial dilutions of whole organ homogenates on nutrient 7H11 agar and counting colony-forming units after 3 weeks incubation at 37° C. in humidified air. For histology, cranial lung lobes from each mouse is harvested and fixed with 4% paraformaldehyde in phosphate buffered saline (PBS). Sections are prepared and stained using haematoxylin and eosin (H & E).

Yeast induce IL-6 (Cereda et al, *Vaccine* (2011)), a major factor in the generation of Th17 and modulation of CD8+ T cell activation. Experimental evidence generated previously (data not shown here) indicates that increasing the yeast administered, either by increasing the dose or decreasing the interval between immunizations, can increase Th17 activity. As scheme 2 is more likely to lead to increased Th17 activity versus scheme 1, efficacy is followed to determine if it is related to dosing. It is expected that vigorously engaging the Th17 pathway is of benefit and that immunization scheme 2 is therefore more efficacious. However, if a less dominant Th17 response provides more efficacy, then scheme 1 should perform better.

Part 2:

If partial protection occurs as a result of the experiments performed in Part 1 above, other modifications target an increase or decrease in Th17 frequencies associated with CD8+ T cell modulation to determine if the efficacy signal can be enhanced by "fine tuning" the critical yeast-induced Th17 CD4+ T cell pathway. One way to enhance Th17 activity is to increase the frequency of yeast immunization which increases the amount of IL-6, e.g., modulating scheme 2 further by immunizing weekly. In another experiment, animals are evaluated to determine whether decreasing Th17 activity modifies outcome. In this experiment, the animals are treated with an anti-IL-6 blocking antibody (R&D systems). It is expected that Th17 responses will be reduced and CD8+ responses enhanced using this protocol and therefore, it is determined how modulation of Th17 activity, either by increase or decrease, affects challenge outcomes.

Part 3:

In a third set of experiments, in order to assist with the interpretation of immunologic data regarding T cell subsets in animals both immunized with yeast-based immunotherapy and challenged with TB, a parallel group of animals where immune correlative data, as defined by the assays described above, are followed as a consequence of immunization only. These data on the evolution of the immune response are of value in selecting the immune studies most relevant to be performed in infected animals or animals infected that were subsequently cured. A major focus of these experiments identifies the immune phenotype of the yeast-induced response and correlates it with clinical outcome in infected animals, wherein it is expected that a Th17 response is important in overall efficacy.

Example 6

The following example describes testing yeast-based immunotherapeutics for efficacy in the more clinically relevant and sensitive guinea pig challenge model.

The guinea pig model has the advantage over mouse models of being more clinically relevant. To test for prophylactic activity, guinea pigs are vaccinated using information and guidance provided by the results of the experiments in mice in Example 5. Dosing is initiated at 20 million yeast s.c. as described in Example 5. In addition, in this experiment, a BCG prime is given to guinea pigs to determine whether BCG interferes with, enhances or has no effect on subsequent yeast immunization. These experiments are designed to model humans who have already been treated with BCG. Animals are vaccinated with BCG ($10^4$ bacilli/colony forming units s.c.), then ten weeks later vaccinated with yeast expressing TB antigens (e.g., any of the yeast-based TB immunotherapeutics from Examples 1 or 4, including GI-19004 or the yeast expressing hypoxia pool antigens).

Specific pathogen-free albino Hartley-strain guinea pigs (Charles River Breeding Laboratories, Inc., Wilmington, Mass.) are housed in the CSU ABL-III facility and provided commercial chow in stainless-steel feeders and tap water ad libitum. The guinea pigs are maintained in a temperature- and humidity-controlled environment and exposed to a 12-hour light/dark cycle. After approximately two weeks to acclimate, each guinea pig is weighed, implanted with a microchip, and then assigned into specific groups based on mean weights. Each animal is implanted with an individual glass-encapsulated transponder (IMI-1000; Bio Medic Data Systems, Inc., Rockville, Md.) each pre-programmed with its own 10-digit alphanumeric code and pre-loaded into its own sterile needle assembly. These are given s.c. into the scruff of the neck.

Low Dose Aerosol Challenge.

For each aerosol infection, a thawed aliquot of the particular strain of *M. tuberculosis* is diluted in sterile water up to a total volume of 20 ml ($10^6$ CFU/ml). Guinea pigs from each treatment group are aerosolized using a Madison infection chamber (University of Wisconsin Machine Shop, Madison, Wis.) with a starting volume of 15 ml of working stock (nebulization cycle: 5 min; cloud decay cycle: 10 min). The estimated retention of mycobacteria ranges from 25 and 30 CFU/guinea pig as determined (indirectly) by enumerating primary pulmonary lesions five weeks later post-infection, and which has been directly verified by magnetic resonance imaging analysis (Kraft et al, *Infect Immun* 72:5963-71 (2004)).

Animal Monitoring.

Following the aerosol infection, animals are observed daily and evaluated using a modified version of the Karnofsky scale for pain and distress. This includes any potential weight loss, mobility, breathing patterns, and peripheral cyanosis. Guinea pigs scoring a 6 (or more) are deemed moribund necessitating immediate euthanasia. Performing euthanasia allows analysis of lung tissues prior to any tissue autolysis. Guinea pigs are euthanized humanely via an overdose (1 ml per 0.25 kg body weight) of sodium pentobarbital (Sleepaway) via intraperitoneal injection.

Determination of the Bacterial Load in Target Organs.

For bacterial load determinations the abdominal and thoracic cavities are opened aseptically and the right lung, the draining hilar lymph node cluster, and the spleen from individual animals placed into vials filled with 20 ml of sterile saline. Individual tissue samples are homogenized separately using a handheld tissue homogenizer. Serial dilutions of tissue homogenates are then plated onto duplicate Middlebrook 7H11 agar plates and incubated at 37° C. for approximately 21 days. The number of viable colonies from the appropriate dilution quadrants (i.e., 20 CFU <optimal quadrant CFU count <200 CFU) from duplicate plates are averaged and expressed as $\log_{10}$ CFU per total right lung.

Immunopathology.

For histology, the left pulmonary lobes are infused in situ with 5 ml of 10% neutral-buffered formalin and then placed into 30 ml of fixative overnight. Specimens are separately embedded in paraffin, sectioned at 4 µm slices from equivalent areas of the left cranial lung lobe (i.e., along the left primary bronchus) and stained separately with H&E and by the Ziehl-Neelsen method for histologic and acid-fast evaluations, respectively. Additional stains used are Masson's trichrome (for fibrin) and Prussian blue (for iron deposition). A board-certified veterinary pathologist then performs a blinded review and scores sections according to the following parameters: % of lung affected, rank score, the number and associated severity of primary lesions and finally, the severity of secondary lesions (Basaraba, 2008).

It is expected that the highest efficacy will occur with the generation of a multi-subset immune response including CD8+ and Th1/Th17 CD4+ T cell subsets.

In an additional experiment evaluating post-exposure treatment, guinea pigs are infected, then ten days later, given the yeast-based immunotherapeutic product s.c. Some animals are also given 10-30 days co-treatment with TMC207 [15 mg/kg/day] by gentle gavage. Assays are performed 10, 30, and 60 days after vaccination.

Example 7

The following example describes the use of yeast-based immunotherapy for TB in the clinic.

MDR TB (defined as resistance to at least the front line drugs isoniazid and rifampin) and XDR TB (also resistant to fluoroquinolones, and at least one "injectable" such as capreomycin or amikacin) have likely emerged due to non-compliance with or ineffectiveness of current multi-agent regimens. Controlled clinical trials are initially conducted using a TB-yeast-based immunotherapy product identified as a result of the experiments performed in Examples 1-6, plus a multiple drug regimen in subjects with MDR and XDR TB, to get an early assessment of safety, immunogenicity, and therapeutic utility. Efficacy endpoints include mycobacterial clearance in sputum samples and time to complete response. Safety and immunology data also serve as a crucial basis for the potential use as a post-exposure prophylactic agent in a public emergency exposure scenario.

In addition to data from therapeutic trials in MDR and XDR TB, a clinical program to establish the safety and immunogenicity in healthy volunteers is conducted to support the implementation of a post-exposure vaccine program for the purpose of creating a vaccine stockpile that can be deployed to first responders and victims of an event involving MDR TB or XDR TB. The goal of such treatment is to prevent the establishment of chronic infection and to reduce infectivity, morbidity, and mortality. This strategy meets an immediate public emergency contingency need and establishes a basis to do further development of the TB-yeast immunotherapy product as a general prophylactic agent. The efficient and scalable manufacturing process as well as long shelf life of lyophilized TB-yeast-based immunotherapy products are ideally suited to a preemptive stockpiling strategy.

Initially the pre-exposure prophylactic use of stockpiled TB-yeast immunotherapy product is used in the context of a public safety event where confirmed secondary cases are detected. Such deployment of vaccine would serve to limit secondary exposures and mitigate public panic. Additionally, further development of a TB-yeast immunotherapy product for pre-exposure prophylaxis is highly useful for first responders, or persons having a likelihood of being exposed to TB. A TB-yeast immunotherapy product is also useful in combination with BCG to augment current vaccination programs.

Example 8

The following example describes the initial testing of the yeast-based immunotherapeutic known as GI-19004 for dosing and vaccination protocol evaluation and initial evaluation of potential efficacy in the clinically relevant and sensitive guinea pig post-exposure model.

In this pilot experiment to evaluate dosing and preliminary post-exposure data using a yeast-based TB immunotherapeutic, guinea pigs were infected with low dose aerosol of an *M. tuberculosis* strain (Midori X004619), and then ten days later, given GI-19004, which is the yeast-based immunotherapy composition expressing the "3-iron" fusion protein of SEQ ID NO:15 (see Examples 1 and 2), subcutaneously every two weeks for three doses, followed by evaluation of lung, spleen and lymph node cfu's, histology, and survival.

Specifically, pathogen-free female Hartley Outbred guinea pigs (Charles River Breeding Laboratories, Inc., Wilmington, Mass.) were housed in the CSU ABL-III facility and provided commercial chow in stainless-steel feeders and tap water ad libitum. The guinea pigs were maintained in a temperature- and humidity-controlled environment and exposed to a 12-hour light/dark cycle. After approximately two weeks to acclimate, each guinea pig was weighed, implanted with a microchip, and then assigned into specific groups based on mean weights. Each animal was implanted with an individual glass-encapsulated transponder (IMI-1000; Bio Medic Data Systems, Inc., Rockville, Md.) each pre-programmed with its own 10-digit alphanumeric code and pre-loaded into its own sterile needle assembly. These were given s.c. into the scruff of the neck. The guinea pig weight range was 500-550 grams.

Low Dose Aerosol Challenge.

For each aerosol infection, a thawed aliquot of *M. tuberculosis* Midori X004619 was diluted in sterile water (1.17× $10^7$ CFU/ml). Guinea pigs from each treatment group were aerosolized using a Madison infection chamber (University of Wisconsin Machine Shop, Madison, Wis.) with a starting volume of 15 ml of working stock (nebulization cycle: 5 min; cloud decay cycle: 10 min). The estimated retention of mycobacteria ranges from 25 and 30 CFU/guinea pig as determined (indirectly) by enumerating primary pulmonary lesions five weeks later post-infection, and which has been directly verified by magnetic resonance imaging analysis (Kraft et al, *Infect Immun* 72:5963-71 (2004)).

Vaccination with GI-19004 Yeast-Based Immunotherapeutic. 10 days post-infection with the Mtb strain, the guinea pigs were divided into four groups (15 guinea pigs were assigned to each group; one guinea pig in Group 1 died prior to the start of the study, and so that group proceeded with 14 guinea pigs). The four groups were vaccinated as follows:

Group 1 (untreated control): 100 µl saline administered subcutaneously;

Group 2 (antigen control): 3 Y.U. of a control yeast-immunotherapeutic known as "Ovax" or "Oval-Tarm" (whole, heat-killed yeast expressing irrelevant control antigen ovalbumin), administered subcutaneously as a divided dose to two separate sites (1.5 Y.U. administered in 100 µl to the scruff and 1.5 Y.U. administered in 100 µl to the flank);

Group 3 (low dose treatment): 3 Y.U. of GI-19004 ("3-Iron fusion Tarm (low)") administered subcutaneously as a divided dose to two separate sites (1.5 Y.U. administered in 100 µl to the scruff and 1.5 Y.U. administered in 100 µl to the flank); or Group 4 (high dose treatment): 6 Y.U. of GI-19004 ("3-Iron fusion Tarm (high)") administered subcutaneously as a divided dose to two separate sites (3 Y.U. administered in 100 µl to the scruff and 3 Y.U. administered in 100 µl to the flank).

A second vaccination (same dosing as above) was administered two weeks later (Day 25 post-infection), followed by a third vaccination (same dosing as above) two weeks after that (Day 40 post-infection). At Day 50 post infection, five guinea pigs from each group were euthanized and lung, spleen and lymph nodes were collected for CFU determination and histology. RNA was also isolated from lung lobes to evaluate interleukin-17 (IL-17) production by real time PCR. The remaining animals (9 in Group 1 and 10 in each of Groups 2, 3 and 4) were followed to track survival. The experiment was terminated at Day 109.

Animal Monitoring.

Following the aerosol infection, animals were observed daily and evaluated using a modified version of the Karnofsky scale for pain and distress. This included any potential weight loss, mobility, breathing patterns, and peripheral cyanosis. Guinea pigs scoring a 6 (or more) are deemed moribund necessitating immediate euthanasia. Performing euthanasia allows analysis of lung tissues prior to any tissue autolysis. Guinea pigs were euthanized humanely via an overdose (1 ml per 0.25 kg body weight) of sodium pentobarbital (Sleepaway) via intraperitoneal injection.

Determination of the Bacterial Load in Target Organs.

For bacterial load determinations the abdominal and thoracic cavities were opened aseptically and the right lung, the draining hilar lymph node cluster, and the spleen from individual animals was placed into vials filled with 20 ml of sterile saline. Individual tissue samples were homogenized separately using a handheld tissue homogenizer. Serial dilutions of tissue homogenates were then plated onto duplicate Middlebrook 7H11 agar plates and incubated at 37° C. for approximately 21 days. The number of viable colonies from the appropriate dilution quadrants (i.e., 20 CFU <optimal quadrant CFU count <200 CFU) from duplicate plates were averaged and expressed as $\log_{10}$ CFU per total right lung.

Immunopathology.

For histology, the left pulmonary lobes were infused in situ with 5 ml of 10% neutral-buffered formalin and then placed into 30 ml of fixative overnight. Specimens were separately embedded in paraffin, sectioned at 4 µm slices from equivalent areas of the left cranial lung lobe (i.e., along the left primary bronchus) and stained separately with H&E and by the Ziehl-Neelsen method for histologic and acid-fast evaluations, respectively. Additional stains used were Masson's trichrome (for fibrin) and Prussian blue (for iron deposition).

RNA Real Time PCR Analysis.

Lung tissue was homogenized in an RNA lysis solution and RNA and cDNA were prepared according to standard procedures. IL17A mRNA level was evaluated by real time PCR and the results were normalized to the level of a housekeeping gene (GAPDH) in the same sample.

Results.

This experiment was a pilot experiment to evaluate initial yeast-immunotherapeutic dosing and potential efficacy in a post-infection guinea pig model for tuberculosis, and the bacterial load and histology were only evaluated at a single time point. While none of the results from the Day 50 bacterial load evaluation in all target organs examined were statistically significant, the lower dose of GI-19004 ("3-iron Tarm Low) appeared to show a trend toward a lower CFU in the lung (the organ of initial infection) as compared to the saline control (data not shown). Results in the spleen and lymph node did not show this trend for either low or high dose GI-19004 (data not shown). Survival rates were not distinguishable among the groups in this pilot study (data not shown) and so the study was terminated early at Day 109. Further dosing and immunization optimization will be performed as discussed below. Results from the RNA analysis for IL-17 were not available at the time of this filing.

Given that GI-19004 does not target the immunodominant antigens that are typically the focus of therapeutic vaccines, but instead targets latency antigens, including those that emerge as *M. tuberculosis* infection progresses, GI-19004 is expected to be most beneficial in reducing, slowing, or halting secondary lesion formation rather than by reducing primary lesions. One goal of ameliorating or delaying secondary lesion formation is to extend survival long enough to allow antimicrobial chemotherapeutic agents to bring the infection under control. However, this initial study was not designed to fully evaluate these parameters and was terminated early; therefore, the results are viewed as preliminary and primarily useful for evaluating additional dosing and protocol optimization. Nonetheless, the results from low dose GI-19004 in lung cfu may be viewed as encouraging. Future experiments will look at CFU data and histology at multiple time points, in order to track the impact of yeast-based TB immunotherapy on a variety of parameters in vivo including reduction or slowing of secondary lesion formation, reduction of dissemination of infection to the lymph nodes, and the ability to elicit long lasting, protective immunity against the most relevant strains of TB. In additional experiments, a board-certified veterinary pathologist will perform a blinded review and scores sections according to the following parameters (data not available): % of lung affected, rank score, the number and associated severity of primary lesions and finally, the severity of secondary lesions (Basaraba, 2008).

Taken together, the results in Examples 2 and 8 show that the yeast-based TB immunotherapeutic known as GI-19004 is immunogenic in vivo, and may have an impact on lung bacterial load at some doses. Future studies will focus on the type and quality of immune response generated by GI-19004 and other yeast-based immunotherapeutics in vivo, and on the ability of these compositions to: (i) reduce or ameliorate the formation or severity of secondary tuberculosis lesions, (ii) reduce the dissemination of the *M. tuberculosis* bacilli to lymph nodes and other organs, (iii) extend survival of the infected subject, (iv) provide long-lasting immunity against

*M. tuberculosis* infection, and, (v) enhance the efficacy of other drugs used to treat infection.

Example 9

The following example describes the initial testing of a yeast-based immunotherapeutic expressing the *M. tuberculosis* antigen known as Ag85A in a murine TB challenge model.

In this pilot experiment, the yeast-based immunotherapeutic described in Example 4 which expresses an antigen from the TB Ag85a protein (SEQ ID NO:37) was used in a murine TB challenge model. Briefly, mice were immunized with the yeast-based Ag85A immunotherapy composition (referred to in this example as "Tarm-Ag85A") every three weeks for three doses, and then challenged with the highly virulent *M. tuberculosis* strain Midori X004619.

More specifically, pathogen-free female, 6- to 8-week-old C57BL/6 mice (Jackson Laboratories, Bar Harbor, Me.) were maintained in the biosafety level-III biohazard facility at Colorado State University (CSU), and given sterile water and mouse chow ad libitum. The mice were divided into five groups (20 mice in Group 1 and 17 mice in each of Groups 2-5). The five groups were immunized three times, immunizations spaced three weeks apart, as follows:

Group 1 (untreated control): Sham immunized with 100 µl of saline subcutaneously;

Group 2 (BCG control): Immunized with $10^6$ BCG delivered subcutaneously in 100 µl;

Group 3 (Ag85 control): Immunized with 0.5 µg recombinant Ag85 (IDRI) delivered intramuscularly in 100 µl;

Group 4 (treatment): Immunized with 4 Y.U. of a the yeast-immunotherapeutic expressing Ag85A known as "Tarm-Ag85A", administered subcutaneously as a divided dose to four separate sites (1 Y.U. administered in 100 µl to the inner right thigh; 1 Y.U. administered in 100 µl to the inner left thigh; 1 Y.U. administered in 100 µl to the right shoulder blade; and 1 Y.U. administered in 100 µl to the left shoulder blade).

Group 5 (antigen control): Immunized with 4 Y.U. of a control yeast-immunotherapeutic known as "Ovax" or "Tarm-Oval" (whole, heat-killed yeast expressing irrelevant control antigen ovalbumin), administered subcutaneously as a divided dose to four separate sites (1 Y.U. administered in 100 µl to the inner right thigh; 1 Y.U. administered in 100 µl to the inner left thigh; 1 Y.U. administered in 100 µl to the right shoulder blade; and 1 Y.U. administered in 100 µl to the left shoulder blade).

Six weeks after the third and final immunization, two mice from each group were humanely euthanized. Lung and spleen were collected and cells stimulated with IDRI recombinant Ag85A. Cells were evaluated for IFN-γ production by ELISA and by real time PCR.

The remaining mice, also rested for six weeks after the third and final immunization, were then infected by low-dose aerosol exposure to *M. tuberculosis* strain Midori X004619 using a Glas-Col exposure device (Terre Haute, Ind.) calibrated to deliver 50-100 bacteria into the lungs of each mouse. Subgroups of mice were humanely euthanized at Day 1 post-exposure (Group 1 saline control only); Day 15 (all five groups); Day 30 (all five groups) and Day 49 (all five groups), and lung and spleen were collected for CFU evaluation. Lungs were also collected for histology, real time PCR analysis (cytokines) and flow cytometry (evaluation of CD4-CD44, 62L, IL-17, and Ly6A expression; IFN-γ expression; and Foxp3+ cells).

Bacterial burden in the lungs of infected animals at indicated time points was determined by plating serial dilutions of whole organ homogenates on nutrient 7H11 agar and counting colony-forming units after 3 weeks incubation at 37° C. in humidified air. For histology, cranial lung lobes from each mouse were harvested and fixed with 4% paraformaldehyde in phosphate buffered saline (PBS). Sections were prepared and stained using haematoxylin and eosin (H & E).

Results were not available at the time of this filing, but it is expected that mice immunized with Tarm-Ag85A will show at least a trend toward lower lung CFU as compared to saline control mice, indications of improved histology as compared to saline control mice, and/or the development of IFN-γ production and Th17-type immune responses against tuberculosis antigens. A major focus of these experiments identifies the immune phenotype of the yeast-induced response and correlates it with clinical outcome in infected animals, wherein it is expected that the induction of a Th17 response, and the relative magnitude of Th17 and Th1 responses are important factors determining the overall efficacy of yeast-based TB immunotherapeutics.

Example 10

The following example describes testing of a yeast-based immunotherapeutic for TB in a prime-boost protocol in a murine model for TB.

In this experiment, the yeast-based immunotherapeutic known as GI-19004, which is the yeast-based immunotherapy composition expressing the "3-iron" fusion protein of SEQ ID NO:15 (see Examples 1 and 2) is used in a murine TB challenge model (a similar design can readily be adapted for use in guinea pigs, using dosing appropriate for that animal model and as determined or used in other examples described herein). In additional experiments, designed in a substantially similar protocol, yeast-based TB immunotherapeutics expressing different antigens, such as the hypoxia pool antigens or combinations of hypoxia pool antigens, iron accumulation antigens and TLR agonist antigens, all described in Example 4, are used.

Briefly, mice are first immunized with the Bacillus Calmette-Guérin (BCG) vaccine, followed by immunization with the yeast-based GI-19004 immunotherapy composition every three weeks for three doses, followed by challenge with the highly virulent *M. tuberculosis* strain Midori X004619.

More specifically, pathogen-free female, 6- to 8-week-old C57BL/6 mice (Jackson Laboratories, Bar Harbor, Me.) are maintained in the biosafety level-III biohazard facility at Colorado State University (CSU), and given sterile water and mouse chow ad libitum. The mice are divided into groups and immunized as follows:

Group 1 (untreated control): Sham immunized with 100 µl of saline subcutaneously;

Group 2 (BCG alone control): Immunized once with $10^6$ BCG delivered subcutaneously in 100 µl;

Group 3 (treatment): Immunized with $10^6$ BCG delivered subcutaneously in 100 µl; followed 10 weeks later by a first booster with between 4 Y.U. and 10 Y.U. of GI-19004 ("3-Iron fusion Tarm), administered subcutaneously as a divided dose to four separate sites (e.g., at 4 Y.U. total: 1 Y.U. administered in 100 µl to the inner right thigh; 1 Y.U. administered in 100 µl to the inner left thigh; 1 Y.U. administered in 100 µl to the right shoulder blade; and 1 Y.U. administered in 100 μl to the left shoulder blade). A second immunization with GI-19004 (same dosing as above) is administered 2, 3 or 4 weeks after the first booster, and a third immunization with GI-19004 (same dosing as above) is administered 2, 3 or 4 weeks after the second booster.

Group 5 (antigen control): Immunized with $10^6$ BCG delivered subcutaneously in 100 μl; followed 10 weeks later by a first booster with between 4 Y.U. and 10 Y.U. of a control yeast-immunotherapeutic known as "Ovax" or "Tarm-Oval" (whole, heat-killed yeast expressing irrelevant control antigen ovalbumin), administered subcutaneously as a divided dose to four separate sites (e.g., at 4 Y.U. total: 1 Y.U. administered in 100 μl to the inner right thigh; 1 Y.U. administered in 100 μl to the inner left thigh; 1 Y.U. administered in 100 μl to the right shoulder blade; and 1 Y.U. administered in 100 μl to the left shoulder blade). A second immunization with Tarm-Oval (same dosing as above) is administered 2, 3 or 4 weeks after the first booster, and a third immunization with Tarm-Oval (same dosing as above) is administered 2, 3 or 4 weeks after the second booster.

Between 6-8 weeks after the third and final booster with yeast-based immunotherapy, a few mice from each group are humanely euthanized. Lung and spleen are collected and cells stimulated with recombinant antigen for in vitro analysis. Cells are evaluated for IFN-γ production by ELISA and by real time PCR.

The remaining mice, also rested for 6-8 weeks after the third and final immunization, are then infected by low-dose aerosol exposure to *M. tuberculosis* strain (e.g., Midori X004619) using a Glas-Col exposure device (Terre Haute, Ind.) calibrated to deliver 50-100 bacteria into the lungs of each mouse. Subgroups of mice are humanely euthanized at Day 1 post-exposure (Group 1 saline control only); Day 15 (all groups); Day 30 (all groups) and Day 49 (all groups), and lung and spleen are collected for CFU evaluation. Lungs are also collected for histology, real time PCR analysis (cytokines) and flow cytometry (evaluation of CD4-CD44, 62L, IL-17, and Ly6A expression; IFN-γ expression; and Foxp3+ cells). Bacterial burden in the lungs of infected animals at indicated time points is determined by plating serial dilutions of whole organ homogenates on nutrient 7H11 agar and counting colony-forming units after 3 weeks incubation at 37° C. in humidified air. For histology, cranial lung lobes from each mouse are harvested and fixed with 4% paraformaldehyde in phosphate buffered saline (PBS). Sections are prepared and stained using haematoxylin and eosin (H & E).

It is expected that mice immunized with BCG and boosted with GI-19004 will show lower lung CFU as compared to saline control mice, indications of improved histology as compared to saline control mice, and/or the development of IFN-γ production and Th17-type immune responses against tuberculosis antigens. It is also expected that GI-19004 will show improved immunity and/or protection against tuberculosis infection as compared to the BCG immunization alone.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An immunotherapeutic composition comprising:
   a) a yeast vehicle; and
   b) a fusion protein comprising:
      a) an N-terminal amino acid sequence of SEQ ID NO:1; and
      b) a second amino acid sequence that is at least 95% identical to an amino acid sequence selected from SEQ ID NO:13, SEQ ID NO:31, SEQ ID NO:34, SEQ ID NO:43, or SEQ ID NO:46.

2. The immunotherapeutic composition of claim 1, wherein the yeast vehicle is a whole yeast.

3. The immunotherapeutic composition of claim 1, wherein the yeast vehicle is a whole, killed or inactivated yeast.

4. The immunotherapeutic composition of claim 1, wherein the yeast vehicle is a whole, heat-inactivated yeast.

5. The immunotherapeutic composition of claim 1, wherein the yeast is from a yeast genus selected from the group consisting of: *Saccharomyces, Candida, Cryptococcus, Hansenula, Kluyveromyces, Pichia, Rhodotorula, Schizosaccharomyces* and *Yarrowia*.

6. The immunotherapeutic composition of claim 1, wherein the composition is formulated in a pharmaceutically acceptable excipient suitable for administration to a subject by injection.

7. A fusion protein comprising
   a) an N-terminal amino acid sequence of SEQ ID NO:1; and
   b) a second amino acid sequence that is at least 95% identical to an amino acid sequence selected from SEQ ID NO:13, SEQ ID NO:31, SEQ ID NO:34, SEQ ID NO:43, or SEQ ID NO:46.

8. An immunotherapeutic composition comprising:
   a) a yeast vehicle; and
   b) a fusion protein comprising:
      a) an N-terminal amino acid sequence of SEQ ID NO:1; and
      b) a second amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46.

9. The immunotherapeutic composition of claim 8, wherein the fusion protein has an amino acid sequence selected from: SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, SEQ ID NO:42, SEQ ID NO:45 or SEQ ID NO:48.

10. The immunotherapeutic composition of claim 8, wherein the yeast vehicle is a whole yeast.

11. The immunotherapeutic composition of claim 8, wherein the yeast vehicle is a whole, killed or inactivated yeast.

12. The immunotherapeutic composition of claim 8, wherein the yeast vehicle is a whole, heat-inactivated yeast.

13. The immunotherapeutic composition of claim 8, wherein the yeast is from a yeast genus selected from the group consisting of: *Saccharomyces, Candida, Cryptococcus, Hansenula, Kluyveromyces, Pichia, Rhodotorula, Schizosaccharomyces* and *Yarrowia*.

14. The immunotherapeutic composition of claim 8, wherein the composition is formulated in a pharmaceutically acceptable excipient suitable for administration to a subject by injection.

15. A fusion protein comprising:
   a) an N-terminal amino acid sequence of SEQ ID NO:1, and
   b) a second amino acid sequence selected from: SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:43, or SEQ ID NO:46.

16. The fusion protein of claim 15, wherein the fusion protein comprises an amino acid sequence selected from SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, SEQ ID NO:42, SEQ ID NO:45 or SEQ ID NO:48.

* * * * *

SEQUENCE LISTING

```
<160> NUMBER OF SEQ ID NOS: 48

<210> SEQ ID NO 1
<211> LENGTH: 6
<212> TYPE: PRT
<213> ORGANISM: Artificial
<220> FEATURE:
<223> OTHER INFORMATION: synthetic peptide

<400> SEQUENCE: 1

Met Ala Asp Glu Ala Pro
1               5

<210> SEQ ID NO 2
<211> LENGTH: 89
<212> TYPE: PRT
<213> ORGANISM: Saccharomyces cerevisiae

<400> SEQUENCE: 2

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80
```

```
Ser Leu Asp Lys Arg Glu Ala Glu Ala
                85

<210> SEQ ID NO 3
<211> LENGTH: 89
<212> TYPE: PRT
<213> ORGANISM: Saccharomyces cerevisiae

<400> SEQUENCE: 3

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 4
<211> LENGTH: 129
<212> TYPE: PRT
<213> ORGANISM: Mycobacterium tuberculosis

<400> SEQUENCE: 4

Ser Ala Ala Gly Val Arg Ser Thr Arg Gln Arg Ala Ala Ile Ser Thr
1               5                   10                  15

Leu Leu Glu Thr Leu Asp Asp Phe Arg Ser Ala Gln Glu Leu His Asp
            20                  25                  30

Glu Leu Arg Arg Arg Gly Glu Asn Ile Gly Leu Thr Thr Val Tyr Arg
        35                  40                  45

Thr Leu Gln Ser Met Ala Ser Ser Gly Leu Val Asp Thr Leu His Thr
    50                  55                  60

Asp Thr Gly Glu Ser Val Tyr Arg Arg Cys Ser Glu His His His His
65                  70                  75                  80

His Leu Val Cys Arg Ser Cys Gly Ser Thr Ile Glu Val Gly Asp His
                85                  90                  95

Glu Val Glu Ala Trp Ala Ala Gly Val Ala Thr Lys His Gly Phe Ser
            100                 105                 110

Asp Val Ser His Thr Ile Glu Ile Phe Gly Thr Cys Ser Asp Cys Arg
        115                 120                 125

Ser

<210> SEQ ID NO 5
<211> LENGTH: 452
<212> TYPE: DNA
<213> ORGANISM: Artificial
<220> FEATURE:
<223> OTHER INFORMATION: synthetic sequence
<220> FEATURE:
<221> NAME/KEY: CDS
<222> LOCATION: (13)..(444)

<400> SEQUENCE: 5
gaattcgcca cc atg gcc gat gaa gcc cca act agt tct gct gct ggt gtt    51
              Met Ala Asp Glu Ala Pro Thr Ser Ser Ala Ala Gly Val
```

```
                1               5                       10
aga tcc act aga caa aga gct gct att tca act ctc ctt gag aca ttg         99
Arg Ser Thr Arg Gln Arg Ala Ala Ile Ser Thr Leu Leu Glu Thr Leu
         15                  20                  25 gac gac ttt aga tcc gcg cag gaa cta cat gac gaa ctt cgt aga aga        147
Asp Asp Phe Arg Ser Ala Gln Glu Leu His Asp Glu Leu Arg Arg Arg
 30                  35                  40                  45 ggg gag aat ata gga ctg acc acg gtc tat agg aca ttg caa agc atg        195
Gly Glu Asn Ile Gly Leu Thr Thr Val Tyr Arg Thr Leu Gln Ser Met
                 50                  55                  60 gct tcc tct ggt tta gta gat aca ttg cat aca gat act gga gaa tct        243
Ala Ser Ser Gly Leu Val Asp Thr Leu His Thr Asp Thr Gly Glu Ser
             65                  70                  75 gta tac cga aga tgt tct gaa cac cat cac cac cac tta gtc tgt aga        291
Val Tyr Arg Arg Cys Ser Glu His His His His His Leu Val Cys Arg
         80                  85                  90 tca tgc ggc tct act atc gaa gtt ggt gat cat gaa gtg gaa gcc tgg        339
Ser Cys Gly Ser Thr Ile Glu Val Gly Asp His Glu Val Glu Ala Trp
     95                 100                 105 gca gca gaa gtg gca acc aaa cat ggt ttt agt gat gtt tct cat aca        387
Ala Ala Glu Val Ala Thr Lys His Gly Phe Ser Asp Val Ser His Thr
110                 115                 120                 125 atc gag att ttc ggc aca tgt tca gat tgc aga tca cat cac cac cat        435
Ile Glu Ile Phe Gly Thr Cys Ser Asp Cys Arg Ser His His His His
                130                 135                 140 cac cat tag gcggccgc                                                   452
His His
```

<210> SEQ ID NO 6
<211> LENGTH: 143
<212> TYPE: PRT
<213> ORGANISM: Artificial
<220> FEATURE:
<223> OTHER INFORMATION: Synthetic Construct

<400> SEQUENCE: 6

Met Ala Asp Glu Ala Pro Thr Ser Ser Ala Ala Gly Val Arg Ser Thr
1               5                   10                  15

Arg Gln Arg Ala Ala Ile Ser Thr Leu Leu Glu Thr Leu Asp Asp Phe
            20                  25                  30

Arg Ser Ala Gln Glu Leu His Asp Glu Leu Arg Arg Arg Gly Glu Asn
        35                  40                  45

Ile Gly Leu Thr Thr Val Tyr Arg Thr Leu Gln Ser Met Ala Ser Ser
    50                  55                  60

Gly Leu Val Asp Thr Leu His Thr Asp Thr Gly Glu Ser Val Tyr Arg
65                  70                  75                  80

Arg Cys Ser Glu His His His His Leu Val Cys Arg Ser Cys Gly
                85                  90                  95

Ser Thr Ile Glu Val Gly Asp His Glu Val Glu Ala Trp Ala Ala Glu
            100                 105                 110

Val Ala Thr Lys His Gly Phe Ser Asp Val Ser His Thr Ile Glu Ile
        115                 120                 125

Phe Gly Thr Cys Ser Asp Cys Arg Ser His His His His His
    130                 135                 140

<210> SEQ ID NO 7
<211> LENGTH: 229
<212> TYPE: PRT
<213> ORGANISM: Mycobacterium tuberculosis

<400> SEQUENCE: 7

Asn Glu Leu Val Asp Thr Thr Glu Met Tyr Leu Arg Thr Ile Tyr Asp
1               5                   10                  15

Leu Glu Glu Glu Gly Val Thr Pro Leu Arg Ala Arg Ile Ala Glu Arg
            20                  25                  30

Leu Asp Gln Ser Gly Pro Thr Val Ser Gln Thr Val Ser Arg Met Glu
        35                  40                  45

Arg Asp Gly Leu Leu Arg Val Ala Gly Asp Arg His Leu Glu Leu Thr
    50                  55                  60

Glu Lys Gly Arg Ala Leu Ala Ile Ala Val Met Arg Lys His Arg Leu
65                  70                  75                  80

Ala Glu Arg Leu Leu Val Asp Val Ile Gly Leu Pro Trp Glu Val
                85                  90                  95

His Ala Glu Ala Cys Arg Trp Glu His Val Met Ser Glu Asp Val Glu
            100                 105                 110

Arg Arg Leu Val Lys Val Leu Asn Asn Pro Thr Thr Ser Pro Phe Gly
            115                 120                 125

Asn Pro Ile Pro Gly Leu Val Glu Leu Gly Val Gly Pro Glu Pro Gly
130                 135                 140

Ala Asp Asp Ala Asn Leu Val Arg Leu Thr Glu Leu Pro Ala Gly Ser
145                 150                 155                 160

Pro Val Ala Val Val Val Arg Gln Leu Thr Glu His Val Gln Gly Asp
                165                 170                 175

Ile Asp Leu Ile Thr Arg Leu Lys Asp Ala Gly Val Val Pro Asn Ala
            180                 185                 190

Arg Val Thr Val Glu Thr Thr Pro Gly Gly Gly Val Thr Ile Val Ile
            195                 200                 205

Pro Gly His Glu Asn Val Thr Leu Pro His Glu Met Ala His Ala Val
        210                 215                 220

Lys Val Glu Lys Val
225

<210> SEQ ID NO 8
<211> LENGTH: 752
<212> TYPE: DNA
<213> ORGANISM: Artificial
<220> FEATURE:
<223> OTHER INFORMATION: synthetic sequence
<220> FEATURE:
<221> NAME/KEY: CDS
<222> LOCATION: (13)..(744)

<400> SEQUENCE: 8

```
gaattcgcca cc atg gcg gac gag gcg cct act agt aat gaa tta gta gac    51
              Met Ala Asp Glu Ala Pro Thr Ser Asn Glu Leu Val Asp
              1               5                   10 acc act gaa atg tat ctt aga aca ata tac gac tta gag gaa gag ggc     99
Thr Thr Glu Met Tyr Leu Arg Thr Ile Tyr Asp Leu Glu Glu Glu Gly
    15                  20                  25 gtg acc cca tta aga gcc aga atc gcc gaa aga tta gac caa tcc ggt    147
Val Thr Pro Leu Arg Ala Arg Ile Ala Glu Arg Leu Asp Gln Ser Gly
30                  35                  40                  45 cca act gtt tct caa aca gtg tct agg atg gaa aga gat ggt ttg tta    195
Pro Thr Val Ser Gln Thr Val Ser Arg Met Glu Arg Asp Gly Leu Leu
                50                  55                  60 agg gtt gct gga gat cgt cac ctc gaa ctc aca gag aaa ggt aga gct    243
Arg Val Ala Gly Asp Arg His Leu Glu Leu Thr Glu Lys Gly Arg Ala
```

```
                  65                  70                  75
ttg gca atc gca gtc atg aga aag cat aga cta gcg gaa cga ttg cta       291
Leu Ala Ile Ala Val Met Arg Lys His Arg Leu Ala Glu Arg Leu Leu
            80                  85                  90 gtg gac gtg atc gga ctg cct tgg gaa gag gtc cat gct gaa gca tgt       339
Val Asp Val Ile Gly Leu Pro Trp Glu Glu Val His Ala Glu Ala Cys
    95                 100                 105 aga tgg gaa cat gtt atg tct gag gat gta gag aga aga ttg gtc aaa       387
Arg Trp Glu His Val Met Ser Glu Asp Val Glu Arg Arg Leu Val Lys
110                 115                 120                 125 gta ttg aat aat cca acc aca tca cct ttt gga aac cct att cct ggg       435
Val Leu Asn Asn Pro Thr Thr Ser Pro Phe Gly Asn Pro Ile Pro Gly
                130                 135                 140 cta gtt gaa ctt ggt gtg ggt cct gaa cca ggc gca gat gat gcg aat       483
Leu Val Glu Leu Gly Val Gly Pro Glu Pro Gly Ala Asp Asp Ala Asn
            145                 150                 155 ctg gta aga ttg aca gaa tta cca gca ggg tca cca gtt gca gtt gtt       531
Leu Val Arg Leu Thr Glu Leu Pro Ala Gly Ser Pro Val Ala Val Val
    160                 165                 170 gta aga caa ctg acg gaa cac gtg cag ggt gat att gat ctt atc aca       579
Val Arg Gln Leu Thr Glu His Val Gln Gly Asp Ile Asp Leu Ile Thr
175                 180                 185 aga ttg aag gac gct ggt gtt gta cca aac gcc cgt gtc act gtt gaa       627
Arg Leu Lys Asp Ala Gly Val Val Pro Asn Ala Arg Val Thr Val Glu
                190                 195                 200                 205 aca act cct gga ggt ggc gtc aca att gtt ata cca ggc cac gaa aac       675
Thr Thr Pro Gly Gly Gly Val Thr Ile Val Ile Pro Gly His Glu Asn
            210                 215                 220 gtt act ctt cca cat gaa atg gcc cat gct gta aaa gtc gag aag gtt       723
Val Thr Leu Pro His Glu Met Ala His Ala Val Lys Val Glu Lys Val
    225                 230                 235 cat cac cac cat cac cat tag gcggccgc                                  752
His His His His His His
        240

<210> SEQ ID NO 9
<211> LENGTH: 243
<212> TYPE: PRT
<213> ORGANISM: Artificial
<220> FEATURE:
<223> OTHER INFORMATION: Synthetic Construct

<400> SEQUENCE: 9

Met Ala Asp Glu Ala Pro Thr Ser Asn Glu Leu Val Asp Thr Thr Glu
1               5                   10                  15

Met Tyr Leu Arg Thr Ile Tyr Asp Leu Glu Glu Gly Val Thr Pro
            20                  25                  30

Leu Arg Ala Arg Ile Ala Glu Arg Leu Asp Gln Ser Gly Pro Thr Val
        35                  40                  45

Ser Gln Thr Val Ser Arg Met Glu Arg Asp Gly Leu Leu Arg Val Ala
    50                  55                  60

Gly Asp Arg His Leu Glu Leu Thr Glu Lys Gly Arg Ala Leu Ala Ile
65                  70                  75                  80

Ala Val Met Arg Lys His Arg Leu Ala Glu Arg Leu Leu Val Asp Val
                85                  90                  95

Ile Gly Leu Pro Trp Glu Glu Val His Ala Glu Ala Cys Arg Trp Glu
            100                 105                 110

His Val Met Ser Glu Asp Val Glu Arg Arg Leu Val Lys Val Leu Asn
        115                 120                 125
```

```
Asn Pro Thr Thr Ser Pro Phe Gly Asn Pro Ile Pro Gly Leu Val Glu
        130                 135                 140

Leu Gly Val Gly Pro Glu Pro Gly Ala Asp Asp Ala Asn Leu Val Arg
145                 150                 155                 160

Leu Thr Glu Leu Pro Ala Gly Ser Pro Val Ala Val Val Arg Gln
            165                 170                 175

Leu Thr Glu His Val Gln Gly Asp Ile Asp Leu Ile Thr Arg Leu Lys
            180                 185                 190

Asp Ala Gly Val Val Pro Asn Ala Arg Val Thr Val Glu Thr Thr Pro
        195                 200                 205

Gly Gly Gly Val Thr Ile Val Ile Pro Gly His Glu Asn Val Thr Leu
        210                 215                 220

Pro His Glu Met Ala His Ala Val Lys Val Glu Lys Val His His His
225                 230                 235                 240

His His His
```

<210> SEQ ID NO 10
<211> LENGTH: 147
<212> TYPE: PRT
<213> ORGANISM: Mycobacterium tuberculosis

<400> SEQUENCE: 10

```
Val Ser Ser Ile Pro Asp Tyr Ala Glu Gln Leu Arg Thr Ala Asp Leu
1               5                   10                  15

Arg Val Thr Arg Pro Arg Val Ala Val Leu Glu Ala Val Asn Ala His
                20                  25                  30

Pro His Ala Asp Thr Glu Thr Ile Phe Gly Ala Val Arg Phe Ala Leu
            35                  40                  45

Pro Asp Val Ser Arg Gln Ala Val Tyr Asp Val Leu His Ala Leu Thr
        50                  55                  60

Ala Ala Gly Leu Val Arg Lys Ile Gln Pro Ser Gly Ser Val Ala Arg
65                  70                  75                  80

Tyr Glu Ser Arg Val Gly Asp Asn His His His Ile Val Cys Arg Ser
                85                  90                  95

Cys Gly Val Ile Ala Asp Val Asp Cys Ala Val Gly Glu Ala Pro Cys
            100                 105                 110

Leu Thr Ala Ser Asp His Asn Gly Phe Leu Leu Asp Glu Ala Glu Val
        115                 120                 125

Ile Tyr Trp Gly Leu Cys Pro Asp Cys Ser Ile Ser Asp Thr Ser Arg
130                 135                 140

Ser His Pro
145
```

<210> SEQ ID NO 11
<211> LENGTH: 506
<212> TYPE: DNA
<213> ORGANISM: Artificial
<220> FEATURE:
<223> OTHER INFORMATION: synthetic sequence
<220> FEATURE:
<221> NAME/KEY: CDS
<222> LOCATION: (13)..(498)

<400> SEQUENCE: 11

```
gaattcgcca cc atg gcg gac gag gcg cct act agt gtg tca tca att cct    51
              Met Ala Asp Glu Ala Pro Thr Ser Val Ser Ser Ile Pro
              1               5                   10
```

| | | |
|---|---|---|
| gat tac gca gag cag ctc aga acc gct gat ctg aga gta aca aga cca<br>Asp Tyr Ala Glu Gln Leu Arg Thr Ala Asp Leu Arg Val Thr Arg Pro<br>     15                    20                 25 | | 99 |
| agg gtc gcc gtt tta gaa gct gtt aat gca cat cca cat gca gat aca<br>Arg Val Ala Val Leu Glu Ala Val Asn Ala His Pro His Ala Asp Thr<br>30                    35                 40                45 | | 147 |
| gaa act ata ttt ggc gct gta aga ttc gcg tta cca gat gtt tcc cgt<br>Glu Thr Ile Phe Gly Ala Val Arg Phe Ala Leu Pro Asp Val Ser Arg<br>                 50                 55                60 | | 195 |
| caa gcc gtc tac gat gta ttg cac gct cta aca gcc gct ggc ttg gtc<br>Gln Ala Val Tyr Asp Val Leu His Ala Leu Thr Ala Ala Gly Leu Val<br>            65                 70                75 | | 243 |
| cga aaa atc caa cca tct ggg tct gtc gct aga tat gaa agt aga gtg<br>Arg Lys Ile Gln Pro Ser Gly Ser Val Ala Arg Tyr Glu Ser Arg Val<br>                80                 85                90 | | 291 |
| ggt gac aat cat cat cat atc gtt tgc aga agc tgt ggt gtg att gca<br>Gly Asp Asn His His His Ile Val Cys Arg Ser Cys Gly Val Ile Ala<br>95                   100                   105 | | 339 |
| gat gtt gac tgc gcg gtt gga gaa gca cca tgt ctt act gca tct gat<br>Asp Val Asp Cys Ala Val Gly Glu Ala Pro Cys Leu Thr Ala Ser Asp<br>110                 115                120              125 | | 387 |
| cac aac gga ttt ttg cta gac gaa gct gaa gtt atc tac tgg ggt ctt<br>His Asn Gly Phe Leu Leu Asp Glu Ala Glu Val Ile Tyr Trp Gly Leu<br>                130                   135               140 | | 435 |
| tgt cct gac tgt tct att tct gat acg tca aga tcc cac cct cac cat<br>Cys Pro Asp Cys Ser Ile Ser Asp Thr Ser Arg Ser His Pro His His<br>                  145                   150               155 | | 483 |
| cat cac cat cac tag gcggccgc<br>His His His His<br>           160 | | 506 |

<210> SEQ ID NO 12
<211> LENGTH: 161
<212> TYPE: PRT
<213> ORGANISM: Artificial
<220> FEATURE:
<223> OTHER INFORMATION: Synthetic Construct

<400> SEQUENCE: 12

Met Ala Asp Glu Ala Pro Thr Ser Val Ser Ser Ile Pro Asp Tyr Ala
1               5                   10                  15

Glu Gln Leu Arg Thr Ala Asp Leu Arg Val Thr Arg Pro Arg Val Ala
            20                  25                  30

Val Leu Glu Ala Val Asn Ala His Pro His Ala Asp Thr Glu Thr Ile
        35                  40                  45

Phe Gly Ala Val Arg Phe Ala Leu Pro Asp Val Ser Arg Gln Ala Val
    50                  55                  60

Tyr Asp Val Leu His Ala Leu Thr Ala Ala Gly Leu Val Arg Lys Ile
65                  70                  75                  80

Gln Pro Ser Gly Ser Val Ala Arg Tyr Glu Ser Arg Val Gly Asp Asn
                85                  90                  95

His His His Ile Val Cys Arg Ser Cys Gly Val Ile Ala Asp Val Asp
            100                 105                 110

Cys Ala Val Gly Glu Ala Pro Cys Leu Thr Ala Ser Asp His Asn Gly
        115                 120                 125

Phe Leu Leu Asp Glu Ala Glu Val Ile Tyr Trp Gly Leu Cys Pro Asp
    130                 135                 140

Cys Ser Ile Ser Asp Thr Ser Arg Ser His Pro His His His His
145                 150                 155                 160

His

<210> SEQ ID NO 13
<211> LENGTH: 505
<212> TYPE: PRT
<213> ORGANISM: Artificial
<220> FEATURE:
<223> OTHER INFORMATION: synthetic sequence

<400> SEQUENCE: 13

Ser Ala Ala Gly Val Arg Ser Thr Arg Gln Arg Ala Ala Ile Ser Thr
1               5                   10                  15

Leu Leu Glu Thr Leu Asp Asp Phe Arg Ser Ala Gln Glu Leu His Asp
            20                  25                  30

Glu Leu Arg Arg Arg Gly Glu Asn Ile Gly Leu Thr Thr Val Tyr Arg
        35                  40                  45

Thr Leu Gln Ser Met Ala Ser Ser Gly Leu Val Asp Thr Leu His Thr
    50                  55                  60

Asp Thr Gly Glu Ser Val Tyr Arg Arg Cys Ser Glu His His His His
65                  70                  75                  80

His Leu Val Cys Arg Ser Cys Gly Ser Thr Ile Glu Val Gly Asp His
                85                  90                  95

Glu Val Glu Ala Trp Ala Ala Glu Val Ala Thr Lys His Gly Phe Ser
            100                 105                 110

Asp Val Ser His Thr Ile Glu Ile Phe Gly Thr Cys Ser Asp Cys Arg
        115                 120                 125

Ser Asn Glu Leu Val Asp Thr Thr Glu Met Tyr Leu Arg Thr Ile Tyr
    130                 135                 140

Asp Leu Glu Glu Glu Gly Val Thr Pro Leu Arg Ala Arg Ile Ala Glu
145                 150                 155                 160

Arg Leu Asp Gln Ser Gly Pro Thr Val Ser Gln Thr Val Ser Arg Met
                165                 170                 175

Glu Arg Asp Gly Leu Leu Arg Val Ala Gly Asp Arg His Leu Glu Leu
            180                 185                 190

Thr Glu Lys Gly Arg Ala Leu Ala Ile Ala Val Met Arg Lys His Arg
        195                 200                 205

Leu Ala Glu Arg Leu Leu Val Asp Val Ile Gly Leu Pro Trp Glu Glu
    210                 215                 220

Val His Ala Glu Ala Cys Arg Trp Glu His Val Met Ser Glu Asp Val
225                 230                 235                 240

Glu Arg Arg Leu Val Lys Val Leu Asn Asn Pro Thr Thr Ser Pro Phe
                245                 250                 255

Gly Asn Pro Ile Pro Gly Leu Val Glu Leu Gly Val Gly Pro Glu Pro
            260                 265                 270

Gly Ala Asp Asp Ala Asn Leu Val Arg Leu Thr Glu Leu Pro Ala Gly
        275                 280                 285

Ser Pro Val Ala Val Val Arg Gln Leu Thr Glu His Val Gln Gly
    290                 295                 300

Asp Ile Asp Leu Ile Thr Arg Leu Lys Asp Ala Gly Val Val Pro Asn
305                 310                 315                 320

Ala Arg Val Thr Val Glu Thr Thr Pro Gly Gly Val Thr Ile Val
                325                 330                 335

Ile Pro Gly His Glu Asn Val Thr Leu Pro His Glu Met Ala His Ala
            340                 345                 350

```
Val Lys Val Glu Lys Val Val Ser Ile Pro Asp Tyr Ala Glu Gln
            355                 360                 365

Leu Arg Thr Ala Asp Leu Arg Val Thr Arg Pro Arg Val Ala Val Leu
    370                 375                 380

Glu Ala Val Asn Ala His Pro His Ala Asp Thr Glu Thr Ile Phe Gly
385                 390                 395                 400

Ala Val Arg Phe Ala Leu Pro Asp Val Ser Arg Gln Ala Val Tyr Asp
                405                 410                 415

Val Leu His Ala Leu Thr Ala Ala Gly Leu Val Arg Lys Ile Gln Pro
            420                 425                 430

Ser Gly Ser Val Ala Arg Tyr Glu Ser Arg Val Gly Asp Asn His His
        435                 440                 445

His Ile Val Cys Arg Ser Cys Gly Val Ile Ala Asp Val Asp Cys Ala
    450                 455                 460

Val Gly Glu Ala Pro Cys Leu Thr Ala Ser Asp His Asn Gly Phe Leu
465                 470                 475                 480

Leu Asp Glu Ala Glu Val Ile Tyr Trp Gly Leu Cys Pro Asp Cys Ser
                485                 490                 495

Ile Ser Asp Thr Ser Arg Ser His Pro
            500                 505

<210> SEQ ID NO 14
<211> LENGTH: 1580
<212> TYPE: DNA
<213> ORGANISM: Artificial
<220> FEATURE:
<223> OTHER INFORMATION: synthetic sequence
<220> FEATURE:
<221> NAME/KEY: CDS
<222> LOCATION: (13)..(1572)

<400> SEQUENCE: 14
gaattcgcca cc atg gcc gat gaa gcc cca act agt tct gct gct ggt gtt      51
              Met Ala Asp Glu Ala Pro Thr Ser Ser Ala Ala Gly Val
              1               5                   10 aga tcc act aga caa aga gct gct att tca act ctc ctt gag aca ttg       99
Arg Ser Thr Arg Gln Arg Ala Ala Ile Ser Thr Leu Leu Glu Thr Leu
 15                  20                  25 gac gac ttt aga tcc gcg cag gaa cta cat gac gaa ctt cgt aga aga      147
Asp Asp Phe Arg Ser Ala Gln Glu Leu His Asp Glu Leu Arg Arg Arg
 30                  35                  40                  45 ggg gag aat ata gga ctg acc acg gtc tat agg aca ttg caa agc atg      195
Gly Glu Asn Ile Gly Leu Thr Thr Val Tyr Arg Thr Leu Gln Ser Met
                 50                  55                  60 gct tcc tct ggt tta gta gat aca ttg cat aca gat act gga gaa tct      243
Ala Ser Ser Gly Leu Val Asp Thr Leu His Thr Asp Thr Gly Glu Ser
             65                  70                  75 gta tac cga aga tgt tct gaa cac cat cac cac cac tta gtc tgt aga      291
Val Tyr Arg Arg Cys Ser Glu His His His His His Leu Val Cys Arg
         80                  85                  90 tca tgc ggc tct act atc gaa gtt ggt gat cat gaa gtg gaa gcc tgg      339
Ser Cys Gly Ser Thr Ile Glu Val Gly Asp His Glu Val Glu Ala Trp
 95                 100                 105 gca gca gaa gtg gca acc aaa cat ggt ttt agt gat gtt tct cat aca      387
Ala Ala Glu Val Ala Thr Lys His Gly Phe Ser Asp Val Ser His Thr
110                 115                 120                 125 atc gag att ttc ggc aca tgt tca gat tgc aga tca aat gaa tta gta      435
Ile Glu Ile Phe Gly Thr Cys Ser Asp Cys Arg Ser Asn Glu Leu Val
                130                 135                 140
```

```
gac acc act gaa atg tat ctt aga aca ata tac gac tta gag gaa gag    483
Asp Thr Thr Glu Met Tyr Leu Arg Thr Ile Tyr Asp Leu Glu Glu Glu
            145                 150                 155 ggc gtg acc cca tta aga gcc aga atc gcc gaa aga tta gac caa tcc    531
Gly Val Thr Pro Leu Arg Ala Arg Ile Ala Glu Arg Leu Asp Gln Ser
        160                 165                 170 ggt cca act gtt tct caa aca gtg tct agg atg gaa aga gat ggt ttg    579
Gly Pro Thr Val Ser Gln Thr Val Ser Arg Met Glu Arg Asp Gly Leu
175                 180                 185 tta agg gtt gct gga gat cgt cac ctc gaa ctc aca gag aaa ggt aga    627
Leu Arg Val Ala Gly Asp Arg His Leu Glu Leu Thr Glu Lys Gly Arg
190                 195                 200                 205 gct ttg gca atc gca gtc atg aga aag cat aga cta gcg gaa cga ttg    675
Ala Leu Ala Ile Ala Val Met Arg Lys His Arg Leu Ala Glu Arg Leu
            210                 215                 220 cta gtg gac gtg atc gga ctg cct tgg gaa gag gtc cat gct gaa gca    723
Leu Val Asp Val Ile Gly Leu Pro Trp Glu Glu Val His Ala Glu Ala
        225                 230                 235 tgt aga tgg gaa cat gtt atg tct gag gat gta gag aga aga ttg gtc    771
Cys Arg Trp Glu His Val Met Ser Glu Asp Val Glu Arg Arg Leu Val
    240                 245                 250 aaa gta ttg aat aat cca acc aca tca cct ttt gga aac cct att cct    819
Lys Val Leu Asn Asn Pro Thr Thr Ser Pro Phe Gly Asn Pro Ile Pro
255                 260                 265 ggg cta gtt gaa ctt ggt gtg ggt cct gaa cca ggc gca gat gat gcg    867
Gly Leu Val Glu Leu Gly Val Gly Pro Glu Pro Gly Ala Asp Asp Ala
270                 275                 280                 285 aat ctg gta aga ttg aca gaa tta cca gca ggg tca cca gtt gca gtt    915
Asn Leu Val Arg Leu Thr Glu Leu Pro Ala Gly Ser Pro Val Ala Val
            290                 295                 300 gtt gta aga caa ctg acg gaa cac gtg cag ggt gat att gat ctt atc    963
Val Val Arg Gln Leu Thr Glu His Val Gln Gly Asp Ile Asp Leu Ile
        305                 310                 315 aca aga ttg aag gac gct ggt gtt gta cca aac gcc cgt gtc act gtt   1011
Thr Arg Leu Lys Asp Ala Gly Val Val Pro Asn Ala Arg Val Thr Val
    320                 325                 330 gaa aca act cct gga ggt ggc gtc aca att gtt ata cca ggc cac gaa   1059
Glu Thr Thr Pro Gly Gly Gly Val Thr Ile Val Ile Pro Gly His Glu
335                 340                 345 aac gtt act ctt cca cat gaa atg gcc cat gct gta aaa gtc gag aag   1107
Asn Val Thr Leu Pro His Glu Met Ala His Ala Val Lys Val Glu Lys
350                 355                 360                 365 gtt gtg tca tca att cct gat tac gca gag cag ctc aga acc gct gat   1155
Val Val Ser Ser Ile Pro Asp Tyr Ala Glu Gln Leu Arg Thr Ala Asp
            370                 375                 380 ctg aga gta aca aga cca agg gtc gcc gtt tta gaa gct gtt aat gca   1203
Leu Arg Val Thr Arg Pro Arg Val Ala Val Leu Glu Ala Val Asn Ala
        385                 390                 395 cat cca cat gca gat aca gaa act ata ttt ggc gct gta aga ttc gcg   1251
His Pro His Ala Asp Thr Glu Thr Ile Phe Gly Ala Val Arg Phe Ala
    400                 405                 410 tta cca gat gtt tcc cgt caa gcc gtc tac gat gta ttg cac gct cta   1299
Leu Pro Asp Val Ser Arg Gln Ala Val Tyr Asp Val Leu His Ala Leu
415                 420                 425 aca gcc gct ggc ttg gtc cga aaa atc caa cca tct ggg tct gtc gct   1347
Thr Ala Ala Gly Leu Val Arg Lys Ile Gln Pro Ser Gly Ser Val Ala
430                 435                 440                 445 aga tat gaa agt aga gtg ggt gac aat cat cat cat atc gtt tgc aga   1395
Arg Tyr Glu Ser Arg Val Gly Asp Asn His His His Ile Val Cys Arg
            450                 455                 460
```

-continued

```
agc tgt ggt gtg att gca gat gtt gac tgc gcg gtt gga gaa gca cca    1443
Ser Cys Gly Val Ile Ala Asp Val Asp Cys Ala Val Gly Glu Ala Pro
        465                 470                 475 tgt ctt act gca tct gat cac aac gga ttt ttg cta gac gaa gct gaa    1491
Cys Leu Thr Ala Ser Asp His Asn Gly Phe Leu Leu Asp Glu Ala Glu
    480                 485                 490 gtt atc tac tgg ggt ctt tgt cct gac tgt tct att tct gat acg tca    1539
Val Ile Tyr Trp Gly Leu Cys Pro Asp Cys Ser Ile Ser Asp Thr Ser
495                 500                 505 aga tcc cac cct cac cat cat cac cat cac tag gcggccgc               1580
Arg Ser His Pro His His His His His His
510                 515
```

<210> SEQ ID NO 15
<211> LENGTH: 519
<212> TYPE: PRT
<213> ORGANISM: Artificial
<220> FEATURE:
<223> OTHER INFORMATION: Synthetic Construct

<400> SEQUENCE: 15

```
Met Ala Asp Glu Ala Pro Thr Ser Ser Ala Ala Gly Val Arg Ser Thr
1               5                   10                  15

Arg Gln Arg Ala Ala Ile Ser Thr Leu Leu Glu Thr Leu Asp Asp Phe
            20                  25                  30

Arg Ser Ala Gln Glu Leu His Asp Glu Leu Arg Arg Arg Gly Glu Asn
        35                  40                  45

Ile Gly Leu Thr Thr Val Tyr Arg Thr Leu Gln Ser Met Ala Ser Ser
50                  55                  60

Gly Leu Val Asp Thr Leu His Thr Asp Thr Gly Glu Ser Val Tyr Arg
65                  70                  75                  80

Arg Cys Ser Glu His His His His His Leu Val Cys Arg Ser Cys Gly
                85                  90                  95

Ser Thr Ile Glu Val Gly Asp His Glu Val Ala Trp Ala Ala Glu
            100                 105                 110

Val Ala Thr Lys His Gly Phe Ser Asp Val Ser His Thr Ile Glu Ile
        115                 120                 125

Phe Gly Thr Cys Ser Asp Cys Arg Ser Asn Glu Leu Val Asp Thr Thr
    130                 135                 140

Glu Met Tyr Leu Arg Thr Ile Tyr Asp Leu Glu Glu Gly Val Thr
145                 150                 155                 160

Pro Leu Arg Ala Arg Ile Ala Glu Arg Leu Asp Gln Ser Gly Pro Thr
                165                 170                 175

Val Ser Gln Thr Val Ser Arg Met Glu Arg Asp Gly Leu Leu Arg Val
            180                 185                 190

Ala Gly Asp Arg His Leu Glu Leu Thr Glu Lys Gly Arg Ala Leu Ala
        195                 200                 205

Ile Ala Val Met Arg Lys His Arg Leu Ala Glu Arg Leu Leu Val Asp
    210                 215                 220

Val Ile Gly Leu Pro Trp Glu Glu Val His Ala Glu Ala Cys Arg Trp
225                 230                 235                 240

Glu His Val Met Ser Glu Asp Val Glu Arg Arg Leu Val Lys Val Leu
                245                 250                 255

Asn Asn Pro Thr Thr Ser Pro Phe Gly Asn Pro Ile Pro Gly Leu Val
            260                 265                 270

Glu Leu Gly Val Gly Pro Glu Pro Gly Ala Asp Asp Ala Asn Leu Val
```

```
                275                 280                 285
Arg Leu Thr Glu Leu Pro Ala Gly Ser Pro Val Ala Val Val Arg
    290                 295                 300
Gln Leu Thr Glu His Val Gln Gly Asp Ile Asp Leu Ile Thr Arg Leu
305                 310                 315                 320
Lys Asp Ala Gly Val Val Pro Asn Ala Arg Val Thr Val Glu Thr Thr
                325                 330                 335
Pro Gly Gly Gly Val Thr Ile Val Ile Pro Gly His Glu Asn Val Thr
            340                 345                 350
Leu Pro His Glu Met Ala His Ala Val Lys Val Glu Lys Val Val Ser
            355                 360                 365
Ser Ile Pro Asp Tyr Ala Glu Gln Leu Arg Thr Ala Asp Leu Arg Val
    370                 375                 380
Thr Arg Pro Arg Val Ala Val Leu Glu Ala Val Asn Ala His Pro His
385                 390                 395                 400
Ala Asp Thr Glu Thr Ile Phe Gly Ala Val Arg Phe Ala Leu Pro Asp
                405                 410                 415
Val Ser Arg Gln Ala Val Tyr Asp Val Leu His Ala Leu Thr Ala Ala
            420                 425                 430
Gly Leu Val Arg Lys Ile Gln Pro Ser Gly Ser Val Ala Arg Tyr Glu
            435                 440                 445
Ser Arg Val Gly Asp Asn His His Ile Val Cys Arg Ser Cys Gly
    450                 455                 460
Val Ile Ala Asp Val Asp Cys Ala Val Gly Glu Ala Pro Cys Leu Thr
465                 470                 475                 480
Ala Ser Asp His Asn Gly Phe Leu Leu Asp Glu Ala Glu Val Ile Tyr
                485                 490                 495
Trp Gly Leu Cys Pro Asp Cys Ser Ile Ser Asp Thr Ser Arg Ser His
            500                 505                 510
Pro His His His His His His
        515

<210> SEQ ID NO 16
<211> LENGTH: 94
<212> TYPE: PRT
<213> ORGANISM: Mycobacterium tuberculosis

<400> SEQUENCE: 16

Thr Glu Gln Gln Trp Asn Phe Ala Gly Ile Glu Ala Ala Ser Ala
1               5                   10                  15
Ile Gln Gly Asn Val Thr Ser Ile His Ser Leu Leu Asp Glu Gly Lys
                20                  25                  30
Gln Ser Leu Thr Lys Leu Ala Ala Ala Trp Gly Gly Ser Gly Ser Glu
            35                  40                  45
Ala Tyr Gln Gly Val Gln Gln Lys Trp Asp Ala Thr Ala Thr Glu Leu
        50                  55                  60
Asn Asn Ala Leu Gln Asn Leu Ala Arg Thr Ile Ser Glu Ala Gly Gln
65                  70                  75                  80
Ala Met Ala Ser Thr Glu Gly Asn Val Thr Gly Met Phe Ala
                85                  90

<210> SEQ ID NO 17
<211> LENGTH: 347
<212> TYPE: DNA
<213> ORGANISM: Artificial
<220> FEATURE:
```

```
<223> OTHER INFORMATION: synthetic sequence
<220> FEATURE:
<221> NAME/KEY: CDS
<222> LOCATION: (13)..(339)

<400> SEQUENCE: 17
gaattcgcca cc atg gca gat gaa gcc cca act agt acc gaa cag caa tgg      51
              Met Ala Asp Glu Ala Pro Thr Ser Thr Glu Gln Gln Trp
               1               5                  10 aat ttt gct ggt ata gag gct gcg gcc tct gca atc caa ggc aac gta         99
Asn Phe Ala Gly Ile Glu Ala Ala Ala Ser Ala Ile Gln Gly Asn Val
         15                  20                  25 aca tca att cat tca ctg tta gac gaa ggt aaa cag agc ttg act aag        147
Thr Ser Ile His Ser Leu Leu Asp Glu Gly Lys Gln Ser Leu Thr Lys
 30                  35                  40                  45 ttg gct gcc gcc tgg gga ggt tct ggc tcc gag gct tac caa ggg gtt        195
Leu Ala Ala Ala Trp Gly Gly Ser Gly Ser Glu Ala Tyr Gln Gly Val
                 50                  55                  60 caa caa aaa tgg gat gct acg gca act gaa cta aac aat gct tta caa        243
Gln Gln Lys Trp Asp Ala Thr Ala Thr Glu Leu Asn Asn Ala Leu Gln
             65                  70                  75 aat ctt gct aga aca atc tca gaa gca ggt caa gcg atg gca tct aca        291
Asn Leu Ala Arg Thr Ile Ser Glu Ala Gly Gln Ala Met Ala Ser Thr
 80                  85                  90 gaa ggt aat gtc aca gga atg ttc gca cac cat cat cac cat cac tag        339
Glu Gly Asn Val Thr Gly Met Phe Ala His His His His His His
         95                 100                 105 gcggccgc                                                                347

<210> SEQ ID NO 18
<211> LENGTH: 108
<212> TYPE: PRT
<213> ORGANISM: Artificial
<220> FEATURE:
<223> OTHER INFORMATION: Synthetic Construct

<400> SEQUENCE: 18

Met Ala Asp Glu Ala Pro Thr Ser Thr Glu Gln Gln Trp Asn Phe Ala
 1               5                  10                  15

Gly Ile Glu Ala Ala Ala Ser Ala Ile Gln Gly Asn Val Thr Ser Ile
             20                  25                  30

His Ser Leu Leu Asp Glu Gly Lys Gln Ser Leu Thr Lys Leu Ala Ala
         35                  40                  45

Ala Trp Gly Gly Ser Gly Ser Glu Ala Tyr Gln Gly Val Gln Gln Lys
     50                  55                  60

Trp Asp Ala Thr Ala Thr Glu Leu Asn Asn Ala Leu Gln Asn Leu Ala
65                  70                  75                  80

Arg Thr Ile Ser Glu Ala Gly Gln Ala Met Ala Ser Thr Glu Gly Asn
                 85                  90                  95

Val Thr Gly Met Phe Ala His His His His His His
             100                 105

<210> SEQ ID NO 19
<211> LENGTH: 94
<212> TYPE: PRT
<213> ORGANISM: Mycobacterium tuberculosis

<400> SEQUENCE: 19

Met Cys Gly Asp Gln Ser Asp His Val Leu Gln His Trp Thr Val Asp
 1               5                  10                  15
```

```
Ile Ser Ile Asp Glu His Glu Gly Leu Thr Arg Ala Lys Ala Arg Leu
            20                  25                  30

Arg Trp Arg Glu Lys Glu Leu Val Gly Val Gly Leu Ala Arg Leu Asn
        35                  40                  45

Pro Ala Asp Arg Asn Val Pro Glu Ile Gly Asp Glu Leu Ser Val Ala
    50                  55                  60

Arg Ala Leu Ser Asp Leu Gly Lys Arg Met Leu Lys Val Ser Thr His
65                  70                  75                  80

Asp Ile Glu Ala Val Thr His Gln Pro Ala Arg Leu Leu Tyr
                85                  90

<210> SEQ ID NO 20
<211> LENGTH: 324
<212> TYPE: DNA
<213> ORGANISM: Artificial
<220> FEATURE:
<223> OTHER INFORMATION: synthetic sequence
<220> FEATURE:
<221> NAME/KEY: CDS
<222> LOCATION: (1)..(324)

<400> SEQUENCE: 20 atg gcc gac gag gca cca act agt tgc gga gat caa tca gac cac gtt       48
Met Ala Asp Glu Ala Pro Thr Ser Cys Gly Asp Gln Ser Asp His Val
1               5                   10                  15 tta caa cac tgg acc gta gac att tct atc gat gaa cat gaa ggt ctt       96
Leu Gln His Trp Thr Val Asp Ile Ser Ile Asp Glu His Glu Gly Leu
            20                  25                  30 aca aga gct aaa gct aga ttg aga tgg cgt gaa aag gaa tta gtc ggc      144
Thr Arg Ala Lys Ala Arg Leu Arg Trp Arg Glu Lys Glu Leu Val Gly
        35                  40                  45 gtt ggg cta gct agg tta aat cct gca gat aga aac gtt cca gaa ata      192
Val Gly Leu Ala Arg Leu Asn Pro Ala Asp Arg Asn Val Pro Glu Ile
    50                  55                  60 ggt gat gaa cta tcc gtg gcg aga gcc ctg tct gat ttg ggt aag aga      240
Gly Asp Glu Leu Ser Val Ala Arg Ala Leu Ser Asp Leu Gly Lys Arg
65                  70                  75                  80 atg ttg aaa gtc tca act cat gat atc gag gca gta aca cat cag cca      288
Met Leu Lys Val Ser Thr His Asp Ile Glu Ala Val Thr His Gln Pro
                85                  90                  95 gct aga ctc ctt tac cac cat cat cac cat cat taa                      324
Ala Arg Leu Leu Tyr His His His His His His
            100                 105

<210> SEQ ID NO 21
<211> LENGTH: 107
<212> TYPE: PRT
<213> ORGANISM: Artificial
<220> FEATURE:
<223> OTHER INFORMATION: Synthetic Construct

<400> SEQUENCE: 21

Met Ala Asp Glu Ala Pro Thr Ser Cys Gly Asp Gln Ser Asp His Val
1               5                   10                  15

Leu Gln His Trp Thr Val Asp Ile Ser Ile Asp Glu His Glu Gly Leu
            20                  25                  30

Thr Arg Ala Lys Ala Arg Leu Arg Trp Arg Glu Lys Glu Leu Val Gly
        35                  40                  45

Val Gly Leu Ala Arg Leu Asn Pro Ala Asp Arg Asn Val Pro Glu Ile
    50                  55                  60

Gly Asp Glu Leu Ser Val Ala Arg Ala Leu Ser Asp Leu Gly Lys Arg
```

```
                    65                  70                  75                  80
Met Leu Lys Val Ser Thr His Asp Ile Glu Ala Val Thr His Gln Pro
                    85                  90                  95

Ala Arg Leu Leu Tyr His His His His His
                   100                 105

<210> SEQ ID NO 22
<211> LENGTH: 331
<212> TYPE: PRT
<213> ORGANISM: Mycobacterium tuberculosis

<400> SEQUENCE: 22

Met Pro Asp Thr Met Val Thr Thr Asp Val Ile Lys Ser Arg Val Gln
  1               5                  10                  15

Leu Ala Cys Arg Ala Pro Ser Leu His Asn Ser Gln Pro Trp Arg Trp
                 20                  25                  30

Ile Ala Glu Asp His Thr Val Ala Leu Phe Leu Asp Lys Asp Arg Val
             35                  40                  45

Leu Tyr Ala Thr Asp His Ser Gly Arg Glu Ala Leu Leu Gly Cys Gly
         50                  55                  60

Ala Val Leu Asp His Phe Arg Val Ala Met Ala Ala Gly Thr Thr
 65                  70                  75                  80

Ala Asn Val Glu Arg Phe Pro Asn Pro Asn Asp Pro Leu His Leu Ala
                 85                  90                  95

Ser Ile Asp Phe Ser Pro Ala Asp Phe Val Thr Glu Gly His Arg Leu
                100                 105                 110

Arg Ala Asp Ala Ile Leu Leu Arg Arg Thr Asp Arg Leu Pro Phe Ala
            115                 120                 125

Glu Pro Pro Asp Trp Asp Leu Val Glu Ser Gln Leu Arg Thr Thr Val
        130                 135                 140

Thr Ala Asp Thr Val Arg Ile Asp Val Ile Ala Asp Asp Met Arg Pro
145                 150                 155                 160

Glu Leu Ala Ala Ala Ser Lys Leu Thr Glu Ser Leu Arg Leu Tyr Asp
                165                 170                 175

Ser Ser Tyr His Ala Glu Leu Phe Trp Trp Thr Gly Ala Phe Glu Thr
            180                 185                 190

Ser Glu Gly Ile Pro His Ser Ser Leu Val Ser Ala Ala Glu Ser Asp
        195                 200                 205

Arg Val Thr Phe Gly Arg Asp Phe Pro Val Val Ala Asn Thr Asp Arg
    210                 215                 220

Arg Pro Glu Phe Gly His Asp Arg Ser Lys Val Leu Val Leu Ser Thr
225                 230                 235                 240

Tyr Asp Asn Glu Arg Ala Ser Leu Leu Arg Cys Gly Glu Met Leu Ser
                245                 250                 255

Ala Val Leu Leu Asp Ala Thr Met Ala Gly Leu Ala Thr Cys Thr Leu
            260                 265                 270

Thr His Ile Thr Glu Leu His Ala Ser Arg Asp Leu Val Ala Ala Leu
        275                 280                 285

Ile Gly Gln Pro Ala Thr Pro Gln Ala Leu Val Arg Val Gly Leu Ala
    290                 295                 300

Pro Glu Met Glu Glu Pro Pro Ala Thr Pro Arg Arg Pro Ile Asp
305                 310                 315                 320

Glu Val Phe His Val Arg Ala Lys Asp His Arg
                325                 330
```

<210> SEQ ID NO 23
<211> LENGTH: 1035
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1035)

<400> SEQUENCE: 23

```
atg gcc gac gag gca cca act agt cca gat aca atg gtt aca aca gac      48
Met Ala Asp Glu Ala Pro Thr Ser Pro Asp Thr Met Val Thr Thr Asp
1               5                   10                  15 gtg att aag agc aga gta caa ttg gcc tgt aga gca cct agt tta cat      96
Val Ile Lys Ser Arg Val Gln Leu Ala Cys Arg Ala Pro Ser Leu His
                20                  25                  30 aat tca cag cca tgg aga tgg att gca gaa gat cac aca gtc gca ttg     144
Asn Ser Gln Pro Trp Arg Trp Ile Ala Glu Asp His Thr Val Ala Leu
            35                  40                  45 ttt ctc gac aaa gat aga gta cta tac gct acc gat cat tct ggg aga     192
Phe Leu Asp Lys Asp Arg Val Leu Tyr Ala Thr Asp His Ser Gly Arg
        50                  55                  60 gaa gca ttg ttg ggt tgc ggt gca gtt ctg gat cac ttt aga gta gcc     240
Glu Ala Leu Leu Gly Cys Gly Ala Val Leu Asp His Phe Arg Val Ala
65                  70                  75                  80 atg gcg gct gcc ggt aca acc gct aac gta gag aga ttc cca aac cct     288
Met Ala Ala Ala Gly Thr Thr Ala Asn Val Glu Arg Phe Pro Asn Pro
                85                  90                  95 aat gat cca ctc cac tta gct tca atc gat ttt tcc cca gct gat ttc     336
Asn Asp Pro Leu His Leu Ala Ser Ile Asp Phe Ser Pro Ala Asp Phe
                100                 105                 110 gtg acg gaa ggc cat aga ctc aga gct gat gcc atc ttg ctt agg agg     384
Val Thr Glu Gly His Arg Leu Arg Ala Asp Ala Ile Leu Leu Arg Arg
            115                 120                 125 aca gat aga tta cct ttc gcc gaa cct cca gac tgg gat tta gta gaa     432
Thr Asp Arg Leu Pro Phe Ala Glu Pro Pro Asp Trp Asp Leu Val Glu
        130                 135                 140 agt caa ttg cgt act act gtc act gca gat aca gtt aga att gac gtc     480
Ser Gln Leu Arg Thr Thr Val Thr Ala Asp Thr Val Arg Ile Asp Val
145                 150                 155                 160 atc gcg gat gac atg cgt cca gaa ctg gca gcc gca tca aaa ctg acc     528
Ile Ala Asp Asp Met Arg Pro Glu Leu Ala Ala Ala Ser Lys Leu Thr
                165                 170                 175 gaa tct ttg aga tta tac gat tct tct tac cat gca gaa cta ttc tgg     576
Glu Ser Leu Arg Leu Tyr Asp Ser Ser Tyr His Ala Glu Leu Phe Trp
            180                 185                 190 tgg act ggc gcc ttt gaa aca tct gag ggg ata cca cat tct tct tta     624
Trp Thr Gly Ala Phe Glu Thr Ser Glu Gly Ile Pro His Ser Ser Leu
        195                 200                 205 gtg tca gct gct gaa tct gac aga gtt act ttc gga aga gat ttt cct     672
Val Ser Ala Ala Glu Ser Asp Arg Val Thr Phe Gly Arg Asp Phe Pro
        210                 215                 220 gtg gtc gca aat aca gat cgt aga cca gaa ttt ggc cac gac aga tcc     720
Val Val Ala Asn Thr Asp Arg Arg Pro Glu Phe Gly His Asp Arg Ser
225                 230                 235                 240 aaa gtt ctt gtt tta tcc act tat gat aat gaa aga gcc tcc ttg ctg     768
Lys Val Leu Val Leu Ser Thr Tyr Asp Asn Glu Arg Ala Ser Leu Leu
                245                 250                 255 aga tgt gga gag atg cta tca gct gtt ttg cta gat gca act atg gcg     816
Arg Cys Gly Glu Met Leu Ser Ala Val Leu Leu Asp Ala Thr Met Ala
```

```
gga tta gct aca tgt act cta acc cat att acg gaa ctt cat gct tca      864
Gly Leu Ala Thr Cys Thr Leu Thr His Ile Thr Glu Leu His Ala Ser
        275                 280                 285 agg gac ctt gtc gcg gct ttg ata ggt caa ccc gct aca cca caa gca      912
Arg Asp Leu Val Ala Ala Leu Ile Gly Gln Pro Ala Thr Pro Gln Ala
    290                 295                 300 ctt gtt cgc gtt ggt ttg gct cca gaa atg gag gaa cct cct cct gct      960
Leu Val Arg Val Gly Leu Ala Pro Glu Met Glu Glu Pro Pro Pro Ala
305                 310                 315                 320 act cca aga cga cca atc gac gag gtt ttt cat gtg aga gct aag gat     1008
Thr Pro Arg Arg Pro Ile Asp Glu Val Phe His Val Arg Ala Lys Asp
                325                 330                 335 cat aga cac cat cac cat cat cac taa                                 1035
His Arg His His His His His His
                340
```

<210> SEQ ID NO 24
<211> LENGTH: 344
<212> TYPE: PRT
<213> ORGANISM: Artificial
<220> FEATURE:
<223> OTHER INFORMATION: Synthetic Construct

<400> SEQUENCE: 24

```
Met Ala Asp Glu Ala Pro Thr Ser Pro Asp Thr Met Val Thr Thr Asp
1               5                   10                  15

Val Ile Lys Ser Arg Val Gln Leu Ala Cys Arg Ala Pro Ser Leu His
            20                  25                  30

Asn Ser Gln Pro Trp Arg Trp Ile Ala Glu Asp His Thr Val Ala Leu
        35                  40                  45

Phe Leu Asp Lys Asp Arg Val Leu Tyr Ala Thr Asp His Ser Gly Arg
    50                  55                  60

Glu Ala Leu Leu Gly Cys Gly Ala Val Leu Asp His Phe Arg Val Ala
65                  70                  75                  80

Met Ala Ala Ala Gly Thr Thr Ala Asn Val Glu Arg Phe Pro Asn Pro
                85                  90                  95

Asn Asp Pro Leu His Leu Ala Ser Ile Asp Phe Ser Pro Ala Asp Phe
            100                 105                 110

Val Thr Glu Gly His Arg Leu Arg Ala Asp Ala Ile Leu Leu Arg Arg
        115                 120                 125

Thr Asp Arg Leu Pro Phe Ala Glu Pro Pro Asp Trp Asp Leu Val Glu
    130                 135                 140

Ser Gln Leu Arg Thr Thr Val Thr Ala Asp Thr Val Arg Ile Asp Val
145                 150                 155                 160

Ile Ala Asp Asp Met Arg Pro Glu Leu Ala Ala Ser Lys Leu Thr
                165                 170                 175

Glu Ser Leu Arg Leu Tyr Asp Ser Ser Tyr His Ala Glu Leu Phe Trp
            180                 185                 190

Trp Thr Gly Ala Phe Glu Thr Ser Glu Gly Ile Pro His Ser Ser Leu
        195                 200                 205

Val Ser Ala Ala Glu Ser Asp Arg Val Thr Phe Gly Arg Asp Phe Pro
    210                 215                 220

Val Val Ala Asn Thr Asp Arg Arg Pro Glu Phe Gly His Asp Arg Ser
225                 230                 235                 240

Lys Val Leu Val Leu Ser Thr Tyr Asp Asn Glu Arg Ala Ser Leu Leu
                245                 250                 255
```

```
Arg Cys Gly Glu Met Leu Ser Ala Val Leu Leu Asp Ala Thr Met Ala
            260                 265                 270

Gly Leu Ala Thr Cys Thr Leu Thr His Ile Thr Glu Leu His Ala Ser
            275                 280                 285

Arg Asp Leu Val Ala Ala Leu Ile Gly Gln Pro Ala Thr Pro Gln Ala
            290                 295                 300

Leu Val Arg Val Gly Leu Ala Pro Glu Met Glu Glu Pro Pro Ala
305                 310                 315                 320

Thr Pro Arg Arg Pro Ile Asp Glu Val Phe His Val Arg Ala Lys Asp
                325                 330                 335

His Arg His His His His His
            340

<210> SEQ ID NO 25
<211> LENGTH: 463
<212> TYPE: PRT
<213> ORGANISM: Mycobacterium tuberculosis

<400> SEQUENCE: 25

Met Asn His Leu Thr Thr Leu Asp Ala Gly Phe Leu Lys Ala Glu Asp
1               5                   10                  15

Val Asp Arg His Val Ser Leu Ala Ile Gly Ala Leu Ala Val Ile Glu
            20                  25                  30

Gly Pro Ala Pro Asp Gln Glu Ala Phe Leu Ser Ser Leu Ala Gln Arg
            35                  40                  45

Leu Arg Pro Cys Thr Arg Phe Gly Gln Arg Leu Arg Leu Arg Pro Phe
    50                  55                  60

Asp Leu Gly Ala Pro Lys Trp Val Asp Pro Asp Phe Asp Leu Gly
65                  70                  75                  80

Arg His Val Trp Arg Ile Ala Leu Pro Arg Pro Gly Asn Glu Asp Gln
                85                  90                  95

Leu Phe Glu Leu Ile Ala Asp Leu Met Ala Arg Arg Leu Asp Arg Gly
            100                 105                 110

Arg Pro Leu Trp Glu Val Trp Val Ile Glu Gly Leu Ala Asp Ser Lys
        115                 120                 125

Trp Ala Ile Leu Thr Lys Leu His His Cys Met Ala Asp Gly Ile Ala
130                 135                 140

Ala Thr His Leu Leu Ala Gly Leu Ser Asp Glu Ser Met Ser Asp Ser
145                 150                 155                 160

Phe Ala Ser Asn Ile His Thr Thr Met Gln Ser Gln Ser Ala Ser Val
                165                 170                 175

Arg Arg Gly Gly Phe Arg Val Asn Pro Ser Glu Ala Leu Thr Ala Ser
            180                 185                 190

Thr Ala Val Met Ala Gly Ile Val Arg Ala Ala Lys Gly Ala Ser Glu
            195                 200                 205

Ile Ala Ala Gly Val Leu Ser Pro Ala Ala Ser Leu Asn Gly Pro
        210                 215                 220

Ile Ser Asp Leu Arg Arg Tyr Ser Ala Ala Lys Val Pro Leu Ala Asp
225                 230                 235                 240

Val Glu Gln Val Cys Arg Lys Phe Asp Val Thr Ile Asn Asp Val Ala
                245                 250                 255

Leu Ala Ala Ile Thr Glu Ser Tyr Arg Asn Val Leu Ile Gln Arg Gly
            260                 265                 270

Glu Arg Pro Arg Phe Asp Ser Leu Arg Thr Leu Val Pro Val Ser Thr
```

```
            275                 280                 285
Arg Ser Asn Ser Ala Leu Ser Lys Thr Asp Asn Arg Val Ser Leu Met
    290                 295                 300

Leu Pro Asn Leu Pro Val Asp Gln Glu Asn Pro Leu Gln Arg Leu Arg
305                 310                 315                 320

Ile Val His Ser Arg Leu Thr Arg Ala Lys Ala Gly Gly Gln Arg Gln
                325                 330                 335

Phe Gly Asn Thr Leu Met Ala Ile Ala Asn Arg Leu Pro Phe Pro Met
            340                 345                 350

Thr Ala Trp Ala Val Gly Leu Leu Met Arg Leu Pro Gln Arg Gly Val
        355                 360                 365

Val Thr Val Ala Thr Asn Val Pro Gly Pro Arg Arg Pro Leu Gln Ile
370                 375                 380

Met Gly Arg Arg Val Leu Asp Leu Tyr Pro Val Ser Pro Ile Ala Met
385                 390                 395                 400

Gln Leu Arg Thr Ser Val Ala Met Leu Ser Tyr Ala Asp Asp Leu Tyr
                405                 410                 415

Phe Gly Ile Leu Ala Asp Tyr Asp Val Val Ala Asp Ala Gly Gln Leu
            420                 425                 430

Ala Arg Gly Ile Glu Asp Ala Val Ala Arg Leu Val Ala Ile Ser Lys
        435                 440                 445

Arg Arg Lys Val Thr Arg Arg Gly Ala Leu Ser Leu Val Val
    450                 455                 460

<210> SEQ ID NO 26
<211> LENGTH: 1431
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1431)

<400> SEQUENCE: 26 atg gcc gac gag gca cca act agt aat cac tta aca aca ttg gac gcg      48
Met Ala Asp Glu Ala Pro Thr Ser Asn His Leu Thr Thr Leu Asp Ala
1               5                   10                  15 gga ttc ttg aaa gct gaa gat gta gat aga cat gta tca ttg gca att      96
Gly Phe Leu Lys Ala Glu Asp Val Asp Arg His Val Ser Leu Ala Ile
            20                  25                  30 ggt gcc ctt gct gtg att gaa ggc cca gca cct gat cag gaa gct ttc     144
Gly Ala Leu Ala Val Ile Glu Gly Pro Ala Pro Asp Gln Glu Ala Phe
        35                  40                  45 ctg agt tca tta gca caa cgt tta aga cca tgt act aga ttc ggg caa     192
Leu Ser Ser Leu Ala Gln Arg Leu Arg Pro Cys Thr Arg Phe Gly Gln
    50                  55                  60 aga cta aga ctc aga cca ttt gat ctt ggg gcg cca aag tgg gta gat     240
Arg Leu Arg Leu Arg Pro Phe Asp Leu Gly Ala Pro Lys Trp Val Asp
65                  70                  75                  80 gat cct gat ttt gat ttg ggc aga cat gtt tgg aga atc gca cta cct     288
Asp Pro Asp Phe Asp Leu Gly Arg His Val Trp Arg Ile Ala Leu Pro
                85                  90                  95 aga cca gga aac gag gat caa ttg ttt gaa ttg atc gct gac ctg atg     336
Arg Pro Gly Asn Glu Asp Gln Leu Phe Glu Leu Ile Ala Asp Leu Met
            100                 105                 110 gcc aga agg ctt gac aga ggt agg cca tta tgg gaa gta tgg gtt ata     384
Ala Arg Arg Leu Asp Arg Gly Arg Pro Leu Trp Glu Val Trp Val Ile
        115                 120                 125
```

```
gag ggt ttg gcc gat tct aaa tgg gct att ttg acc aaa ctg cat cac     432
Glu Gly Leu Ala Asp Ser Lys Trp Ala Ile Leu Thr Lys Leu His His
    130                 135                 140 tgc atg gca gac ggt atc gcc gct acg cac tta ctc gct ggt cta tca     480
Cys Met Ala Asp Gly Ile Ala Ala Thr His Leu Leu Ala Gly Leu Ser
145                 150                 155                 160 gat gaa tcc atg tct gac tct ttt gct tct aat atc cac act act atg     528
Asp Glu Ser Met Ser Asp Ser Phe Ala Ser Asn Ile His Thr Thr Met
                165                 170                 175 cag tct caa agt gcg tca gtt aga aga ggt gga ttc aga gtc aac cct     576
Gln Ser Gln Ser Ala Ser Val Arg Arg Gly Gly Phe Arg Val Asn Pro
            180                 185                 190 tct gaa gca tta aca gca tct aca gca gtt atg gca gga ata gtt aga     624
Ser Glu Ala Leu Thr Ala Ser Thr Ala Val Met Ala Gly Ile Val Arg
        195                 200                 205 gct gca aaa ggt gcc tcc gaa att gcc gct ggc gtt cta tcc cca gcc     672
Ala Ala Lys Gly Ala Ser Glu Ile Ala Ala Gly Val Leu Ser Pro Ala
    210                 215                 220 gcc tca agc ctc aac gga cct ata tct gac ttg aga aga tac tca gct     720
Ala Ser Ser Leu Asn Gly Pro Ile Ser Asp Leu Arg Arg Tyr Ser Ala
225                 230                 235                 240 gct aag gtc cct ttg gct gat gta gaa caa gtc tgt cgt aag ttt gat     768
Ala Lys Val Pro Leu Ala Asp Val Glu Gln Val Cys Arg Lys Phe Asp
                245                 250                 255 gtg aca att aac gat gtt gct ttg gca gct att act gaa agc tac aga     816
Val Thr Ile Asn Asp Val Ala Leu Ala Ala Ile Thr Glu Ser Tyr Arg
            260                 265                 270 aac gtc cta atc caa agg gga gaa aga cct aga ttt gat tct ctc aga     864
Asn Val Leu Ile Gln Arg Gly Glu Arg Pro Arg Phe Asp Ser Leu Arg
        275                 280                 285 aca tta gta cca gta agt acc aga tca aat tca gct cta tct aag acc     912
Thr Leu Val Pro Val Ser Thr Arg Ser Asn Ser Ala Leu Ser Lys Thr
    290                 295                 300 gac aat aga gtg tcc cta atg ctt cct aat ctt cca gtc gac cag gag     960
Asp Asn Arg Val Ser Leu Met Leu Pro Asn Leu Pro Val Asp Gln Glu
305                 310                 315                 320 aat cca ctg caa aga ctt aga atc gtg cat tct cgt ttg aca aga gcc    1008
Asn Pro Leu Gln Arg Leu Arg Ile Val His Ser Arg Leu Thr Arg Ala
                325                 330                 335 aaa gcg gga ggt caa cga caa ttt ggt aat act tta atg gca ata gcc    1056
Lys Ala Gly Gly Gln Arg Gln Phe Gly Asn Thr Leu Met Ala Ile Ala
            340                 345                 350 aat aga ttg cca ttt cca atg acg gca tgg gca gtt ggg tta ttg atg    1104
Asn Arg Leu Pro Phe Pro Met Thr Ala Trp Ala Val Gly Leu Leu Met
        355                 360                 365 aga ttg cct caa agg ggc gtt gtg act gtt gca aca aac gtg cca ggg    1152
Arg Leu Pro Gln Arg Gly Val Val Thr Val Ala Thr Asn Val Pro Gly
    370                 375                 380 cca cgc aga cca cta caa atc atg ggt aga aga gtc ttg gat ctt tat    1200
Pro Arg Arg Pro Leu Gln Ile Met Gly Arg Arg Val Leu Asp Leu Tyr
385                 390                 395                 400 cct gtt tct ccc att gcc atg cag ctc cgt aca tcg gtt gct atg ctt    1248
Pro Val Ser Pro Ile Ala Met Gln Leu Arg Thr Ser Val Ala Met Leu
                405                 410                 415 tca tat gct gat gac tta tac ttc ggc att ctg gct gat tac gat gtt    1296
Ser Tyr Ala Asp Asp Leu Tyr Phe Gly Ile Leu Ala Asp Tyr Asp Val
            420                 425                 430 gtt gct gat gcg ggc caa tta gct aga ggt atc gag gac gct gta gca    1344
Val Ala Asp Ala Gly Gln Leu Ala Arg Gly Ile Glu Asp Ala Val Ala
```

|  |  |  |  |  |  |  |  |  |  |  |  |  |  |
|---|---|---|---|---|---|---|---|---|---|---|---|---|---|
| | | | 435 | | | | 440 | | | | 445 | | |
| aga | ttg | gtg | gct | atc | tcc | aag | aga | agg | aaa | gtt | act | aga | cgt | cga | ggt | | 1392 |
| Arg | Leu | Val | Ala | Ile | Ser | Lys | Arg | Arg | Lys | Val | Thr | Arg | Arg | Arg | Gly | | |
| | 450 | | | | | 455 | | | | | 460 | | | | | | |
| gcc | ctg | tct | tta | gtc | gtc | cat | cac | cat | cat | cat | cat | taa | | | | | 1431 |
| Ala | Leu | Ser | Leu | Val | Val | His | His | His | His | His | His | | | | | | |
| 465 | | | | 470 | | | | | 475 | | | | | | | | |

<210> SEQ ID NO 27
<211> LENGTH: 476
<212> TYPE: PRT
<213> ORGANISM: Artificial
<220> FEATURE:
<223> OTHER INFORMATION: Synthetic Construct

<400> SEQUENCE: 27

Met Ala Asp Glu Ala Pro Thr Ser Asn His Leu Thr Thr Leu Asp Ala
1               5                   10                  15

Gly Phe Leu Lys Ala Glu Asp Val Asp Arg His Val Ser Leu Ala Ile
            20                  25                  30

Gly Ala Leu Ala Val Ile Glu Gly Pro Ala Pro Asp Gln Glu Ala Phe
        35                  40                  45

Leu Ser Ser Leu Ala Gln Arg Leu Arg Pro Cys Thr Arg Phe Gly Gln
    50                  55                  60

Arg Leu Arg Leu Arg Pro Phe Asp Leu Gly Ala Pro Lys Trp Val Asp
65                  70                  75                  80

Asp Pro Asp Phe Asp Leu Gly Arg His Val Trp Arg Ile Ala Leu Pro
                85                  90                  95

Arg Pro Gly Asn Glu Asp Gln Leu Phe Glu Leu Ile Ala Asp Leu Met
            100                 105                 110

Ala Arg Arg Leu Asp Arg Gly Arg Pro Leu Trp Glu Val Trp Val Ile
        115                 120                 125

Glu Gly Leu Ala Asp Ser Lys Trp Ala Ile Leu Thr Lys Leu His His
    130                 135                 140

Cys Met Ala Asp Gly Ile Ala Ala Thr His Leu Leu Ala Gly Leu Ser
145                 150                 155                 160

Asp Glu Ser Met Ser Asp Ser Phe Ala Ser Asn Ile His Thr Thr Met
                165                 170                 175

Gln Ser Gln Ser Ala Ser Val Arg Arg Gly Gly Phe Arg Val Asn Pro
            180                 185                 190

Ser Glu Ala Leu Thr Ala Ser Thr Ala Val Met Ala Gly Ile Val Arg
        195                 200                 205

Ala Ala Lys Gly Ala Ser Glu Ile Ala Ala Gly Val Leu Ser Pro Ala
    210                 215                 220

Ala Ser Ser Leu Asn Gly Pro Ile Ser Asp Leu Arg Arg Tyr Ser Ala
225                 230                 235                 240

Ala Lys Val Pro Leu Ala Asp Val Glu Gln Val Cys Arg Lys Phe Asp
                245                 250                 255

Val Thr Ile Asn Asp Val Ala Leu Ala Ala Ile Thr Glu Ser Tyr Arg
            260                 265                 270

Asn Val Leu Ile Gln Arg Gly Glu Arg Pro Arg Phe Asp Ser Leu Arg
        275                 280                 285

Thr Leu Val Pro Val Ser Thr Arg Ser Asn Ser Ala Leu Ser Lys Thr
    290                 295                 300

Asp Asn Arg Val Ser Leu Met Leu Pro Asn Leu Pro Val Asp Gln Glu
305                 310                 315                 320

```
Asn Pro Leu Gln Arg Leu Arg Ile Val His Ser Arg Leu Thr Arg Ala
                325                 330                 335

Lys Ala Gly Gly Gln Arg Gln Phe Gly Asn Thr Leu Met Ala Ile Ala
            340                 345                 350

Asn Arg Leu Pro Phe Pro Met Thr Ala Trp Ala Val Gly Leu Leu Met
        355                 360                 365

Arg Leu Pro Gln Arg Gly Val Val Thr Val Ala Thr Asn Val Pro Gly
    370                 375                 380

Pro Arg Arg Pro Leu Gln Ile Met Gly Arg Arg Val Leu Asp Leu Tyr
385                 390                 395                 400

Pro Val Ser Pro Ile Ala Met Gln Leu Arg Thr Ser Val Ala Met Leu
                405                 410                 415

Ser Tyr Ala Asp Asp Leu Tyr Phe Gly Ile Leu Ala Asp Tyr Asp Val
            420                 425                 430

Val Ala Asp Ala Gly Gln Leu Ala Arg Gly Ile Glu Asp Ala Val Ala
        435                 440                 445

Arg Leu Val Ala Ile Ser Lys Arg Lys Val Thr Arg Arg Gly
    450                 455                 460

Ala Leu Ser Leu Val Val His His His His His His
465                 470                 475
```

<210> SEQ ID NO 28
<211> LENGTH: 181
<212> TYPE: PRT
<213> ORGANISM: Mycobacterium tuberculosis

<400> SEQUENCE: 28

```
Met Thr Glu Tyr Glu Gly Pro Lys Thr Lys Phe His Ala Leu Met Gln
1               5                   10                  15

Glu Gln Ile His Asn Glu Phe Thr Ala Ala Gln Gln Tyr Val Ala Ile
            20                  25                  30

Ala Val Tyr Phe Asp Ser Glu Asp Leu Pro Gln Leu Ala Lys His Phe
        35                  40                  45

Tyr Ser Gln Ala Val Glu Glu Arg Asn His Ala Met Met Leu Val Gln
    50                  55                  60

His Leu Leu Asp Arg Asp Leu Arg Val Glu Ile Pro Gly Val Asp Thr
65                  70                  75                  80

Val Arg Asn Gln Phe Asp Arg Pro Arg Glu Ala Leu Ala Leu Ala Leu
                85                  90                  95

Asp Gln Glu Arg Thr Val Thr Asp Gln Val Gly Arg Leu Thr Ala Val
            100                 105                 110

Ala Arg Asp Glu Gly Asp Phe Leu Gly Glu Gln Phe Met Gln Trp Phe
        115                 120                 125

Leu Gln Glu Gln Ile Glu Glu Val Ala Leu Met Ala Thr Leu Val Arg
    130                 135                 140

Val Ala Asp Arg Ala Gly Ala Asn Leu Phe Glu Leu Glu Asn Phe Val
145                 150                 155                 160

Ala Arg Glu Val Asp Val Ala Pro Ala Ala Ser Gly Ala Pro His Ala
                165                 170                 175

Ala Gly Gly Arg Leu
            180
```

<210> SEQ ID NO 29
<211> LENGTH: 570
<212> TYPE: DNA

```
<213> ORGANISM: Artificial
<220> FEATURE:
<223> OTHER INFORMATION: Synthetic Construct
<220> FEATURE:
<221> NAME/KEY: CDS
<222> LOCATION: (1)..(570)

<400> SEQUENCE: 29 atg gcc gac gag gca cca act agt aca gaa tac gaa gga cca aaa aca      48
Met Ala Asp Glu Ala Pro Thr Ser Thr Glu Tyr Glu Gly Pro Lys Thr
1               5                  10                  15 aag ttt cat gct tta atg caa gag caa att cat aac gaa ttt aca gcg      96
Lys Phe His Ala Leu Met Gln Glu Gln Ile His Asn Glu Phe Thr Ala
            20                  25                  30 gct cag caa tac gtg gct atc gcc gta tac ttt gat tct gaa gat ctt     144
Ala Gln Gln Tyr Val Ala Ile Ala Val Tyr Phe Asp Ser Glu Asp Leu
        35                  40                  45 cct caa ctg gcc aaa cac ttc tat tcc caa gca gta gaa gct atg atg     192
Pro Gln Leu Ala Lys His Phe Tyr Ser Gln Ala Val Glu Ala Met Met
    50                  55                  60 ctt gtc caa cat ttg ctg gac aga gat ttg cga gta gaa atc cct ggt     240
Leu Val Gln His Leu Leu Asp Arg Asp Leu Arg Val Glu Ile Pro Gly
65                  70                  75                  80 gtt gat act gtc aga aat caa ttt gat aga cca aga gaa gca tta gca     288
Val Asp Thr Val Arg Asn Gln Phe Asp Arg Pro Arg Glu Ala Leu Ala
                85                  90                  95 ttg gct cta gat cag gaa agg acg gtt aca gac caa gtt ggg aga ttg     336
Leu Ala Leu Asp Gln Glu Arg Thr Val Thr Asp Gln Val Gly Arg Leu
            100                 105                 110 acc gcc gtt gct aga gat gaa gga gat ttc tta ggt gaa caa ttc atg     384
Thr Ala Val Ala Arg Asp Glu Gly Asp Phe Leu Gly Glu Gln Phe Met
        115                 120                 125 caa tgg ttt ttg caa gag cag ata gag gaa gtc gcc ctt atg gct act     432
Gln Trp Phe Leu Gln Glu Gln Ile Glu Glu Val Ala Leu Met Ala Thr
    130                 135                 140 ctc gtt aga gtg gct gac cgt gct ggt gcg aat cta ttt gaa tta gag     480
Leu Val Arg Val Ala Asp Arg Ala Gly Ala Asn Leu Phe Glu Leu Glu
145                 150                 155                 160 aac ttc gtg gct aga gaa gtc gac gtt gca cca gcc gca tca ggc gca     528
Asn Phe Val Ala Arg Glu Val Asp Val Ala Pro Ala Ala Ser Gly Ala
                165                 170                 175 cct cat gct gca ggc ggt aga cac cat cat cat cac cac taa             570
Pro His Ala Ala Gly Gly Arg His His His His His His
            180                 185

<210> SEQ ID NO 30
<211> LENGTH: 189
<212> TYPE: PRT
<213> ORGANISM: Artificial
<220> FEATURE:
<223> OTHER INFORMATION: Synthetic Construct

<400> SEQUENCE: 30

Met Ala Asp Glu Ala Pro Thr Ser Thr Glu Tyr Glu Gly Pro Lys Thr
1               5                   10                  15

Lys Phe His Ala Leu Met Gln Glu Gln Ile His Asn Glu Phe Thr Ala
            20                  25                  30

Ala Gln Gln Tyr Val Ala Ile Ala Val Tyr Phe Asp Ser Glu Asp Leu
        35                  40                  45

Pro Gln Leu Ala Lys His Phe Tyr Ser Gln Ala Val Glu Ala Met Met
    50                  55                  60
```

```
Leu Val Gln His Leu Leu Asp Arg Asp Leu Arg Val Glu Ile Pro Gly
 65                  70                  75                  80

Val Asp Thr Val Arg Asn Gln Phe Asp Arg Pro Arg Glu Ala Leu Ala
                 85                  90                  95

Leu Ala Leu Asp Gln Glu Arg Thr Val Thr Asp Gln Val Gly Arg Leu
            100                 105                 110

Thr Ala Val Ala Arg Asp Glu Gly Asp Phe Leu Gly Glu Gln Phe Met
        115                 120                 125

Gln Trp Phe Leu Gln Glu Gln Ile Glu Glu Val Ala Leu Met Ala Thr
    130                 135                 140

Leu Val Arg Val Ala Asp Arg Ala Gly Ala Asn Leu Phe Glu Leu Glu
145                 150                 155                 160

Asn Phe Val Ala Arg Glu Val Asp Val Ala Pro Ala Ala Ser Gly Ala
                165                 170                 175

Pro His Ala Ala Gly Gly Arg His His His His His
            180                 185

<210> SEQ ID NO 31
<211> LENGTH: 1060
<212> TYPE: PRT
<213> ORGANISM: Artificial
<220> FEATURE:
<223> OTHER INFORMATION: Synthetic Construct

<400> SEQUENCE: 31

Cys Gly Asp Gln Ser Asp His Val Leu Gln His Trp Thr Val Asp Ile
  1               5                  10                  15

Ser Ile Asp Glu His Glu Gly Leu Thr Arg Ala Lys Ala Arg Leu Arg
                 20                  25                  30

Trp Arg Glu Lys Glu Leu Val Gly Val Gly Leu Ala Arg Leu Asn Pro
             35                  40                  45

Ala Asp Arg Asn Val Pro Glu Ile Gly Asp Glu Leu Ser Val Ala Arg
         50                  55                  60

Ala Leu Ser Asp Leu Gly Lys Arg Met Leu Lys Val Ser Thr His Asp
 65                  70                  75                  80

Ile Glu Ala Val Thr His Gln Pro Ala Arg Leu Leu Tyr Pro Asp Thr
                 85                  90                  95

Met Val Thr Thr Asp Val Ile Lys Ser Arg Val Gln Leu Ala Cys Arg
            100                 105                 110

Ala Pro Ser Leu His Asn Ser Gln Pro Trp Arg Trp Ile Ala Glu Asp
        115                 120                 125

His Thr Val Ala Leu Phe Leu Asp Lys Asp Arg Val Leu Tyr Ala Thr
    130                 135                 140

Asp His Ser Gly Arg Glu Ala Leu Leu Gly Cys Gly Ala Val Leu Asp
145                 150                 155                 160

His Phe Arg Val Ala Met Ala Ala Ala Gly Thr Thr Ala Asn Val Glu
                165                 170                 175

Arg Phe Pro Asn Pro Asn Asp Pro Leu His Leu Ala Ser Ile Asp Phe
            180                 185                 190

Ser Pro Ala Asp Phe Val Thr Glu Gly His Arg Leu Arg Ala Asp Ala
        195                 200                 205

Ile Leu Leu Arg Arg Thr Asp Arg Leu Pro Phe Ala Glu Pro Pro Asp
    210                 215                 220

Trp Asp Leu Val Glu Ser Gln Leu Arg Thr Thr Val Thr Ala Asp Thr
225                 230                 235                 240
```

```
Val Arg Ile Asp Val Ile Ala Asp Asp Met Arg Pro Glu Leu Ala Ala
            245                 250                 255

Ala Ser Lys Leu Thr Glu Ser Leu Arg Leu Tyr Asp Ser Ser Tyr His
        260                 265                 270

Ala Glu Leu Phe Trp Trp Thr Gly Ala Phe Glu Thr Ser Glu Gly Ile
            275                 280                 285

Pro His Ser Ser Leu Val Ser Ala Ala Glu Ser Asp Arg Val Thr Phe
        290                 295                 300

Gly Arg Asp Phe Pro Val Val Ala Asn Thr Asp Arg Arg Pro Glu Phe
305                 310                 315                 320

Gly His Asp Arg Ser Lys Val Leu Val Leu Ser Thr Tyr Asp Asn Glu
            325                 330                 335

Arg Ala Ser Leu Leu Arg Cys Gly Glu Met Leu Ser Ala Val Leu Leu
            340                 345                 350

Asp Ala Thr Met Ala Gly Leu Ala Thr Cys Thr Leu Thr His Ile Thr
            355                 360                 365

Glu Leu His Ala Ser Arg Asp Leu Val Ala Ala Leu Ile Gly Gln Pro
        370                 375                 380

Ala Thr Pro Gln Ala Leu Val Arg Val Gly Leu Ala Pro Glu Met Glu
385                 390                 395                 400

Glu Pro Pro Pro Ala Thr Pro Arg Arg Pro Ile Asp Glu Val Phe His
            405                 410                 415

Val Arg Ala Lys Asp His Arg Asn His Leu Thr Thr Leu Asp Ala Gly
            420                 425                 430

Phe Leu Lys Ala Glu Asp Val Asp Arg His Val Ser Leu Ala Ile Gly
        435                 440                 445

Ala Leu Ala Val Ile Glu Gly Pro Ala Pro Asp Gln Glu Ala Phe Leu
450                 455                 460

Ser Ser Leu Ala Gln Arg Leu Arg Pro Cys Thr Arg Phe Gly Gln Arg
465                 470                 475                 480

Leu Arg Leu Arg Pro Phe Asp Leu Gly Ala Pro Lys Trp Val Asp Asp
            485                 490                 495

Pro Asp Phe Asp Leu Gly Arg His Val Trp Arg Ile Ala Leu Pro Arg
        500                 505                 510

Pro Gly Asn Glu Asp Gln Leu Phe Glu Leu Ile Ala Asp Leu Met Ala
        515                 520                 525

Arg Arg Leu Asp Arg Gly Arg Pro Leu Trp Glu Val Trp Ile Glu
        530                 535                 540

Gly Leu Ala Asp Ser Lys Trp Ala Ile Leu Thr Lys Leu His His Cys
545                 550                 555                 560

Met Ala Asp Gly Ile Ala Ala Thr His Leu Leu Ala Gly Leu Ser Asp
            565                 570                 575

Glu Ser Met Ser Asp Ser Phe Ala Ser Asn Ile His Thr Thr Met Gln
        580                 585                 590

Ser Gln Ser Ala Ser Val Arg Arg Gly Gly Phe Arg Val Asn Pro Ser
        595                 600                 605

Glu Ala Leu Thr Ala Ser Thr Ala Val Met Ala Gly Ile Val Arg Ala
        610                 615                 620

Ala Lys Gly Ala Ser Glu Ile Ala Ala Gly Val Leu Ser Pro Ala Ala
625                 630                 635                 640

Ser Ser Leu Asn Gly Pro Ile Ser Asp Leu Arg Arg Tyr Ser Ala Ala
            645                 650                 655

Lys Val Pro Leu Ala Asp Val Glu Gln Val Cys Arg Lys Phe Asp Val
```

```
                    660                 665                 670
Thr Ile Asn Asp Val Ala Leu Ala Ala Ile Thr Glu Ser Tyr Arg Asn
            675                 680                 685

Val Leu Ile Gln Arg Gly Glu Arg Pro Arg Phe Asp Ser Leu Arg Thr
        690                 695                 700

Leu Val Pro Val Ser Thr Arg Ser Asn Ser Ala Leu Ser Lys Thr Asp
705                 710                 715                 720

Asn Arg Val Ser Leu Met Leu Pro Asn Leu Pro Val Asp Gln Glu Asn
                725                 730                 735

Pro Leu Gln Arg Leu Arg Ile Val His Ser Arg Leu Thr Arg Ala Lys
            740                 745                 750

Ala Gly Gly Gln Arg Gln Phe Gly Asn Thr Leu Met Ala Ile Ala Asn
        755                 760                 765

Arg Leu Pro Phe Pro Met Thr Ala Trp Ala Val Gly Leu Leu Met Arg
    770                 775                 780

Leu Pro Gln Arg Gly Val Val Thr Val Ala Thr Asn Val Pro Gly Pro
785                 790                 795                 800

Arg Arg Pro Leu Gln Ile Met Gly Arg Arg Val Leu Asp Leu Tyr Pro
                805                 810                 815

Val Ser Pro Ile Ala Met Gln Leu Arg Thr Ser Val Ala Met Leu Ser
            820                 825                 830

Tyr Ala Asp Asp Leu Tyr Phe Gly Ile Leu Ala Asp Tyr Asp Val Val
        835                 840                 845

Ala Asp Ala Gly Gln Leu Ala Arg Gly Ile Glu Asp Ala Val Ala Arg
    850                 855                 860

Leu Val Ala Ile Ser Lys Arg Arg Lys Val Thr Arg Arg Arg Gly Ala
865                 870                 875                 880

Leu Ser Leu Val Val Thr Glu Tyr Glu Gly Pro Lys Thr Lys Phe His
                885                 890                 895

Ala Leu Met Gln Glu Gln Ile His Asn Glu Phe Thr Ala Ala Gln Gln
            900                 905                 910

Tyr Val Ala Ile Ala Val Tyr Phe Asp Ser Glu Asp Leu Pro Gln Leu
        915                 920                 925

Ala Lys His Phe Tyr Ser Gln Ala Val Glu Ala Met Met Leu Val Gln
    930                 935                 940

His Leu Leu Asp Arg Asp Leu Arg Val Glu Ile Pro Gly Val Asp Thr
945                 950                 955                 960

Val Arg Asn Gln Phe Asp Arg Pro Arg Glu Ala Leu Ala Leu Ala Leu
                965                 970                 975

Asp Gln Glu Arg Thr Val Thr Asp Gln Val Gly Arg Leu Thr Ala Val
            980                 985                 990

Ala Arg Asp Glu Gly Asp Phe Leu Gly Glu Gln Phe Met Gln Trp Phe
        995                 1000                1005

Leu Gln Glu Gln Ile Glu Glu Val Ala Leu Met Ala Thr Leu Val
    1010                1015                1020

Arg Val Ala Asp Arg Ala Gly Ala Asn Leu Phe Glu Leu Glu Asn
    1025                1030                1035

Phe Val Ala Arg Glu Val Asp Val Ala Pro Ala Ala Ser Gly Ala
    1040                1045                1050

Pro His Ala Ala Gly Gly Arg
    1055                1060

<210> SEQ ID NO 32
```

```
<211> LENGTH: 3225
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(3225)

<400> SEQUENCE: 32 atg gcc gac gag gca cca act agt tgc ggc gac cag tca gat cac gtt      48
Met Ala Asp Glu Ala Pro Thr Ser Cys Gly Asp Gln Ser Asp His Val
1               5                   10                  15 ctg caa cat tgg aca gtc gat atc tca att gat gaa cat gaa ggt ttg      96
Leu Gln His Trp Thr Val Asp Ile Ser Ile Asp Glu His Glu Gly Leu
            20                  25                  30 act aga gct aaa gct aga ctt cga tgg aga gag aag gaa ttg gtt ggt     144
Thr Arg Ala Lys Ala Arg Leu Arg Trp Arg Glu Lys Glu Leu Val Gly
        35                  40                  45 gtg ggt ttg gct agg ctt aat cct gct gac aga aac gta cca gaa att     192
Val Gly Leu Ala Arg Leu Asn Pro Ala Asp Arg Asn Val Pro Glu Ile
50                  55                  60 ggg gat gaa ttg tcc gtc gcc aga gcc ttg agt gat ctc gga aag agg     240
Gly Asp Glu Leu Ser Val Ala Arg Ala Leu Ser Asp Leu Gly Lys Arg
65                  70                  75                  80 atg ttg aaa gtg tcg act cac gac atc gag gca gtg act cat caa cca     288
Met Leu Lys Val Ser Thr His Asp Ile Glu Ala Val Thr His Gln Pro
                85                  90                  95 gca agg ctc ctt tat cct gat aca atg gta aca act gac gtt atc aaa     336
Ala Arg Leu Leu Tyr Pro Asp Thr Met Val Thr Thr Asp Val Ile Lys
            100                 105                 110 tct aga gta caa ttg gct tgc aga gcc cca tca tta cat aat tcc caa     384
Ser Arg Val Gln Leu Ala Cys Arg Ala Pro Ser Leu His Asn Ser Gln
        115                 120                 125 cca tgg cgc tgg att gcc gag gat cac aca gtg gca cta ttc tta gac     432
Pro Trp Arg Trp Ile Ala Glu Asp His Thr Val Ala Leu Phe Leu Asp
130                 135                 140 aaa gat aga gtt ctt tat gct aca gat cat agt ggc aga gaa gca ctg     480
Lys Asp Arg Val Leu Tyr Ala Thr Asp His Ser Gly Arg Glu Ala Leu
145                 150                 155                 160 ctg gga tgt ggt gct gtc cta gac cac ttc aga gtt gct atg gct gcg     528
Leu Gly Cys Gly Ala Val Leu Asp His Phe Arg Val Ala Met Ala Ala
                165                 170                 175 gcg ggc acc aca gca aat gtc gaa cga ttc cca aat cct aac gat cca     576
Ala Gly Thr Thr Ala Asn Val Glu Arg Phe Pro Asn Pro Asn Asp Pro
            180                 185                 190 tta cat ctt gca tct att gac ttt tct cct gct gat ttt gtc aca gaa     624
Leu His Leu Ala Ser Ile Asp Phe Ser Pro Ala Asp Phe Val Thr Glu
        195                 200                 205 ggc cac aga ttg aga gct gat gcg atc tta ttg agg aga aca gat aga     672
Gly His Arg Leu Arg Ala Asp Ala Ile Leu Leu Arg Arg Thr Asp Arg
210                 215                 220 ttg cct ttc gct gag cct cca gac tgg gac tta gta gaa tca cag ttg     720
Leu Pro Phe Ala Glu Pro Pro Asp Trp Asp Leu Val Glu Ser Gln Leu
225                 230                 235                 240 agg act aca gtt act gct gat acc gtt aga atc gat gtt ata gcg gat     768
Arg Thr Thr Val Thr Ala Asp Thr Val Arg Ile Asp Val Ile Ala Asp
                245                 250                 255 gat atg agg cca gaa ctt gca gcc gca tcc aaa ttg acc gaa tct ttg     816
Asp Met Arg Pro Glu Leu Ala Ala Ala Ser Lys Leu Thr Glu Ser Leu
            260                 265                 270
```

```
aga cta tac gat agc tct tac cat gcg gaa ctg ttt tgg tgg act ggt      864
Arg Leu Tyr Asp Ser Ser Tyr His Ala Glu Leu Phe Trp Trp Thr Gly
        275                 280                 285 gct ttc gaa aca tct gaa ggg ata cca cat tct tca tta gtt tca gct      912
Ala Phe Glu Thr Ser Glu Gly Ile Pro His Ser Ser Leu Val Ser Ala
    290                 295                 300 gca gaa tcc gat aga gtc act ttt ggt cgt gat ttc cca gtc gta gca      960
Ala Glu Ser Asp Arg Val Thr Phe Gly Arg Asp Phe Pro Val Val Ala
305                 310                 315                 320 aat act gac aga cga cct gaa ttt ggt cat gac aga tct aaa gta ctt     1008
Asn Thr Asp Arg Arg Pro Glu Phe Gly His Asp Arg Ser Lys Val Leu
            325                 330                 335 gtt ctc agc acc tac gat aat gaa agg gct tct ttg tta aga tgc ggt     1056
Val Leu Ser Thr Tyr Asp Asn Glu Arg Ala Ser Leu Leu Arg Cys Gly
        340                 345                 350 gaa atg cta agt gcc gtc tta ctg gat gcg act atg gct gga ttg gca     1104
Glu Met Leu Ser Ala Val Leu Leu Asp Ala Thr Met Ala Gly Leu Ala
    355                 360                 365 act tgt aca ctg acc cat atc acg gaa ctg cat gca tca aga gat ctc     1152
Thr Cys Thr Leu Thr His Ile Thr Glu Leu His Ala Ser Arg Asp Leu
370                 375                 380 gta gca gcc ttg att ggc caa cca gcc aca cct caa gcc ctt gtg aga     1200
Val Ala Ala Leu Ile Gly Gln Pro Ala Thr Pro Gln Ala Leu Val Arg
385                 390                 395                 400 gta gga ttg gct cca gag atg gag gaa cca cct cct gct act cca cgt     1248
Val Gly Leu Ala Pro Glu Met Glu Glu Pro Pro Pro Ala Thr Pro Arg
            405                 410                 415 aga ccc atc gac gaa gtg ttc cat gtg aga gct aag gat cat aga aat     1296
Arg Pro Ile Asp Glu Val Phe His Val Arg Ala Lys Asp His Arg Asn
        420                 425                 430 cac ctt act aca ctc gac gcc gga ttc ctt aaa gca gaa gat gta gat     1344
His Leu Thr Thr Leu Asp Ala Gly Phe Leu Lys Ala Glu Asp Val Asp
    435                 440                 445 aga cat gtg agt cta gca atc ggc gct ttg gcc gta att gaa ggc cca     1392
Arg His Val Ser Leu Ala Ile Gly Ala Leu Ala Val Ile Glu Gly Pro
450                 455                 460 gca cca gac cag gaa gct ttt cta tct agt ctt gct cag agg tta aga     1440
Ala Pro Asp Gln Glu Ala Phe Leu Ser Ser Leu Ala Gln Arg Leu Arg
465                 470                 475                 480 cca tgt acg cgt ttc ggt caa aga tta aga cta aga cca ttc gat ctt     1488
Pro Cys Thr Arg Phe Gly Gln Arg Leu Arg Leu Arg Pro Phe Asp Leu
            485                 490                 495 ggc gca cca aag tgg gtg gat gat cct gat ttt gac ctt ggc aga cat     1536
Gly Ala Pro Lys Trp Val Asp Asp Pro Asp Phe Asp Leu Gly Arg His
        500                 505                 510 gtt tgg aga ata gca tta cct aga cct gga aat gag gat caa tta ttt     1584
Val Trp Arg Ile Ala Leu Pro Arg Pro Gly Asn Glu Asp Gln Leu Phe
    515                 520                 525 gaa tta atc gcg gac ttg atg gct aga agg ttg gat aga ggt aga cca     1632
Glu Leu Ile Ala Asp Leu Met Ala Arg Arg Leu Asp Arg Gly Arg Pro
530                 535                 540 cta tgg gag gtt tgg gtt att gaa ggg ctt gcg gat tcc aaa tgg gcc     1680
Leu Trp Glu Val Trp Val Ile Glu Gly Leu Ala Asp Ser Lys Trp Ala
545                 550                 555                 560 ata ctg aca aag ctg cat cac tgt atg gcc gat ggg atc gct gca aca     1728
Ile Leu Thr Lys Leu His His Cys Met Ala Asp Gly Ile Ala Ala Thr
            565                 570                 575 cac ttg tta gcc gga ttg tct gac gag tcg atg tca gat tct ttt gca     1776
His Leu Leu Ala Gly Leu Ser Asp Glu Ser Met Ser Asp Ser Phe Ala
        580                 585                 590
```

-continued

```
tct aac atc cat acg aca atg caa tca caa tct gca tct gtc aga cga      1824
Ser Asn Ile His Thr Thr Met Gln Ser Gln Ser Ala Ser Val Arg Arg
            595                 600                 605 gga ggt ttc aga gtt aat cca tct gag gcg cta acc gct tct aca gcg      1872
Gly Gly Phe Arg Val Asn Pro Ser Glu Ala Leu Thr Ala Ser Thr Ala
    610                 615                 620 gtc atg gcc gga atc gta aga gct gct aag ggt gca agt gag att gct      1920
Val Met Ala Gly Ile Val Arg Ala Ala Lys Gly Ala Ser Glu Ile Ala
625                 630                 635                 640 gcc ggt gtt cta tct cca gcg gct tca tca ttg aac gga cca ata tcc      1968
Ala Gly Val Leu Ser Pro Ala Ala Ser Ser Leu Asn Gly Pro Ile Ser
                645                 650                 655 gac ctc aga aga tac tct gca gct aaa gtt cca ctc gcc gat gtt gaa      2016
Asp Leu Arg Arg Tyr Ser Ala Ala Lys Val Pro Leu Ala Asp Val Glu
            660                 665                 670 caa gtt tgt aga aaa ttt gat gtc acc atc aat gac gta gct cta gct      2064
Gln Val Cys Arg Lys Phe Asp Val Thr Ile Asn Asp Val Ala Leu Ala
        675                 680                 685 gcc att aca gaa tct tac aga aat gtt ctt ata caa aga ggt gaa aga      2112
Ala Ile Thr Glu Ser Tyr Arg Asn Val Leu Ile Gln Arg Gly Glu Arg
    690                 695                 700 cct aga ttc gat tct ttg cgt aca ttg gtt cca gtg agc acc aga tct      2160
Pro Arg Phe Asp Ser Leu Arg Thr Leu Val Pro Val Ser Thr Arg Ser
705                 710                 715                 720 aat agc gct cta tct aag aca gat aac aga gtc agt cta atg ctg ccc      2208
Asn Ser Ala Leu Ser Lys Thr Asp Asn Arg Val Ser Leu Met Leu Pro
                725                 730                 735 aat ttg cca gtg gat cag gaa aac cct ctg caa cga ttg aga att gta      2256
Asn Leu Pro Val Asp Gln Glu Asn Pro Leu Gln Arg Leu Arg Ile Val
            740                 745                 750 cat tcc cgt tta act aga gcg aaa gct ggg ggt caa aga caa ttt ggt      2304
His Ser Arg Leu Thr Arg Ala Lys Ala Gly Gly Gln Arg Gln Phe Gly
        755                 760                 765 aat acc tta atg gca att gct aac aga cta cca ttc cca atg act gct      2352
Asn Thr Leu Met Ala Ile Ala Asn Arg Leu Pro Phe Pro Met Thr Ala
    770                 775                 780 tgg gca gtt ggt tta cta atg cgt tta cca caa aga ggc gta gtc aca      2400
Trp Ala Val Gly Leu Leu Met Arg Leu Pro Gln Arg Gly Val Val Thr
785                 790                 795                 800 gtc gct act aat gtt cct ggg ccg cgt aga cct ctg caa atc atg ggt      2448
Val Ala Thr Asn Val Pro Gly Pro Arg Arg Pro Leu Gln Ile Met Gly
                805                 810                 815 aga agg gtt tta gac ttg tac cct gtt tct cct att gct atg caa ctg      2496
Arg Arg Val Leu Asp Leu Tyr Pro Val Ser Pro Ile Ala Met Gln Leu
            820                 825                 830 aga aca tca gtc gca atg ctt tcc tac gct gat gac ttg tat ttt ggt      2544
Arg Thr Ser Val Ala Met Leu Ser Tyr Ala Asp Asp Leu Tyr Phe Gly
        835                 840                 845 atc ttg gcc gat tac gat gta gtt gcc gac gcc ggg caa ctg gct aga      2592
Ile Leu Ala Asp Tyr Asp Val Val Ala Asp Ala Gly Gln Leu Ala Arg
    850                 855                 860 ggt att gag gat gca gtc gca aga ttg gta gcc atc tca aaa aga cgc      2640
Gly Ile Glu Asp Ala Val Ala Arg Leu Val Ala Ile Ser Lys Arg Arg
865                 870                 875                 880 aaa gtg acg cgt aga aga ggc gct ttg tca tta gta gtt aca gaa tac      2688
Lys Val Thr Arg Arg Arg Gly Ala Leu Ser Leu Val Val Thr Glu Tyr
                885                 890                 895 gaa gga cca aag aca aag ttt cac gct ctt atg caa gag caa atc cac      2736
Glu Gly Pro Lys Thr Lys Phe His Ala Leu Met Gln Glu Gln Ile His
```

```
                        900                 905                 910
aac gaa ttt act gct gct cag caa tac gtt gca ata gcc gta tac ttt      2784
Asn Glu Phe Thr Ala Ala Gln Gln Tyr Val Ala Ile Ala Val Tyr Phe
        915                 920                 925 gat tca gaa gat ttg cca caa ttg gca aaa cat ttc tat tcc caa gcc      2832
Asp Ser Glu Asp Leu Pro Gln Leu Ala Lys His Phe Tyr Ser Gln Ala
930                 935                 940 gtg gag gcc atg atg tta gtt caa cac ctc cta gac aga gat ttg aga      2880
Val Glu Ala Met Met Leu Val Gln His Leu Leu Asp Arg Asp Leu Arg
945                 950                 955                 960 gtt gaa att cca ggt gtt gat aca gtc aga aac caa ttt gat aga cct      2928
Val Glu Ile Pro Gly Val Asp Thr Val Arg Asn Gln Phe Asp Arg Pro
            965                 970                 975 cgt gaa gca ttg gct cta gca tta gat cag gag aga act gtg acg gat      2976
Arg Glu Ala Leu Ala Leu Ala Leu Asp Gln Glu Arg Thr Val Thr Asp
        980                 985                 990 caa gtg ggt aga ttg aca gct gtt gca cgt gac gaa gga gac ttt ctt      3024
Gln Val Gly Arg Leu Thr Ala Val Ala Arg Asp Glu Gly Asp Phe Leu
    995                 1000                1005 ggg gag cag ttt atg caa tgg ttt ctc cag gaa caa att gaa gag          3069
Gly Glu Gln Phe Met Gln Trp Phe Leu Gln Glu Gln Ile Glu Glu
1010                1015                1020 gtt gca cta atg gca act tta gtg aga gtc gct gac aga gct ggt          3114
Val Ala Leu Met Ala Thr Leu Val Arg Val Ala Asp Arg Ala Gly
    1025                1030                1035 gct aat ctc ttc gaa tta gaa aac ttt gta gcc aga gag gtt gat          3159
Ala Asn Leu Phe Glu Leu Glu Asn Phe Val Ala Arg Glu Val Asp
    1040                1045                1050 gtt gca cca gca gcc tca ggt gcc cct cac gct gcc ggg ggc aga          3204
Val Ala Pro Ala Ala Ser Gly Ala Pro His Ala Ala Gly Gly Arg
    1055                1060                1065 cat cat cac cat cac cat taa                                          3225
His His His His His His
    1070

<210> SEQ ID NO 33
<211> LENGTH: 1074
<212> TYPE: PRT
<213> ORGANISM: Artificial
<220> FEATURE:
<223> OTHER INFORMATION: Synthetic Construct

<400> SEQUENCE: 33

Met Ala Asp Glu Ala Pro Thr Ser Cys Gly Asp Gln Ser Asp His Val
1               5                   10                  15

Leu Gln His Trp Thr Val Asp Ile Ser Ile Asp Glu His Glu Gly Leu
            20                  25                  30

Thr Arg Ala Lys Ala Arg Leu Arg Trp Arg Glu Lys Glu Leu Val Gly
        35                  40                  45

Val Gly Leu Ala Arg Leu Asn Pro Ala Asp Arg Asn Val Pro Glu Ile
    50                  55                  60

Gly Asp Glu Leu Ser Val Ala Arg Ala Leu Ser Asp Leu Gly Lys Arg
65                  70                  75                  80

Met Leu Lys Val Ser Thr His Asp Ile Glu Ala Val Thr His Gln Pro
                85                  90                  95

Ala Arg Leu Leu Tyr Pro Asp Thr Met Val Thr Thr Asp Val Ile Lys
            100                 105                 110

Ser Arg Val Gln Leu Ala Cys Arg Ala Pro Ser Leu His Asn Ser Gln
        115                 120                 125
```

-continued

```
Pro Trp Arg Trp Ile Ala Glu Asp His Thr Val Ala Leu Phe Leu Asp
    130                 135                 140
Lys Asp Arg Val Leu Tyr Ala Thr Asp His Ser Gly Arg Glu Ala Leu
145                 150                 155                 160
Leu Gly Cys Gly Ala Val Leu Asp His Phe Arg Val Ala Met Ala Ala
                165                 170                 175
Ala Gly Thr Thr Ala Asn Val Glu Arg Phe Pro Asn Pro Asn Asp Pro
            180                 185                 190
Leu His Leu Ala Ser Ile Asp Phe Ser Pro Ala Asp Phe Val Thr Glu
        195                 200                 205
Gly His Arg Leu Arg Ala Asp Ala Ile Leu Leu Arg Arg Thr Asp Arg
    210                 215                 220
Leu Pro Phe Ala Glu Pro Pro Asp Trp Asp Leu Val Glu Ser Gln Leu
225                 230                 235                 240
Arg Thr Thr Val Thr Ala Asp Thr Val Arg Ile Asp Val Ile Ala Asp
                245                 250                 255
Asp Met Arg Pro Glu Leu Ala Ala Ala Ser Lys Leu Thr Glu Ser Leu
            260                 265                 270
Arg Leu Tyr Asp Ser Ser Tyr His Ala Glu Leu Phe Trp Trp Thr Gly
        275                 280                 285
Ala Phe Glu Thr Ser Glu Gly Ile Pro His Ser Ser Leu Val Ser Ala
    290                 295                 300
Ala Glu Ser Asp Arg Val Thr Phe Gly Arg Asp Phe Pro Val Val Ala
305                 310                 315                 320
Asn Thr Asp Arg Arg Pro Glu Phe Gly His Asp Arg Ser Lys Val Leu
                325                 330                 335
Val Leu Ser Thr Tyr Asp Asn Glu Arg Ala Ser Leu Leu Arg Cys Gly
            340                 345                 350
Glu Met Leu Ser Ala Val Leu Leu Asp Ala Thr Met Ala Gly Leu Ala
        355                 360                 365
Thr Cys Thr Leu Thr His Ile Thr Glu Leu His Ala Ser Arg Asp Leu
    370                 375                 380
Val Ala Ala Leu Ile Gly Gln Pro Ala Thr Pro Gln Ala Leu Val Arg
385                 390                 395                 400
Val Gly Leu Ala Pro Glu Met Glu Glu Pro Pro Ala Thr Pro Arg
                405                 410                 415
Arg Pro Ile Asp Glu Val Phe His Val Arg Ala Lys Asp His Arg Asn
            420                 425                 430
His Leu Thr Thr Leu Asp Ala Gly Phe Leu Lys Ala Glu Asp Val Asp
        435                 440                 445
Arg His Val Ser Leu Ala Ile Gly Ala Leu Ala Val Ile Glu Gly Pro
    450                 455                 460
Ala Pro Asp Gln Glu Ala Phe Leu Ser Ser Leu Ala Gln Arg Leu Arg
465                 470                 475                 480
Pro Cys Thr Arg Phe Gly Gln Arg Leu Arg Leu Arg Pro Phe Asp Leu
                485                 490                 495
Gly Ala Pro Lys Trp Val Asp Asp Pro Asp Phe Asp Leu Gly Arg His
            500                 505                 510
Val Trp Arg Ile Ala Leu Pro Arg Pro Gly Asn Glu Asp Gln Leu Phe
        515                 520                 525
Glu Leu Ile Ala Asp Leu Met Ala Arg Arg Leu Asp Arg Gly Arg Pro
    530                 535                 540
```

```
Leu Trp Glu Val Trp Val Ile Glu Gly Leu Ala Asp Ser Lys Trp Ala
545                 550                 555                 560

Ile Leu Thr Lys Leu His His Cys Met Ala Asp Gly Ile Ala Ala Thr
                565                 570                 575

His Leu Leu Ala Gly Leu Ser Asp Glu Ser Met Ser Asp Ser Phe Ala
            580                 585                 590

Ser Asn Ile His Thr Thr Met Gln Ser Gln Ser Ala Ser Val Arg Arg
        595                 600                 605

Gly Gly Phe Arg Val Asn Pro Ser Glu Ala Leu Thr Ala Ser Thr Ala
    610                 615                 620

Val Met Ala Gly Ile Val Arg Ala Ala Lys Gly Ala Ser Glu Ile Ala
625                 630                 635                 640

Ala Gly Val Leu Ser Pro Ala Ala Ser Ser Leu Asn Gly Pro Ile Ser
                645                 650                 655

Asp Leu Arg Arg Tyr Ser Ala Ala Lys Val Pro Leu Ala Asp Val Glu
                660                 665                 670

Gln Val Cys Arg Lys Phe Asp Val Thr Ile Asn Asp Val Ala Leu Ala
            675                 680                 685

Ala Ile Thr Glu Ser Tyr Arg Asn Val Leu Ile Gln Arg Gly Glu Arg
        690                 695                 700

Pro Arg Phe Asp Ser Leu Arg Thr Leu Val Pro Val Ser Thr Arg Ser
705                 710                 715                 720

Asn Ser Ala Leu Ser Lys Thr Asp Asn Arg Val Ser Leu Met Leu Pro
                725                 730                 735

Asn Leu Pro Val Asp Gln Glu Asn Pro Leu Gln Arg Leu Arg Ile Val
                740                 745                 750

His Ser Arg Leu Thr Arg Ala Lys Ala Gly Gly Gln Arg Gln Phe Gly
            755                 760                 765

Asn Thr Leu Met Ala Ile Ala Asn Arg Leu Pro Phe Pro Met Thr Ala
770                 775                 780

Trp Ala Val Gly Leu Leu Met Arg Leu Pro Gln Arg Gly Val Val Thr
785                 790                 795                 800

Val Ala Thr Asn Val Pro Gly Pro Arg Arg Pro Leu Gln Ile Met Gly
                805                 810                 815

Arg Arg Val Leu Asp Leu Tyr Pro Val Ser Pro Ile Ala Met Gln Leu
                820                 825                 830

Arg Thr Ser Val Ala Met Leu Ser Tyr Ala Asp Asp Leu Tyr Phe Gly
            835                 840                 845

Ile Leu Ala Asp Tyr Asp Val Val Ala Asp Ala Gly Gln Leu Ala Arg
        850                 855                 860

Gly Ile Glu Asp Ala Val Ala Arg Leu Val Ala Ile Ser Lys Arg Arg
865                 870                 875                 880

Lys Val Thr Arg Arg Gly Ala Leu Ser Leu Val Val Thr Glu Tyr
                885                 890                 895

Glu Gly Pro Lys Thr Lys Phe His Ala Leu Met Gln Glu Gln Ile His
                900                 905                 910

Asn Glu Phe Thr Ala Ala Gln Gln Tyr Val Ala Ile Ala Val Tyr Phe
            915                 920                 925

Asp Ser Glu Asp Leu Pro Gln Leu Ala Lys His Phe Tyr Ser Gln Ala
        930                 935                 940

Val Glu Ala Met Met Leu Val Gln His Leu Leu Asp Arg Asp Leu Arg
945                 950                 955                 960

Val Glu Ile Pro Gly Val Asp Thr Val Arg Asn Gln Phe Asp Arg Pro
```

-continued

```
                965                 970                 975
Arg Glu Ala Leu Ala Leu Ala Leu Asp Gln Glu Arg Thr Val Thr Asp
            980                 985                 990

Gln Val Gly Arg Leu Thr Ala Val  Ala Arg Asp Glu Gly  Asp Phe Leu
        995                 1000                1005

Gly Glu  Gln Phe Met Gln Trp  Phe Leu Gln Glu Gln  Ile Glu Glu
    1010                1015                1020

Val Ala  Leu Met Ala Thr Leu  Val Arg Val Ala Asp  Arg Ala Gly
    1025                1030                1035

Ala Asn  Leu Phe Glu Leu Glu  Asn Phe Val Ala Arg  Glu Val Asp
    1040                1045                1050

Val Ala  Pro Ala Ala Ser Gly  Ala Pro His Ala Ala  Gly Gly Arg
    1055                1060                1065

His His  His His His His
    1070

<210> SEQ ID NO 34
<211> LENGTH: 505
<212> TYPE: PRT
<213> ORGANISM: Artificial
<220> FEATURE:
<223> OTHER INFORMATION: Synthetic Construct

<400> SEQUENCE: 34

Pro Asp Thr Met Val Thr Thr Asp Val Ile Lys Ser Arg Val Gln Leu
1               5                   10                  15

Ala Cys Arg Ala Pro Ser Leu His Asn Ser Gln Pro Trp Arg Trp Ile
            20                  25                  30

Ala Glu Asp His Thr Val Ala Leu Phe Leu Asp Lys Asp Arg Val Leu
        35                  40                  45

Tyr Ala Thr Asp His Ser Gly Arg Glu Ala Leu Leu Gly Cys Gly Ala
    50                  55                  60

Val Leu Asp His Phe Arg Val Ala Met Ala Ala Ala Gly Thr Thr Ala
65                  70                  75                  80

Asn Val Glu Arg Phe Pro Asn Pro Asn Asp Pro Leu His Leu Ala Ser
                85                  90                  95

Ile Asp Phe Ser Pro Ala Asp Phe Val Thr Glu Gly His Arg Leu Arg
            100                 105                 110

Ala Asp Ala Ile Leu Leu Arg Arg Thr Asp Arg Leu Pro Phe Ala Glu
        115                 120                 125

Pro Pro Asp Trp Asp Leu Val Glu Ser Gln Leu Arg Thr Thr Val Thr
    130                 135                 140

Ala Asp Thr Val Arg Ile Asp Val Ile Ala Asp Asp Met Arg Pro Glu
145                 150                 155                 160

Leu Ala Ala Ala Ser Lys Leu Thr Glu Ser Leu Arg Leu Tyr Asp Ser
                165                 170                 175

Ser Tyr His Ala Glu Leu Phe Trp Trp Thr Gly Ala Phe Glu Thr Ser
            180                 185                 190

Glu Gly Ile Pro His Ser Ser Leu Val Ser Ala Ala Glu Ser Asp Arg
        195                 200                 205

Val Thr Phe Gly Arg Asp Phe Pro Val Val Ala Asn Thr Asp Arg Arg
    210                 215                 220

Pro Glu Phe Gly His Asp Arg Ser Lys Val Leu Val Leu Ser Thr Tyr
225                 230                 235                 240

Asp Asn Glu Arg Ala Ser Leu Leu Arg Cys Gly Glu Met Leu Ser Ala
```

```
                    245                 250                 255
Val Leu Leu Asp Ala Thr Met Ala Gly Leu Ala Thr Cys Thr Leu Thr
            260                 265                 270

His Ile Thr Glu Leu His Ala Ser Arg Asp Leu Val Ala Ala Leu Ile
        275                 280                 285

Gly Gln Pro Ala Thr Pro Gln Ala Leu Val Arg Val Gly Leu Ala Pro
    290                 295                 300

Glu Met Glu Glu Pro Pro Ala Thr Pro Arg Arg Pro Ile Asp Glu
305                 310                 315                 320

Val Phe His Val Arg Ala Lys Asp His Arg Thr Glu Tyr Glu Gly Pro
                325                 330                 335

Lys Thr Lys Phe His Ala Leu Met Gln Glu Gln Ile His Asn Glu Phe
            340                 345                 350

Thr Ala Ala Gln Gln Tyr Val Ala Ile Ala Val Tyr Phe Asp Ser Glu
        355                 360                 365

Asp Leu Pro Gln Leu Ala Lys His Phe Tyr Ser Gln Ala Val Glu Ala
    370                 375                 380

Met Met Leu Val Gln His Leu Leu Asp Arg Asp Leu Arg Val Glu Ile
385                 390                 395                 400

Pro Gly Val Asp Thr Val Arg Asn Gln Phe Asp Arg Pro Arg Glu Ala
                405                 410                 415

Leu Ala Leu Ala Leu Asp Gln Glu Arg Thr Val Thr Asp Gln Val Gly
            420                 425                 430

Arg Leu Thr Ala Val Ala Arg Asp Glu Gly Asp Phe Leu Gly Glu Gln
        435                 440                 445

Phe Met Gln Trp Phe Leu Gln Glu Gln Ile Glu Glu Val Ala Leu Met
    450                 455                 460

Ala Thr Leu Val Arg Val Ala Asp Arg Ala Gly Ala Asn Leu Phe Glu
465                 470                 475                 480

Leu Glu Asn Phe Val Ala Arg Glu Val Asp Val Ala Pro Ala Ala Ser
                485                 490                 495

Gly Ala Pro His Ala Ala Gly Gly Arg
            500                 505

<210> SEQ ID NO 35
<211> LENGTH: 1560
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1560)

<400> SEQUENCE: 35 atg gcc gac gag gca cca act agt cct gat aca atg gta aca act gac      48
Met Ala Asp Glu Ala Pro Thr Ser Pro Asp Thr Met Val Thr Thr Asp
1               5                   10                  15 gtt atc aaa tct aga gta caa ttg gct tgc aga gcc cca tca tta cat      96
Val Ile Lys Ser Arg Val Gln Leu Ala Cys Arg Ala Pro Ser Leu His
                20                  25                  30 aat tcc caa cca tgg cgc tgg att gcc gag gat cac aca gtg gca cta     144
Asn Ser Gln Pro Trp Arg Trp Ile Ala Glu Asp His Thr Val Ala Leu
            35                  40                  45 ttc tta gac aaa gat aga gtt ctt tat gct aca gat cat agt ggc aga     192
Phe Leu Asp Lys Asp Arg Val Leu Tyr Ala Thr Asp His Ser Gly Arg
        50                  55                  60
```

```
gaa gca ctg ctg gga tgt ggt gct gtc cta gac cac ttc aga gtt gct    240
Glu Ala Leu Leu Gly Cys Gly Ala Val Leu Asp His Phe Arg Val Ala
65                  70                  75                  80 atg gct gcg gcg ggc acc aca gca aat gtc gaa cga ttc cca aat cct    288
Met Ala Ala Ala Gly Thr Thr Ala Asn Val Glu Arg Phe Pro Asn Pro
                85                  90                  95 aac gat cca tta cat ctt gca tct att gac ttt tct cct gct gat ttt    336
Asn Asp Pro Leu His Leu Ala Ser Ile Asp Phe Ser Pro Ala Asp Phe
            100                 105                 110 gtc aca gaa ggc cac aga ttg aga gct gat gcg atc tta ttg agg aga    384
Val Thr Glu Gly His Arg Leu Arg Ala Asp Ala Ile Leu Leu Arg Arg
        115                 120                 125 aca gat aga ttg cct ttc gct gag cct cca gac tgg gac tta gta gaa    432
Thr Asp Arg Leu Pro Phe Ala Glu Pro Pro Asp Trp Asp Leu Val Glu
    130                 135                 140 tca cag ttg agg act aca gtt act gct gat acc gtt aga atc gat gtt    480
Ser Gln Leu Arg Thr Thr Val Thr Ala Asp Thr Val Arg Ile Asp Val
145                 150                 155                 160 ata gcg gat gat atg agg cca gaa ctt gca gcc gca tcc aaa ttg acc    528
Ile Ala Asp Asp Met Arg Pro Glu Leu Ala Ala Ala Ser Lys Leu Thr
                165                 170                 175 gaa tct ttg aga cta tac gat agc tct tac cat gcg gaa ctg ttt tgg    576
Glu Ser Leu Arg Leu Tyr Asp Ser Ser Tyr His Ala Glu Leu Phe Trp
            180                 185                 190 tgg act ggt gct ttc gaa aca tct gaa ggg ata cca cat tct tca tta    624
Trp Thr Gly Ala Phe Glu Thr Ser Glu Gly Ile Pro His Ser Ser Leu
        195                 200                 205 gtt tca gct gca gaa tcc gat aga gtc act ttt ggt cgt gat ttc cca    672
Val Ser Ala Ala Glu Ser Asp Arg Val Thr Phe Gly Arg Asp Phe Pro
    210                 215                 220 gtc gta gca aat act gac aga cga cct gaa ttt ggt cat gac aga tct    720
Val Val Ala Asn Thr Asp Arg Arg Pro Glu Phe Gly His Asp Arg Ser
225                 230                 235                 240 aaa gta ctt gtt ctc agc acc tac gat aat gaa agg gct tct ttg tta    768
Lys Val Leu Val Leu Ser Thr Tyr Asp Asn Glu Arg Ala Ser Leu Leu
                245                 250                 255 aga tgc ggt gaa atg cta agt gcc gtc tta ctg gat gcg act atg gct    816
Arg Cys Gly Glu Met Leu Ser Ala Val Leu Leu Asp Ala Thr Met Ala
            260                 265                 270 gga ttg gca act tgt aca ctg acc cat atc acg gaa ctg cat gca tca    864
Gly Leu Ala Thr Cys Thr Leu Thr His Ile Thr Glu Leu His Ala Ser
        275                 280                 285 aga gat ctc gta gca gcc ttg att ggc caa cca gcc aca cct caa gcc    912
Arg Asp Leu Val Ala Ala Leu Ile Gly Gln Pro Ala Thr Pro Gln Ala
    290                 295                 300 ctt gtg aga gta gga ttg gct cca gag atg gag gaa cca cct cct gct    960
Leu Val Arg Val Gly Leu Ala Pro Glu Met Glu Glu Pro Pro Pro Ala
305                 310                 315                 320 act cca cgt aga ccc atc gac gaa gtg ttc cat gtg aga gct aag gat   1008
Thr Pro Arg Arg Pro Ile Asp Glu Val Phe His Val Arg Ala Lys Asp
                325                 330                 335 cat aga aca gaa tac gaa gga cca aag aca aag ttt cac gct ctt atg   1056
His Arg Thr Glu Tyr Glu Gly Pro Lys Thr Lys Phe His Ala Leu Met
            340                 345                 350 caa gag caa atc cac aac gaa ttt act gct gct cag caa tac gtt gca   1104
Gln Glu Gln Ile His Asn Glu Phe Thr Ala Ala Gln Gln Tyr Val Ala
        355                 360                 365 ata gcc gta tac ttt gat tca gaa gat ttg cca caa ttg gca aaa cat   1152
Ile Ala Val Tyr Phe Asp Ser Glu Asp Leu Pro Gln Leu Ala Lys His
    370                 375                 380
```

```
ttc tat tcc caa gcc gtg gag gcc atg atg tta gtt caa cac ctc cta    1200
Phe Tyr Ser Gln Ala Val Glu Ala Met Met Leu Val Gln His Leu Leu
385                 390                 395                 400 gac aga gat ttg aga gtt gaa att cca ggt gtt gat aca gtc aga aac    1248
Asp Arg Asp Leu Arg Val Glu Ile Pro Gly Val Asp Thr Val Arg Asn
            405                 410                 415 caa ttt gat aga cct cgt gaa gca ttg gct cta gca tta gat cag gag    1296
Gln Phe Asp Arg Pro Arg Glu Ala Leu Ala Leu Ala Leu Asp Gln Glu
        420                 425                 430 aga act gtg acg gat caa gtg ggt aga ttg aca gct gtt gca cgt gac    1344
Arg Thr Val Thr Asp Gln Val Gly Arg Leu Thr Ala Val Ala Arg Asp
    435                 440                 445 gaa gga gac ttt ctt ggg gag cag ttt atg caa tgg ttt ctc cag gaa    1392
Glu Gly Asp Phe Leu Gly Glu Gln Phe Met Gln Trp Phe Leu Gln Glu
450                 455                 460 caa att gaa gag gtt gca cta atg gca act tta gtg aga gtc gct gac    1440
Gln Ile Glu Glu Val Ala Leu Met Ala Thr Leu Val Arg Val Ala Asp
465                 470                 475                 480 aga gct ggt gct aat ctc ttc gaa tta gaa aac ttt gta gcc aga gag    1488
Arg Ala Gly Ala Asn Leu Phe Glu Leu Glu Asn Phe Val Ala Arg Glu
            485                 490                 495 gtt gat gtt gca cca gca gcc tca ggt gcc cct cac gct gcc ggg ggc    1536
Val Asp Val Ala Pro Ala Ala Ser Gly Ala Pro His Ala Ala Gly Gly
        500                 505                 510 aga cat cat cac cat cac cat taa                                    1560
Arg His His His His His His
    515

<210> SEQ ID NO 36
<211> LENGTH: 519
<212> TYPE: PRT
<213> ORGANISM: Artificial
<220> FEATURE:
<223> OTHER INFORMATION: Synthetic Construct

<400> SEQUENCE: 36

Met Ala Asp Glu Ala Pro Thr Ser Pro Asp Thr Met Val Thr Thr Asp
1               5                   10                  15

Val Ile Lys Ser Arg Val Gln Leu Ala Cys Arg Ala Pro Ser Leu His
                20                  25                  30

Asn Ser Gln Pro Trp Arg Trp Ile Ala Glu Asp His Thr Val Ala Leu
            35                  40                  45

Phe Leu Asp Lys Asp Arg Val Leu Tyr Ala Thr Asp His Ser Gly Arg
        50                  55                  60

Glu Ala Leu Leu Gly Cys Gly Ala Val Leu Asp His Phe Arg Val Ala
65                  70                  75                  80

Met Ala Ala Ala Gly Thr Thr Ala Asn Val Glu Arg Phe Pro Asn Pro
                85                  90                  95

Asn Asp Pro Leu His Leu Ala Ser Ile Asp Phe Ser Pro Ala Asp Phe
            100                 105                 110

Val Thr Glu Gly His Arg Leu Arg Ala Asp Ala Ile Leu Leu Arg Arg
        115                 120                 125

Thr Asp Arg Leu Pro Phe Ala Glu Pro Pro Asp Trp Asp Leu Val Glu
    130                 135                 140

Ser Gln Leu Arg Thr Thr Val Thr Ala Asp Thr Val Arg Ile Asp Val
145                 150                 155                 160

Ile Ala Asp Asp Met Arg Pro Glu Leu Ala Ala Ala Ser Lys Leu Thr
                165                 170                 175
```

```
Glu Ser Leu Arg Leu Tyr Asp Ser Ser Tyr His Ala Glu Leu Phe Trp
            180                 185                 190

Trp Thr Gly Ala Phe Glu Thr Ser Glu Gly Ile Pro His Ser Ser Leu
        195                 200                 205

Val Ser Ala Ala Glu Ser Asp Arg Val Thr Phe Gly Arg Asp Phe Pro
210                 215                 220

Val Val Ala Asn Thr Asp Arg Arg Pro Glu Phe Gly His Asp Arg Ser
225                 230                 235                 240

Lys Val Leu Val Leu Ser Thr Tyr Asp Asn Glu Arg Ala Ser Leu Leu
            245                 250                 255

Arg Cys Gly Glu Met Leu Ser Ala Val Leu Leu Asp Ala Thr Met Ala
            260                 265                 270

Gly Leu Ala Thr Cys Thr Leu Thr His Ile Thr Glu Leu His Ala Ser
            275                 280                 285

Arg Asp Leu Val Ala Ala Leu Ile Gly Gln Pro Ala Thr Pro Gln Ala
        290                 295                 300

Leu Val Arg Val Gly Leu Ala Pro Glu Met Glu Pro Pro Ala
305                 310                 315                 320

Thr Pro Arg Arg Pro Ile Asp Glu Val Phe His Val Arg Ala Lys Asp
                325                 330                 335

His Arg Thr Glu Tyr Glu Gly Pro Lys Thr Lys Phe His Ala Leu Met
            340                 345                 350

Gln Glu Gln Ile His Asn Glu Phe Thr Ala Ala Gln Tyr Val Ala
        355                 360                 365

Ile Ala Val Tyr Phe Asp Ser Glu Asp Leu Pro Gln Leu Ala Lys His
        370                 375                 380

Phe Tyr Ser Gln Ala Val Glu Ala Met Met Leu Val Gln His Leu Leu
385                 390                 395                 400

Asp Arg Asp Leu Arg Val Glu Ile Pro Gly Val Asp Thr Val Arg Asn
                405                 410                 415

Gln Phe Asp Arg Pro Arg Glu Ala Leu Ala Leu Ala Leu Asp Gln Glu
            420                 425                 430

Arg Thr Val Thr Asp Gln Val Gly Arg Leu Thr Ala Val Ala Arg Asp
            435                 440                 445

Glu Gly Asp Phe Leu Gly Glu Gln Phe Met Gln Trp Phe Leu Gln Glu
450                 455                 460

Gln Ile Glu Glu Val Ala Leu Met Ala Thr Leu Val Arg Val Ala Asp
465                 470                 475                 480

Arg Ala Gly Ala Asn Leu Phe Glu Leu Glu Asn Phe Val Ala Arg Glu
                485                 490                 495

Val Asp Val Ala Pro Ala Ala Ser Gly Ala Pro His Ala Ala Gly Gly
            500                 505                 510

Arg His His His His His
        515

<210> SEQ ID NO 37
<211> LENGTH: 337
<212> TYPE: PRT
<213> ORGANISM: Mycobacterium tuberculosis

<400> SEQUENCE: 37

Gln Leu Val Asp Arg Val Arg Gly Ala Val Thr Gly Met Ser Arg Arg
1               5                   10                  15

Leu Val Val Gly Ala Val Gly Ala Ala Leu Val Ser Gly Leu Val Gly
```

-continued

```
                    20                  25                  30
Ala Val Gly Gly Thr Ala Thr Ala Gly Ala Phe Ser Arg Pro Gly Leu
         35                  40                  45
Pro Val Glu Tyr Leu Gln Val Pro Ser Pro Ser Met Gly Arg Asp Ile
 50                  55                  60
Lys Val Gln Phe Gln Ser Gly Gly Ala Asn Ser Pro Ala Leu Tyr Leu
 65                  70                  75                  80
Leu Asp Gly Leu Arg Ala Gln Asp Asp Phe Ser Gly Trp Asp Ile Asn
                 85                  90                  95
Thr Pro Ala Phe Glu Trp Tyr Asp Gln Ser Gly Leu Ser Val Val Met
            100                 105                 110
Pro Val Gly Gly Gln Ser Ser Phe Tyr Ser Asp Trp Tyr Gln Pro Ala
        115                 120                 125
Cys Gly Lys Ala Gly Cys Gln Thr Tyr Lys Trp Glu Thr Phe Leu Thr
    130                 135                 140
Ser Glu Leu Pro Gly Trp Leu Gln Ala Asn Arg His Val Lys Pro Thr
145                 150                 155                 160
Gly Ser Ala Val Val Gly Leu Ser Met Ala Ala Ser Ser Ala Leu Thr
                165                 170                 175
Leu Ala Ile Tyr His Pro Gln Gln Phe Val Tyr Ala Gly Ala Met Ser
            180                 185                 190
Gly Leu Leu Asp Pro Ser Gln Ala Met Gly Pro Thr Leu Ile Gly Leu
        195                 200                 205
Ala Met Gly Asp Ala Gly Gly Tyr Lys Ala Ser Asp Met Trp Gly Pro
    210                 215                 220
Lys Glu Asp Pro Ala Trp Gln Arg Asn Asp Pro Leu Leu Asn Val Gly
225                 230                 235                 240
Lys Leu Ile Ala Asn Asn Thr Arg Val Trp Val Tyr Cys Gly Asn Gly
                245                 250                 255
Lys Pro Ser Asp Leu Gly Gly Asn Asn Leu Pro Ala Lys Phe Leu Glu
            260                 265                 270
Gly Phe Val Arg Thr Ser Asn Ile Lys Phe Gln Asp Ala Tyr Asn Ala
        275                 280                 285
Gly Gly Gly His Asn Gly Val Phe Asp Phe Pro Asp Ser Gly Thr His
    290                 295                 300
Ser Trp Glu Tyr Trp Gly Ala Gln Leu Asn Ala Met Lys Pro Asp Leu
305                 310                 315                 320
Gln Arg Ala Leu Gly Ala Thr Pro Asn Thr Gly Pro Ala Pro Gln Gly
                325                 330                 335
Ala
```

<210> SEQ ID NO 38
<211> LENGTH: 1056
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1056)

<400> SEQUENCE: 38

```
atg gcc gac gag gca cca act agt caa tta gta gat aga gtc aga gga    48
Met Ala Asp Glu Ala Pro Thr Ser Gln Leu Val Asp Arg Val Arg Gly
 1               5                  10                  15 gca gtt aca ggt atg tcc aga aga ttg gtt gta ggt gcc gtt ggg gct    96
```

```
Ala Val Thr Gly Met Ser Arg Arg Leu Val Val Gly Ala Val Gly Ala
             20                  25                  30 gct ttg gtt tca ggt ttg gtt ggg gct gtg ggc ggt aca gct act gca    144
Ala Leu Val Ser Gly Leu Val Gly Ala Val Gly Gly Thr Ala Thr Ala
                 35                  40                  45 ggg gct ttt tct aga cct ggc ctg cca gtg gaa tac ctt caa gtc cct    192
Gly Ala Phe Ser Arg Pro Gly Leu Pro Val Glu Tyr Leu Gln Val Pro
 50                  55                  60 tca cca tca atg ggt cgt gac att aag gtc caa ttt caa tca ggt ggt    240
Ser Pro Ser Met Gly Arg Asp Ile Lys Val Gln Phe Gln Ser Gly Gly
 65                  70                  75                  80 gca aat tcc cca gct ctg tac ctg tta gat gga ctt aga gca caa gat    288
Ala Asn Ser Pro Ala Leu Tyr Leu Leu Asp Gly Leu Arg Ala Gln Asp
                 85                  90                  95 gat ttt tct gga tgg gat atc aac act cct gcc ttt gaa tgg tat gat    336
Asp Phe Ser Gly Trp Asp Ile Asn Thr Pro Ala Phe Glu Trp Tyr Asp
                100                 105                 110 cag tct ggt tta agc gtt gtt atg cca gtc ggt ggt caa tcg tca ttc    384
Gln Ser Gly Leu Ser Val Val Met Pro Val Gly Gly Gln Ser Ser Phe
                115                 120                 125 tac tct gat tgg tat caa cca gcc tgt ggt aag gct gga tgc caa aca    432
Tyr Ser Asp Trp Tyr Gln Pro Ala Cys Gly Lys Ala Gly Cys Gln Thr
            130                 135                 140 tac aaa tgg gaa acc ttt ttg acg tct gaa tta cct gga tgg ttg caa    480
Tyr Lys Trp Glu Thr Phe Leu Thr Ser Glu Leu Pro Gly Trp Leu Gln
145                 150                 155                 160 gct aat aga cac gtg aag cct act ggc tca gct gtt gta ggg ctt tca    528
Ala Asn Arg His Val Lys Pro Thr Gly Ser Ala Val Val Gly Leu Ser
                165                 170                 175 atg gca gcc agt agt gca cta aca cta gcc ata tac cat cca caa cag    576
Met Ala Ala Ser Ser Ala Leu Thr Leu Ala Ile Tyr His Pro Gln Gln
            180                 185                 190 ttc gta tat gcg ggt gct atg agc ggc ttg ttg gac cca tct caa gca    624
Phe Val Tyr Ala Gly Ala Met Ser Gly Leu Leu Asp Pro Ser Gln Ala
            195                 200                 205 atg gga cct act ctc atc ggt cta gca atg gga gat gca gga gga tac    672
Met Gly Pro Thr Leu Ile Gly Leu Ala Met Gly Asp Ala Gly Gly Tyr
        210                 215                 220 aaa gcc tcc gat atg tgg ggc ccc aaa gag gat cca gct tgg cag aga    720
Lys Ala Ser Asp Met Trp Gly Pro Lys Glu Asp Pro Ala Trp Gln Arg
225                 230                 235                 240 aat gac cca ttg ttg aat gta ggt aaa cta att gcg aac aac aca cga    768
Asn Asp Pro Leu Leu Asn Val Gly Lys Leu Ile Ala Asn Asn Thr Arg
                245                 250                 255 gtg tgg gtc tat tgt ggc aac ggc aag cca tct gat ctt ggg ggt aat    816
Val Trp Val Tyr Cys Gly Asn Gly Lys Pro Ser Asp Leu Gly Gly Asn
            260                 265                 270 aac ctt cct gct aaa ttc tta gaa ggc ttc gtg aga aca tct aac atc    864
Asn Leu Pro Ala Lys Phe Leu Glu Gly Phe Val Arg Thr Ser Asn Ile
        275                 280                 285 aag ttc caa gac gcc tac aat gct ggc ggt ggt cat aat ggg gtt ttt    912
Lys Phe Gln Asp Ala Tyr Asn Ala Gly Gly Gly His Asn Gly Val Phe
        290                 295                 300 gac ttt cca gat tcc ggt act cac tct tgg gaa tac tgg gga gca cag    960
Asp Phe Pro Asp Ser Gly Thr His Ser Trp Glu Tyr Trp Gly Ala Gln
305                 310                 315                 320 tta aat gct atg aaa cct gac tta caa agg gct ctc ggt gcc aca cca   1008
Leu Asn Ala Met Lys Pro Asp Leu Gln Arg Ala Leu Gly Ala Thr Pro
                325                 330                 335
```

```
aat acc ggt cca gcg cct caa ggc gcg cat cac cat cat cat cac taa        1056
Asn Thr Gly Pro Ala Pro Gln Gly Ala His His His His His His
            340                 345                 350
```

<210> SEQ ID NO 39
<211> LENGTH: 351
<212> TYPE: PRT
<213> ORGANISM: Artificial
<220> FEATURE:
<223> OTHER INFORMATION: Synthetic Construct

<400> SEQUENCE: 39

```
Met Ala Asp Glu Ala Pro Thr Ser Gln Leu Val Asp Arg Val Arg Gly
1               5                   10                  15

Ala Val Thr Gly Met Ser Arg Arg Leu Val Val Gly Ala Val Gly Ala
            20                  25                  30

Ala Leu Val Ser Gly Leu Val Gly Ala Val Gly Gly Thr Ala Thr Ala
        35                  40                  45

Gly Ala Phe Ser Arg Pro Gly Leu Pro Val Glu Tyr Leu Gln Val Pro
    50                  55                  60

Ser Pro Ser Met Gly Arg Asp Ile Lys Val Gln Phe Gln Ser Gly Gly
65                  70                  75                  80

Ala Asn Ser Pro Ala Leu Tyr Leu Leu Asp Gly Leu Arg Ala Gln Asp
                85                  90                  95

Asp Phe Ser Gly Trp Asp Ile Asn Thr Pro Ala Phe Glu Trp Tyr Asp
            100                 105                 110

Gln Ser Gly Leu Ser Val Val Met Pro Val Gly Gly Gln Ser Ser Phe
        115                 120                 125

Tyr Ser Asp Trp Tyr Gln Pro Ala Cys Gly Lys Ala Gly Cys Gln Thr
    130                 135                 140

Tyr Lys Trp Glu Thr Phe Leu Thr Ser Glu Leu Pro Gly Trp Leu Gln
145                 150                 155                 160

Ala Asn Arg His Val Lys Pro Thr Gly Ser Ala Val Val Gly Leu Ser
                165                 170                 175

Met Ala Ala Ser Ser Ala Leu Thr Leu Ala Ile Tyr His Pro Gln Gln
            180                 185                 190

Phe Val Tyr Ala Gly Ala Met Ser Gly Leu Leu Asp Pro Ser Gln Ala
        195                 200                 205

Met Gly Pro Thr Leu Ile Gly Leu Ala Met Gly Asp Ala Gly Gly Tyr
    210                 215                 220

Lys Ala Ser Asp Met Trp Gly Pro Lys Glu Asp Pro Ala Trp Gln Arg
225                 230                 235                 240

Asn Asp Pro Leu Leu Asn Val Gly Lys Leu Ile Ala Asn Asn Thr Arg
                245                 250                 255

Val Trp Val Tyr Cys Gly Asn Gly Lys Pro Ser Asp Leu Gly Gly Asn
            260                 265                 270

Asn Leu Pro Ala Lys Phe Leu Glu Gly Phe Val Arg Thr Ser Asn Ile
        275                 280                 285

Lys Phe Gln Asp Ala Tyr Asn Ala Gly Gly Gly His Asn Gly Val Phe
    290                 295                 300

Asp Phe Pro Asp Ser Gly Thr His Ser Trp Glu Tyr Trp Gly Ala Gln
305                 310                 315                 320

Leu Asn Ala Met Lys Pro Asp Leu Gln Arg Ala Leu Gly Ala Thr Pro
                325                 330                 335

Asn Thr Gly Pro Ala Pro Gln Gly Ala His His His His His His
            340                 345                 350
```

<210> SEQ ID NO 40
<211> LENGTH: 236
<212> TYPE: PRT
<213> ORGANISM: Mycobacterium tuberculosis

<400> SEQUENCE: 40

Met Arg Thr Pro Arg His Cys Arg Arg Ile Ala Val Leu Ala Ala
1               5                   10                  15

Val Ser Ile Ala Ala Thr Val Val Ala Gly Cys Ser Ser Gly Ser Lys
                20                  25                  30

Pro Ser Gly Gly Pro Leu Pro Asp Ala Lys Pro Leu Val Glu Glu Ala
            35                  40                  45

Thr Ala Gln Thr Lys Ala Leu Lys Ser Ala His Met Val Leu Thr Val
        50                  55                  60

Asn Gly Lys Ile Pro Gly Leu Ser Leu Lys Thr Leu Ser Gly Asp Leu
65                  70                  75                  80

Thr Thr Asn Pro Thr Ala Ala Thr Gly Asn Trp Lys Leu Thr Leu Gly
                85                  90                  95

Gly Ser Asp Ile Asp Ala Asp Phe Val Val Phe Asp Gly Ile Leu Tyr
            100                 105                 110

Ala Thr Leu Thr Pro Asn Gln Trp Ser Asp Phe Gly Pro Ala Ala Asp
        115                 120                 125

Ile Tyr Asp Pro Ala Gln Val Leu Asn Pro Asp Thr Gly Leu Ala Asn
130                 135                 140

Val Leu Ala Asn Phe Ala Asp Ala Lys Ala Glu Gly Arg Asp Thr Ile
145                 150                 155                 160

Asn Gly Gln Asn Thr Ile Arg Ile Ser Gly Lys Val Ser Ala Gln Ala
                165                 170                 175

Val Asn Gln Ile Ala Pro Pro Phe Asn Ala Thr Gln Pro Val Pro Ala
            180                 185                 190

Thr Val Trp Ile Gln Glu Thr Gly Asp His Gly Leu Ala Gln Ala Gln
        195                 200                 205

Leu Asp Arg Gly Ser Gly Asn Ser Val Gln Met Thr Leu Ser Lys Trp
210                 215                 220

Gly Glu Lys Val Gln Val Thr Lys Pro Pro Val Ser
225                 230                 235

<210> SEQ ID NO 41
<211> LENGTH: 753
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(753)

<400> SEQUENCE: 41 atg gcc gac gag gca cca act agt atg aga aca cca aga cgt cac tgt     48
Met Ala Asp Glu Ala Pro Thr Ser Met Arg Thr Pro Arg Arg His Cys
1               5                   10                  15 agg aga ata gcc gtt tta gct gca gtc tca att gca gca aca gta gtc     96
Arg Arg Ile Ala Val Leu Ala Ala Val Ser Ile Ala Ala Thr Val Val
                20                  25                  30 gct ggt tgc tca tct ggc tca aag cca tcc gga ggc cct ttg ccc gat    144
Ala Gly Cys Ser Ser Gly Ser Lys Pro Ser Gly Gly Pro Leu Pro Asp
        35                  40                  45

| | | |
|---|---|---|
| gct aag cca ctc gta gaa gag gcc aca gct caa act aaa gca cta aag<br>Ala Lys Pro Leu Val Glu Glu Ala Thr Ala Gln Thr Lys Ala Leu Lys<br>50                         55                       60 | | 192 |
| tct gcg cat atg gtg ctt aca gta aat ggt aaa atc cca ggg ctt tca<br>Ser Ala His Met Val Leu Thr Val Asn Gly Lys Ile Pro Gly Leu Ser<br>65                     70                       75                   80 | | 240 |
| ttg aaa act cta tct ggt gat tta aca acc aat cca acg gct gct aca<br>Leu Lys Thr Leu Ser Gly Asp Leu Thr Thr Asn Pro Thr Ala Ala Thr<br>                   85                       90                      95 | | 288 |
| ggt aac tgg aag tta aca cta gga ggc tca gac atc gat gcg gat ttt<br>Gly Asn Trp Lys Leu Thr Leu Gly Gly Ser Asp Ile Asp Ala Asp Phe<br>               100                      105                     110 | | 336 |
| gtt gtg ttt gac gga atc ttg tat gct acc ttg act cca aac caa tgg<br>Val Val Phe Asp Gly Ile Leu Tyr Ala Thr Leu Thr Pro Asn Gln Trp<br>          115                     120                     125 | | 384 |
| tct gat ttc ggt cca gcc gct gac att tac gat cct gca caa gtt ctt<br>Ser Asp Phe Gly Pro Ala Ala Asp Ile Tyr Asp Pro Ala Gln Val Leu<br>130                        135                     140 | | 432 |
| aac cct gat aca gga ttg gca aat gta ctg gca aat ttc gct gac gcg<br>Asn Pro Asp Thr Gly Leu Ala Asn Val Leu Ala Asn Phe Ala Asp Ala<br>145                        150                     155                     160 | | 480 |
| aaa gcc gaa ggg aga gat acc atc aat ggt caa aac acg att aga ata<br>Lys Ala Glu Gly Arg Asp Thr Ile Asn Gly Gln Asn Thr Ile Arg Ile<br>               165                      170                     175 | | 528 |
| agc ggt aaa gtg tct gcc caa gca gtc aat caa atc gct cct cca ttt<br>Ser Gly Lys Val Ser Ala Gln Ala Val Asn Gln Ile Ala Pro Pro Phe<br>          180                     185                     190 | | 576 |
| aac gct act cag cct gtt cct gca act gtt tgg att cag gaa act ggt<br>Asn Ala Thr Gln Pro Val Pro Ala Thr Val Trp Ile Gln Glu Thr Gly<br>          195                     200                     205 | | 624 |
| gat cat cag tta gcc caa gct caa ctc gat aga ggc tcc gga aat agt<br>Asp His Gln Leu Ala Gln Ala Gln Leu Asp Arg Gly Ser Gly Asn Ser<br>210                        215                     220 | | 672 |
| gtt caa atg act ctg tcc aag tgg ggt gaa aaa gtg caa gtt aca aaa<br>Val Gln Met Thr Leu Ser Lys Trp Gly Glu Lys Val Gln Val Thr Lys<br>225                        230                     235                     240 | | 720 |
| cca cca gtc tct cac cat cac cat cat cat taa<br>Pro Pro Val Ser His His His His His His<br>               245                      250 | | 753 |

<210> SEQ ID NO 42
<211> LENGTH: 250
<212> TYPE: PRT
<213> ORGANISM: Artificial
<220> FEATURE:
<223> OTHER INFORMATION: Synthetic Construct

<400> SEQUENCE: 42

Met Ala Asp Glu Ala Pro Thr Ser Met Arg Thr Pro Arg Arg His Cys
1                   5                       10                       15

Arg Arg Ile Ala Val Leu Ala Val Ser Ile Ala Ala Thr Val Val
               20                      25                      30

Ala Gly Cys Ser Ser Gly Ser Lys Pro Ser Gly Gly Pro Leu Pro Asp
          35                     40                     45

Ala Lys Pro Leu Val Glu Glu Ala Thr Ala Gln Thr Lys Ala Leu Lys
50                        55                       60

Ser Ala His Met Val Leu Thr Val Asn Gly Lys Ile Pro Gly Leu Ser
65                  70                      75                   80

Leu Lys Thr Leu Ser Gly Asp Leu Thr Thr Asn Pro Thr Ala Ala Thr
               85                      90                     95

```
Gly Asn Trp Lys Leu Thr Leu Gly Gly Ser Asp Ile Asp Ala Asp Phe
                100                 105                 110

Val Val Phe Asp Gly Ile Leu Tyr Ala Thr Leu Thr Pro Asn Gln Trp
            115                 120                 125

Ser Asp Phe Gly Pro Ala Ala Asp Ile Tyr Asp Pro Ala Gln Val Leu
    130                 135                 140

Asn Pro Asp Thr Gly Leu Ala Asn Val Leu Ala Asn Phe Ala Asp Ala
145                 150                 155                 160

Lys Ala Glu Gly Arg Asp Thr Ile Asn Gly Gln Asn Thr Ile Arg Ile
                165                 170                 175

Ser Gly Lys Val Ser Ala Gln Ala Val Asn Gln Ile Ala Pro Pro Phe
            180                 185                 190

Asn Ala Thr Gln Pro Val Pro Ala Thr Val Trp Ile Gln Glu Thr Gly
        195                 200                 205

Asp His Gln Leu Ala Gln Ala Gln Leu Asp Arg Gly Ser Gly Asn Ser
    210                 215                 220

Val Gln Met Thr Leu Ser Lys Trp Gly Glu Lys Val Gln Val Thr Lys
225                 230                 235                 240

Pro Pro Val Ser His His His His His His
                245                 250

<210> SEQ ID NO 43
<211> LENGTH: 695
<212> TYPE: PRT
<213> ORGANISM: Artificial
<220> FEATURE:
<223> OTHER INFORMATION: Synthetic Construct

<400> SEQUENCE: 43

Pro Asp Thr Met Val Thr Thr Asp Val Ile Lys Ser Arg Val Gln Leu
1               5                   10                  15

Ala Cys Arg Ala Pro Ser Leu His Asn Ser Gln Pro Trp Arg Trp Ile
            20                  25                  30

Ala Glu Asp His Thr Val Ala Leu Phe Leu Asp Lys Asp Arg Val Leu
        35                  40                  45

Tyr Ala Thr Asp His Ser Gly Arg Glu Ala Leu Leu Gly Cys Gly Ala
    50                  55                  60

Val Leu Asp His Phe Arg Val Ala Met Ala Ala Ala Gly Thr Thr Ala
65                  70                  75                  80

Asn Val Glu Arg Phe Pro Asn Pro Asn Asp Pro Leu His Leu Ala Ser
                85                  90                  95

Ile Asp Phe Ser Pro Ala Asp Phe Val Thr Glu Gly His Arg Leu Arg
                100                 105                 110

Ala Asp Ala Ile Leu Leu Arg Arg Thr Asp Arg Leu Pro Phe Ala Glu
            115                 120                 125

Pro Pro Asp Trp Asp Leu Val Glu Ser Gln Leu Arg Thr Thr Val Thr
        130                 135                 140

Ala Asp Thr Val Arg Ile Asp Val Ile Ala Asp Asp Met Arg Pro Glu
145                 150                 155                 160

Leu Ala Ala Ala Ser Lys Leu Thr Glu Ser Leu Arg Leu Tyr Asp Ser
                165                 170                 175

Ser Tyr His Ala Glu Leu Phe Trp Trp Thr Gly Ala Phe Glu Thr Ser
            180                 185                 190

Glu Gly Ile Pro His Ser Ser Leu Val Ser Ala Ala Glu Ser Asp Arg
        195                 200                 205
```

```
Val Thr Phe Gly Arg Asp Phe Pro Val Val Ala Asn Thr Asp Arg Arg
    210                 215                 220
Pro Glu Phe Gly His Asp Arg Ser Lys Val Leu Val Leu Ser Thr Tyr
225                 230                 235                 240
Asp Asn Glu Arg Ala Ser Leu Leu Arg Cys Gly Glu Met Leu Ser Ala
                245                 250                 255
Val Leu Leu Asp Ala Thr Met Ala Gly Leu Ala Thr Cys Thr Leu Thr
            260                 265                 270
His Ile Thr Glu Leu His Ala Ser Arg Asp Leu Val Ala Ala Leu Ile
        275                 280                 285
Gly Gln Pro Ala Thr Pro Gln Ala Leu Val Arg Val Gly Leu Ala Pro
    290                 295                 300
Glu Met Glu Glu Pro Pro Pro Ala Thr Pro Arg Arg Pro Ile Asp Glu
305                 310                 315                 320
Val Phe His Val Arg Ala Lys Asp His Arg Met Arg Thr Pro Arg Arg
                325                 330                 335
His Cys Arg Arg Ile Ala Val Leu Ala Ala Val Ser Ile Ala Ala Thr
            340                 345                 350
Val Val Ala Gly Cys Ser Ser Gly Ser Lys Pro Ser Gly Gly Pro Leu
        355                 360                 365
Pro Asp Ala Lys Pro Leu Val Glu Glu Ala Thr Ala Gln Thr Lys Ala
    370                 375                 380
Leu Lys Ser Ala His Met Val Leu Thr Val Asn Gly Lys Ile Pro Gly
385                 390                 395                 400
Leu Ser Leu Lys Thr Leu Ser Gly Asp Leu Thr Thr Asn Pro Thr Ala
                405                 410                 415
Ala Thr Gly Asn Trp Lys Leu Thr Leu Gly Gly Ser Asp Ile Asp Ala
            420                 425                 430
Asp Phe Val Val Phe Asp Gly Ile Leu Tyr Ala Thr Leu Thr Pro Asn
        435                 440                 445
Gln Trp Ser Asp Phe Gly Pro Ala Ala Asp Ile Tyr Asp Pro Ala Gln
    450                 455                 460
Val Leu Asn Pro Asp Thr Gly Leu Ala Asn Val Leu Ala Asn Phe Ala
465                 470                 475                 480
Asp Ala Lys Ala Glu Gly Arg Asp Thr Ile Asn Gly Gln Asn Thr Ile
                485                 490                 495
Arg Ile Ser Gly Lys Val Ser Ala Gln Ala Val Asn Gln Ile Ala Pro
            500                 505                 510
Pro Phe Asn Ala Thr Gln Pro Val Pro Ala Thr Val Trp Ile Gln Glu
        515                 520                 525
Thr Gly Asp His Gln Leu Ala Gln Ala Gln Leu Asp Arg Gly Ser Gly
    530                 535                 540
Asn Ser Val Gln Met Thr Leu Ser Lys Trp Gly Glu Lys Val Gln Val
545                 550                 555                 560
Thr Lys Pro Pro Val Ser Ser Ala Ala Gly Val Arg Ser Thr Arg Gln
                565                 570                 575
Arg Ala Ala Ile Ser Thr Leu Leu Glu Thr Leu Asp Asp Phe Arg Ser
            580                 585                 590
Ala Gln Glu Leu His Asp Glu Leu Arg Arg Arg Gly Glu Asn Ile Gly
        595                 600                 605
Leu Thr Thr Val Tyr Arg Thr Leu Gln Ser Met Ala Ser Ser Gly Leu
    610                 615                 620
```

```
Val Asp Thr Leu His Thr Asp Thr Gly Glu Ser Val Tyr Arg Arg Cys
625                 630                 635                 640

Ser Glu His His His His His Leu Val Cys Arg Ser Cys Gly Ser Thr
                645                 650                 655

Ile Glu Val Gly Asp His Glu Val Ala Trp Ala Ala Glu Val Ala
            660                 665                 670

Thr Lys His Gly Phe Ser Asp Val Ser His Thr Ile Glu Ile Phe Gly
        675                 680                 685

Thr Cys Ser Asp Cys Arg Ser
    690                 695

<210> SEQ ID NO 44
<211> LENGTH: 2130
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(2130)

<400> SEQUENCE: 44 atg gcc gac gag gca cca act agt cct gat aca atg gta aca act gac      48
Met Ala Asp Glu Ala Pro Thr Ser Pro Asp Thr Met Val Thr Thr Asp
1               5                   10                  15 gtt atc aaa tct aga gta caa ttg gct tgc aga gcc cca tca tta cat      96
Val Ile Lys Ser Arg Val Gln Leu Ala Cys Arg Ala Pro Ser Leu His
                20                  25                  30 aat tcc caa cca tgg cgc tgg att gcc gag gat cac aca gtg gca cta     144
Asn Ser Gln Pro Trp Arg Trp Ile Ala Glu Asp His Thr Val Ala Leu
            35                  40                  45 ttc tta gac aaa gat aga gtt ctt tat gct aca gat cat agt ggc aga     192
Phe Leu Asp Lys Asp Arg Val Leu Tyr Ala Thr Asp His Ser Gly Arg
        50                  55                  60 gaa gca ctg ctg gga tgt ggt gct gtc cta gac cac ttc aga gtt gct     240
Glu Ala Leu Leu Gly Cys Gly Ala Val Leu Asp His Phe Arg Val Ala
65                  70                  75                  80 atg gct gcg gcg ggc acc aca gca aat gtc gaa cga ttc cca aat cct     288
Met Ala Ala Ala Gly Thr Thr Ala Asn Val Glu Arg Phe Pro Asn Pro
                85                  90                  95 aac gat cca tta cat ctt gca tct att gac ttt tct cct gct gat ttt     336
Asn Asp Pro Leu His Leu Ala Ser Ile Asp Phe Ser Pro Ala Asp Phe
            100                 105                 110 gtc aca gaa ggc cac aga ttg aga gct gat gcg atc tta ttg agg aga     384
Val Thr Glu Gly His Arg Leu Arg Ala Asp Ala Ile Leu Leu Arg Arg
        115                 120                 125 aca gat aga ttg cct ttc gct gag cct cca gac tgg gac tta gta gaa     432
Thr Asp Arg Leu Pro Phe Ala Glu Pro Pro Asp Trp Asp Leu Val Glu
    130                 135                 140 tca cag ttg agg act aca gtt act gct gat acc gtt aga atc gat gtt     480
Ser Gln Leu Arg Thr Thr Val Thr Ala Asp Thr Val Arg Ile Asp Val
145                 150                 155                 160 ata gcg gat gat atg agg cca gaa ctt gca gcc gca tcc aaa ttg acc     528
Ile Ala Asp Asp Met Arg Pro Glu Leu Ala Ala Ala Ser Lys Leu Thr
                165                 170                 175 gaa tct ttg aga cta tac gat agc tct tac cat gcg gaa ctg ttt tgg     576
Glu Ser Leu Arg Leu Tyr Asp Ser Ser Tyr His Ala Glu Leu Phe Trp
            180                 185                 190 tgg act ggt gct ttc gaa aca tct gaa ggg ata cca cat tct tca tta     624
Trp Thr Gly Ala Phe Glu Thr Ser Glu Gly Ile Pro His Ser Ser Leu
        195                 200                 205
```

|  |  |  |  |  |  |  |  |  |  |  |  |  |  |  |  |
|---|---|---|---|---|---|---|---|---|---|---|---|---|---|---|---|
| gtt | tca | gct | gca | gaa | tcc | gat | aga | gtc | act | ttt | ggt | cgt | gat | ttc | cca | 672 |
| Val | Ser | Ala | Ala | Glu | Ser | Asp | Arg | Val | Thr | Phe | Gly | Arg | Asp | Phe | Pro |
| 210 |  |  |  |  | 215 |  |  |  |  | 220 |  |  |  |  |  |

```
gtt tca gct gca gaa tcc gat aga gtc act ttt ggt cgt gat ttc cca    672
Val Ser Ala Ala Glu Ser Asp Arg Val Thr Phe Gly Arg Asp Phe Pro
210                 215                 220 gtc gta gca aat act gac aga cga cct gaa ttt ggt cat gac aga tct    720
Val Val Ala Asn Thr Asp Arg Arg Pro Glu Phe Gly His Asp Arg Ser
225                 230                 235                 240 aaa gta ctt gtt ctc agc acc tac gat aat gaa agg gct tct ttg tta    768
Lys Val Leu Val Leu Ser Thr Tyr Asp Asn Glu Arg Ala Ser Leu Leu
                245                 250                 255 aga tgc ggt gaa atg cta agt gcc gtc tta ctg gat gcg act atg gct    816
Arg Cys Gly Glu Met Leu Ser Ala Val Leu Leu Asp Ala Thr Met Ala
            260                 265                 270 gga ttg gca act tgt aca ctg acc cat atc acg gaa ctg cat gca tca    864
Gly Leu Ala Thr Cys Thr Leu Thr His Ile Thr Glu Leu His Ala Ser
        275                 280                 285 aga gat ctc gta gca gcc ttg att ggc caa cca gcc aca cct caa gcc    912
Arg Asp Leu Val Ala Ala Leu Ile Gly Gln Pro Ala Thr Pro Gln Ala
    290                 295                 300 ctt gtg aga gta gga ttg gct cca gag atg gag gaa cca cct cct gct    960
Leu Val Arg Val Gly Leu Ala Pro Glu Met Glu Glu Pro Pro Pro Ala
305                 310                 315                 320 act cca cgt aga ccc atc gac gaa gtg ttc cat gtg aga gct aag gat   1008
Thr Pro Arg Arg Pro Ile Asp Glu Val Phe His Val Arg Ala Lys Asp
                325                 330                 335 cat aga atg aga act cca agg aga cat tgt cgt aga atc gcc gtg ctc   1056
His Arg Met Arg Thr Pro Arg Arg His Cys Arg Arg Ile Ala Val Leu
                340                 345                 350 gca gca gtc agt atc gcc gca aca gtc gtt gct ggt tgc tca tct ggt   1104
Ala Ala Val Ser Ile Ala Ala Thr Val Val Ala Gly Cys Ser Ser Gly
            355                 360                 365 tca aaa cca tct ggt ggc cca ctt cca gac gcc aag cct ttg gtg gaa   1152
Ser Lys Pro Ser Gly Gly Pro Leu Pro Asp Ala Lys Pro Leu Val Glu
        370                 375                 380 gag gca aca gct cag act aag gcg ttg aag tcc gca cac atg gtt cta   1200
Glu Ala Thr Ala Gln Thr Lys Ala Leu Lys Ser Ala His Met Val Leu
385                 390                 395                 400 act gtt aat ggt aaa att cct ggg cta tca ctt aag aca cta tct gga   1248
Thr Val Asn Gly Lys Ile Pro Gly Leu Ser Leu Lys Thr Leu Ser Gly
                405                 410                 415 gat ctc act acc aat cca aca gct gct acg ggt aac tgg aaa ctt aca   1296
Asp Leu Thr Thr Asn Pro Thr Ala Ala Thr Gly Asn Trp Lys Leu Thr
                420                 425                 430 ttg gga ggt tca gac atc gat gct gac ttt gtg gta ttt gat ggt att   1344
Leu Gly Gly Ser Asp Ile Asp Ala Asp Phe Val Val Phe Asp Gly Ile
            435                 440                 445 ttg tac gct acc tta aca cca aac caa tgg tca gat ttt gga cca gcc   1392
Leu Tyr Ala Thr Leu Thr Pro Asn Gln Trp Ser Asp Phe Gly Pro Ala
        450                 455                 460 gca gat atc tac gat cct gct caa gtt cta aat cca gac aca ggt tta   1440
Ala Asp Ile Tyr Asp Pro Ala Gln Val Leu Asn Pro Asp Thr Gly Leu
465                 470                 475                 480 gcg aac gtt ctt gct aat ttc gct gat gct aag gcc gaa ggg aga gac   1488
Ala Asn Val Leu Ala Asn Phe Ala Asp Ala Lys Ala Glu Gly Arg Asp
                485                 490                 495 acc att aac ggt caa aat act att aga ata tct ggc aag gta tct gca   1536
Thr Ile Asn Gly Gln Asn Thr Ile Arg Ile Ser Gly Lys Val Ser Ala
                500                 505                 510 caa gcc gtc aac caa att gca cct cct ttt aac gct acc caa cca gtc   1584
Gln Ala Val Asn Gln Ile Ala Pro Pro Phe Asn Ala Thr Gln Pro Val
```

```
cca gct act gta tgg atc caa gag act gga gat cat cag tta gct caa    1632
Pro Ala Thr Val Trp Ile Gln Glu Thr Gly Asp His Gln Leu Ala Gln
    530                 535                 540 gct caa ctg gac aga ggg agt ggc aat tcc gtt cag atg aca ctc tcc    1680
Ala Gln Leu Asp Arg Gly Ser Gly Asn Ser Val Gln Met Thr Leu Ser
545                 550                 555                 560 aaa tgg ggc gag aag gtt caa gtc aca aaa cca cct gtt tca agt gct    1728
Lys Trp Gly Glu Lys Val Gln Val Thr Lys Pro Pro Val Ser Ser Ala
                565                 570                 575 gcc ggt gtg aga agc acg aga caa aga gca gcc atc tct acg ttg ctt    1776
Ala Gly Val Arg Ser Thr Arg Gln Arg Ala Ala Ile Ser Thr Leu Leu
            580                 585                 590 gaa aca cta gat gac ttc aga tct gcc cag gag tta cac gat gaa tta    1824
Glu Thr Leu Asp Asp Phe Arg Ser Ala Gln Glu Leu His Asp Glu Leu
        595                 600                 605 aga cgt agg ggg gag aat att ggc ttg act act gtt tac aga acc tta    1872
Arg Arg Arg Gly Glu Asn Ile Gly Leu Thr Thr Val Tyr Arg Thr Leu
    610                 615                 620 caa tca atg gca tcc tcg gga ttg gtg gat act ttg cat act gat acg    1920
Gln Ser Met Ala Ser Ser Gly Leu Val Asp Thr Leu His Thr Asp Thr
625                 630                 635                 640 gga gaa tca gtt tat aga aga tgc tct gaa cac cat cat cat cat ttg    1968
Gly Glu Ser Val Tyr Arg Arg Cys Ser Glu His His His His His Leu
                645                 650                 655 gtt tgt aga tca tgt gga tca aca ata gag gta ggt gac cat gaa gtc    2016
Val Cys Arg Ser Cys Gly Ser Thr Ile Glu Val Gly Asp His Glu Val
            660                 665                 670 gaa gca tgg gca gcc gag gtg gct act aaa cat ggt ttt tct gat gtt    2064
Glu Ala Trp Ala Ala Glu Val Ala Thr Lys His Gly Phe Ser Asp Val
        675                 680                 685 tct cat aca att gaa ata ttt ggc aca tgt agt gat tgt cgt tcc cac    2112
Ser His Thr Ile Glu Ile Phe Gly Thr Cys Ser Asp Cys Arg Ser His
    690                 695                 700 cat cac cac cac cat taa                                            2130
His His His His His
705

<210> SEQ ID NO 45
<211> LENGTH: 709
<212> TYPE: PRT
<213> ORGANISM: Artificial
<220> FEATURE:
<223> OTHER INFORMATION: Synthetic Construct

<400> SEQUENCE: 45

Met Ala Asp Glu Ala Pro Thr Ser Pro Asp Thr Met Val Thr Thr Asp
1               5                   10                  15

Val Ile Lys Ser Arg Val Gln Leu Ala Cys Arg Ala Pro Ser Leu His
                20                  25                  30

Asn Ser Gln Pro Trp Arg Trp Ile Ala Glu Asp His Thr Val Ala Leu
            35                  40                  45

Phe Leu Asp Lys Asp Arg Val Leu Tyr Ala Thr Asp His Ser Gly Arg
        50                  55                  60

Glu Ala Leu Leu Gly Cys Gly Ala Val Leu Asp His Phe Arg Val Ala
65                  70                  75                  80

Met Ala Ala Ala Gly Thr Thr Ala Asn Val Glu Arg Phe Pro Asn Pro
                85                  90                  95

Asn Asp Pro Leu His Leu Ala Ser Ile Asp Phe Ser Pro Ala Asp Phe
```

```
                100                 105                 110
Val Thr Glu Gly His Arg Leu Arg Ala Asp Ala Ile Leu Leu Arg Arg
            115                 120                 125

Thr Asp Arg Leu Pro Phe Ala Glu Pro Pro Asp Trp Asp Leu Val Glu
        130                 135                 140

Ser Gln Leu Arg Thr Thr Val Thr Ala Asp Thr Val Arg Ile Asp Val
145                 150                 155                 160

Ile Ala Asp Asp Met Arg Pro Glu Leu Ala Ala Ser Lys Leu Thr
                165                 170                 175

Glu Ser Leu Arg Leu Tyr Asp Ser Ser Tyr His Ala Glu Leu Phe Trp
            180                 185                 190

Trp Thr Gly Ala Phe Glu Thr Ser Glu Gly Ile Pro His Ser Ser Leu
        195                 200                 205

Val Ser Ala Ala Glu Ser Asp Arg Val Thr Phe Gly Arg Asp Phe Pro
    210                 215                 220

Val Val Ala Asn Thr Asp Arg Arg Pro Glu Phe Gly His Asp Arg Ser
225                 230                 235                 240

Lys Val Leu Val Leu Ser Thr Tyr Asp Asn Glu Arg Ala Ser Leu Leu
                245                 250                 255

Arg Cys Gly Glu Met Leu Ser Ala Val Leu Leu Asp Ala Thr Met Ala
            260                 265                 270

Gly Leu Ala Thr Cys Thr Leu Thr His Ile Thr Glu Leu His Ala Ser
        275                 280                 285

Arg Asp Leu Val Ala Ala Leu Ile Gly Gln Pro Ala Thr Pro Gln Ala
    290                 295                 300

Leu Val Arg Val Gly Leu Ala Pro Glu Met Glu Glu Pro Pro Ala
305                 310                 315                 320

Thr Pro Arg Arg Pro Ile Asp Glu Val Phe His Val Arg Ala Lys Asp
                325                 330                 335

His Arg Met Arg Thr Pro Arg Arg His Cys Arg Arg Ile Ala Val Leu
            340                 345                 350

Ala Ala Val Ser Ile Ala Ala Thr Val Val Ala Gly Cys Ser Ser Gly
        355                 360                 365

Ser Lys Pro Ser Gly Gly Pro Leu Pro Asp Ala Lys Pro Leu Val Glu
    370                 375                 380

Glu Ala Thr Ala Gln Thr Lys Ala Leu Lys Ser Ala His Met Val Leu
385                 390                 395                 400

Thr Val Asn Gly Lys Ile Pro Gly Leu Ser Leu Lys Thr Leu Ser Gly
                405                 410                 415

Asp Leu Thr Thr Asn Pro Thr Ala Ala Thr Gly Asn Trp Lys Leu Thr
            420                 425                 430

Leu Gly Gly Ser Asp Ile Asp Ala Asp Phe Val Val Phe Asp Gly Ile
        435                 440                 445

Leu Tyr Ala Thr Leu Thr Pro Asn Gln Trp Ser Asp Phe Gly Pro Ala
    450                 455                 460

Ala Asp Ile Tyr Asp Pro Ala Gln Val Leu Asn Pro Asp Thr Gly Leu
465                 470                 475                 480

Ala Asn Val Leu Ala Asn Phe Asp Ala Lys Ala Glu Gly Arg Asp
                485                 490                 495

Thr Ile Asn Gly Gln Asn Thr Ile Arg Ile Ser Gly Lys Val Ser Ala
            500                 505                 510

Gln Ala Val Asn Gln Ile Ala Pro Pro Phe Asn Ala Thr Gln Pro Val
        515                 520                 525
```

```
Pro Ala Thr Val Trp Ile Gln Glu Thr Gly Asp His Gln Leu Ala Gln
        530                 535                 540

Ala Gln Leu Asp Arg Gly Ser Gly Asn Ser Val Gln Met Thr Leu Ser
545                 550                 555                 560

Lys Trp Gly Glu Lys Val Gln Val Thr Lys Pro Pro Val Ser Ser Ala
                565                 570                 575

Ala Gly Val Arg Ser Thr Arg Gln Arg Ala Ala Ile Ser Thr Leu Leu
                580                 585                 590

Glu Thr Leu Asp Asp Phe Arg Ser Ala Gln Glu Leu His Asp Glu Leu
            595                 600                 605

Arg Arg Arg Gly Glu Asn Ile Gly Leu Thr Thr Val Tyr Arg Thr Leu
610                 615                 620

Gln Ser Met Ala Ser Ser Gly Leu Val Asp Thr Leu His Thr Asp Thr
625                 630                 635                 640

Gly Glu Ser Val Tyr Arg Arg Cys Ser Glu His His His His His Leu
                645                 650                 655

Val Cys Arg Ser Cys Gly Ser Thr Ile Glu Val Gly Asp His Glu Val
                660                 665                 670

Glu Ala Trp Ala Ala Glu Val Ala Thr Lys His Gly Phe Ser Asp Val
            675                 680                 685

Ser His Thr Ile Glu Ile Phe Gly Thr Cys Ser Asp Cys Arg Ser His
        690                 695                 700

His His His His His
705

<210> SEQ ID NO 46
<211> LENGTH: 795
<212> TYPE: PRT
<213> ORGANISM: Artificial
<220> FEATURE:
<223> OTHER INFORMATION: Synthetic Construct

<400> SEQUENCE: 46

Pro Asp Thr Met Val Thr Thr Asp Val Ile Lys Ser Arg Val Gln Leu
1               5                   10                  15

Ala Cys Arg Ala Pro Ser Leu His Asn Ser Gln Pro Trp Arg Trp Ile
                20                  25                  30

Ala Glu Asp His Thr Val Ala Leu Phe Leu Asp Lys Asp Arg Val Leu
            35                  40                  45

Tyr Ala Thr Asp His Ser Gly Arg Glu Ala Leu Leu Gly Cys Gly Ala
        50                  55                  60

Val Leu Asp His Phe Arg Val Ala Met Ala Ala Ala Gly Thr Thr Ala
65                  70                  75                  80

Asn Val Glu Arg Phe Pro Asn Pro Asn Asp Pro Leu His Leu Ala Ser
                85                  90                  95

Ile Asp Phe Ser Pro Ala Asp Phe Val Thr Glu Gly His Arg Leu Arg
                100                 105                 110

Ala Asp Ala Ile Leu Leu Arg Arg Thr Asp Arg Leu Pro Phe Ala Glu
            115                 120                 125

Pro Pro Asp Trp Asp Leu Val Glu Ser Gln Leu Arg Thr Thr Val Thr
        130                 135                 140

Ala Asp Thr Val Arg Ile Asp Val Ile Ala Asp Asp Met Arg Pro Glu
145                 150                 155                 160

Leu Ala Ala Ala Ser Lys Leu Thr Glu Ser Leu Arg Leu Tyr Asp Ser
                165                 170                 175
```

```
Ser Tyr His Ala Glu Leu Phe Trp Trp Thr Gly Ala Phe Glu Thr Ser
            180                 185                 190

Glu Gly Ile Pro His Ser Ser Leu Val Ser Ala Ala Glu Ser Asp Arg
            195                 200                 205

Val Thr Phe Gly Arg Asp Phe Pro Val Val Ala Asn Thr Asp Arg Arg
210                 215                 220

Pro Glu Phe Gly His Asp Arg Ser Lys Val Leu Val Leu Ser Thr Tyr
225                 230                 235                 240

Asp Asn Glu Arg Ala Ser Leu Leu Arg Cys Gly Glu Met Leu Ser Ala
                245                 250                 255

Val Leu Leu Asp Ala Thr Met Ala Gly Leu Ala Thr Cys Thr Leu Thr
            260                 265                 270

His Ile Thr Glu Leu His Ala Ser Arg Asp Leu Val Ala Ala Leu Ile
            275                 280                 285

Gly Gln Pro Ala Thr Pro Gln Ala Leu Val Arg Val Gly Leu Ala Pro
290                 295                 300

Glu Met Glu Glu Pro Pro Ala Thr Pro Arg Arg Pro Ile Asp Glu
305                 310                 315                 320

Val Phe His Val Arg Ala Lys Asp His Arg Met Arg Thr Pro Arg Arg
                325                 330                 335

His Cys Arg Arg Ile Ala Val Leu Ala Ala Val Ser Ile Ala Ala Thr
                340                 345                 350

Val Val Ala Gly Cys Ser Ser Gly Ser Lys Pro Ser Gly Gly Pro Leu
            355                 360                 365

Pro Asp Ala Lys Pro Leu Val Glu Ala Thr Ala Gln Thr Lys Ala
370                 375                 380

Leu Lys Ser Ala His Met Val Leu Thr Val Asn Gly Lys Ile Pro Gly
385                 390                 395                 400

Leu Ser Leu Lys Thr Leu Ser Gly Asp Leu Thr Thr Asn Pro Thr Ala
                405                 410                 415

Ala Thr Gly Asn Trp Lys Leu Thr Leu Gly Gly Ser Asp Ile Asp Ala
            420                 425                 430

Asp Phe Val Val Phe Asp Gly Ile Leu Tyr Ala Thr Leu Thr Pro Asn
            435                 440                 445

Gln Trp Ser Asp Phe Gly Pro Ala Ala Asp Ile Tyr Asp Pro Ala Gln
    450                 455                 460

Val Leu Asn Pro Asp Thr Gly Leu Ala Asn Val Leu Ala Asn Phe Ala
465                 470                 475                 480

Asp Ala Lys Ala Glu Gly Arg Asp Thr Ile Asn Gly Gln Asn Thr Ile
                485                 490                 495

Arg Ile Ser Gly Lys Val Ser Ala Gln Ala Val Asn Gln Ile Ala Pro
            500                 505                 510

Pro Phe Asn Ala Thr Gln Pro Val Pro Ala Thr Val Trp Ile Gln Glu
    515                 520                 525

Thr Gly Asp His Gln Leu Ala Gln Ala Gln Leu Asp Arg Gly Ser Gly
    530                 535                 540

Asn Ser Val Gln Met Thr Leu Ser Lys Trp Gly Glu Lys Val Gln Val
545                 550                 555                 560

Thr Lys Pro Pro Val Ser Asn Glu Leu Val Asp Thr Glu Met Tyr
                565                 570                 575

Leu Arg Thr Ile Tyr Asp Leu Glu Glu Glu Gly Val Thr Pro Leu Arg
            580                 585                 590
```

```
Ala Arg Ile Ala Glu Arg Leu Asp Gln Ser Gly Pro Thr Val Ser Gln
        595                 600                 605

Thr Val Ser Arg Met Glu Arg Asp Gly Leu Leu Arg Val Ala Gly Asp
    610                 615                 620

Arg His Leu Glu Leu Thr Glu Lys Gly Arg Ala Leu Ala Ile Ala Val
625                 630                 635                 640

Met Arg Lys His Arg Leu Ala Glu Arg Leu Val Asp Val Ile Gly
                645                 650                 655

Leu Pro Trp Glu Val His Ala Glu Ala Cys Arg Trp Glu His Val
            660                 665                 670

Met Ser Glu Asp Val Glu Arg Leu Val Lys Val Leu Asn Asn Pro
    675                 680                 685

Thr Thr Ser Pro Phe Gly Asn Pro Ile Pro Gly Leu Val Glu Leu Gly
    690                 695                 700

Val Gly Pro Glu Pro Gly Ala Asp Asp Ala Asn Leu Val Arg Leu Thr
705                 710                 715                 720

Glu Leu Pro Ala Gly Ser Pro Val Ala Val Val Arg Gln Leu Thr
            725                 730                 735

Glu His Val Gln Gly Asp Ile Asp Leu Ile Thr Arg Leu Lys Asp Ala
                740                 745                 750

Gly Val Val Pro Asn Ala Arg Val Thr Val Glu Thr Pro Gly Gly
    755                 760                 765

Gly Val Thr Ile Val Ile Pro Gly His Glu Asn Val Thr Leu Pro His
    770                 775                 780

Glu Met Ala His Ala Val Lys Val Glu Lys Val
785                 790                 795

<210> SEQ ID NO 47
<211> LENGTH: 2430
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(2430)

<400> SEQUENCE: 47 atg gcc gac gag gca cca act agt cct gat aca atg gta aca act gac      48
Met Ala Asp Glu Ala Pro Thr Ser Pro Asp Thr Met Val Thr Thr Asp
1               5                   10                  15 gtt atc aaa tct aga gta caa ttg gct tgc aga gcc cca tca tta cat      96
Val Ile Lys Ser Arg Val Gln Leu Ala Cys Arg Ala Pro Ser Leu His
            20                  25                  30 aat tcc caa cca tgg cgc tgg att gcc gag gat cac aca gtg gca cta     144
Asn Ser Gln Pro Trp Arg Trp Ile Ala Glu Asp His Thr Val Ala Leu
        35                  40                  45 ttc tta gac aaa gat aga gtt ctt tat gct aca gat cat agt ggc aga     192
Phe Leu Asp Lys Asp Arg Val Leu Tyr Ala Thr Asp His Ser Gly Arg
    50                  55                  60 gaa gca ctg ctg gga tgt ggt gct gtc cta gac cac ttc aga gtt gct     240
Glu Ala Leu Leu Gly Cys Gly Ala Val Leu Asp His Phe Arg Val Ala
65                  70                  75                  80 atg gct gcg gcg ggc acc aca gca aat gtc gaa cga ttc cca aat cct     288
Met Ala Ala Ala Gly Thr Thr Ala Asn Val Glu Arg Phe Pro Asn Pro
                85                  90                  95 aac gat cca tta cat ctt gca tct att gac ttt tct cct gct gat ttt     336
Asn Asp Pro Leu His Leu Ala Ser Ile Asp Phe Ser Pro Ala Asp Phe
            100                 105                 110
```

```
gtc aca gaa ggc cac aga ttg aga gct gat gcg atc tta ttg agg aga      384
Val Thr Glu Gly His Arg Leu Arg Ala Asp Ala Ile Leu Leu Arg Arg
            115                 120                 125 aca gat aga ttg cct ttc gct gag cct cca gac tgg gac tta gta gaa      432
Thr Asp Arg Leu Pro Phe Ala Glu Pro Pro Asp Trp Asp Leu Val Glu
        130                 135                 140 tca cag ttg agg act aca gtt act gct gat acc gtt aga atc gat gtt      480
Ser Gln Leu Arg Thr Thr Val Thr Ala Asp Thr Val Arg Ile Asp Val
145                 150                 155                 160 ata gcg gat gat atg agg cca gaa ctt gca gcc gca tcc aaa ttg acc      528
Ile Ala Asp Asp Met Arg Pro Glu Leu Ala Ala Ala Ser Lys Leu Thr
                165                 170                 175 gaa tct ttg aga cta tac gat agc tct tac cat gcg gaa ctg ttt tgg      576
Glu Ser Leu Arg Leu Tyr Asp Ser Ser Tyr His Ala Glu Leu Phe Trp
            180                 185                 190 tgg act ggt gct ttc gaa aca tct gaa ggg ata cca cat tct tca tta      624
Trp Thr Gly Ala Phe Glu Thr Ser Glu Gly Ile Pro His Ser Ser Leu
        195                 200                 205 gtt tca gct gca gaa tcc gat aga gtc act ttt ggt cgt gat ttc cca      672
Val Ser Ala Ala Glu Ser Asp Arg Val Thr Phe Gly Arg Asp Phe Pro
    210                 215                 220 gtc gta gca aat act gac aga cga cct gaa ttt ggt cat gac aga tct      720
Val Val Ala Asn Thr Asp Arg Arg Pro Glu Phe Gly His Asp Arg Ser
225                 230                 235                 240 aaa gta ctt gtt ctc agc acc tac gat aat gaa agg gct tct ttg tta      768
Lys Val Leu Val Leu Ser Thr Tyr Asp Asn Glu Arg Ala Ser Leu Leu
                245                 250                 255 aga tgc ggt gaa atg cta agt gcc gtc tta ctg gat gcg act atg gct      816
Arg Cys Gly Glu Met Leu Ser Ala Val Leu Leu Asp Ala Thr Met Ala
            260                 265                 270 gga ttg gca act tgt aca ctg acc cat atc acg gaa ctg cat gca tca      864
Gly Leu Ala Thr Cys Thr Leu Thr His Ile Thr Glu Leu His Ala Ser
        275                 280                 285 aga gat ctc gta gca gcc ttg att ggc caa cca gcc aca cct caa gcc      912
Arg Asp Leu Val Ala Ala Leu Ile Gly Gln Pro Ala Thr Pro Gln Ala
    290                 295                 300 ctt gtg aga gta gga ttg gct cca gag atg gag gaa cca cct cct gct      960
Leu Val Arg Val Gly Leu Ala Pro Glu Met Glu Glu Pro Pro Pro Ala
305                 310                 315                 320 act cca cgt aga ccc atc gac gaa gtg ttc cat gtg aga gct aag gat     1008
Thr Pro Arg Arg Pro Ile Asp Glu Val Phe His Val Arg Ala Lys Asp
                325                 330                 335 cat aga atg aga act cca agg aga cat tgt cgt aga atc gcc gtg ctc     1056
His Arg Met Arg Thr Pro Arg Arg His Cys Arg Arg Ile Ala Val Leu
            340                 345                 350 gca gca gtc agt atc gcc gca aca gtc gtt gct ggt tgc tca tct ggt     1104
Ala Ala Val Ser Ile Ala Ala Thr Val Val Ala Gly Cys Ser Ser Gly
        355                 360                 365 tca aaa cca tct ggt ggc cca ctt cca gac gcc aag cct ttg gtg gaa     1152
Ser Lys Pro Ser Gly Gly Pro Leu Pro Asp Ala Lys Pro Leu Val Glu
    370                 375                 380 gag gca aca gct cag act aag gcg ttg aag tcc gca cac atg gtt cta     1200
Glu Ala Thr Ala Gln Thr Lys Ala Leu Lys Ser Ala His Met Val Leu
385                 390                 395                 400 act gtt aat ggt aaa att cct ggg cta tca ctt aag aca cta tct gga     1248
Thr Val Asn Gly Lys Ile Pro Gly Leu Ser Leu Lys Thr Leu Ser Gly
                405                 410                 415 gat ctc act acc aat cca aca gct gct acg ggt aac tgg aaa ctt aca     1296
Asp Leu Thr Thr Asn Pro Thr Ala Ala Thr Gly Asn Trp Lys Leu Thr
```

```
                    420                 425                 430
ttg gga ggt tca gac atc gat gct gac ttt gtg gta ttt gat ggt att     1344
Leu Gly Gly Ser Asp Ile Asp Ala Asp Phe Val Val Phe Asp Gly Ile
            435                 440                 445 ttg tac gct acc tta aca cca aac caa tgg tca gat ttt gga cca gcc     1392
Leu Tyr Ala Thr Leu Thr Pro Asn Gln Trp Ser Asp Phe Gly Pro Ala
450                 455                 460 gca gat atc tac gat cct gct caa gtt cta aat cca gac aca ggt tta     1440
Ala Asp Ile Tyr Asp Pro Ala Gln Val Leu Asn Pro Asp Thr Gly Leu
465                 470                 475                 480 gcg aac gtt ctt gct aat ttc gct gat gct aag gcc gaa ggg aga gac     1488
Ala Asn Val Leu Ala Asn Phe Ala Asp Ala Lys Ala Glu Gly Arg Asp
            485                 490                 495 acc att aac ggt caa aat act att aga ata tct ggc aag gta tct gca     1536
Thr Ile Asn Gly Gln Asn Thr Ile Arg Ile Ser Gly Lys Val Ser Ala
            500                 505                 510 caa gcc gtc aac caa att gca cct cct ttt aac gct acc caa cca gtc     1584
Gln Ala Val Asn Gln Ile Ala Pro Pro Phe Asn Ala Thr Gln Pro Val
            515                 520                 525 cca gct act gta tgg atc caa gag act gga gat cat cag tta gct caa     1632
Pro Ala Thr Val Trp Ile Gln Glu Thr Gly Asp His Gln Leu Ala Gln
530                 535                 540 gct caa ctg gac aga ggg agt ggc aat tcc gtt cag atg aca ctc tcc     1680
Ala Gln Leu Asp Arg Gly Ser Gly Asn Ser Val Gln Met Thr Leu Ser
545                 550                 555                 560 aaa tgg ggc gag aag gtt caa gtc aca aaa cca cct gtt tca aat gaa     1728
Lys Trp Gly Glu Lys Val Gln Val Thr Lys Pro Pro Val Ser Asn Glu
            565                 570                 575 tta gta gac acc act gaa atg tat ctt aga aca ata tac gac tta gag     1776
Leu Val Asp Thr Thr Glu Met Tyr Leu Arg Thr Ile Tyr Asp Leu Glu
            580                 585                 590 gaa gag ggc gtg acc cca tta aga gcc aga atc gcc gaa aga tta gac     1824
Glu Glu Gly Val Thr Pro Leu Arg Ala Arg Ile Ala Glu Arg Leu Asp
            595                 600                 605 caa tcc ggt cca act gtt tct caa aca gtg tct agg atg gaa aga gat     1872
Gln Ser Gly Pro Thr Val Ser Gln Thr Val Ser Arg Met Glu Arg Asp
610                 615                 620 ggt ttg tta agg gtt gct gga gat cgt cac ctc gaa ctc aca gag aaa     1920
Gly Leu Leu Arg Val Ala Gly Asp Arg His Leu Glu Leu Thr Glu Lys
625                 630                 635                 640 ggt aga gct ttg gca atc gca gtc atg aga aag cat aga cta gcg gaa     1968
Gly Arg Ala Leu Ala Ile Ala Val Met Arg Lys His Arg Leu Ala Glu
            645                 650                 655 cga ttg cta gtg gac gtg atc gga ctg cct tgg gaa gag gtc cat gct     2016
Arg Leu Leu Val Asp Val Ile Gly Leu Pro Trp Glu Glu Val His Ala
            660                 665                 670 gaa gca tgt aga tgg gaa cat gtt atg tct gag gat gta gag aga aga     2064
Glu Ala Cys Arg Trp Glu His Val Met Ser Glu Asp Val Glu Arg Arg
            675                 680                 685 ttg gtc aaa gta ttg aat aat cca acc aca tca cct ttt gga aac cct     2112
Leu Val Lys Val Leu Asn Asn Pro Thr Thr Ser Pro Phe Gly Asn Pro
            690                 695                 700 att cct ggg cta gtt gaa ctt ggt gtg ggt cct gaa cca ggc gca gat     2160
Ile Pro Gly Leu Val Glu Leu Gly Val Gly Pro Glu Pro Gly Ala Asp
705                 710                 715                 720 gat gcg aat ctg gta aga ttg aca gaa tta cca gca ggg tca cca gtt     2208
Asp Ala Asn Leu Val Arg Leu Thr Glu Leu Pro Ala Gly Ser Pro Val
            725                 730                 735 gca gtt gtt gta aga caa ctg acg gaa cac gtg cag ggt gat att gat     2256
```

```
Ala Val Val Val Arg Gln Leu Thr Glu His Val Gln Gly Asp Ile Asp
                740                 745                 750 ctt atc aca aga ttg aag gac gct ggt gtt gta cca aac gcc cgt gtc      2304
Leu Ile Thr Arg Leu Lys Asp Ala Gly Val Val Pro Asn Ala Arg Val
                755                 760                 765 act gtt gaa aca act cct gga ggt ggc gtc aca att gtt ata cca ggc      2352
Thr Val Glu Thr Thr Pro Gly Gly Gly Val Thr Ile Val Ile Pro Gly
        770                 775                 780 cac gaa aac gtt act ctt cca cat gaa atg gcc cat gct gta aaa gtc      2400
His Glu Asn Val Thr Leu Pro His Glu Met Ala His Ala Val Lys Val
785                 790                 795                 800 gag aag gtt cac cat cac cac cac cat taa                              2430
Glu Lys Val His His His His His His
                805
```

<210> SEQ ID NO 48
<211> LENGTH: 809
<212> TYPE: PRT
<213> ORGANISM: Artificial
<220> FEATURE:
<223> OTHER INFORMATION: Synthetic Construct

<400> SEQUENCE: 48

```
Met Ala Asp Glu Ala Pro Thr Ser Pro Asp Thr Met Val Thr Thr Asp
1               5                   10                  15

Val Ile Lys Ser Arg Val Gln Leu Ala Cys Arg Ala Pro Ser Leu His
                20                  25                  30

Asn Ser Gln Pro Trp Arg Trp Ile Ala Glu Asp His Thr Val Ala Leu
            35                  40                  45

Phe Leu Asp Lys Asp Arg Val Leu Tyr Ala Thr Asp His Ser Gly Arg
    50                  55                  60

Glu Ala Leu Leu Gly Cys Gly Ala Val Leu Asp His Phe Arg Val Ala
65                  70                  75                  80

Met Ala Ala Ala Gly Thr Thr Ala Asn Val Glu Arg Phe Pro Asn Pro
                85                  90                  95

Asn Asp Pro Leu His Leu Ala Ser Ile Asp Phe Ser Pro Ala Asp Phe
            100                 105                 110

Val Thr Glu Gly His Arg Leu Arg Ala Asp Ala Ile Leu Leu Arg Arg
        115                 120                 125

Thr Asp Arg Leu Pro Phe Ala Glu Pro Pro Asp Trp Asp Leu Val Glu
    130                 135                 140

Ser Gln Leu Arg Thr Thr Val Thr Ala Asp Thr Val Arg Ile Asp Val
145                 150                 155                 160

Ile Ala Asp Asp Met Arg Pro Glu Leu Ala Ala Ala Ser Lys Leu Thr
                165                 170                 175

Glu Ser Leu Arg Leu Tyr Asp Ser Ser Tyr His Ala Glu Leu Phe Trp
            180                 185                 190

Trp Thr Gly Ala Phe Glu Thr Ser Glu Gly Ile Pro His Ser Ser Leu
        195                 200                 205

Val Ser Ala Ala Glu Ser Asp Arg Val Thr Phe Gly Arg Asp Phe Pro
    210                 215                 220

Val Val Ala Asn Thr Asp Arg Arg Pro Glu Phe Gly His Asp Arg Ser
225                 230                 235                 240

Lys Val Leu Val Leu Ser Thr Tyr Asp Asn Glu Arg Ala Ser Leu Leu
                245                 250                 255

Arg Cys Gly Glu Met Leu Ser Ala Val Leu Leu Asp Ala Thr Met Ala
            260                 265                 270
```

```
Gly Leu Ala Thr Cys Thr Leu Thr His Ile Thr Glu Leu His Ala Ser
            275                 280                 285

Arg Asp Leu Val Ala Ala Leu Ile Gly Gln Pro Ala Thr Pro Gln Ala
    290                 295                 300

Leu Val Arg Val Gly Leu Ala Pro Glu Met Glu Glu Pro Pro Ala
305                 310                 315                 320

Thr Pro Arg Arg Pro Ile Asp Glu Val Phe His Val Arg Ala Lys Asp
                325                 330                 335

His Arg Met Arg Thr Pro Arg Arg His Cys Arg Arg Ile Ala Val Leu
            340                 345                 350

Ala Ala Val Ser Ile Ala Ala Thr Val Ala Gly Cys Ser Ser Gly
            355                 360                 365

Ser Lys Pro Ser Gly Gly Pro Leu Pro Asp Ala Lys Pro Leu Val Glu
    370                 375                 380

Glu Ala Thr Ala Gln Thr Lys Ala Leu Lys Ser Ala His Met Val Leu
385                 390                 395                 400

Thr Val Asn Gly Lys Ile Pro Gly Leu Ser Leu Lys Thr Leu Ser Gly
                405                 410                 415

Asp Leu Thr Thr Asn Pro Thr Ala Ala Thr Gly Asn Trp Lys Leu Thr
            420                 425                 430

Leu Gly Gly Ser Asp Ile Asp Ala Asp Phe Val Val Phe Asp Gly Ile
        435                 440                 445

Leu Tyr Ala Thr Leu Thr Pro Asn Gln Trp Ser Asp Phe Gly Pro Ala
        450                 455                 460

Ala Asp Ile Tyr Asp Pro Ala Gln Val Leu Asn Pro Asp Thr Gly Leu
465                 470                 475                 480

Ala Asn Val Leu Ala Asn Phe Ala Asp Ala Lys Ala Glu Gly Arg Asp
                485                 490                 495

Thr Ile Asn Gly Gln Asn Thr Ile Arg Ile Ser Gly Lys Val Ser Ala
            500                 505                 510

Gln Ala Val Asn Gln Ile Ala Pro Pro Phe Asn Ala Thr Gln Pro Val
    515                 520                 525

Pro Ala Thr Val Trp Ile Gln Glu Thr Gly Asp His Gln Leu Ala Gln
    530                 535                 540

Ala Gln Leu Asp Arg Gly Ser Gly Asn Ser Val Gln Met Thr Leu Ser
545                 550                 555                 560

Lys Trp Gly Glu Lys Val Gln Val Thr Lys Pro Pro Val Ser Asn Glu
                565                 570                 575

Leu Val Asp Thr Thr Glu Met Tyr Leu Arg Thr Ile Tyr Asp Leu Glu
            580                 585                 590

Glu Glu Gly Val Thr Pro Leu Arg Ala Arg Ile Ala Glu Arg Leu Asp
        595                 600                 605

Gln Ser Gly Pro Thr Val Ser Gln Thr Val Ser Arg Met Glu Arg Asp
    610                 615                 620

Gly Leu Leu Arg Val Ala Gly Asp Arg His Leu Glu Leu Thr Glu Lys
625                 630                 635                 640

Gly Arg Ala Leu Ala Ile Ala Val Met Arg Lys His Arg Leu Ala Glu
                645                 650                 655

Arg Leu Leu Val Asp Val Ile Gly Leu Pro Trp Glu Val His Ala
            660                 665                 670

Glu Ala Cys Arg Trp Glu His Val Met Ser Glu Asp Val Glu Arg Arg
            675                 680                 685
```

-continued

```
Leu Val Lys Val Leu Asn Asn Pro Thr Thr Ser Pro Phe Gly Asn Pro
    690             695             700
Ile Pro Gly Leu Val Glu Leu Gly Val Gly Pro Glu Pro Gly Ala Asp
705             710             715             720
Asp Ala Asn Leu Val Arg Leu Thr Glu Leu Pro Ala Gly Ser Pro Val
            725             730             735
Ala Val Val Val Arg Gln Leu Thr Glu His Val Gln Gly Asp Ile Asp
            740             745             750
Leu Ile Thr Arg Leu Lys Asp Ala Gly Val Val Pro Asn Ala Arg Val
        755             760             765
Thr Val Glu Thr Thr Pro Gly Gly Gly Val Thr Ile Val Ile Pro Gly
    770             775             780
His Glu Asn Val Thr Leu Pro His Glu Met Ala His Ala Val Lys Val
785             790             795             800
Glu Lys Val His His His His His His
                805
```